US010336768B2

(12) United States Patent
Cuny et al.

(10) Patent No.: US 10,336,768 B2
(45) Date of Patent: Jul. 2, 2019

(54) PYRIMIDINE COMPOUNDS AND METHODS USING THE SAME

(71) Applicants: Yuma Therapeutics, Inc., Cambridge, MA (US); The Brigham and Women's Hospital, Inc., Boston, MA (US)

(72) Inventors: Gregory D. Cuny, Houston, TX (US); Marcie A. Glicksman, Boston, MA (US); Kevin J. Hodgetts, Framingham, MA (US); Steven L. Mathieu, Somerville, MA (US); Yukari Y. Perrella, Cambridge, MA (US); Vincent Darmency, Bougy Villars (CH); Hrvoje Lusic, Boston, MA (US)

(73) Assignees: Yuma Therapeutics, Inc., Cambridge, MA (US); The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 15/317,999

(22) PCT Filed: Jun. 15, 2015

(86) PCT No.: PCT/US2015/035735
§ 371 (c)(1),
(2) Date: Dec. 12, 2016

(87) PCT Pub. No.: WO2015/192119
PCT Pub. Date: Dec. 17, 2015

(65) Prior Publication Data
US 2017/0107228 A1 Apr. 20, 2017

Related U.S. Application Data

(60) Provisional application No. 62/012,152, filed on Jun. 13, 2014.

(51) Int. Cl.
| C07D 495/04 | (2006.01) |
| C07D 487/04 | (2006.01) |
| C07D 405/04 | (2006.01) |
| C07D 239/42 | (2006.01) |
| C07D 239/70 | (2006.01) |
| C07D 471/04 | (2006.01) |
| C07D 239/84 | (2006.01) |
| C07D 251/16 | (2006.01) |
| C07D 251/22 | (2006.01) |
| C07D 405/10 | (2006.01) |

(52) U.S. Cl.
CPC ........ *C07D 495/04* (2013.01); *C07D 239/42* (2013.01); *C07D 239/70* (2013.01); *C07D 239/84* (2013.01); *C07D 251/16* (2013.01); *C07D 251/22* (2013.01); *C07D 405/04* (2013.01); *C07D 405/10* (2013.01); *C07D 471/04* (2013.01); *C07D 487/04* (2013.01)

(58) Field of Classification Search
CPC .................................................. C07D 405/04
See application file for complete search history.

(56) References Cited

U.S. PATENT DOCUMENTS

| 2,691,655 A * | 10/1954 | Hitchings | C07D 239/47 544/321 |
| 5,863,924 A * | 1/1999 | Berger | C07D 239/42 514/217.01 |
| 8,642,594 B2 | 2/2014 | Dymock et al. | |
| 2010/0093696 A1* | 4/2010 | Bennett | C07D 487/04 514/210.21 |
| 2011/0201587 A1 | 8/2011 | Shapiro | |

FOREIGN PATENT DOCUMENTS

| DE | 102006008880 A1 | 9/2007 | |
| JP | 2001-525794 A | 12/2001 | |
| JP | 2007-533611 A | 11/2007 | |
| JP | 2008-506758 A | 3/2008 | |
| JP | 2008-540587 A | 11/2008 | |
| JP | 2008-540626 A | 11/2008 | |
| JP | 2009-067729 A | 4/2009 | |
| JP | 2009-533323 A | 9/2009 | |
| JP | 2010-518066 A | 5/2010 | |
| JP | 2017-516826 A | 6/2017 | |
| WO | WO-9911633 A1 * | 3/1999 | ........... C07D 251/18 |
| WO | WO-2006/008503 A1 | 1/2006 | |
| WO | WO-2006/090094 A1 | 8/2006 | |
| WO | WO-2006/122631 A1 | 11/2006 | |
| WO | WO-2006/123165 A2 | 11/2006 | |
| WO | WO-2006123165 A2 * | 11/2006 | ........... C07D 239/42 |
| WO | WO-2007/104944 A1 | 9/2007 | |

(Continued)

OTHER PUBLICATIONS

A. Wittmann-Regis, International Preliminary Report on Patentability (dated Dec. 15, 2016).*
CAS Abstract and Indexed Compounds WO 2006/123165 (Dec. 12, 1995).*
CAS Abstract and Indexed Compounds U.S. Pat. No. 2,691,655 (1954).*
CAS Abstract and Indexed Compounds U.S. Pat. No. 5,863,924 (1999).*
M.K. Lakshnnan et al., 4 Organic Letters, 1479-1482 (2002) (Year: 2002).*
R. Geller et al., 1823 Biochimica et Biophysica Acta, 698-706 (2012) (Year: 2012).*
L. Cowen et al., 106 PNAS, 2818-2823 (2009) (Year: 2009).*
L. Whitesell et al., 5 Nature Reviews Cancer (2005) (Year: 2005).*
D. Solit et al., 13 Drug Discovery Today (2008) (Year: 2008).*

(Continued)

*Primary Examiner* — Alexander R Pagano
(74) *Attorney, Agent, or Firm* — Clark & Elbing LLP

(57) ABSTRACT

The present invention relates to 2-amino-4-arylpyrimidine and 2-amino-4-aryltriazine compounds as inhibitors of heat shock protein 90 family of chaperone proteins. The invention also features pharmaceutical compositions and kits that include the compounds and compositions of the invention. The invention further relates to the medical use of these compounds and compositions for the treatment of a disorder in a subject. For example, the disorder is a neurodegenerative disease.

33 Claims, 10 Drawing Sheets

(56) References Cited

FOREIGN PATENT DOCUMENTS

| WO | WO-2007/138994 A1 | 12/2007 | | |
|----|-------------------|---------|---|---|
| WO | WO-2008/059368 A2 | 5/2008 | | |
| WO | WO-2008059368 A2 * | 5/2008 | ........... | A61K 31/519 |
| WO | WO 2008059368 A2 * | 5/2008 | ........... | A61K 31/519 |
| WO | WO-2008/096218 A1 | 8/2008 | | |
| WO | WO-2013/157021 A1 | 10/2013 | | |
| WO | WO-2013/177535 A2 | 11/2013 | | |
| WO | WO-2015/187089 A1 | 12/2015 | | |

OTHER PUBLICATIONS

T. Guo et al., 133 Acta Neuropathol (2017) (Year: 2017).*
A. Salminen et al., 93 Progress in Neurobiology (2011) (Year: 2011).*
"CellTiter-Glo® Luminescent Cell Viability Assay," Promega, revised Dec. 2012 (14 pages).
"ELISA to Alpha Immunoassay Conversion Guide," PerkinElmer, Inc., Aug. 2012 (24 pages).
Corcoran et al., "Sodium selenate specifically activates PP2A phosphatase, dephosphorylates tau and reverses memory deficits in an Alzheimer's disease model," J Clin Neurosci. 17(8):1025-33 (2010).
Geller et al., "Broad action of Hsp90 as a host chaperone required for viral replication," available in PMC Mar. 1, 2013, published in final edited form as: Biochim Biophys Acta. 1823(3):698-706 (2012) (21 pages).
International Preliminary Report on Patentability for International Application No. PCT/US2015/035735, dated Dec. 15, 2016 (5 pages).
International Search Report and Written Opinion for International Application No. PCT/US2015/035735, dated Sep. 14, 2015 (13 pages).
Liu et al., "Kinetic mechanistic studies of Cdk5/p25-catalyzed H1P phosphorylation: metal effect and solvent kinetic isotope effect," available in PMC Jun. 15, 2011, published in final edited form as: Biochemistry. 49(23):4921-9 (2010) (24 pages).
Löffler et al., "Stable mutated tau441 transfected SH-SY5Y cells as screening tool for Alzheimer's disease drug candidates," J Mol Neurosci. 47(1):192-203 (2012).
Shukla et al., "Role of hsp90 in systemic lupus erythematosus and its clinical relevance," Autoimmune Dis. 2012:728605 (2012) (6 pages).
Suda et al., "Design and synthesis of 2-amino-6-(1H,3H-benzo[de]isochromen-6-yl)-1,3,5-triazines as novel Hsp90 inhibitors," Bioorg Med Chem. 22(2):892-905 (2014).
Extended European Search Report for European Application No. 15806816.3, dated Jan. 3, 2018 (8 pages).
Office Action for Chinese Patent Application No. 201580043036.0, dated Dec. 27, 2018 (10 pages) (Chinese language only).
Jia et al., "Identification, design and bio-evaluation of novel Hsp90 inhibitors by ligand-based virtual screening," PLoS One. 8(4):e59315 (2013) (15 pages).
Brough et al., "Combining hit identification strategies: fragment-based and in silico approaches to orally active 2-aminothieno[2,3-d]pyrimidine inhibitors of the Hsp90 molecular chaperone," J Med Chem. 52(15):4794-809 (2009).

* cited by examiner

PYRIMIDINE COMPOUNDS AND METHODS USING THE SAME

STATEMENT AS TO FEDERALLY FUNDED RESEARCH

This invention was made with government support under Grant No. STTR 1 R41 G042205-01 awarded by the National Institutes of Health. The government has certain rights in the invention.

FIELD OF THE INVENTION

In general, the present invention relates to pyrimidine-based small molecule inhibitors of heat shock protein 90 (Hsp90) and pharmaceutical compositions thereof. The invention further relates to methods of treatment of a subject having a neurodegenerative disease.

BACKGROUND OF THE INVENTION

Hsp90 proteins are implicated in stabilizing protein conformations, maintaining the function of many cell-signaling proteins, and ATPase activity. Hsp90 activity is also required for the proper folding, stabilization, activation, and localization of oncoproteins involved in tumor progression. The N-terminus ATP binding domain is responsible for the ATPase activity of this protein: this adenine nucleotide binding pocket is highly conserved among all Hsp90 proteins from bacteria to mammals but is not present in other chaperones.

Hsp90 protein has emerged as an important target in cancer treatment, as many Hsp90 client proteins themselves were identified as targets for cancer therapies. The exemplary Hsp90 client proteins that are associated with cancer include HER2 (breast cancer), Raf-1/mutant BRAF (melanoma), Mutant EGFR (non-small cell lung cancer, glioblastoma), c-Kit (GIST), c-Met (gastric, lung, glioblastoma), HIF-1α (renal cancer), Zap70 (chronic lymphocytic leukemia), Bcr-Abl (chronic myelogenous leukemia), mBcr-Abl (chronic myelogenous leukemia), Flt-3 (acute myeloid leukemia), IGF-1R/Akt (myeloma), NMP-ALK (lymphoma), and Akt (small cell lung cancer). Overexpression of mutated Hsp90 client or amplification of its clients, such as HER2, leads to the increased dependency of tumor cells on Hsp90 chaperone function. Accordingly, Hsp90 provides a compelling target for treating different classes of tumors.

Increased levels of Hsp90 have also been implicated in neurodegenerative disorders, including Alzheimer's, Parkinson's, and Huntington's disease, and tauopathies. Tauopathies are neurodegenerative diseases characterized by tau protein abnormalities, which then result in the accumulation of hyperphosphorylated and aggregated tau protein. It has been proposed that hyperphosphorylated tau in Alzheimer's disease is a pathogenic process caused by aberrant activation of kinases, particularly cdk5 and GSK β3. Studies have shown that Hsp90 stabilizes p35, an activator of cdk5, leading to increased tau phosphorylation. It has also been shown that Hsp90 inhibition activates heat shock factor 1 (HSF1), which in turn increases the expression of Hsp70. Increased expression of Hsp70 promotes tau solubility and binding to microtubules, inhibits Aβ peptide aggregation, and enhances Aβ peptide degradation.

Hsp90 has also emerged as a target for treating viral, fungal, and bacterial infections. For example, an Hsp90 inhibitor (geldanamycin) has been shown to delay the growth of influenza virus in cell culture. Other viruses that rely on Hsp90 dependent processes include those belonging to the families: Herpesviridae (e.g., herpes simplex virus-1, herpes simplex virus-2, herpes herpesvirus-5, Kaposi's sarcoma-associated herpesvirus, varicella zoster virus, or Epstein-Barr virus), Polyomaviridae (e.g., SV40), Poxviridae (e.g., vaccinia virus), Reoviridae (e.g., rotavirus), Birnaviridae (e.g., infectious bursal disease virus), picornaviridae (e.g., poliovirus, rhinovirus, or coxsackievirus), flaviviridae (e.g., hepatitis C virus or dengue virus), arenaviridae (e.g., lymphocytic choriomeningitis virus), Hepeviridae (e.g., Hepatitis E virus), Rhabdoviridae (e.g., vesicular stomatitis virus), Paramoxyviridae (e.g., human parainfluenza virus 2, human parainfluenza virus 3, SV5, SV41, measles virus, or Sendai virus), Bunyaviridae (e.g., La Crosse virus), Orthomoxyviridae (e.g., influenza A virus), Filoviridae (e.g., Ebola virus), Retroviridae (e.g., HTLV1 or HIV1), and Hepadnaviridae (e.g., hepatitis B virus). Hsp90 inhibitors have also been used in vivo for the treatment of fungal infectious diseases, e.g., treatment of *Candida albicans, Aspergillus fumigates,* or *Pneumocystis jiroveci.* Moreover, Hsp90 inhibitors are also useful in the treatment of bacterial infections, e.g., mycobacteria, anthrax, or bacterial pneumonia.

In view of the above, inhibitors of Hsp90 represent beneficial therapeutics for the treatment of disorders, e.g., cancer, neurodegenerative diseases, and infectious diseases.

SUMMARY OF THE INVENTION

In one aspect, the invention features a compound according to formula (I):

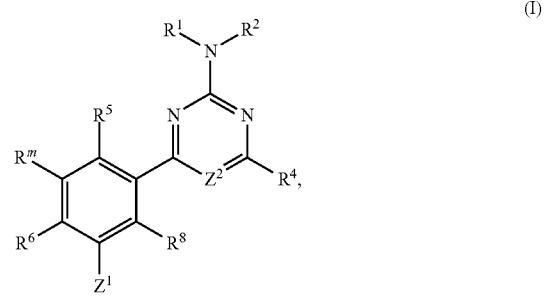

or a pharmaceutically acceptable salt thereof,
where
$Z^1$ is —OR$^7$, —N(R$^{10}$)R$^7$, —SR$^7$, or —C(R$^{10}$)(R$^{11}$)R$^7$;
$Z^2$ is —N= or —C(R$^3$)=;
each $R^1$ and $R^2$ is, independently, H or optionally substituted $C_{1-3}$ alkyl (e.g., $C_{1-3}$ acyl);
$R^3$ is H, halogen, cyano, optionally substituted $C_{1-6}$ alkyl, optionally substituted $C_{1-3}$ alkoxy, or optionally substituted amino, and $R^4$ is halogen, cyano, optionally substituted $C_{1-6}$ alkyl, optionally substituted $C_{1-3}$ alkoxy, optionally substituted amino, optionally substituted $C_{1-6}$ thioalkoxy, or optionally substituted $C_{6-10}$ aryl, or $R^3$ and $R^4$, together with the atoms to which each is attached, join to form an optionally substituted five- or six-membered ring optionally comprising from one to three heteroatoms selected from the group consisting of nitrogen, oxygen, and sulfur, where the nitrogen is optionally substituted with $R^9$;
each $R^5$ and $R^6$ is, independently, H, optionally substituted $C_{1-3}$ alkyl, optionally substituted $C_{1-3}$ alkoxy, halogen, or CN;

$R^7$ is optionally substituted $C_{1-3}$ alkyl, optionally substituted $C_{1-3}$ alkcycloalkyl, optionally substituted $C_{1-3}$ alkheterocyclyl, or optionally substituted $C_{1-3}$ alkaryl, and $R^8$ is H; or $R^7$ and $R^8$, together with the atoms to which each is attached, join to form an optionally substituted five-, six-, or seven-membered ring optionally comprising one or two heteroatoms selected from nitrogen, oxygen, and sulfur;

$R^9$ is H, optionally substituted $C_{1-3}$ alkyl, optionally substituted $C_{3-8}$ cycloalkyl, optionally substituted $C_{6-10}$ aryl, optionally substituted $C_{2-9}$ heteroaryl, optionally substituted $C_{2-9}$ heterocyclyl, optionally substituted $C_{1-3}$ alkcycloalkyl, optionally substituted $C_{1-3}$ alkheterocyclyl, or optionally substituted $C_{1-3}$ alkaryl;

$R^{10}$ is H, optionally substituted $C_{1-3}$ alkyl, optionally substituted $C_{3-8}$ cycloalkyl, optionally substituted $C_{6-10}$ aryl, optionally substituted $C_{2-9}$ heteroaryl, optionally substituted $C_{2-9}$ heterocyclyl, optionally substituted $C_{1-3}$ alkcycloalkyl, optionally substituted $C_{1-3}$ alkheterocyclyl, or optionally substituted $C_{1-3}$ alkaryl, and $R^{11}$ is H, optionally substituted $C_{1-3}$ alkyl, or $R^{10}$ and $R^{11}$ combine to form =O or =S; and $R'''$ is H, halogen, cyano, optionally substituted $C_{1-4}$ alkyl (e.g., $C_{1-4}$ acyl), or optionally substituted $C_{1-3}$ alkoxy.

In particular embodiments of formula (I), $R'''$ is H (e.g., the compound of formula (I) has the following structure:

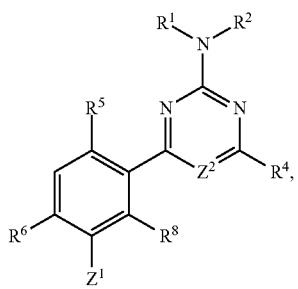

(I)

or a pharmaceutically acceptable salt thereof).

In certain embodiments of formula (I), when $Z^2$ is $CR^3$, each of $R^1$ and $R^2$ is H, $R^3$ is H, $R^4$ is methyl or halogen (e.g., chloro), and each of $R^5$ and $R^6$ is halogen (e.g., chloro), $Z^1$ is not methoxy.

In certain embodiments of formula (I), when $Z^2$ is $CR^3$, $R^3$ is H, $R^4$ is methyl or halogen (e.g., chloro), each of $R^5$ and $R^6$ is halogen (e.g., chloro), $Z^2$ is not unsubstituted $C_{1-3}$ alkoxy.

In particular embodiments of formula (I), when $Z^2$ is N, $R^3$ is H, $R^4$ is optionally substituted $C_{1-6}$ thioalkoxy, and each of $R^5$ and $R^6$ is halogen (e.g., chloro), $Z^1$ is not cyanomethoxy or aminomethoxy.

In other embodiments of formula (I), when $Z^2$ is N, $R^3$ is H, each of $R^5$ and $R^6$ is halogen (e.g., chloro), $R^4$ is substituted $C_{1-6}$ thioalkoxy, $Z^1$ is not cyanomethoxy or aminomethoxy.

In some embodiments of formula (I), when $Z^2$ is N, $R^3$ is H, $R^4$ is optionally substituted $C_{1-6}$ thioalkoxy, $Z^1$ is not cyanomethoxy or aminomethoxy.

In certain embodiments of formula (I), when $Z^2$ is N, $R^3$ is H, $R^4$ is substituted $C_{1-6}$ thioalkoxy, $Z^1$ is not cyanomethoxy or aminomethoxy.

In further embodiments of formula (I), when $Z^2$ is N, $R^3$ is H, $R^4$ is substituted $C_{1-6}$ thioalkoxy, Z is not substituted $C_1$ alkoxy.

In particular embodiments of formula (I), when $Z^2$ is N, $R^3$ is H, $R^4$ is substituted $C_{1-6}$ thioalkoxy, $Z^1$ is —$OR^7$, —$N(R^7)R^{10}$, —$SR^7$, or —$C(R^7)(R^{10})R^{11}$, in which $R^7$ is methyl, dialkylaminoethyl, optionally substituted $C_{1-3}$ alkcycloalkyl, optionally substituted $C_{1-3}$ alkheterocyclyl, or optionally substituted $C_{1-3}$ alkaryl, or $R^7$ and $R^8$, together with the atoms to which each is attached, join to form an optionally substituted five- or six-membered ring optionally comprising one or two heteroatoms selected from nitrogen, oxygen, and sulfur.

In other embodiments of formula (I), when $Z^2$ is $CR^3$, each of $R^5$ and $R^6$ is chloro, $R^3$ is H, and $R^4$ is halogen (e.g., chloro), $Z^1$ is not 2-amino-2oxoethoxy, 2-(N,N-diethylamino)ethoxy, methoxy, or benzyloxy.

In yet other embodiments of formula (I), when $Z^2$ is $CR^3$, $R^3$ is H, and $R^4$ is halogen (e.g., chloro), $Z^1$ is not 2-amino-2oxoethoxy, 2-(N,N-diethylamino)ethoxy, methoxy, or benzyloxy.

In still other embodiments of formula (I), when $Z^2$ is $CR^3$, each of $R^5$ and $R^6$ is chloro, $R^3$ is H, and $R^4$ is halogen (e.g., chloro), $Z^1$ is —$OR^7$, —$N(R^7)R^{10}$, —$SR^7$, or —$C(R^7)(R^{10})R^{11}$, in which $R^7$ is dimethylaminoethyl, optionally substituted $C_{1-3}$ alkcycloalkyl, or optionally substituted $C_{1-3}$ alkheterocyclyl, or $R^7$ and $R^8$, together with the atoms to which each is attached, join to form an optionally substituted five- or six-membered ring optionally comprising one or two heteroatoms selected from nitrogen, oxygen, and sulfur.

In further embodiments of formula (I), when $Z^2$ is $CR^3$, each of $R^5$ and $R^6$ is chloro, $R^3$ is H, and $R^4$ is halogen (e.g., chloro), $Z^1$ is —$OR^7$, —$N(R^7)R^{10}$, —$SR^7$, or —$C(R^7)(R^{10})R^{11}$, in which $R^7$ is optionally substituted $C_{1-3}$ alkcycloalkyl, or optionally substituted $C_{1-3}$ alkheterocyclyl, or $R^7$ and $R^8$, together with the atoms to which each is attached, join to form an optionally substituted five- or six-membered ring optionally comprising one or two heteroatoms selected from nitrogen, oxygen, and sulfur.

In particular embodiments of formula (I), when $Z^2$ is $CR^3$, $R^3$ is H, and $R^4$ is halogen (e.g., chloro), $Z^1$ is —$OR^7$, —$N(R^7)R^{10}$, —$SR^7$, or —$C(R^7)(R^{10})R^{11}$, in which $R^7$ is optionally substituted $C_{1-3}$ alkcycloalkyl, or optionally substituted $C_{1-3}$ alkheterocyclyl, or $R^7$ and $R^8$, together with the atoms to which each is attached, join to form an optionally substituted five- or six-membered ring optionally comprising one or two heteroatoms selected from nitrogen, oxygen, and sulfur.

In some embodiments of formula (I), when $R^5$ is chloro, $R^6$ is bromo, $Z^1$ is —$OR^7$, $Z^2$ is $CR^3$, and $R^3$ and $R^4$ combine to form a group according to formula (IIa):

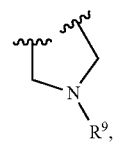

(IIa)

$R^7$ is not methyl, ethyl, n-propyl, 2-(N-pyrazolyl)ethyl, 2-(N-imidazolyl)ethyl, 3-hydroxypropyl, cyanomethyl, 2-chloroethyl, 2-hydroxyethyl, 2-oxo-propyl, 2-(N,N-dimethylamino)ethyl, difluoromethyl, or 2-(t-butylamino)ethyl.

In certain embodiments of formula (I), when R$^5$ is chloro, R$^6$ is bromo, Z$^1$ is —OR$^7$, Z$^2$ is CR$^3$, and R$^3$ and R$^4$ combine to form a group according to formula (IIa),
R$^7$ is not substituted alkyl, unsubstituted alkyl, or unsubstituted C$_2$ alkheteroaryl.

In some embodiments of formula (I), when R$^5$ is chloro, R$^6$ is bromo, Z$^1$ is —OR$^7$, Z$^2$ is CR$^3$, and R$^3$ and R$^4$ combine to form a group according to formula (IIa),
R$^7$ is not alkyl or unsubstituted C$_2$ alkheteroaryl.

In particular embodiments of formula (I), when R$^5$ is chloro, R$^6$ is bromo, Z$^1$ is —OR$^7$, Z$^2$ is CR$^3$, and R$^3$ and R$^4$ combine to form a group according to formula (IIa),
R$^7$ is not substituted alkyl, unsubstituted alkyl, or unsubstituted C$_2$ alkheterocyclyl.

In other embodiments of formula (I), when R$^5$ is chloro, R$^6$ is bromo, Z$^1$ is —OR$^7$, Z$^2$ is CR$^3$, and R$^3$ and R$^4$ combine to form a group according to formula (IIa),
R$^7$ is not alkyl or C$_2$ alkheterocyclyl.

In still other embodiments of formula (I), when R$^5$ is chloro, R$^6$ is bromo, Z$^1$ is —OR$^7$, Z$^2$ is CR$^3$, and R$^3$ and R$^4$ combine to form a group according to formula (IIa),
R$^7$ and R$^8$, together with the atoms to which each is attached, join to form an optionally substituted five- or six-membered ring optionally comprising one or two heteroatoms selected from nitrogen, oxygen, and sulfur.

In yet other embodiments of formula (I), when R$^5$ is chloro, R$^6$ is bromo, Z$^2$ is CR$^3$, and R$^3$ and R$^4$ combine to form a group according to formula (IIa),
Z is —OR$^7$, and R$^7$ and R$^8$ combine to form —CH$_2$—CH$_2$—.

In some embodiments of formula (I), when each R$^5$ and R$^6$ is bromo, Z$^1$ is —OR$^7$, Z$^2$ is CR$^3$, and R$^3$ and R$^4$ combine to form a group according to formula (IIa),
R$^7$ is not methyl.

In particular embodiments of formula (I), when each R$^5$ and R$^6$ is chloro, Z$^1$ is —OR$^7$, Z$^2$ is CR$^3$, and R$^3$ and R$^4$ combine to form a group according to formula (IIa),
R$^7$ is not methyl, 2-(N-imidazolyl)ethyl, methoxymethyl, 2-(N-pyrazolyl)ethyl, 2-(3-methylpyrazol-1-yl)ethyl, 2-pyridyl-methyl, 1,3-dimethyl-1H-1,2,4-triazol-5-yl-methyl, 2-pyrimidinylmethyl, imidazol-2-yl-methyl, 5-methyl-isoxazol-3-yl-methyl, 4-methyl-imidazol-5-yl-methyl, or 3-methyl-1,2,4-oxadiazol-5-yl-methyl.

In other embodiments of formula (I), when each R$^5$ and R$^6$ is chloro, Z$^1$ is —OR$^7$, Z$^2$ is CR$^3$, and R$^3$ and R$^4$ combine to form a group according to formula (IIa),
R$^7$ is not unsubstituted alkyl, substituted alkyl, unsubstituted alkheteroaryl, or substituted alkheteroaryl.

In other embodiments of formula (I), when each R$^5$ and R$^6$ is chloro, Z$^1$ is —OR$^7$, Z$^2$ is CR$^3$, and R$^3$ and R$^4$ combine to form a group according to formula (IIa),
R$^7$ is not unsubstituted alkyl, substituted alkyl, unsubstituted alkheterocyclyl, or substituted alkheterocyclyl.

In certain embodiments of formula (I), when each R$^5$ and R$^6$ is chloro, Z$^1$ is —OR$^7$, R$^7$ and R$^8$ combine to form —CH$_2$—CH$_2$—, Z$^2$ is CR$^3$, and R$^3$ and R$^4$ combine to form a group according to formula (IIa),
R$^9$ is not ethoxycarbonyl, cyclobutylaminocarbonyl, or cyclobutadienylaminocarbonyl.

In other embodiments of formula (I), when each R$^5$ and R$^6$ is chloro, Z$^1$ is —OR$^7$, R$^7$ and R$^8$ combine to form —CH$_2$—CH$_2$—, Z$^2$ is CR$^3$, and R$^3$ and R$^4$ combine to form a group according to formula (IIa),
R$^9$ is H or —C(O)—N(H)-(linear C$_{1-3}$ alkyl).

In particular embodiments of formula (I), when each R$^5$ and R$^6$ is halo, Z$^2$ is CR$^3$, and R$^3$ and R$^4$ combine to form a group according to formula (IIa),
Z is —OR$^7$, R$^7$ is not methyl or 2-chloroethyl, and R$^9$ is H or —C(O)—N(H)-(linear C$_{1-3}$ alkyl).

In some embodiments of formula (I), when R$^5$ is methoxy, R$^6$ is methyl, Z$^1$ is —OR$^7$, Z$^2$ is CR$^3$, and R$^3$ and R$^4$ combine to form a group according to formula (IIa),
R$^7$ is not methyl.

In certain embodiments of formula (I), when R$^5$ is chloro, R$^6$ is ethyl, Z$^1$ is —OR$^7$, Z$^2$ is CR$^3$, and R$^3$ and R$^4$ combine to form a group according to formula (IIa),
R$^7$ is not methyl.

In some embodiments of formula (I), when each R$^5$ and R$^6$ is chloro, Z$^1$ is —OR$^7$, Z$^2$ is CR$^3$, and R$^3$ and R$^4$ combine to form a group according to formula (IIb) or (IIc),

(IIb)

or (IIc)

R$^7$ is not methyl or 2-(N,N-diethylamino)ethyl.

In other embodiments of formula (I), when each R$^5$ and R$^6$ is chloro, Z$^1$ is —OR$^7$, Z$^2$ is CR$^3$, and R$^3$ and R$^4$ combine to form a group according to formula (IIb) or (IIc),
R$^7$ and R$^8$, together with the atoms to which each is attached, join to form an optionally substituted five- or six-membered ring optionally comprising one or two heteroatoms selected from nitrogen, oxygen, and sulfur.

In certain embodiments of formula (I), when each R$^5$ and R$^6$ is chloro, Z$^2$ is CR$^3$, and R$^3$ and R$^4$ combine to form a group according to formula (IIb) or (IIc),
Z$^1$ is —OR$^7$, and R$^7$ and R$^8$ combine to form —CH$_2$—CH$_2$—.

In some embodiments of formula (I), when R$^7$ is methyl, R$^5$ is chloro, Z$^1$ is —OR$^7$, Z$^2$ is CR$^3$, and R$^3$ and R$^4$ combine to form a group according to formula (IIIa),

(IIIa)

R$^6$ is not bromo.

In particular embodiments of formula (I), when each R$^5$ and R$^6$ is chloro, Z$^1$ is —OR$^7$, Z$^2$ is CR$^3$, and R$^3$ and R$^4$ combine to form a group according to formula (IIIa),
R$^7$ is not isopropyl, 3,3,3-trifluoropropyl, or 2-(N,N-dimethylamino)ethyl.

In certain embodiments of formula (I), when each R$^5$ and R$^6$ is chloro, Z$^1$ is —OR$^7$, Z$^2$ is CR$^3$, and R$^3$ and R$^4$ combine to form a group according to formula (IIIa),
R$^8$ is not H.

In some embodiments of formula (I), when Z$^2$ is CR$^3$, and R$^3$ and R$^4$ combine to form a group according to formula (IIIa),
each R$^5$ and R$^6$ is chloro, and
R$^7$ is methyl and R$^8$ is H, or R$^7$ and R$^8$, together with the atoms to which each is attached, join to form an optionally substituted five- or six-membered ring optionally comprising one or two heteroatoms selected from nitrogen, oxygen, and sulfur.

In other embodiments of formula (I), when $R^5$ is chloro, $R^6$ is methoxy, $Z^1$ is —$OR^7$, $Z^2$ is $CR^3$, and $R^3$ and $R^4$ combine to form a group according to formula (IIIb):

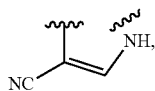

(IIIb)

neither $R^1$ nor $R^2$ is 2-(N,N-diethylamino)ethyl.

In certain embodiments of formula (I), when $R^5$ is chloro, $R^6$ is methoxy, $Z^1$ is —$OR^7$, $Z^2$ is $CR^3$, and $R^3$ and $R^4$ combine to form a group according to formula (IIIb), each $R^1$ and $R^2$ is H.

In some embodiments of formula (I), when each $R^5$ and $R^6$ is chloro, $Z^1$ is —$OR^7$, $Z^2$ is $CR^3$, and $R^3$ and $R^4$ combine to form a group according to formula (IVa):

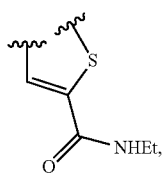

(IVa)

$R^7$ is not 3-(N-morpholinyl)propyl, benzyl, 1-ethyl-pyrrolydin-3-yl, 1-methyl-piperidin-4-yl, 2-(1-methyl-pyrrolidin-2-yl)ethyl, or 3-(N,N-diethylamino)propyl.

In particular embodiments of formula (I), when each $R^5$ and $R^6$ is chloro, $Z^1$ is —$OR^7$, $Z^2$ is $CR^3$, and $R^3$ and $R^4$ combine to form a group according to formula (IVa),
$R^7$ is not substituted alkyl, heterocyclyl, alkheterocyclyl, or alkaryl.

In some embodiments of formula (I), when each $R^5$ and $R^6$ is chloro, $Z^1$ is —$OR^7$, $Z^2$ is $CR^3$, and $R^3$ and $R^4$ combine to form a group according to formula (IVb):

c(IVb), $R^7$ is not 2-methoxyethyl or benzyl.

In certain embodiments of formula (I), when each $R^5$ and $R^6$ is chloro, $Z^1$ is —$OR^7$, $Z^2$ is $CR^3$, and $R^3$ and $R^4$ combine to form a group according to formula (IVb),
$R^7$ is not substituted alkyl or alkaryl.

In some embodiments of formula (I), when each $R^5$ and $R^6$ is chloro, $Z^1$ is —$OR^7$, $Z^2$ is $CR^3$, and $R^3$ and $R^4$ combine to form a group according to formula (IVc):

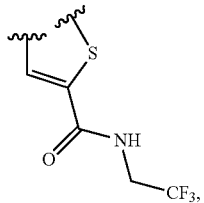

(IVc)

$R^7$ is not 2-(N,N-diethylamino)ethyl or 3-(N,N-dimethylamino)propyl.

In other embodiments of formula (I), when each $R^5$ and $R^6$ is chloro, $Z^1$ is —$OR^7$, $Z^2$ is $CR^3$, and $R^3$ and $R^4$ combine to form a group according to formula (IVc),
$R^7$ is not substituted alkyl.

In particular embodiments of formula (I), when each $R^5$ and $R^6$ is chloro, $Z^1$ is —$OR^7$, $Z^2$ is $CR^3$, and $R^3$ and $R^4$ combine to form a group according to formula (IVd):

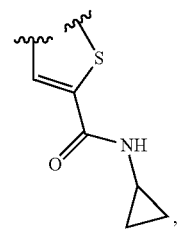

(IVd)

$R^7$ is not 2-(pyrrolidin-1-yl)ethyl or 2-hydroxyethyl.

In certain embodiments of formula (I), when each $R^5$ and $R^6$ is chloro, $Z^1$ is —$OR^7$, $Z^2$ is $CR^3$, and $R^3$ and $R^4$ combine to form a group according to formula (IVd),
$R^7$ is not substituted alkyl or alkheterocyclyl.

In some embodiments of formula (I), when each $R^5$ and $R^6$ is chloro, $Z^1$ is —$OR^7$, $Z^2$ is $CR^3$, and $R^3$ and $R^4$ combine to form a group according to formula (IVe) or (IVf):

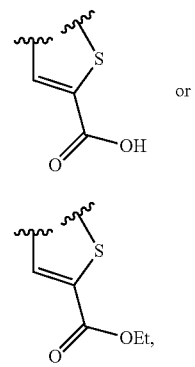

(IVe)

(IVf)

$R^7$ is not benzyl.

In other embodiments of formula (I), when each $R^5$ and $R^6$ is chloro, $Z^1$ is —$OR^7$, $Z^2$ is $CR^3$, and $R^3$ and $R^4$ combine to form a group according to formula (IVe) or (IVf),
$R^7$ is not alkaryl.

In certain embodiments of formula (I), when $R^5$ is chloro, $R^6$ is bromo, $Z^1$ is —$OR^7$, $Z^2$ is $CR^3$, and $R^3$ and $R^4$ combine to form a group according to formula (IVg), (IVh), (IVi), (IVj), or (IVk):

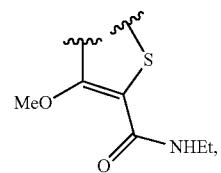

(IVg)

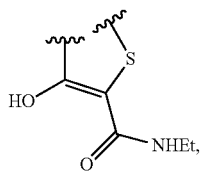
(IVh)

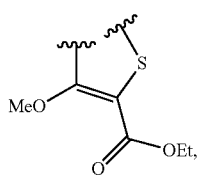
(IVi)

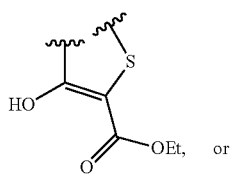
(IVj)

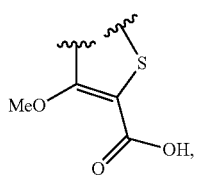
(IVk)

$R^7$ is not methyl.

In certain embodiments of formula (I), when $R^5$ is chloro, $R^6$ is bromo, $Z^1$ is —$OR^7$, $Z^2$ is $CR^3$, and $R^3$ and $R^4$ combine to form a group according to formula (IVg), (IVh), (IVi), (IVj), or (IVk), $R^7$ is not alkyl.

In some embodiments of formula (I), when $R^5$ is chloro, $R^6$ is bromo, $Z^1$ is —$OR^7$, $Z^2$ is $CR^3$, and $R^3$ and $R^4$ combine to form a group according to formula (IVg), (IVh), (IVi), (IVj), or (IVk), $R^7$ and $R^8$, together with the atoms to which each is attached, join to form an optionally substituted five- or six-membered ring optionally comprising one or two heteroatoms selected from nitrogen, oxygen, and sulfur.

In particular embodiments of formula (I), when $R^5$ is chloro, $R^6$ is bromo, $Z^1$ is —$OR^7$, and $Z^2$ is $CR^3$, $R^3$ and $R^4$ do not combine to form a group according to formula (IVg), (IVh), (IVi), (IVj), or (IVk).

In particular embodiments of formula (I), when $R^6$ is methyl, each $R^1$ and $R^2$ is H.

In certain embodiments of formula (I), when $R^3$ is H, and each $R^5$ and $R^6$ is chloro, $R^7$ is not methyl.

In particular embodiments, the compound is according to formula (Ia):

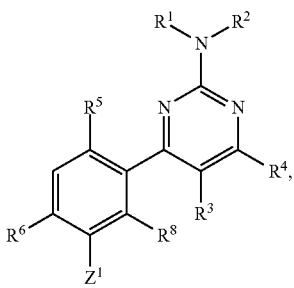
(Ia)

or a pharmaceutically acceptable salt thereof,
where
$Z^1$ is —$OR^7$, —$N(R^{10})R^7$, —$SR^7$, or —$C(R^{10})(R^{11})R^7$;
each $R^1$ and $R^2$ is, independently, H or optionally substituted $C_{1-3}$ alkyl;
$R^3$ is H, halogen, optionally substituted $C_{1-3}$ alkyl, or optionally substituted $C_{1-3}$ alkoxy, and $R^4$ is halogen, optionally substituted $C_{1-3}$ alkyl, optionally substituted $C_{1-3}$ alkoxy, optionally substituted amino, optionally substituted $C_{1-6}$ thioalkyl, or optionally substituted $C_{6-10}$ aryl, or $R^3$ and $R^4$, together with the atoms to which each is attached, join to form an optionally substituted five-, six-, or seven-membered ring optionally comprising from one to three heteroatoms selected from the group consisting of nitrogen, oxygen, and sulfur, where the nitrogen is optionally substituted with $R^9$;
each $R^5$ and $R^6$ is, independently, H, optionally substituted $C_{1-3}$ alkyl, optionally substituted $C_{1-3}$ alkoxy, halogen, or CN;
$R^7$ is optionally substituted $C_{1-3}$ alkyl, optionally substituted $C_{1-3}$ alkcycloalkyl, optionally substituted $C_{1-3}$ alkheterocyclyl, or optionally substituted $C_{1-3}$ alkaryl, and $R^8$ is H; or $R^7$ and $R^8$, together with the atoms to which each is attached, join to form an optionally substituted five-, six-, or seven-membered ring optionally comprising one or two heteroatoms selected from nitrogen, oxygen, and sulfur;
$R^9$ is H, optionally substituted $C_{1-3}$ alkyl, optionally substituted $C_{3-8}$ cycloalkyl, optionally substituted $C_{6-10}$ aryl, optionally substituted $C_{2-9}$ heteroaryl, optionally substituted $C_{2-9}$ heterocyclyl, optionally substituted $C_{1-3}$ alkcycloalkyl, optionally substituted $C_{1-3}$ alkheterocyclyl, or optionally substituted $C_{1-3}$ alkaryl;
$R^{10}$ is H, optionally substituted $C_{1-3}$ alkyl (e.g., optionally substituted $C_{1-3}$ acyl), optionally substituted $C_{3-8}$ cycloalkyl, optionally substituted $C_{6-10}$ aryl, optionally substituted $C_{2-9}$ heteroaryl, optionally substituted $C_{2-9}$ heterocyclyl, optionally substituted $C_{1-3}$ alkcycloalkyl, optionally substituted $C_{1-3}$ alkheterocyclyl, or optionally substituted $C_{1-3}$ alkaryl, and $R^{11}$ is H, optionally substituted $C_{1-3}$ alkyl, or $R^{10}$ and $R^{11}$ combine to form =O or =S.

In other embodiments, when each of $R^1$ and $R^2$ is H, $R^3$ is H, $R^4$ is methyl or chloro, and each of $R^5$ and $R^6$ is chloro, Z is not methoxy.

In yet other embodiments, when $R^3$ is H, and $R^4$ is halogen (e.g., chloro),
$Z^1$ is not 2-amino-2oxoethoxy, 2-(N,N-diethylamino) ethoxy, methoxy, or benzyloxy.

In still other embodiments, when each of $R^5$ and $R^6$ is chloro, $R^3$ is H, and $R^4$ is halogen (e.g., chloro), $Z^1$ is —$OR^7$, —$N(R^7)R^{10}$, —$SR^7$, or —$C(R^7)(R^{10})R^{11}$, in which $R^7$ is dimethylaminoethyl, optionally substituted $C_{1-3}$ alkcycloalkyl, or optionally substituted $C_{1-3}$ alkheterocyclyl, or $R^7$ and $R^8$, together with the atoms to which each is attached, join to form an optionally substituted five- or six-membered ring optionally comprising one or two heteroatoms selected from nitrogen, oxygen, and sulfur.

In further embodiments, when each of $R^5$ and $R^6$ is chloro, $R^3$ is H, and $R^4$ is halogen (e.g., chloro), $Z^1$ is —$OR^7$, —$N(R^7)R^{10}$, —$SR^7$, or —$C(R^7)(R^{10})R^{11}$, in which $R^7$ is optionally substituted $C_{1-3}$ alkcycloalkyl, or optionally substituted $C_{1-3}$ alkheterocyclyl, or $R^7$ and $R^8$, together with the atoms to which each is attached, join to form an optionally substituted five- or six-membered ring optionally comprising one or two heteroatoms selected from nitrogen, oxygen, and sulfur.

In particular embodiments, when $R^3$ is H, and $R^4$ is halogen (e.g., chloro), $Z^1$ is —$OR^7$, —$N(R^7)R^{10}$, —$SR^7$, or —$C(R^7)(R^{10})R^{11}$, in which $R^7$ is optionally substituted $C_{1-3}$ alkcycloalkyl, or optionally substituted $C_{1-3}$ alkheterocyclyl, or $R^7$ and $R^8$, together with the atoms to which each is attached, join to form an optionally substituted five- or six-membered ring optionally comprising one or two heteroatoms selected from nitrogen, oxygen, and sulfur.

In some embodiments, when $R^5$ is chloro, $R^6$ is bromo, $Z^1$ is —$OR^7$, and $R^3$ and $R^4$ combine to form a group according to formula (IIa):

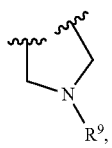

(IIa)

$R^7$ is not methyl, ethyl, n-propyl, 2-(N-pyrazolyl)ethyl, 2-(N-imidazolyl)ethyl, 3-hydroxypropyl, cyanomethyl, 2-chloroethyl, 2-hydroxyethyl, 2-oxo-propyl, 2-(N,N-dimethylamino)ethyl, difluoromethyl, or 2-(t-butylamino)ethyl.

In certain embodiments, when $R^5$ is chloro, $R^6$ is bromo, $Z^1$ is —$OR^7$, and $R^3$ and $R^4$ combine to form a group according to formula (IIa), $R^7$ is not substituted alkyl, unsubstituted alkyl, or unsubstituted $C_2$ alkheteroaryl.

In some embodiments, when $R^5$ is chloro, $R^6$ is bromo, $Z^1$ is —$OR^7$, and $R^3$ and $R^4$ combine to form a group according to formula (IIa), $R^7$ is not alkyl or unsubstituted $C_2$ alkheteroaryl.

In particular embodiments, when $R^5$ is chloro, $R^6$ is bromo, $Z^1$ is —$OR^7$, and $R^3$ and $R^4$ combine to form a group according to formula (IIa), $R^7$ is not substituted alkyl, unsubstituted alkyl, or unsubstituted $C_2$ alkheterocyclyl.

In other embodiments, when $R^5$ is chloro, $R^6$ is bromo, $Z^1$ is —$OR^7$, and $R^3$ and $R^4$ combine to form a group according to formula (IIa), $R^7$ is not alkyl or $C_2$ alkheterocyclyl.

In still other embodiments, when $R^5$ is chloro, $R^6$ is bromo, $Z^1$ is —$OR^7$, and $R^3$ and $R^4$ combine to form a group according to formula (IIa), $R^7$ and $R^8$, together with the atoms to which each is attached, join to form an optionally substituted five- or six-membered ring optionally comprising one or two heteroatoms selected from nitrogen, oxygen, and sulfur.

In yet other embodiments, when $R^5$ is chloro, $R^6$ is bromo, and $R^3$ and $R^4$ combine to form a group according to formula (IIa), Z is —$OR^7$, and $R^7$ and $R^8$ combine to form —$CH_2$—$CH_2$—.

In some embodiments, when each $R^5$ and $R^6$ is bromo, $Z^1$ is —$OR^7$, and $R^3$ and $R^4$ combine to form a group according to formula (IIa), $R^7$ is not methyl.

In particular embodiments, when each $R^5$ and $R^6$ is chloro, $Z^1$ is —$OR^7$, and $R^3$ and $R^4$ combine to form a group according to formula (IIa), $R^7$ is not methyl, 2-(N-imidazolyl)ethyl, methoxymethyl, 2-(N-pyrazolyl)ethyl, 2-(3-methylpyrazol-1-yl)ethyl, 2-pyridyl-methyl, 1,3-dimethyl-1H-1,2,4-triazol-5-yl-methyl, 2-pyrimidinylmethyl, imidazol-2-yl-methyl, 5-methyl-isoxazol-3-yl-methyl, 4-methyl-imidazol-5-yl-methyl, or 3-methyl-1,2,4-oxadiazol-5-yl-methyl.

In other embodiments, when each $R^5$ and $R^6$ is chloro, $Z^1$ is —$OR^7$, and $R^3$ and $R^4$ combine to form a group according to formula (IIa), $R^7$ is not unsubstituted alkyl, substituted alkyl, unsubstituted alkheteroaryl, or substituted alkheteroaryl.

In other embodiments, when each $R^5$ and $R^6$ is chloro, $Z^1$ is —$OR^7$, and $R^3$ and $R^4$ combine to form a group according to formula (IIa), $R^7$ is not unsubstituted alkyl, substituted alkyl, unsubstituted alkheterocyclyl, or substituted alkheterocyclyl.

In certain embodiments, when each $R^5$ and $R^6$ is chloro, $Z^1$ is —$OR^7$, $R^7$ and $R^8$ combine to form —$CH_2$—$CH_2$—, and $R^3$ and $R^4$ combine to form a group according to formula (IIa), $R^9$ is not ethoxycarbonyl, cyclobutylaminocarbonyl, or cyclobutadienylaminocarbonyl.

In other embodiments, when each $R^5$ and $R^6$ is chloro, $Z^1$ is —$OR^7$, $R^7$ and $R^8$ combine to form —$CH_2$—$CH_2$—, and $R^3$ and $R^4$ combine to form a group according to formula (IIa), $R^9$ is H or —C(O)—N(H)-(linear $C_{1-3}$ alkyl).

In particular embodiments, when each $R^5$ and $R^6$ is halo, and $R^3$ and $R^4$ combine to form a group according to formula (IIa), Z is —$OR^7$, $R^7$ is not methyl or 2-chloroethyl, and $R^9$ is H or —C(O)—N(H)-(linear $C_{1-3}$ alkyl).

In some embodiments, when $R^5$ is methoxy, $R^6$ is methyl, $Z^1$ is —$OR^7$, and $R^3$ and $R^4$ combine to form a group according to formula (IIa), $R^7$ is not methyl.

In certain embodiments, when $R^5$ is chloro, $R^6$ is ethyl, $Z^1$ is —$OR^7$, and $R^3$ and $R^4$ combine to form a group according to formula (IIa), $R^7$ is not methyl.

In some embodiments, when each $R^5$ and $R^6$ is chloro, $Z^1$ is —$OR^7$, and $R^3$ and $R^4$ combine to form a group according to formula (IIb) or (IIc),

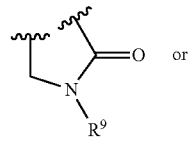

(IIb)

or

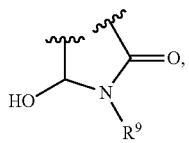
(IIc)

$R^7$ is not methyl or 2-(N,N-diethylamino)ethyl.

In other embodiments, when each $R^5$ and $R^6$ is chloro, $Z^1$ is —$OR^7$, and $R^3$ and $R^4$ combine to form a group according to formula (IIb) or (IIc), $R^7$ and $R^8$, together with the atoms to which each is attached, join to form an optionally substituted five- or six-membered ring optionally comprising one or two heteroatoms selected from nitrogen, oxygen, and sulfur.

In certain embodiments, when each $R^5$ and $R^6$ is chloro, and $R^3$ and $R^4$ combine to form a group according to formula (IIb) or (IIc), $Z^1$ is —$OR^7$, and $R^7$ and $R^8$ combine to form —$CH_2$—$CH_2$—.

In some embodiments, when $R^7$ is methyl, $R^5$ is chloro, $Z^1$ is —$OR^7$, and $R^3$ and $R^4$ combine to form a group according to formula (IIIa),

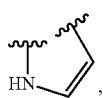
(IIIa)

$R^6$ is not bromo.

In particular embodiments, when each $R^5$ and $R^6$ is chloro, $Z^1$ is —$OR^7$, and $R^3$ and $R^4$ combine to form a group according to formula (IIIa), $R^7$ is not isopropyl, 3,3,3-trifluoropropyl, or 2-(N,N-dimethylamino)ethyl.

In certain embodiments, when each $R^5$ and $R^6$ is chloro, $Z^1$ is —$OR^7$, and $R^3$ and $R^4$ combine to form a group according to formula (IIIa), $R^8$ is not H.

In some embodiments, when $R^3$ and $R^4$ combine to form a group according to formula (IIIa), each $R^5$ and $R^6$ is chloro, and $R^7$ is methyl and $R^8$ is H, or $R^7$ and $R^8$, together with the atoms to which each is attached, join to form an optionally substituted five- or six-membered ring optionally comprising one or two heteroatoms selected from nitrogen, oxygen, and sulfur.

In other embodiments, when $R^5$ is chloro, $R^6$ is methoxy, $Z^1$ is —$OR^7$, and $R^3$ and $R^4$ combine to form a group according to formula (IIIb):

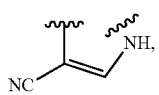
(IIIb)

neither $R^1$ nor $R^2$ is 2-(N,N-diethylamino)ethyl.

In certain embodiments, when $R^5$ is chloro, $R^6$ is methoxy, $Z^1$ is —$OR^7$, and $R^3$ and $R^4$ combine to form a group according to formula (IIIb), each $R^1$ and $R^2$ is H.

In some embodiments, when each $R^5$ and $R^6$ is chloro, $Z^1$ is —$OR^7$, and $R^3$ and $R^4$ combine to form a group according to formula (IVa):

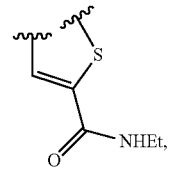
(IVa)

$R^7$ is not 3-(N-morpholinyl)propyl, benzyl, 1-ethyl-pyrrolydin-3-yl, 1-methyl-piperidin-4-yl, 2-(1-methyl-pyrrolidin-2-yl)ethyl, or 3-(N,N-diethylamino)propyl.

In particular embodiments, when each $R^5$ and $R^6$ is chloro, $Z^1$ is —$OR^7$, and $R^3$ and $R^4$ combine to form a group according to formula (IVa), $R^7$ is not substituted alkyl, heterocyclyl, alkheterocyclyl, or alkaryl.

In some embodiments, when each $R^5$ and $R^6$ is chloro, $Z^1$ is —$OR^7$, and $R^3$ and $R^4$ combine to form a group according to formula (IVb):

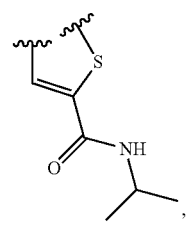
(IVb)

$R^7$ is not 2-methoxyethyl or benzyl.

In certain embodiments, when each $R^5$ and $R^6$ is chloro, $Z^1$ is —$OR^7$, and $R^3$ and $R^4$ combine to form a group according to formula (IVb), $R^7$ is not substituted alkyl or alkaryl.

In some embodiments, when each $R^5$ and $R^6$ is chloro, $Z^1$ is —$OR^7$, and $R^3$ and $R^4$ combine to form a group according to formula (IVc):

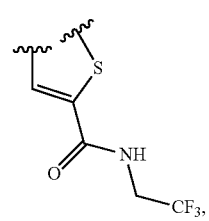
(IVc)

$R^7$ is not 2-(N,N-diethylamino)ethyl or 3-(N,N-dimethylamino)propyl.

In other embodiments, when each $R^5$ and $R^6$ is chloro, $Z^1$ is —$OR^7$, and $R^3$ and $R^4$ combine to form a group according to formula (IVc), $R^7$ is not substituted alkyl.

In particular embodiments, when each $R^5$ and $R^6$ is chloro, $Z^1$ is —$OR^7$, and $R^3$ and $R^4$ combine to form a group according to formula (IVd):

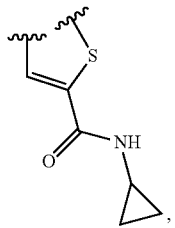

(IVd)

$R^7$ is not 2-(pyrrolidin-1-yl)ethyl or 2-hydroxyethyl.

In certain embodiments, when each $R^5$ and $R^6$ is chloro, $Z^1$ is —$OR^7$, and $R^3$ and $R^4$ combine to form a group according to formula (IVd), $R^7$ is not substituted alkyl or alkheterocyclyl.

In some embodiments, when each $R^5$ and $R^6$ is chloro, $Z^1$ is —$OR^7$, and $R^3$ and $R^4$ combine to form a group according to formula (IVe) or (IVf):

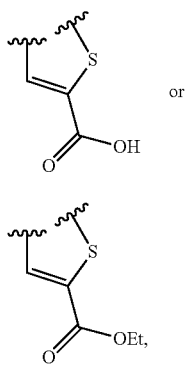

(IVe)

or (IVf)

$R^7$ is not benzyl.

In other embodiments, when each $R^5$ and $R^6$ is chloro, $Z^1$ is —$OR^7$, and $R^3$ and $R^4$ combine to form a group according to formula (IVe) or (IVf), $R^7$ is not alkaryl.

In certain embodiments, when $R^5$ is chloro, $R^6$ is bromo, $Z^1$ is —$OR^7$, and $R^3$ and $R^4$ combine to form a group according to formula (IVg), (IVh), (IVi), (IVj), or (IVk):

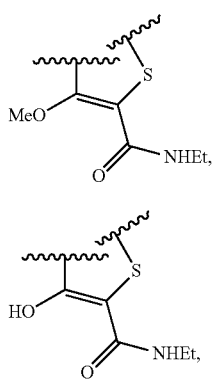

(IVg)

(IVh)

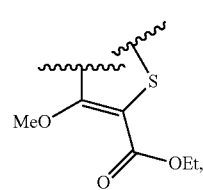

(IVi)

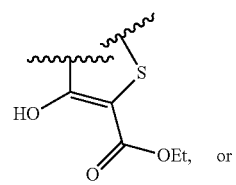

(IVj)

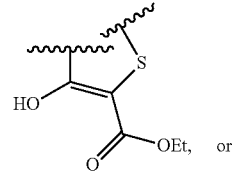

or

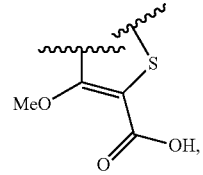

(IVk)

$R^7$ is not methyl.

In certain embodiments, when $R^5$ is chloro, $R^6$ is bromo, $Z^1$ is —$OR^7$, and $R^3$ and $R^4$ combine to form a group according to formula (IVg), (IVh), (IVi), (IVj), or (IVk), $R^7$ is not alkyl.

In some embodiments, when $R^5$ is chloro, $R^6$ is bromo, $Z^1$ is —$OR^7$, and $R^3$ and $R^4$ combine to form a group according to formula (IVg), (IVh), (IVi), (IVj), or (IVk), $R^7$ and $R^8$, together with the atoms to which each is attached, join to form an optionally substituted five- or six-membered ring optionally comprising one or two heteroatoms selected from nitrogen, oxygen, and sulfur.

In particular embodiments, when $R^5$ is chloro, $R^6$ is bromo, and $Z^1$ is —$OR^7$, $R^3$ and $R^4$ do not combine to form a group according to formula (IVg), (IVh), (IVi), (IVj), or (IVk).

In particular embodiments, when $R^6$ is methyl, each $R^1$ and $R^2$ is H.

In certain embodiments, when $R^3$ is H, and each $R^5$ and $R^6$ is chloro, $R^7$ is not methyl.

In certain embodiments, when $R^3$ and $R^4$, together with the atoms to which each is attached, join to form a substituted five-membered ring comprising one nitrogen, the five-membered ring is not substituted with oxo. In particular embodiments, when $R^3$ and $R^4$, together with the atoms to which each is attached, join to form a substituted five-membered ring comprising one sulfur, the five-membered ring is not substituted with hydroxy or $C_{1-3}$ alkoxy. In further embodiments, when $R^3$ and $R^4$, together with the atoms to which each is attached, join to form an optionally substituted five-membered ring comprising one sulfur, $R^7$ and $R^8$, together with the atoms to which each is attached, join to form an optionally substituted five- or six-membered ring optionally comprising one or two heteroatoms selected from nitrogen, oxygen, and sulfur.

In particular embodiments, $R^7$ and $R^8$, together with the atoms to which each is attached, join to form an optionally substituted five- or six-membered ring optionally comprising one or two heteroatoms selected from nitrogen, oxygen, and sulfur. In other embodiments, $R^7$ and $R^8$, together with the atoms to which each is attached, join to form an optionally substituted five- or six-membered saturated ring optionally comprising one or two heteroatoms selected from nitrogen, oxygen, and sulfur. In yet other embodiments, $R^7$ and $R^8$, together with the atoms to which each is attached, join to form an optionally substituted five- of six-membered ring optionally comprising one or two heteroatoms selected from nitrogen and oxygen. In certain embodiments, $R^7$ and $R^8$, together with the atoms to which each is attached, join to form an optionally substituted five-membered ring.

In some embodiments, a compound is according to formula (Ib):

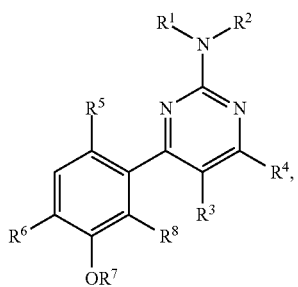

(Ib)

or a pharmaceutically acceptable salt thereof,
where
each of $R^1$ and $R^2$ is, independently, H or optionally substituted $C_{1-3}$ alkyl;
$R^3$ is H, halogen, optionally substituted $C_{1-3}$ alkyl, or optionally substituted $C_{1-3}$ alkoxy, and $R^4$ is halogen, optionally substituted $C_{1-3}$ alkyl, optionally substituted $C_{1-3}$ alkoxy, optionally substituted amino, optionally substituted $C_{1-6}$ thioalkoxy, or optionally substituted $C_{6-10}$ aryl, or $R^3$ and $R^4$, together with the atoms to which each is attached, join to form an optionally substituted five- or six-membered ring optionally comprising one nitrogen, one sulfur, or one oxygen, where the nitrogen is optionally substituted with $R^9$;
each of $R^5$ and $R^6$ is, independently, optionally substituted $C_{1-3}$ alkyl (e.g., optionally substituted $C_{1-3}$ acyl), optionally substituted $C_{1-3}$ alkoxy, halogen, or CN;
$R^7$ is optionally substituted $C_{1-3}$ alkyl, optionally substituted $C_{1-3}$ alkcycloalkyl, optionally substituted $C_{1-3}$ alkheterocyclyl, or optionally substituted $C_{1-3}$ alkaryl, and $R^8$ is H; or $R^7$ and $R^8$, together with the atoms to which each is attached, join to form an optionally substituted five- or six-membered ring; and
$R^9$ is H, optionally substituted $C_{1-3}$ alkyl, optionally substituted $C_{3-8}$ cycloalkyl, optionally substituted $C_{6-10}$ aryl, optionally substituted $C_{2-9}$ heteroaryl, optionally substituted $C_{2-9}$ heterocyclyl, optionally substituted $C_{1-3}$ alkcycloalkyl, optionally substituted $C_{1-3}$ alkheterocyclyl, or optionally substituted $C_{1-3}$ alkaryl.

In other embodiments, when each of $R^1$ and $R^2$ is H, $R^3$ is H, $R^4$ is methyl or chloro, and each of $R^5$ and $R^6$ is chloro, $R^7$ is not methyl.

In yet other embodiments, when $R^3$ is H, and $R^4$ is halogen (e.g., chloro),
$R^7$ is not 2-amino-2oxoethyl, 2-(N,N-diethylamino)ethyl, methyl, or benzyl.

In still other embodiments, when each of $R^5$ and $R^6$ is chloro, $R^3$ is H, and $R^4$ is halogen (e.g., chloro),
$R^7$ is dimethylaminoethyl, optionally substituted $C_{1-3}$ alkcycloalkyl, or optionally substituted $C_{1-3}$ alkheterocyclyl, or $R^7$ and $R^8$, together with the atoms to which each is attached, join to form an optionally substituted five- or six-membered ring optionally comprising one or two heteroatoms selected from nitrogen, oxygen, and sulfur.

In further embodiments, when each of $R^5$ and $R^6$ is chloro, $R^3$ is H, and $R^4$ is halogen (e.g., chloro),
$R^7$ is optionally substituted $C_{1-3}$ alkcycloalkyl, or optionally substituted $C_{1-3}$ alkheterocyclyl, or $R^7$ and $R^8$, together with the atoms to which each is attached, join to form an optionally substituted five- or six-membered ring optionally comprising one or two heteroatoms selected from nitrogen, oxygen, and sulfur.

In particular embodiments, when $R^3$ is H, and $R^4$ is halogen (e.g., chloro),
$R^7$ is optionally substituted $C_{1-3}$ alkcycloalkyl, or optionally substituted $C_{1-3}$ alkheterocyclyl, or $R^7$ and $R^8$, together with the atoms to which each is attached, join to form an optionally substituted five- or six-membered ring optionally comprising one or two heteroatoms selected from nitrogen, oxygen, and sulfur.

In some embodiments, when $R^5$ is chloro, $R^6$ is bromo, and $R^3$ and $R^4$ combine to form a group according to formula (IIa):

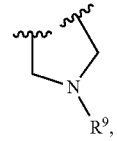

(IIa)

$R^7$ is not methyl, ethyl, n-propyl, 2-(N-pyrazolyl)ethyl, 2-(N-imidazolyl)ethyl, 3-hydroxypropyl, cyanomethyl, 2-chloroethyl, 2-hydroxyethyl, 2-oxo-propyl, 2-(N,N-dimethylamino)-ethyl, difluoromethyl, or 2-(t-butylamino)ethyl.

In certain embodiments, when $R^5$ is chloro, $R^6$ is bromo, and $R^3$ and $R^4$ combine to form a group according to formula (IIa),
$R^7$ is not substituted alkyl, unsubstituted alkyl, or unsubstituted $C_2$ alkheteroaryl.

In other embodiments, when $R^5$ is chloro, $R^6$ is bromo, and $R^3$ and $R^4$ combine to form a group according to formula (IIa),
$R^7$ is not alkyl or $C_2$ alkheteroaryl.

In particular embodiments, when $R^5$ is chloro, $R^6$ is bromo, and $R^3$ and $R^4$ combine to form a group according to formula (IIa),
$R^7$ is not substituted alkyl, unsubstituted alkyl, or unsubstituted $C_2$ alkheterocyclyl.

In some embodiments, when $R^5$ is chloro, $R^6$ is bromo, and $R^3$ and $R^4$ combine to form a group according to formula (IIa),
$R^7$ is not alkyl or $C_2$ alkheterocyclyl.

In still other embodiments, when $R^5$ is chloro, $R^6$ is bromo, and $R^3$ and $R^4$ combine to form a group according to formula (IIa),
$R^7$ and $R^8$, together with the atoms to which each is attached, join to form an optionally substituted five- or six-membered ring comprising one oxygen atom and optionally comprising one more heteroatom selected from nitrogen, oxygen, and sulfur.

In yet other embodiments, when $R^5$ is chloro, $R^6$ is bromo, and $R^3$ and $R^4$ combine to form a group according to formula (IIa),
$R^7$ and $R^8$ combine to form —$CH_2$—$CH_2$—.

In some embodiments, when each $R^5$ and $R^6$ is bromo, and $R^3$ and $R^4$ combine to form a group according to formula (IIa), $R^7$ is not methyl.

In particular embodiments, when each $R^5$ and $R^6$ is chloro, and $R^3$ and $R^4$ combine to form a group according to formula (IIa), $R^7$ is not methyl, 2-(N-imidazolyl)ethyl, methoxymethyl, 2-(N-pyrazolyl)ethyl, 2-(3-methylpyrazol-1-yl)ethyl, 2-pyridyl-methyl, 1,3-dimethyl-1H-1,2,4-triazol-5-yl-methyl, 2-pyrimidinylmethyl, imidazol-2-yl-methyl, 5-methyl-isoxazol-3-yl-methyl, 4-methyl-imidazol-5-yl-methyl, or 3-methyl-1,2,4-oxadiazol-5-yl-methyl.

In other embodiments, when each $R^5$ and $R^6$ is chloro, and $R^3$ and $R^4$ combine to form a group according to formula (IIa), $R^7$ is not unsubstituted alkyl, substituted alkyl, unsubstituted alkheteroaryl, or substituted alkheteroaryl.

In other embodiments, when each $R^5$ and $R^6$ is chloro, and $R^3$ and $R^4$ combine to form a group according to formula (IIa), $R^7$ is not unsubstituted alkyl, substituted alkyl, unsubstituted alkheterocyclyl, or substituted alkheterocyclyl.

In certain embodiments, when each $R^5$ and $R^6$ is chloro, $R^7$ and $R^8$ combine to form —CH$_2$—CH$_2$—, and $R^3$ and $R^4$ combine to form a group according to formula (IIIa), $R^9$ is not ethoxycarbonyl, cyclobutylaminocarbonyl, or cyclobutadienylaminocarbonyl.

In other embodiments, when each $R^5$ and $R^6$ is chloro, $R^7$ and $R^8$ combine to form —CH$_2$—CH$_2$—, and $R^3$ and $R^4$ combine to form a group according to formula (IIa), $R^9$ is H or —C(O)—N(H)-(linear C$_{1-3}$ alkyl).

In particular embodiments, when each $R^5$ and $R^6$ is halo, and $R^3$ and $R^4$ combine to form a group according to formula (IIa), and $R^9$ is H or —C(O)—N(H)-(linear C$_{1-3}$ alkyl).

In some embodiments, when $R^5$ is methoxy, $R^6$ is methyl, and $R^3$ and $R^4$ combine to form a group according to formula (IIa), $R^7$ is not methyl.

In certain embodiments, when $R^5$ is chloro, $R^6$ is ethyl, and $R^3$ and $R^4$ combine to form a group according to formula (IIa), $R^7$ is not methyl.

In some embodiments, when each $R^5$ and $R^6$ is chloro, and $R^3$ and $R^4$ combine to form a group according to formula (IIb) or (IIc),

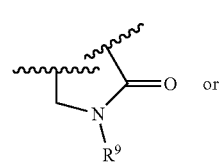
(IIb)

or

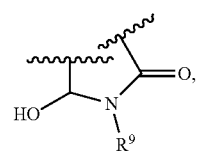
(IIc)

$R^7$ is not methyl or 2-(N,N-diethylamino)ethyl.

In other embodiments, when each $R^5$ and $R^6$ is chloro and $R^3$ and $R^4$ combine to form a group according to formula (IIb) or (IIc), $R^7$ and $R^8$, together with the atoms to which each is attached, join to form an optionally substituted five- or six-membered ring comprising one oxygen atom and optionally comprising one more heteroatom selected from nitrogen, oxygen, and sulfur.

In certain embodiments, when each $R^5$ and $R^6$ is chloro and $R^3$ and $R^4$ combine to form a group according to formula (IIb) or (IIc), $R^7$ and $R^8$ combine to form —CH$_2$—CH$_2$—.

In some embodiments, when $R^7$ is methyl, $R^5$ is chloro, and $R^3$ and $R^4$ combine to form a group according to formula (IIIa),

(IIIa)

$R^6$ is not bromo.

In particular embodiments, when each $R^5$ and $R^6$ is chloro, and $R^3$ and $R^4$ combine to form a group according to formula (IIIa), $R^7$ is not isopropyl, 3,3,3-trifluoropropyl, or 2-(N,N-dimethylamino)ethyl.

In particular embodiments, when each $R^5$ and $R^6$ is chloro, and $R^3$ and $R^4$ combine to form a group according to formula (IIIa), $R^8$ is not H.

In some embodiments, when $R^3$ and $R^4$ combine to form a group according to formula (IIIa), each $R^5$ and $R^6$ is chloro, $R^7$ is methyl, and $R^8$ is H, or $R^7$ and $R^8$, together with the atoms to which each is attached, join to form an optionally substituted five- or six-membered ring comprising one oxygen atom and optionally comprising one more heteroatom selected from nitrogen, oxygen, and sulfur.

In other embodiments, when $R^5$ is chloro, $R^6$ is methoxy, and $R^3$ and $R^4$ combine to form a group according to formula (IIIb):

(IIIb)

neither $R^1$ nor $R^2$ is 2-(N,N-diethylamino)ethyl.

In certain embodiments, when $R^5$ is chloro, $R^6$ is methoxy, and $R^3$ and $R^4$ combine to form a group according to formula (IIIb), each $R^1$ and $R^2$ is H.

In some embodiments, when each $R^5$ and $R^6$ is chloro, and $R^3$ and $R^4$ combine to form a group according to formula (IVa):

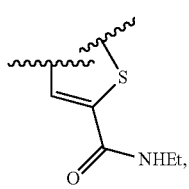

(IVa)

R[7] is not 3-(N-morpholinyl)propyl, benzyl, 1-ethyl-pyrrolydin-3-yl, 1-methyl-piperidin-4-yl, 2-(1-methyl-pyrrolidin-2-yl)ethyl, or 3-(N,N-diethylamino)propyl.

In particular embodiments, when each $R^5$ and $R^6$ is chloro, and $R^3$ and $R^4$ combine to form a group according to formula (IVa), R[7] is not substituted alkyl, heterocyclyl, alkheterocyclyl, or alkaryl.

In some embodiments, when each $R^5$ and $R^6$ is chloro, and $R^3$ and $R^4$ combine to form a group according to formula (IVb):

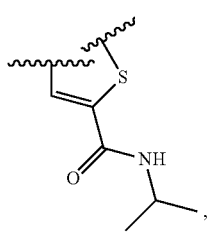

(IVb)

R[7] is not 2-methoxyethyl or benzyl.

In certain embodiments, when each $R^5$ and $R^6$ is chloro, and $R^3$ and $R^4$ combine to form a group according to formula (IVb), R[7] is not substituted alkyl or alkaryl.

In some embodiments, when each $R^5$ and $R^6$ is chloro, and $R^3$ and $R^4$ combine to form a group according to formula (IVc):

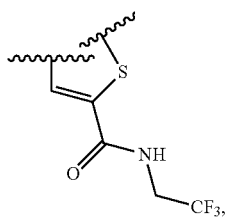

(IVc)

R[7] is not 2-(N,N-diethylamino)ethyl or 3-(N,N-dimethylamino)propyl.

In other embodiments, when each $R^5$ and $R^6$ is chloro, and $R^3$ and $R^4$ combine to form a group according to formula (IVc), R[7] is not substituted alkyl.

In particular embodiments, when each $R^5$ and $R^6$ is chloro, and $R^3$ and $R^4$ combine to form a group according to formula (IVd):

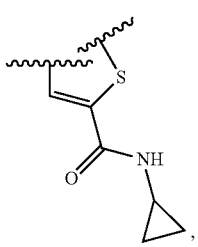

(IVd)

R[7] is not 2-(pyrrolidin-1-yl)ethyl or 2-hydroxyethyl.

In certain embodiments, when each $R^5$ and $R^6$ is chloro, and $R^3$ and $R^4$ combine to form a group according to formula (IVd), R[7] is not substituted alkyl or alkheterocyclyl.

In some embodiments, when each $R^5$ and $R^6$ is chloro, and $R^3$ and $R^4$ combine to form a group according to formula (IVe) or (IVf):

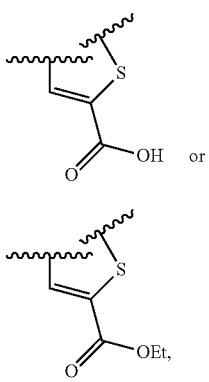

(IVe)

or (IVf)

R[7] is not benzyl.

In other embodiments, when each $R^5$ and $R^6$ is chloro, and $R^3$ and $R^4$ combine to form a group according to formula (IVe) or (IVf), R[7] is not substituted alkyl or alkaryl.

In certain embodiments, when $R^5$ is chloro, $R^6$ is bromo, and $R^3$ and $R^4$ combine to form a group according to formula (IVg), (IVh), (IVi), (IVj), or (IVk):

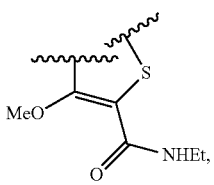

(IVg)

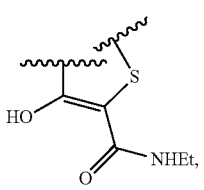

(IVh)

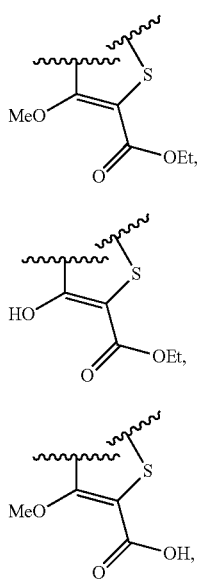

$R^7$ is not methyl.

In some embodiments, when $R^5$ is chloro, $R^6$ is bromo, and $R^3$ and $R^4$ combine to form a group according to formula (IVg), (IVh), (IVi), (IVj), or (IVk), $R^7$ and $R^8$ together with the atoms to which each is attached, join to form an optionally substituted five- or six-membered ring optionally comprising one or two heteroatoms selected from nitrogen, oxygen, and sulfur.

In particular embodiments, when $R^5$ is chloro, $R^6$ is bromo, $R^3$ and $R^4$ do not combine to form a group according to formula (IVg), (IVh), (IVi), (IVj), or (IVk).

In particular embodiments, when $R^6$ is methoxy, each $R^1$ and $R^2$ is H.

In certain embodiments, when $R^3$ is H, and each $R^5$ and $R^6$ is chloro, $R^7$ is not methyl.

In some embodiments of formula (I), (Ia), or (Ib), $R^3$ is H, halogen, optionally substituted $C_{1-3}$ alkyl (e.g., optionally substituted $C_{1-3}$ acyl), or optionally substituted $C_{1-3}$ alkoxy, and $R^4$ is halogen, optionally substituted $C_{1-3}$ alkyl (e.g., optionally substituted $C_{1-3}$ acyl), optionally substituted $C_{1-3}$ alkoxy, optionally substituted amino, optionally substituted $C_{1-6}$ thioalkyl, or optionally substituted $C_{6-10}$ aryl, or $R^3$ and $R^4$, together with the atoms to which each is attached, join to form an optionally substituted five- or six-membered ring optionally comprising one nitrogen, one oxygen, or one sulfur, where the nitrogen is optionally substituted with $R^9$.

In further embodiments of formula (I), (Ia), or (Ib), $R^7$ is optionally substituted $C_{1-3}$ alkyl, optionally substituted $C_{1-3}$ alkcycloalkyl, optionally substituted $C_{1-3}$ alkheterocyclyl, or optionally substituted $C_{1-3}$ alkaryl, and $R^8$ is H; or $R^7$ and $R^8$, together with the atoms to which each is attached, join to form an optionally substituted five- or six-membered ring optionally comprising one or two heteroatoms selected from nitrogen, oxygen, and sulfur.

In particular embodiments, when $R^3$ and $R^4$ combine to form a group according formula (IIb) or (IIc), the carbonyl group of formula (IIb) or (IIc) is proximal to $C^6$. In other embodiments, when $R^3$ and $R^4$ combine to form a group according to formula (IIb) or (IIc), the carbonyl group of formula (IIb) or (IIc) is proximal to $C^5$ or $C^6$.

In certain embodiments, when $R^3$ and $R^4$ combine to form a group according to formula (IIIa), the N atom of the group according to formula (IIIa) is proximal to $C^5$. In particular embodiments, when $R^3$ and $R^4$ combine to form a group according to formula (IIIa), the N atom of the group according to formula (IIIb) is proximal to $C^5$ or $C^6$.

In some embodiments, when $R^3$ and $R^4$ combine to form a group according to formula (IIIb), the N atom of the group according to formula (IIIb) is proximal to $C^6$. In other embodiments, when $R^3$ and $R^4$ combine to form a group according to formula (IIIb), the N atom of the group according to formula (IIIb) is proximal to $C^5$ or $C^6$.

In particular embodiments, when $R^3$ and $R^4$ combine to form a group according to any one of formulae (IVa)-(IVk), the S atom of the group according to any one of formulae (IVa)-(IVk) is proximal to $C^6$. In particular embodiments, when $R^3$ and $R^4$ combine to form a group according to any one of formulae (IVa)-(IVk), the S atom of the group according to any one of formulae (IVa)-(IVk) is proximal to $C^5$ or $C^6$.

In some embodiments, when $R^3$ and $R^4$, together with the atoms to which each is attached, join to form an optionally substituted five-membered ring comprising one sulfur, $R^7$ and $R^8$, together with the atoms to which each is attached, join to form an optionally substituted five- or six-membered ring. In certain embodiments, when $R^3$ and $R^4$, together with the atoms to which each is attached, join to form an optionally substituted five-membered ring comprising one sulfur, $R^7$ and $R^8$, together with the atoms to which each is attached, join to form an optionally substituted five-membered ring. In particular embodiments, when $R^3$ and $R^4$, together with the atoms to which each is attached, join to form an optionally substituted five-membered ring comprising one sulfur, $R^7$ and $R^8$ combine to form a —$CH_2CH_2$— group.

In other embodiments, $R^7$ and $R^8$, together with the atoms to which each is attached, join to form a five- or six-membered ring.

In particular embodiments, $R^7$ is optionally substituted $C_{1-3}$ alkyl. In other embodiments, $R^7$ is unsubstituted $C_{1-3}$ alkyl, $C_{1-3}$ alkylamino-$C_{1-3}$-alkyl (e.g., $C_{1-3}$ haloalkylamino-$C_{1-3}$-alkyl (e.g., $C_{1-3}$ fluoroalkylamino-$C_{1-3}$-alkyl)), di-($C_{1-3}$ alkyl)amino-$C_{1-3}$-alkyl (e.g., $R^{Y1}N(R^{Y2})$—($C_{1-3}$ alkyl)-, where each of $R^{Y1}$ and $R^{Y2}$ is, independently, unsubstituted $C_{1-3}$ alkyl or $C_{1-3}$ haloalkylamino-$C_{1-3}$-alkyl, (e.g., $C_{1-3}$ fluoroalkylamino-$C_{1-3}$-alkyl), or $C_{1-3}$ haloalkyl (e.g., $C_{1-3}$ fluoroalkyl). In particular embodiments, $R^7$ is unsubstituted $C_{1-3}$ alkyl, $C_{1-3}$ alkylamino-$C_{1-3}$-alkyl (e.g., $C_{1-3}$ haloalkylamino-$C_{1-3}$-alkyl, e.g., $C_{1-3}$ fluoroalkylamino-$C_{1-3}$-alkyl), or di-($C_{1-3}$ alkyl)amino-$C_{1-3}$-alkyl (e.g., $R^{Y1}N(R^{Y2})$—($C_{1-3}$ alkyl)-, where each of $R^{Y1}$ and $R^{Y2}$ is, independently, unsubstituted $C_{1-3}$ alkyl, or $C_{1-3}$ haloalkylamino-$C_{1-3}$-alkyl, e.g., $C_{1-3}$ fluoroalkylamino-$C_{1-3}$-alkyl).

In still other embodiments, $R^7$ is optionally substituted $C_{1-3}$ alkyl (e.g., $R^7$ is methyl), or $R^7$ is —$(CH_2)_k$—$N(R^{24})R^{25}$, where k is 2 or 3 (e.g., k is 2), and where each of $R^{24}$ and $R^{25}$ is, independently, H or optionally substituted $C_{1-3}$ alkyl (e.g., each of $R^{24}$ and $R^{25}$ is, independently, optionally substituted $C_{1-3}$ alkyl, e.g., each of $R^{24}$ and $R^{25}$ is, independently, $C_{1-3}$ haloalkyl (e.g., $C_{1-3}$ fluoroalkyl); alternatively each of $R^{24}$ and $R^{25}$ is, independently, unsubstituted $C_{1-3}$ alkyl, e.g., methyl).

In other embodiments, when $R^3$ and $R^4$, together with the atoms to which each is attached, join to form an optionally substituted five-membered ring comprising one nitrogen, an optional substituent on the ring is not oxo. In certain embodiments, when $R^3$ and $R^4$, together with the atoms to which each is attached, join to form an optionally substituted five-membered ring comprising one sulfur, an optional substitutent on the ring is not hydroxyl or $C_{1-3}$ alkoxy.

In yet other embodiments, each $R^1$ and $R^2$ is H. In particular embodiments, each $R^3$ and $R^4$ is, independently, optionally substituted $C_{1-3}$ alkyl or optionally substituted $C_{1-3}$ alkoxy; or $R^3$ and $R^4$, together with the atoms to which each is attached, join to form an optionally substituted five- or six-membered ring optionally comprising one nitrogen, one sulfur, or one oxygen, where the nitrogen is optionally substituted with $R^9$. In some embodiments, $R^3$ and $R^4$, together with the atoms to which each is attached, join to form an optionally substituted five-membered ring. In certain embodiments, $R^3$ and $R^4$ combine to form —$CH_2CH_2CH_2$—. In particular embodiments, $R^3$ and $R^4$, together with the atoms to which each is attached, join to form an optionally substituted five-membered ring comprising one nitrogen. In some embodiments, $R^3$ and $R^4$ combine to form —N($R^9$)—CH=CH— (e.g., $R^9$ is H or optionally substituted $C_{1-3}$ alkyl, e.g., $C_{1-3}$ haloalkyl (e.g., $C_{1-3}$ fluoroalkyl); alternatively $R^9$ is H). In certain embodiments, the N atom is proximal to $C^5$ of Formula (I). In particular embodiments, $R^3$ and $R^4$, together with the atoms to which each is attached, join to form an optionally substituted five-membered ring comprising one sulfur. In yet other embodiments, $R^3$ and $R^4$ combine to form —C($R^{13A}$)=C($R^{13B}$)—S—, where $R^{13A}$ is H, and $R^{13B}$ is H or optionally substituted $C_{1-3}$ alkyl. In particular embodiments, the S atom is proximal to $C^6$ of the compound of the invention. In some embodiments, $R^{13}$ is optionally substituted $C_{1-3}$ alkyl, e.g., $R^{13B}$ is —C(O)—$R^{13C}$, where $R^{13C}$ is optionally substituted $C_{1-3}$ alkoxy or optionally substituted amino. In other embodiments, $R^4$ is $C_{1-3}$ alkyl. In specific embodiments, $R^4$ is methyl, ethyl, or isopropyl. In certain embodiments, $R^4$ is $C_{1-3}$ alkoxy (e.g., $R^4$ is methoxy). In other embodiments, $R^4$ is optionally substituted $C_{1-6}$ thioalkoxy (e.g., $R^4$ is 4-amino-4-oxobutyl). In yet other embodiments, $R^4$ is optionally substituted amino (e.g., $R^4$ is methylamino). In still other embodiments, $R^4$ is halogen (e.g., $R^4$ is chloro). In particular embodiments, $R^3$ is hydrogen or $C_{1-3}$ alkyl (e.g., $R^3$ is hydrogen, methyl, or ethyl). In further embodiments, $R^3$ and $R^4$ combine to form —C($R^{13A}$)=C($R^{13B}$)—S— group, where $R^{13A}$ is H, and $R^{13B}$ is H or —C(O)—$R^{13C}$, where $R^{13C}$ is optionally substituted $C_{1-3}$ alkyl, optionally substituted $C_{1-3}$ alkoxy, optionally substituted amino, or optionally substituted $C_{2-9}$ heterocyclyl.

In some embodiments, $R^3$ and $R^4$ combine to form —$X^1$—$X^2$—$X^3$—, where
  $X^1$ is —S—, —O—, —(C$R^{14}R^{15}$)—, —OC($R^{16}$)=, —N($R^9$)—, —N=, H, or optionally substituted $C_{1-3}$ alkyl;
  $X^2$ is absent, —(C$R^{17}R^{18}$)$_n$—, —S—, —O—, —N=, —N($R^9$)—, —C($R^{19}$)=, =N—, =C($R^{20}$)—, or =C($R^{21}$)—C($R^{22}$)=;
  $X^3$ is —(C$R^{14}R^{15}$)—, —S—, —O—, —N($R^9$)—, =N—, =C($R^{23}$)—, halogen, optionally substituted $C_{1-3}$ alkyl, optionally substituted $C_{1-6}$ thioalkoxy, optionally substituted $C_{1-3}$ alkoxy, or optionally substituted $C_{6-10}$ aryl;
  each $R^{14}$ and $R^{15}$ is, independently, H or optionally substituted $C_{1-3}$ alkyl, or $R^{14}$ and $R^{15}$ combine to form =O or =S;
  each $R^{17}$ and $R^{18}$ is, independently, H or optionally substituted $C_{1-3}$ alkyl, or $R^{17}$ and $R^{18}$ combine to form =O or =S;
  each $R^{16}$, $R^{19}$, $R^{20}$, $R^{21}$, $R^{22}$, and $R^{23}$ is, independently, H, or optionally substituted $C_{1-3}$ alkyl; and
  n is 1 or 2.

In some embodiments, when $X^2$ is not absent,
  the chain of atoms —$X^1$—$X^2$—$X^3$— includes no more than one heteroatom, the heteroatom being selected from nitrogen, oxygen, and sulfur.

In particular embodiments, $X^1$ is —(C$R^{14}R^{15}$)—, —C($R^{16}$)=, —N($R^9$)—, —N=, or optionally substituted $C_{1-3}$ alkyl.

In certain embodiments, $X^1$ is —(C$R^{14}R^{15}$)—. In particular embodiments, each $R^{14}$ and $R^{15}$ is H. In other embodiments, $X^1$ is —C($R^{16}$)=. In yet other embodiments, $R^{16}$ is H. In still other embodiments, $X^1$ is —N($R^9$)—. In some embodiments, $R^9$ is H or optionally substituted $C_{1-3}$ alkyl. In certain embodiments, $R^9$ is hydrogen, methyl, or ethyl. In particular embodiments, $X^1$ is —N=. In other embodiments, $X^1$ is optionally substituted $C_{1-3}$ alkyl. In yet other embodiments, $X^2$ is absent, —(CH$_2$)$_n$—, —N($R^9$)—, —C(H)=, =C($R^{20}$)—, or =C(H)—C(H)=. In still other embodiments, $X^2$ is —C(H)=. In further embodiments, $X^2$ is —N($R^9$)—. In some embodiments, $R^9$ is H. In certain embodiments, $R^9$ is optionally substituted $C_{1-3}$ alkyl (e.g., $R^9$ is —C(O)—N(H)-Et). In particular embodiments, $X^2$ is =C($R^{20}$)—. In other embodiments, $R^{20}$ is optionally substituted $C_{1-3}$ alkyl. In yet other embodiments, $X^2$ is absent. In still other embodiments, $X^3$ is —CH$_2$—, —S—, =C(H)—, —N($R^9$)—, halogen, optionally substituted $C_{1-3}$ alkyl, optionally substituted $C_{1-3}$ alkoxy, optionally substituted $C_{1-6}$ thioalkoxy, optionally substituted $C_{6-10}$ aryl. In certain embodiments, $X^3$ is —CH$_2$—. In particular embodiments, $X^3$ is —S—. In some embodiments, $X^3$ is =C(H)—. In other embodiments, $X^3$ is —N($R^9$)—. In yet other embodiments, $X^3$ is halogen, optionally substituted $C_{1-3}$ alkyl, optionally substituted $C_{1-3}$ alkoxy, optionally substituted $C_{1-6}$ thioalkoxy, or optionally substituted $C_{6-10}$ aryl.

In certain embodiments, $Z^1$ and $R^8$ combine to form —$Z^3$—$Y^1$—$Y^2$—, where
  $Z^3$ is —O—, —N($R^{10}$)—, —N=, —S—, or —(C$R^{11}R^{12}$)—;
  $Y^1$ is —O—, —N($R^{10}$)—, —S—, —(C$R^{26}R^{27}$)$_m$—, —C($R^{20}$)=, =C($R^{20}$)—, =C($R^{21}$)—C($R^{22}$)=, optionally substituted $C_{1-3}$ alkyl, optionally substituted $C_{1-3}$ alkheterocyclyl, optionally substituted $C_{1-3}$ alkcycloalkyl, or optionally substituted $C_{1-3}$ alkaryl; and
  $Y^2$ is —O—, —S—, —N($R^{10}$)—, —(C$R^{26}R^{27}$)—, =C($R^{20}$)—, =N—, or H; where
  each $R^{20}$, $R^{21}$, and $R^{22}$ is, independently, H or optionally substituted $C_{1-3}$ alkyl; and
  each $R^{26}$ and $R^{27}$ is, independently, H or optionally substituted $C_{1-3}$ alkyl, or $R^{26}$ and $R^{27}$ combine to form =O or =S;
  m is 1 or 2; and
  where, when $Y^2$ is H,
    the chain of atoms —$Z^3$—$Y^1$—$Y^2$— comprises no more than two heteroatoms, the heteroatom selected from nitrogen, oxygen, and sulfur.

In yet other embodiments, $R^7$ and $R^8$ form a group —$Y^1$—$Y^2$—, where:
  $Y^1$ is —(C$R^{26}R^{27}$)$_m$—, —C($R^{20}$)=, optionally substituted $C_{1-3}$ alkyl, optionally substituted $C_{1-3}$ alkheterocyclyl, optionally substituted $C_{1-3}$ alkcycloalkyl, or optionally substituted $C_{1-3}$ alkaryl; and
  $Y^2$ is —(C$R^{26}R^{27}$)—, =C($R^{20}$)—, or H; where
  each $R^{26}$ and $R^{27}$ is, independently, H or optionally substituted $C_{1-3}$ alkyl; and
  m is 1 or 2.

In particular embodiments, $Z^3$ is oxygen. In some embodiments, $Y^1$ is —(C$R^{26}R^{27}$)$_m$—, —C($R^{20}$)=, optionally substituted $C_{1-3}$ alkyl, optionally substituted $C_{1-3}$ alkheterocyclyl, optionally substituted $C_{1-3}$ alkcycloalkyl, or optionally substituted $C_{1-3}$ alkaryl. In further embodiments, $Y^1$ is —$(CR^{26}R^{27})_m$— or optionally substituted $C_{1-3}$ alkyl. In other embodiments, $Y^1$ is —$(CR^{26}R^{27})_m$—. In other embodiments, $Y^1$ is optionally substituted $C_{1-3}$ alkyl (e.g., $Y^1$ is methyl). In yet other embodiments, $Y^1$ is —$(CH_2)_k$—$N(R^{24})R^{25}$, where k is 2 or 3, and where each $R^{24}$ and $R^{25}$ is, independently, H or optionally substituted $C_{1-3}$ alkyl. In still other embodiments, k is 2. In further embodiments, each $R^{24}$ and $R^{25}$ is, independently, optionally substituted $C_{1-3}$ alkyl (e.g., each $R^{24}$ and $R^{25}$ is methyl). In certain embodiments, $Y^2$ is —$(CR^{26}R^{27})$— or H. In other embodiments, $Y^2$ is —$(CR^{26}R^{27})$—.

In some embodiments of any aspect, each $R^1$ and $R^2$ is H

In certain embodiments of formula (I) or (Ia), a compound of the invention has a structure according to formula (Va):

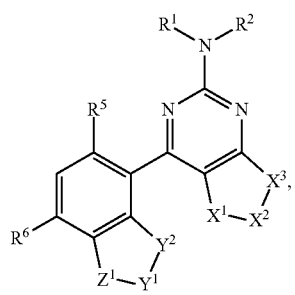

(Va)

or a pharmaceutically acceptable salt thereof, where all substituents are as defined herein.

In particular embodiments of formula (I), (Ia), or (Ib), a compound of the invention has a structure according to formula (Vb):

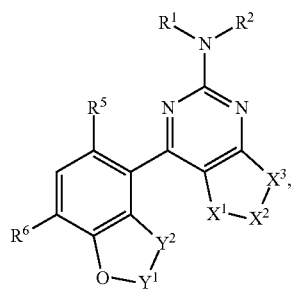

(Vb)

or a pharmaceutically acceptable salt thereof,
where
$X^1$ is —S—, —O—, —$(CR^{14}R^{15})$—, —$OC(R^{16})$=, —$N(R^9)$—, —N=, —H, or optionally substituted $C_{1-3}$ alkyl; $X^2$ is absent, —$(CR^{17}R^{18})_n$—, —S—, —O—, —N=, —$N(R^9)$—, —$C(R^{19})$=, =N—, =$C(R^{20})$—, or =$C(R^{21})$—$C(R^{22})$=;
$X^3$ is —$(CR^{14}R^{15})$—, —S—, —O—, —$N(R^9)$—, =N—, =$C(R^{23})$—, halogen, optionally substituted $C_{1-3}$ alkyl, optionally substituted $C_{1-6}$ thioalkoxy, optionally substituted $C_{1-3}$ alkoxy, or optionally substituted $C_{6-10}$ aryl;
$Y^1$ is —$(CR^{26}R^{27})_m$—, —$C(R^{20})$=, =$C(R^{20})$—, =$C(R^{21})$—$OC(R^{22})$=, optionally substituted $C_{1-3}$ alkyl, optionally substituted $C_{1-3}$ alkheterocyclyl, optionally substituted $C_{1-3}$ alkcycloalkyl, or optionally substituted $C_{1-3}$ alkaryl;
$Y^2$ is —O—, —S—, —$N(R^{10})$—, —$(CR^{26}R^{27})$—, =$C(R^{20})$—, =N—, or H;
each $R^1$ and $R^2$ is, independently, H or optionally substituted $C_{1-3}$ alkyl;
each $R^5$ and $R^6$ is, independently, optionally substituted $C_{1-3}$ alkyl, optionally substituted $C_{1-3}$ alkoxy, halogen, or CN;
each $R^{14}$, $R^{15}$, $R^{16}$, $R^{17}$, $R^{17}$, $R^{18}$, $R^{20}$, $R^{19}$, $R^{20}$, $R^{21}$, $R^{22}$, $R^{23}$, $R^{26}$, and $R^{27}$ is, independently, H or optionally substituted $C_{1-3}$ alkyl;
n is 1 or 2; and
m is 1 or 2.

In some embodiments, when $R^5$ is chloro, $R^6$ is bromo, and —$X^1$—$X^2$—$X^3$— forms a group according to formula (IIa):

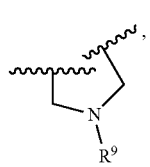

(IIa)

$Y^1$ is not methyl, ethyl, n-propyl, 2-(N-pyrazolyl)ethyl, 2-(N-imidazolyl)ethyl, 3-hydroxypropyl, cyanomethyl, 2-chloroethyl, 2-hydroxyethyl, 2-oxo-propyl, 2-(N,N-dimethylamino)-ethyl, difluoromethyl, or 2-(t-butylamino)ethyl.

In certain embodiments, when $R^5$ is chloro, $R^6$ is bromo, and —$X^1$—$X^2$—$X^3$— forms a group according to formula (IIa),
$Y^1$ is not optionally substituted $C_{1-3}$ alkyl or optionally substituted $C_2$ alkheteroaryl.

In particular embodiments, when $R^5$ is chloro, $R^6$ is bromo, and —$X^1$—$X^2$—$X^3$— forms a group according to formula (IIa),
$Y^1$ is not optionally substituted $C_{1-3}$ alkyl or optionally substituted $C_2$ alkheterocyclyl.

In still other embodiments, when $R^5$ is chloro, $R^6$ is bromo, and —$X^1$—$X^2$—$X^3$— forms a group according to formula (IIa),
$Y^2$ is not H.

In yet other embodiments, when $R^5$ is chloro, $R^6$ is bromo, and —$X^1$—$X^2$—$X^3$— forms a group according to formula (IIa),
each $Y^1$ and $Y^2$ is —$CH_2$—.

In some embodiments, when each $R^5$ and $R^6$ is bromo, and —$X^1$—$X^2$—$X^3$— forms a group according to formula (IIa),
$Y^1$ is not methyl.

In particular embodiments, when each $R^5$ and $R^6$ is chloro, and —$X^1$—$X^2$—$X^3$— forms a group according to formula (IIa),
$Y^1$ is not methyl, 2-(N-imidazolyl)ethyl, methoxymethyl, 2-(N-pyrazolyl)ethyl, 2-(3-methylpyrazol-1-yl)ethyl, 2-pyridyl-methyl, 1,3-dimethyl-1H-1,2,4-triazol-5-yl-methyl, 2-pyrimidinylmethyl, imidazol-2-yl-methyl, 5-methyl-isoxazol-3-yl-methyl, 4-methyl-imidazol-5-yl-methyl, or 3-methyl-1,2,4-oxadiazol-5-yl-methyl.

In other embodiments, when each $R^5$ and $R^6$ is chloro, and —$X^1$—$X^2$—$X^3$— forms a group according to formula (IIa), $Y^1$ is not unsubstituted alkyl, substituted alkyl, unsubstituted alkheteroaryl, or substituted alkheteroaryl.

In some embodiments, when each $R^5$ and $R^6$ is chloro, and —$X^1$—$X^2$—$X^3$— forms a group according to formula (IIa), $Y^1$ is not unsubstituted alkyl, substituted alkyl, unsubstituted alkheterocyclyl, or substituted alkheterocyclyl.

In certain embodiments, when each $R^5$ and $R^6$ is chloro, each $Y^1$ and $Y^2$ is —$CH_2$—, and —$X^1$—$X^2$—$X^3$— forms a group according to formula (IIa), $R^9$ is not ethoxycarbonyl, cyclobutylaminocarbonyl, or cyclobutadienylaminocarbonyl.

In other embodiments, when each $R^5$ and $R^6$ is chloro, $R^7$ and $R^8$ combine to form —$CH_2$—$CH_2$—, and —$X^1$—$X^2$—$X^3$— forms a group according to formula (IIa), $R^9$ is H or —C(O)—N(H)-(linear $C_{1-3}$ alkyl).

In particular embodiments, when each $R^5$ and $R^6$ is halo, and —$X^1$—$X^2$—$X^3$— forms a group according to formula (IIa), and $R^9$ is H or —C(O)—N(H)-(linear $C_{1-3}$ alkyl).

In some embodiments, when $R^5$ is methoxy, $R^6$ is methyl, and —$X^1$—$X^2$—$X^3$— forms a group according to formula (IIa), $Y^1$ is not methyl.

In certain embodiments, when $R^5$ is chloro, $R^6$ is ethyl, and —$X^1$—$X^2$—$X^3$— forms a group according to formula (IIa), $Y^1$ is not methyl.

In some embodiments, when each $R^5$ and $R^6$ is chloro, and —$X^1$—$X^2$—$X^3$— forms a group according to formula (IIb) or (IIc), (IIb)

(IIc)

$Y^1$ is not methyl or 2-(N,N-diethylamino)ethyl.

In other embodiments, when each $R^5$ and $R^6$ is chloro and —$X^1$—$X^2$—$X^3$— forms a group according to formula (IIb) or (IIc), $Y^2$ is not H.

In certain embodiments, when each $R^5$ and $R^6$ is chloro and —$X^1$—$X^2$—$X^3$— forms a group according to formula (IIb) or (IIc), each $Y^1$ and $Y^2$ is —$CH_2$—.

In some embodiments, when $R^7$ is methyl, $R^5$ is chloro, and —$X^1$—$X^2$—$X^3$— forms a group according to formula (IIIa), (IIIa)

$R^6$ is not bromo.

In particular embodiments, when each $R^5$ and $R^6$ is chloro, and —$X^1$—$X^2$—$X^3$— forms a group according to formula (IIIa), $R^7$ is not isopropyl, 3,3,3-trifluoropropyl, or 2-(N,N-dimethylamino)ethyl.

In some embodiments, when —$X^1$—$X^2$—$X^3$— forms a group according to formula (IIIa), each $R^5$ and $R^6$ is chloro, and $Y^1$ is methyl and $Y^2$ is H, or $Y^1$ is —$(CR^{26}R^{27})_m$—, —$C(R^{20})$=, =$C(R^{20})$—, or =$C(R^{21})$—$C(R^{22})$=, and $Y^2$ is —O—, —S—, —N($R^{10}$)—, —$(CR^{26}R^{27})$—, =$C(R^{20})$—, or =N—.

In some embodiments, when —$X^1$—$X^2$—$X^3$— forms a group according to formula (IIIa), each $R^5$ and $R^6$ is chloro, and $Y^2$ is not H.

In other embodiments, when $R^5$ is chloro, $R^6$ is methoxy, and —$X^1$—$X^2$—$X^3$— forms a group according to formula (IIIb):

(IIIb)

neither $R^1$ nor $R^2$ is 2-(N,N-diethylamino)ethyl.

In certain embodiments, when $R^5$ is chloro, $R^6$ is methoxy, and —$X^1$—$X^2$—$X^3$— forms a group according to formula (IIIb), each $R^1$ and $R^2$ is H.

In some embodiments, when each $R^5$ and $R^6$ is chloro, and —$X^1$—$X^2$—$X^3$— forms a group according to formula (IVa):

(IVa)

$Y^1$ is not 3-(N-morpholinyl)propyl, benzyl, 1-ethyl-pyrrolydin-3-yl, 1-methyl-piperidin-4-yl, 2-(1-methyl-pyrrolidin-2-yl)ethyl, or 3-(N,N-diethylamino)propyl.

In particular embodiments, when each $R^5$ and $R^6$ is chloro, and —$X^1$—$X^2$—$X^3$— forms a group according to formula (IVa), $Y^1$ is not heterocyclyl, alkheterocyclyl, or alkaryl.

In some embodiments, when each $R^5$ and $R^6$ is chloro, and —$X^1$—$X^2$—$X^3$— forms a group according to formula (IVb):

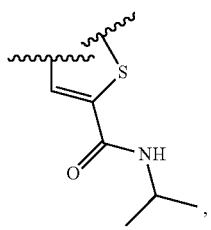
(IVb)

Y$^1$ is not 2-methoxyethyl or benzyl.

In certain embodiments, when each R$^5$ and R$^6$ is chloro, and —X$^1$—X$^2$—X$^3$— forms a group according to formula (IVb), Y$^1$ is not substituted alkyl or alkaryl.

In some embodiments, when each R$^5$ and R$^6$ is chloro, and —X$^1$—X$^2$—X$^3$— forms a group according to formula (IVc):

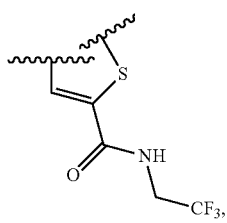
(IVc)

Y$^1$ is not 2-(N,N-diethylamino)ethyl or 3-(N,N-dimethylamino)propyl.

In other embodiments, when each R$^5$ and R$^6$ is chloro, and —X$^1$—X$^2$—X$^3$— forms a group according to formula (IVc), Y$^1$ is not substituted alkyl.

In particular embodiments, when each R$^5$ and R$^6$ is chloro, and —X$^1$—X$^2$—X$^3$— forms a group according to formula (IVd):

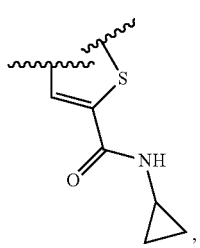
(IVd)

Y$^1$ is not 2-(pyrrolidin-1-yl)ethyl or 2-hydroxyethyl.

In certain embodiments, when each R$^5$ and R$^6$ is chloro, and R$^3$ and R$^4$ combine to form a group according to formula (IVd), Y$^1$ is not substituted alkyl or alkheterocyclyl.

In some embodiments, when each R$^5$ and R$^6$ is chloro, and —X$^1$—X$^2$—X$^3$— forms a group according to formula (IVe) or (IVf):

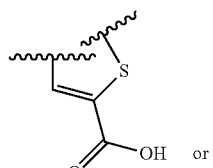
(IVe)

or

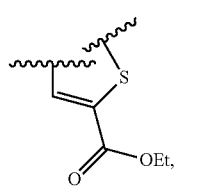
(IVf)

Y$^1$ is not benzyl.

In other embodiments, when each R$^5$ and R$^6$ is chloro, and —X$^1$—X$^2$—X$^3$— forms a group according to formula (IVe) or (IVf), Y$^1$ is not alkaryl or substituted alkyl.

In certain embodiments, when R$^5$ is chloro, R$^6$ is bromo, and —X$^1$—X$^2$—X$^3$— forms a group according to formula (IVg), (IVh), (IVi), (IVj), or (IVk):

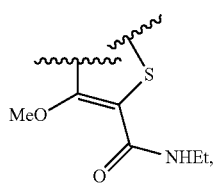
(IVg)

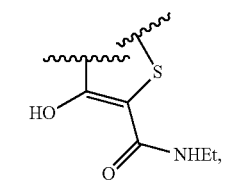
(IVh)

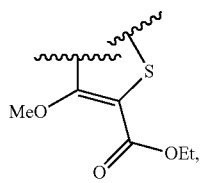
(IVi)

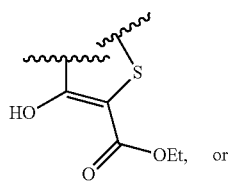
(IVj)

or

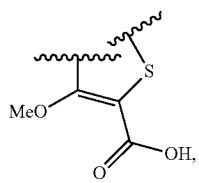
(IVk)

Y$^1$ is not methyl.

In some embodiments, when R⁵ is chloro, R⁶ is bromo, —X¹—X²—X³— forms a group according to formula (IVg), (IVh), (IVi), (IVj), or (IVk),
Y² is not H.
In particular embodiments, when R⁵ is chloro, R⁶ is bromo,
R³ and R⁴ do not combine to form a group according to formula (IVg), (IVh), (IVi), (IVj), or (IVk).
In particular embodiments, when R⁶ is methoxy, each R¹ and R² is H.
In certain embodiments, when X¹ is H, and each R⁵ and R⁶ is chloro,
Y¹ is not methyl.
In some embodiments, R¹⁰ is H, optionally substituted $C_{1-3}$ alkyl, optionally substituted $C_{3-8}$ cycloalkyl, optionally substituted $C_{1-3}$ alkcycloalkyl, optionally substituted $C_{1-3}$ alkheterocyclyl, or optionally substituted $C_{1-3}$ alkaryl. In other embodiments, R¹⁰ is H, optionally substituted $C_{1-3}$ alkyl, optionally substituted $C_{1-3}$ alkcycloalkyl, optionally substituted $C_{1-3}$ alkheterocyclyl, or optionally substituted $C_{1-3}$ alkaryl.
In particular embodiments, when X¹ is —(CR¹⁴R¹⁵)—, X² is —N(R⁹)—, X³ is —(CR¹⁴R¹⁵)—, and each of R¹⁴ and R¹⁵ is H, R⁹ is H or —C(O)—N(H)-Et, and each of Y¹ and Y² is —CH₂—. In other embodiments, when X¹ is —(CR¹⁴R¹⁵)—, X² is —N(R⁹)—, and X³ is —(CR¹⁴R¹⁵)—, R⁹ is H or —C(O)—N(H)-Et, and each of Y¹ and Y² is —CH₂—. In some embodiments, when X¹ is —N(R⁹)—, X² is —C(R¹⁹)=, X³ is =C(R²³)—, and each of R¹⁷, R¹⁹, and R²³ is H, Y¹ is —(CR²⁶R²⁷)ₘ—, and Y² is —(CR²⁶R²⁷)—. In other embodiments, when X¹ is —N(R⁹)—, X² is —C(R¹⁹)=, X³ is =C(R²³)—, and each of R⁹, R¹⁹, and R²³ is H, each of Y¹ and Y² is —CH₂—. In some embodiments, when X¹ is —N(R⁹)—, X² is —C(R¹⁹)=, X³ is =C(R²³)—, and each of R¹⁹ and R²³ is H, Y¹ is —(CR²⁶R²⁷)ₘ—, and Y² is —(CR²⁶R²⁷)—. In certain embodiments, when X¹ is —N(R⁹)—, X² is —C(R¹⁹)=, X³ is =C(R²³)—, Y² is H, and each of R⁵ and R⁶ is —Cl, Y¹ is Me. In particular embodiments, when X¹ is —C(R¹⁶)=, X² is =C(R²⁰)—, and X³ is —S—, R¹⁶ is H. In some embodiments, when X¹ is —C(R¹⁶)=, X² is =C(R²⁰)—, and X³ is —S—, Y¹ is —(CR²⁶R²⁷)ₘ—, and Y² is —(CR²⁶R²⁷)—. In certain embodiments, when X¹ is —C(R¹⁶)=, X² is =C(R²⁰)—, and X³ is —S—, each of Y¹ and Y² is —CH₂—. In some embodiments, when X¹ is —C(R¹⁶)=, X² is =C(R²⁰)—, and X³ is —S—, each of R⁵ and R⁶ is —Cl. In certain embodiments, when X¹ is H, and each of R⁵ and R⁶ is Cl, Y¹ is —(CR²⁶R²⁷)ₘ—, and Y² is —(CR²⁶R²⁷)—. In particular embodiments, when X¹ is H, and each of R⁵ and R⁶ is hal, Y¹ is —(CR²⁶R²⁷)ₘ—, and Y² is —(CR²⁶R²⁷)— (e.g., each of Y¹ and Y² is —CH₂—). In particular embodiments, when X¹ is H, Y¹ is —(CR²⁶R²⁷)ₘ—, and Y² is —(CR²⁶R²⁷)— (e.g., each of Y¹ and Y² is —CH₂—).
In particular embodiments, X¹ is —(CR¹⁴R¹⁵)—, —C(R¹⁶)=, —N(R⁹)—, or optionally substituted $C_{1-3}$ alkyl (e.g., —CH₂—, —C(H)=, —N=, optionally substituted $C_{1-3}$ alkyl, or —N(R⁹)— (e.g., R¹⁷ is H or optionally substituted $C_{1-3}$ alkyl (e.g., R⁹ is H, -Me, or -Et).
In some embodiments, X² is absent, —(CH₂)ₙ—, —N(R⁹)—, —C(H)=, =C(R²⁰)—, or =C(H)—C(H)=. In certain embodiments, X² is absent, —C(H)=, —N(R⁹)— (e.g., R⁹ is H or optionally substituted $C_{1-3}$ alkyl (e.g., R⁹ is $C_{1-3}$ haloalkyl, e.g., $C_{1-3}$ fluoroalkyl), or R⁹ is —C(O)—N(H)-Et), or =C(R²⁰)—, where R²⁰ is, e.g., optionally substituted $C_{1-3}$ alkyl.
In certain embodiments, X³ is —CH₂—, —S—, =C(H)—, or optionally substituted $C_{1-3}$ alkyl.

In some embodiments, each of R⁵ and R⁶ is, independently, halo, or optionally substituted $C_{1-3}$ alkyl, e.g., each of R⁵ and R⁶ is halo (e.g., each of R⁵ and R⁶ is —Cl).
In some embodiments, R²⁶ is H. In other embodiments, R²⁷ is H. In certain embodiments, n is 1. In other embodiments, m is 1. In particular embodiments, Y¹ is optionally substituted $C_{1-3}$ alkyl. In other embodiments, Y¹ is unsubstituted $C_{1-3}$ alkyl, $C_{1-3}$ alkylamino-$C_{1-3}$-alkyl (e.g., $C_{1-3}$ haloalkylamino-$C_{1-3}$-alkyl, e.g., $C_{1-3}$ fluoroalkylamino-$C_{1-3}$-alkyl), di-($C_{1-3}$ alkyl)amino-$C_{1-3}$-alkyl (e.g., $R^{Y1}N(R^{Y2})$—($C_{1-3}$ alkyl)-, where each of $R^{Y1}$ and $R^{Y2}$ is, independently, unsubstituted $C_{1-3}$ alkyl, or $C_{1-3}$ haloalkylamino-$C_{1-3}$-alkyl, e.g., $C_{1-3}$ fluoroalkylamino-$C_{1-3}$-alkyl), or $C_{1-3}$ haloalkyl (e.g., $C_{1-3}$ fluoroalkyl). In particular embodiments, Y¹ is unsubstituted $C_{1-3}$ alkyl, $C_{1-3}$ alkylamino-$C_{1-3}$-alkyl (e.g., $C_{1-3}$ haloalkylamino-$C_{1-3}$-alkyl, e.g., $C_{1-3}$ fluoroalkylamino-$C_{1-3}$-alkyl), or di-($C_{1-3}$ alkyl)amino-$C_{1-3}$-alkyl (e.g., $R^{Y1}N(R^{Y2})$—($C_{1-3}$ alkyl)-, where each of $R^{Y1}$ and $R^{Y2}$ is, independently, unsubstituted $C_{1-3}$ alkyl, or $C_{1-3}$ haloalkylamino-$C_{1-3}$-alkyl, e.g., $C_{1-3}$ fluoroalkylamino-$C_{1-3}$-alkyl).

In certain embodiments, a compound of the invention has the formula as shown in Table 1:

TABLE 1

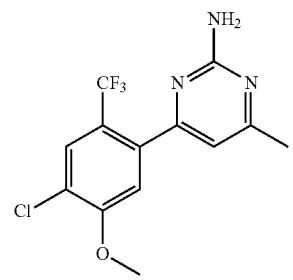
1

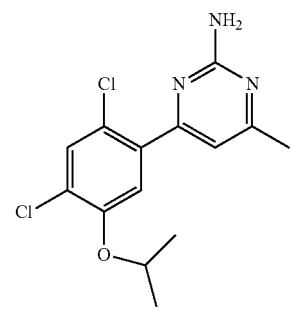
2

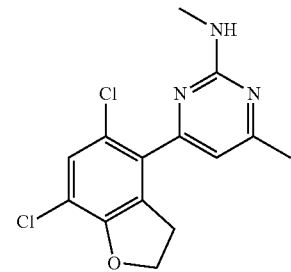
3

TABLE 1-continued
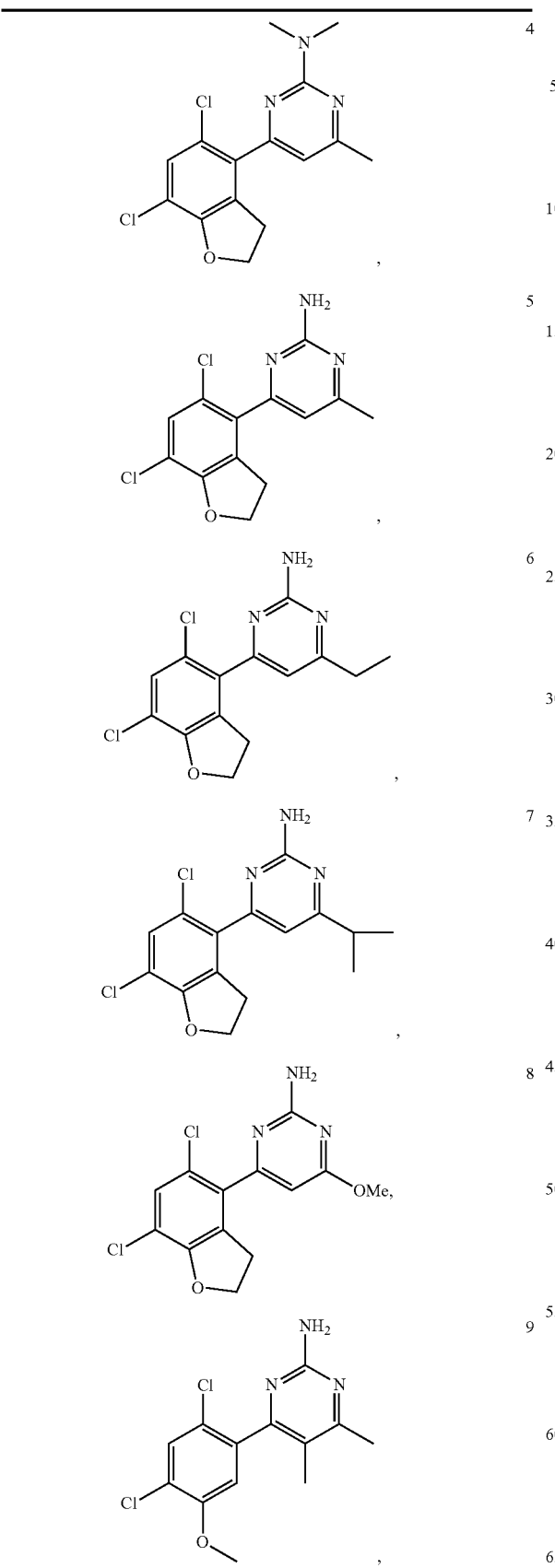
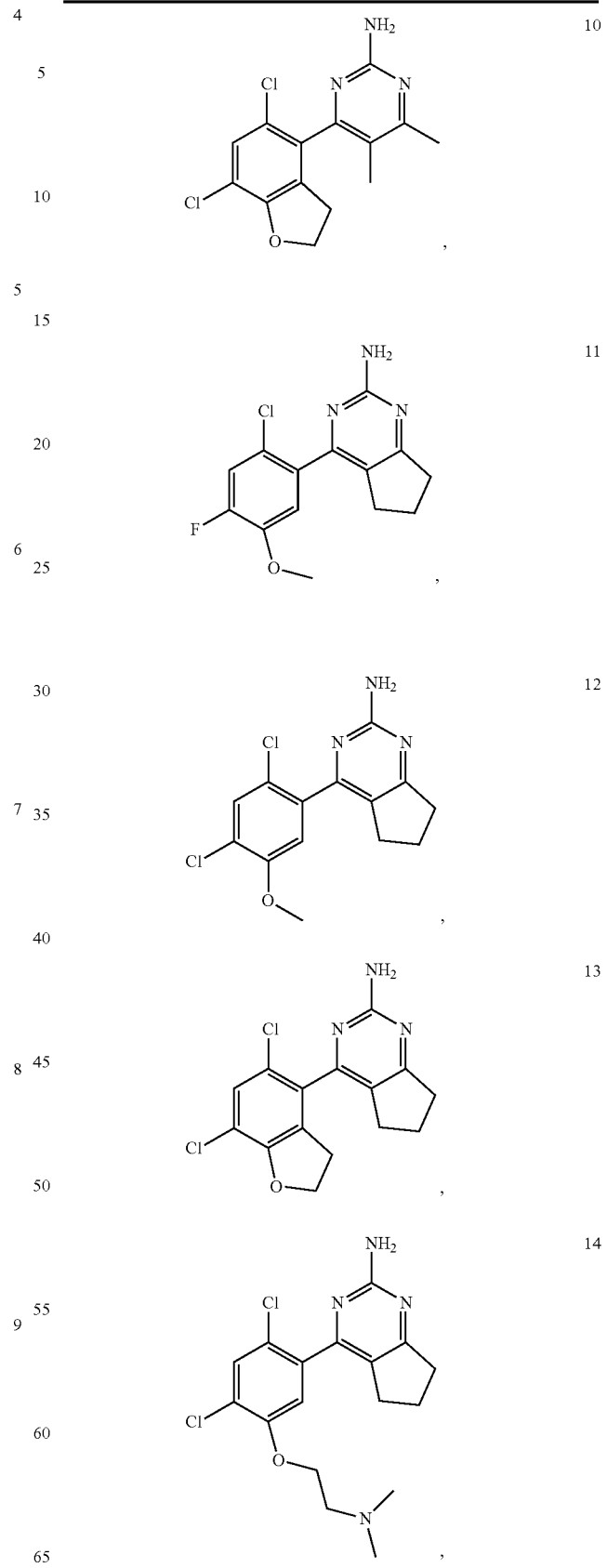

TABLE 1-continued
| | |
|---|---|
| 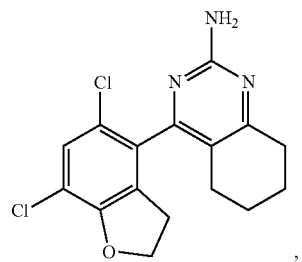 [SMILES: Nc1nc2c(c(-c3c(Cl)cc(Cl)c4c3CCO4)n1)CCCC2] | 15 |
| 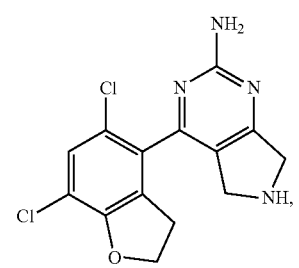 [SMILES: Nc1nc2c(c(-c3c(Cl)cc(Cl)c4c3CCO4)n1)CNC2] | 16 |
| 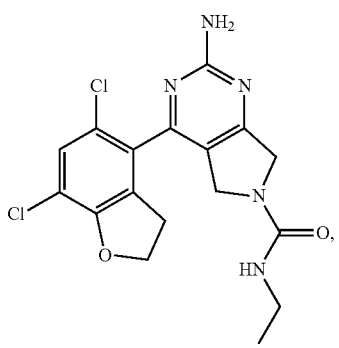 [SMILES: CCNC(=O)N1Cc2nc(N)nc(-c3c(Cl)cc(Cl)c4c3CCO4)c2C1] | 17 |
| 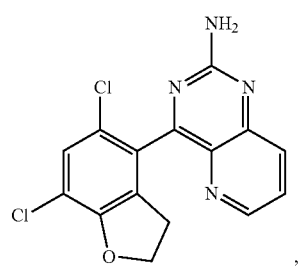 [SMILES: Nc1nc(-c2c(Cl)cc(Cl)c3c2CCO3)c2ncccc2n1] | 18 |
| 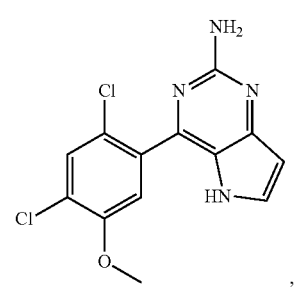 | 19 |
TABLE 1-continued
| | |
|---|---|
| 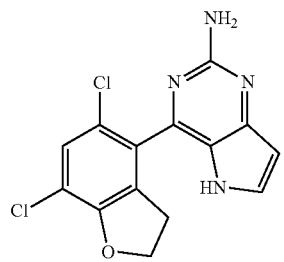 | 20 |
| 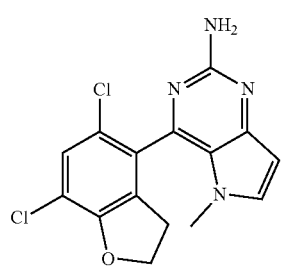 | 21 |
| 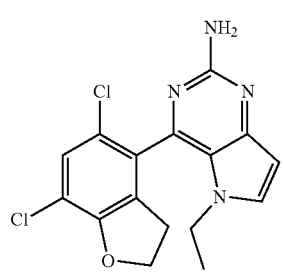 | 22 |
| 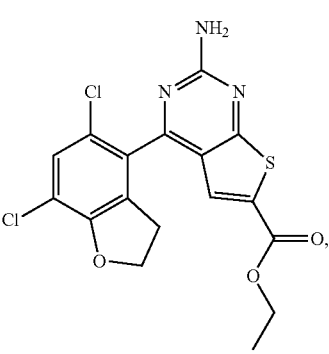 [SMILES: CCOC(=O)c1cc2c(-c3c(Cl)cc(Cl)c4c3CCO4)nc(N)nc2s1] | 23 |
| 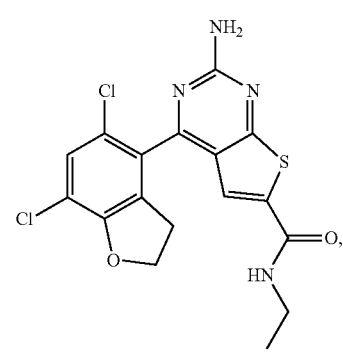 [SMILES: CCNC(=O)c1cc2c(-c3c(Cl)cc(Cl)c4c3CCO4)nc(N)nc2s1] | 24 |

TABLE 1-continued
| 25 | 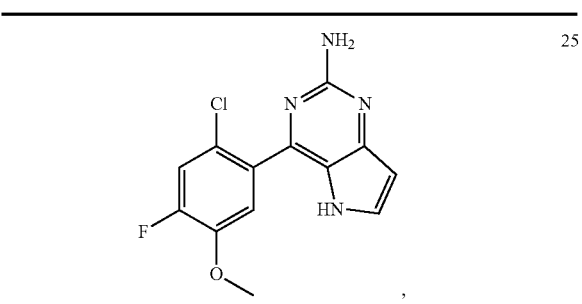 |
| 26 | 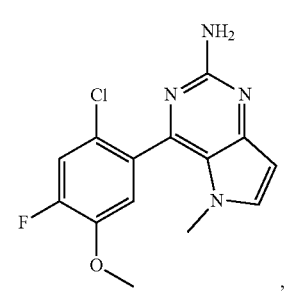 |
| 27 | 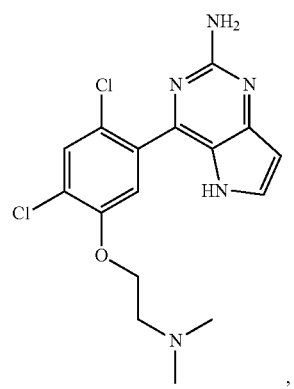 [SMILES: CN(C)CCOc1cc(-c2nc(N)nc3cc[nH]c23)c(Cl)cc1Cl] |
| 28 | 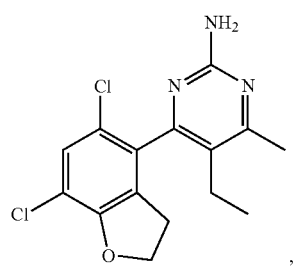 [SMILES: CCc1c(C)nc(N)nc1-c1c(Cl)cc(Cl)c2c1CCO2] |
| 29 | 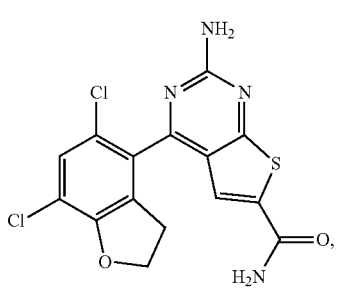 [SMILES: NC(=O)c1cc2c(-c3c(Cl)cc(Cl)c4c3CCO4)nc(N)nc2s1] |
TABLE 1-continued
| 30 | 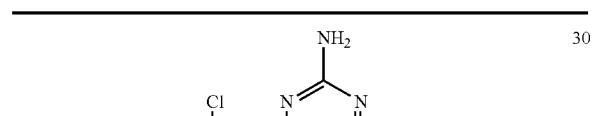 |
| 31 | 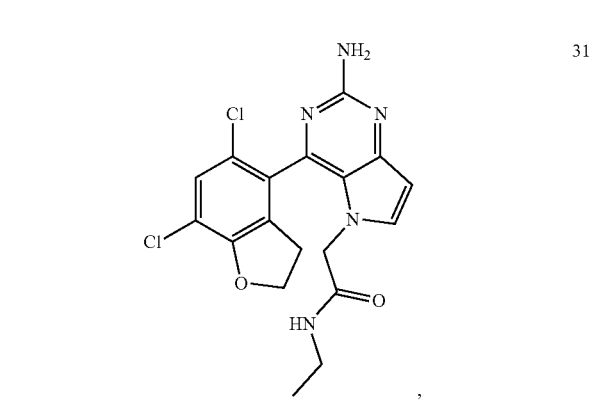 |
| 32 | 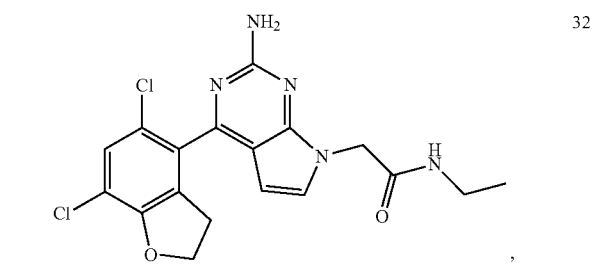 |
| 33 | 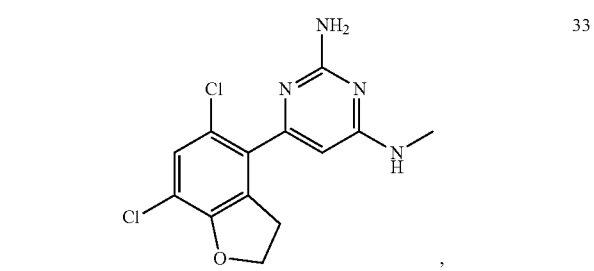 |
| 34 | 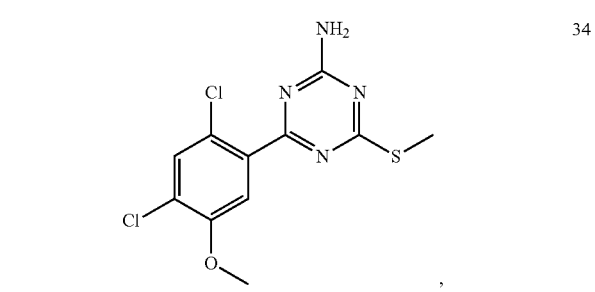 |

TABLE 1-continued
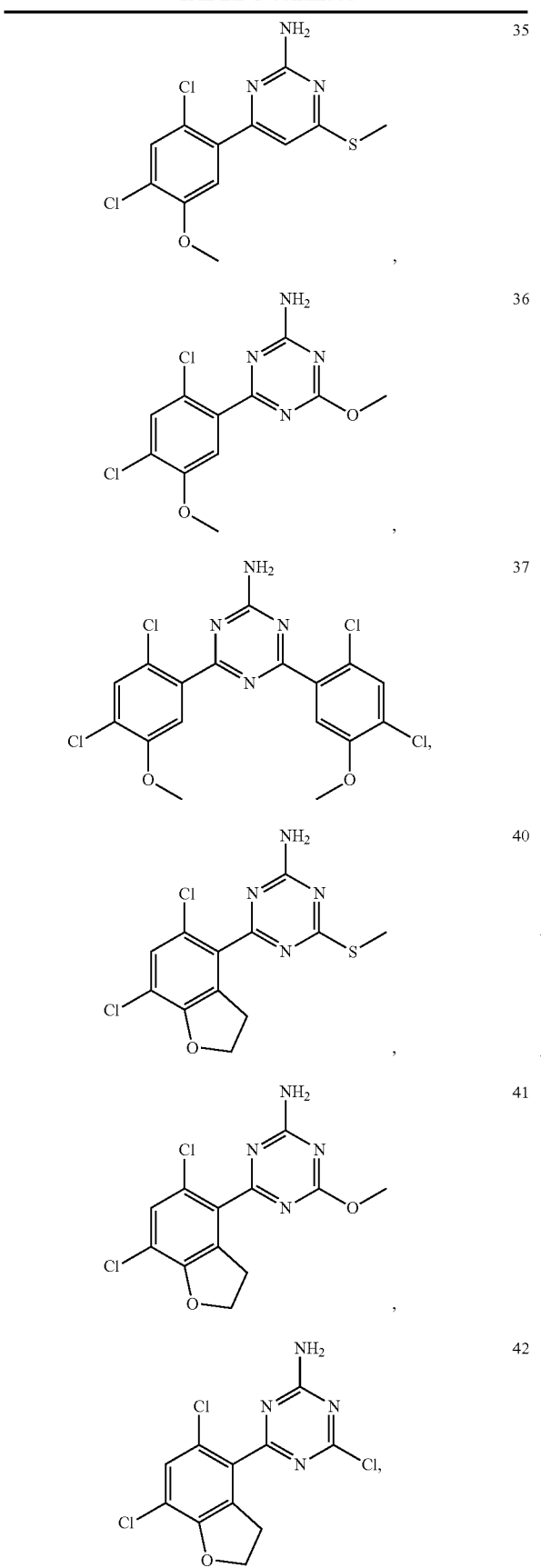
TABLE 1-continued
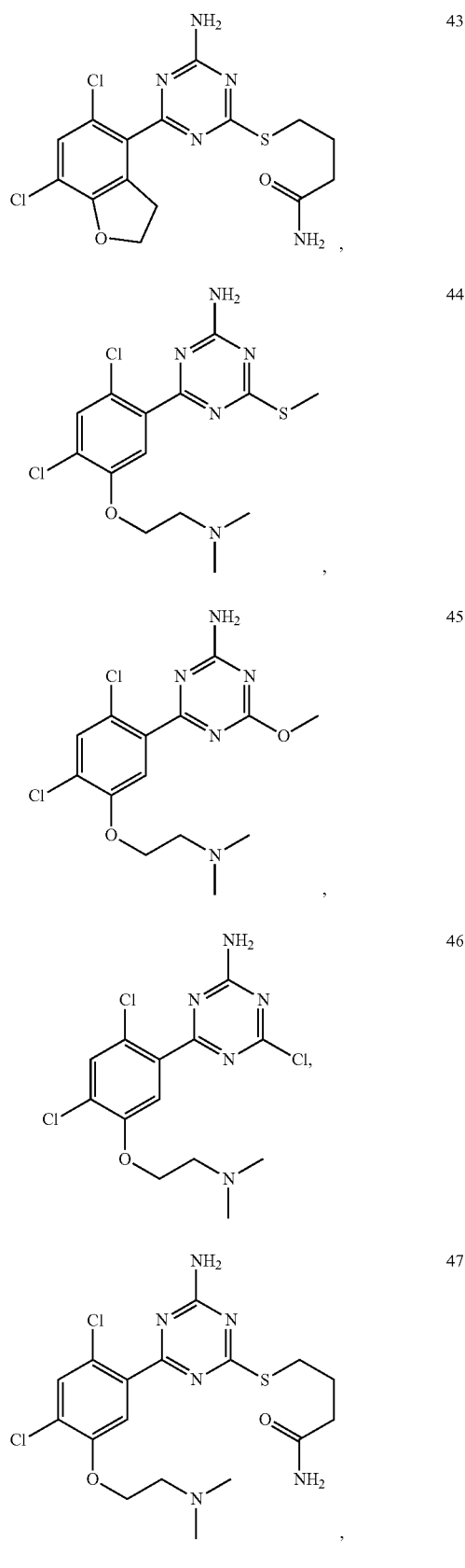

TABLE 1-continued
| | |
|---|---|
| 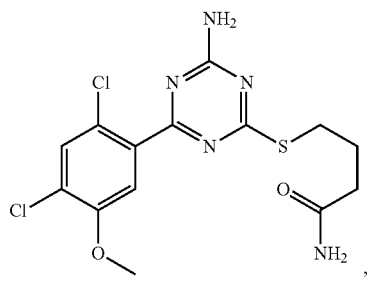 [SMILES: COc1cc(-c2nc(N)nc(SCCCC(N)=O)n2)c(Cl)cc1Cl] | 48 |
| 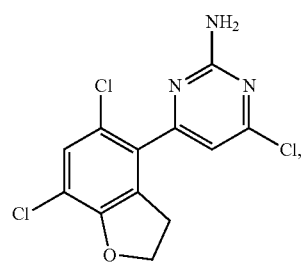 [SMILES: Nc1nc(Cl)cc(-c2c(Cl)cc(Cl)c3c2CCO3)n1] | 49 |
| 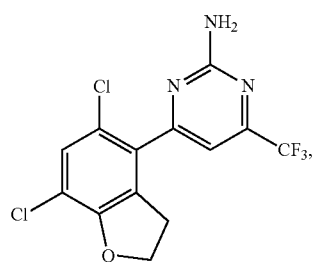 [SMILES: Nc1nc(-c2c(Cl)cc(Cl)c3c2CCO3)cc(C(F)(F)F)n1] | 50 |
| 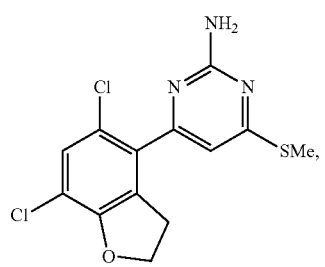 | 51 |
| 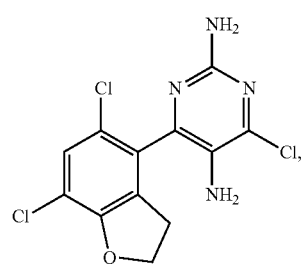 [SMILES: Nc1nc(Cl)c(N)c(-c2c(Cl)cc(Cl)c3c2CCO3)n1] | 52 |
| 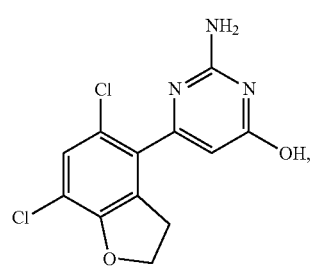 [SMILES: Nc1nc(O)cc(-c2c(Cl)cc(Cl)c3c2CCO3)n1] | 53 |
TABLE 1-continued
| | |
|---|---|
| 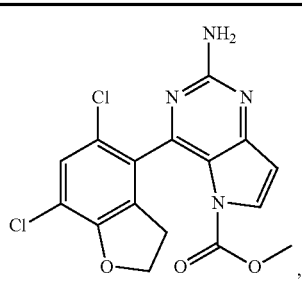 | 54 |
| 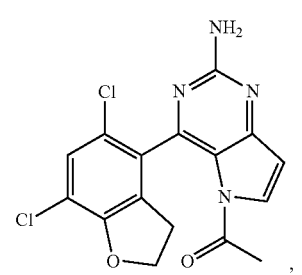 [SMILES: CC(=O)n1ccc2nc(N)nc(-c3c(Cl)cc(Cl)c4c3CCO4)c21] | 55 |
| 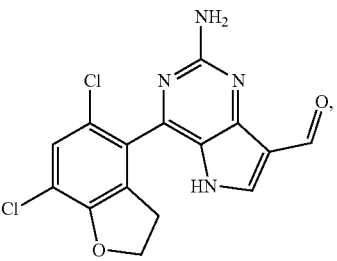 [SMILES: Nc1nc(-c2c(Cl)cc(Cl)c3c2CCO3)c2[nH]cc(C=O)c2n1] | 56 |
| 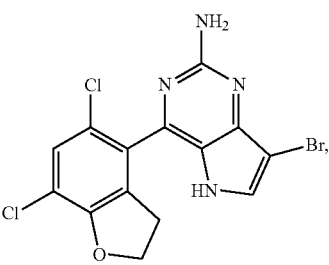 [SMILES: Nc1nc(-c2c(Cl)cc(Cl)c3c2CCO3)c2[nH]cc(Br)c2n1] | 57 |
| 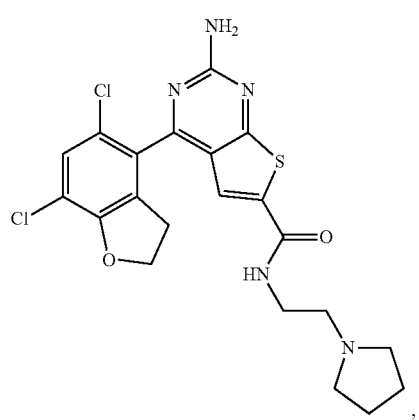 [SMILES: Nc1nc(-c2c(Cl)cc(Cl)c3c2CCO3)c2cc(C(=O)NCCN3CCCC3)sc2n1] | 58 |

TABLE 1-continued
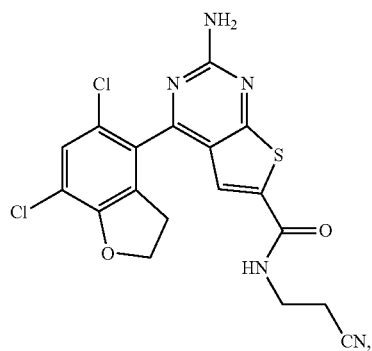 [SMILES: Nc1nc(-c2c(Cl)cc(Cl)c3c2CCO3)c2cc(C(=O)NCCO)sc2n1] 59
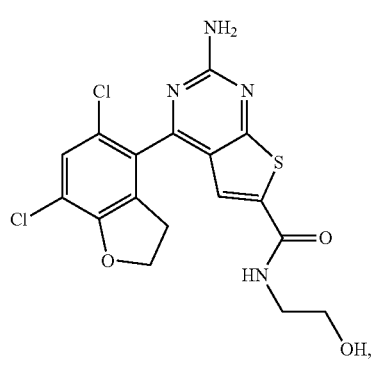 60
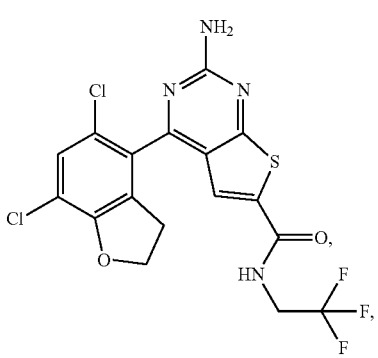 61
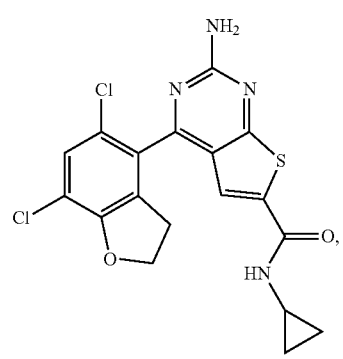 62
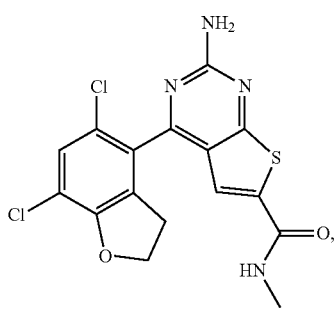 63
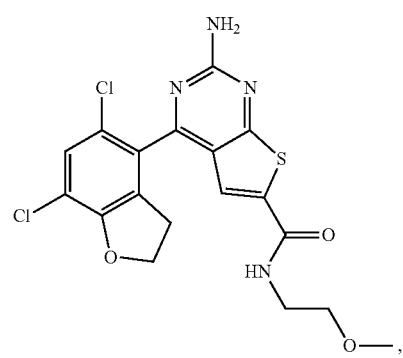 [SMILES: COCCNC(=O)c1cc2c(-c3c(Cl)cc(Cl)c4c3CCO4)nc(N)nc2s1] 64
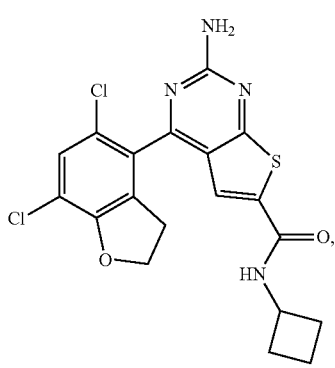 [SMILES: Nc1nc(-c2c(Cl)cc(Cl)c3c2CCO3)c2cc(C(=O)NC3CCC3)sc2n1] 65
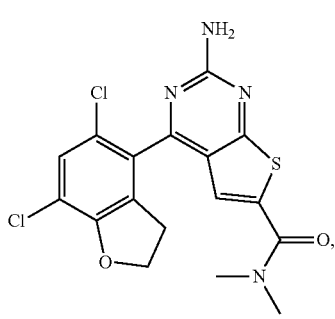 [SMILES: CN(C)C(=O)c1cc2c(-c3c(Cl)cc(Cl)c4c3CCO4)nc(N)nc2s1] 66

TABLE 1-continued
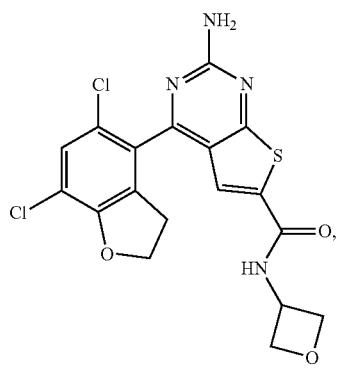 [SMILES: Nc1nc(-c2c(Cl)cc(Cl)c3c2CCO3)c2cc(C(=O)NC3COC3)sc2n1]
67
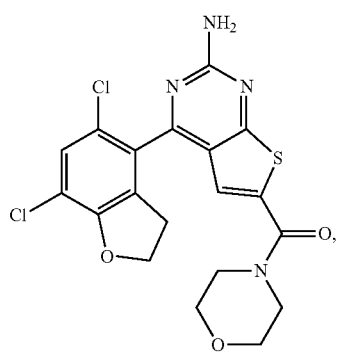 [SMILES: Nc1nc(-c2c(Cl)cc(Cl)c3c2CCO3)c2cc(C(=O)N3CCOCC3)sc2n1]
68
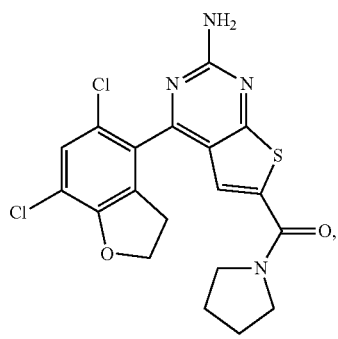 [SMILES: Nc1nc(-c2c(Cl)cc(Cl)c3c2CCO3)c2cc(C(=O)N3CCCC3)sc2n1]
69
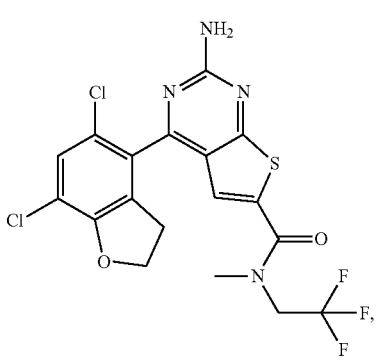 [SMILES: CN(CC(F)(F)F)C(=O)c1cc2c(-c3c(Cl)cc(Cl)c4c3CCO4)nc(N)nc2s1]
70
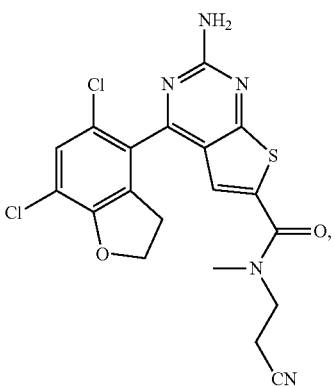 [SMILES: CN(CCC#N)C(=O)c1cc2c(-c3c(Cl)cc(Cl)c4c3CCO4)nc(N)nc2s1]
71
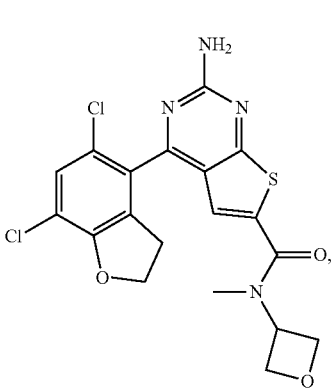
72
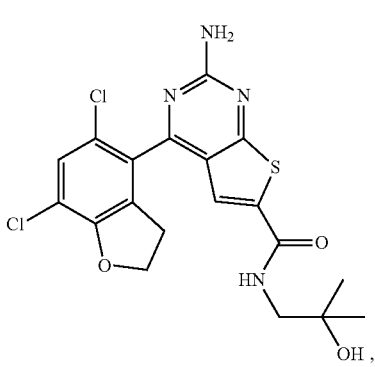 [SMILES: CC(C)(O)CNC(=O)c1cc2c(-c3c(Cl)cc(Cl)c4c3CCO4)nc(N)nc2s1]
73
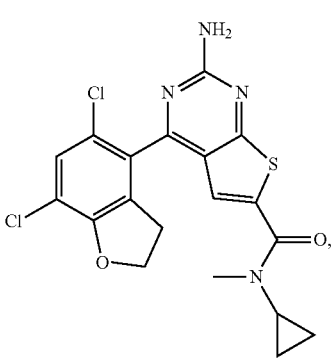
74

TABLE 1-continued
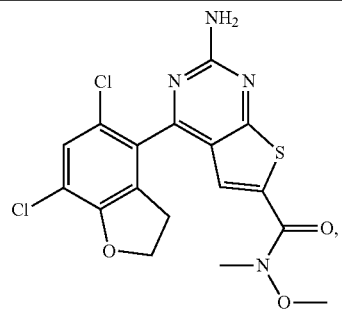 75
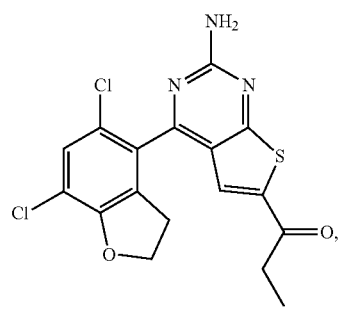 [SMILES: CCC(=O)c1cc2c(-c3c(Cl)cc(Cl)c4c3CCO4)nc(N)nc2s1] 76
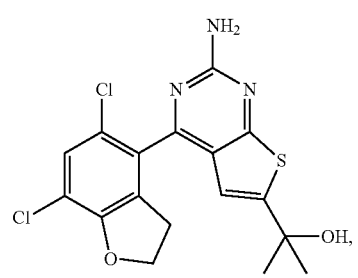 [SMILES: CC(C)(O)c1cc2c(-c3c(Cl)cc(Cl)c4c3CCO4)nc(N)nc2s1] 77
or a pharmaceutically acceptable salt thereof.
In particular embodiments, a compound of the invention has the formula:
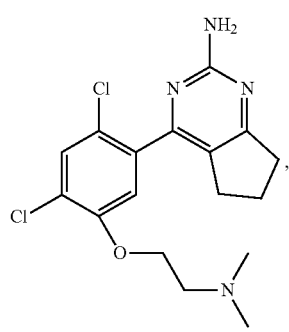 14
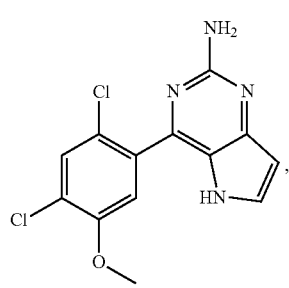 19
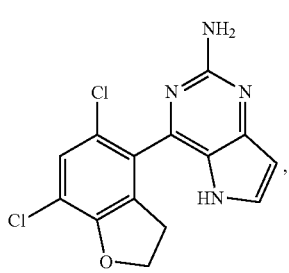 20
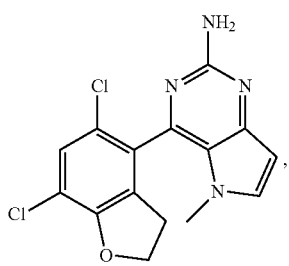 21
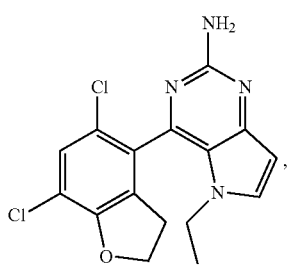 22
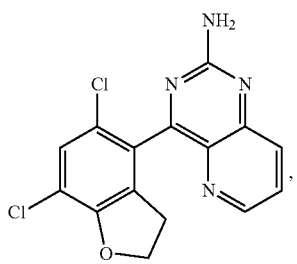 18
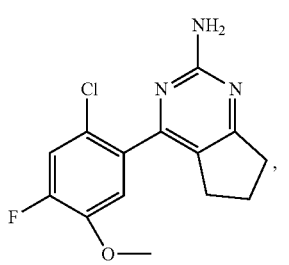 11
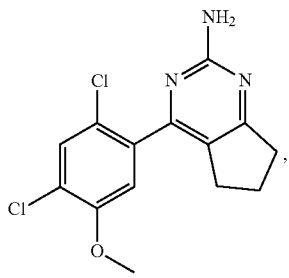 12

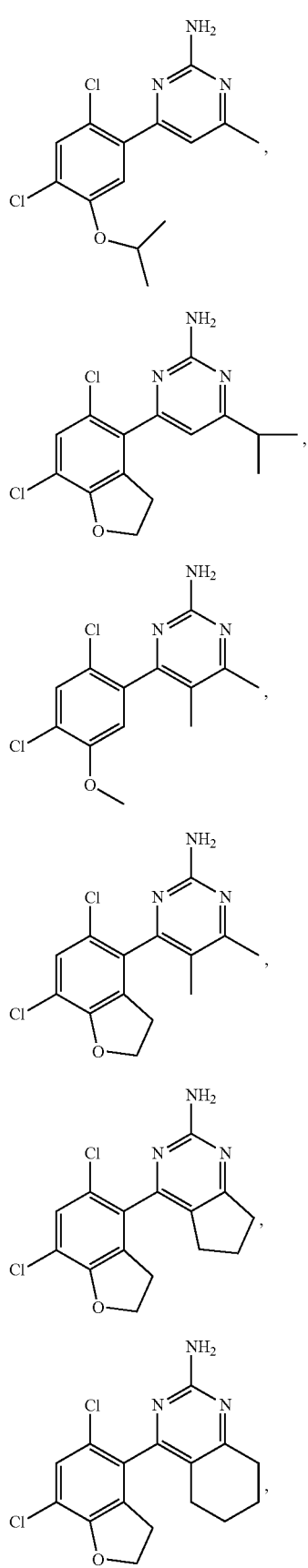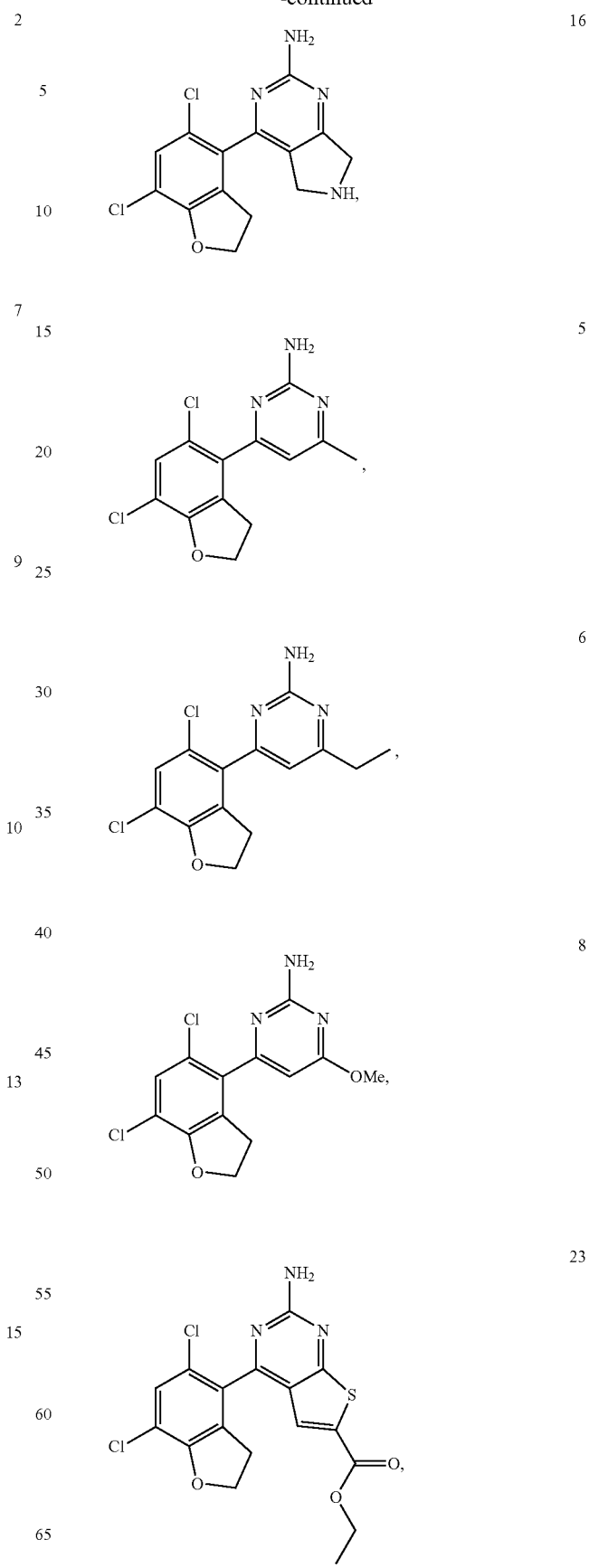

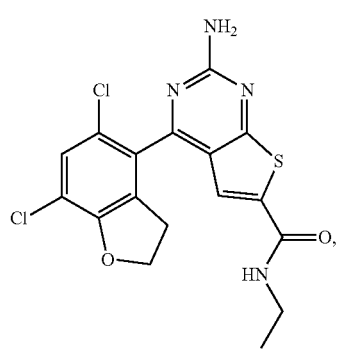
24
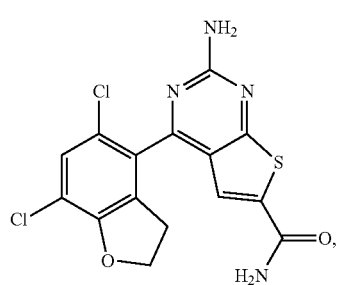
29
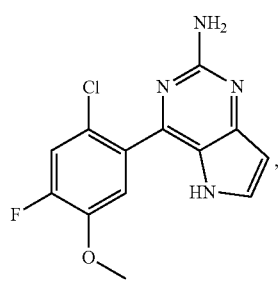
25
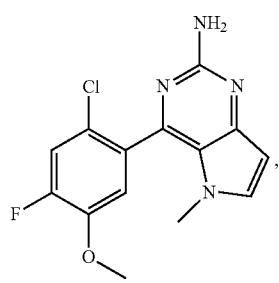
26
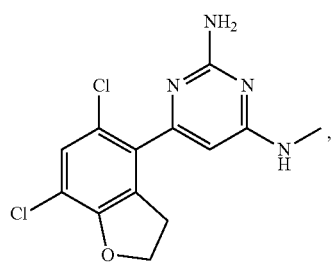
33
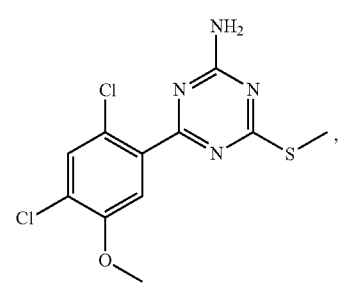
34
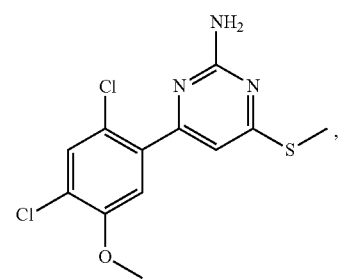
35
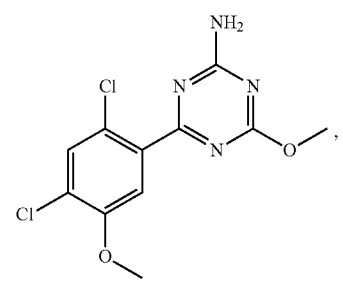
36
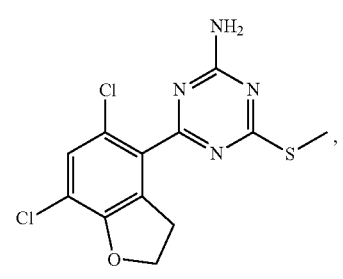
40
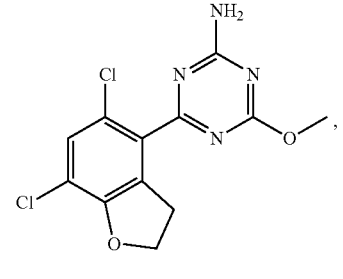
41
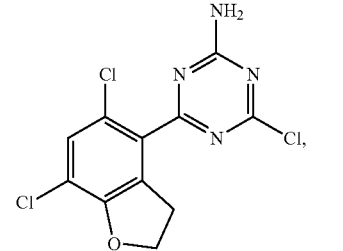
42

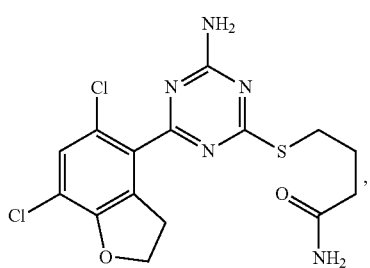
43
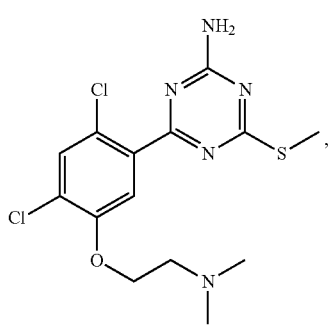
44
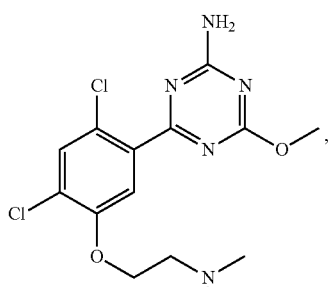
45
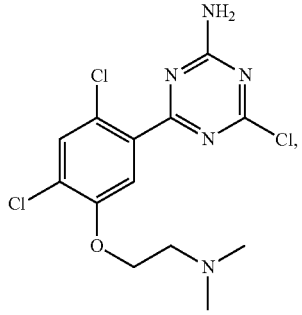
46
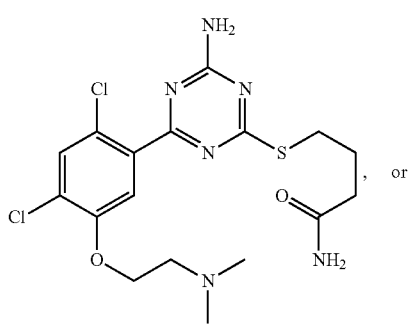
, or
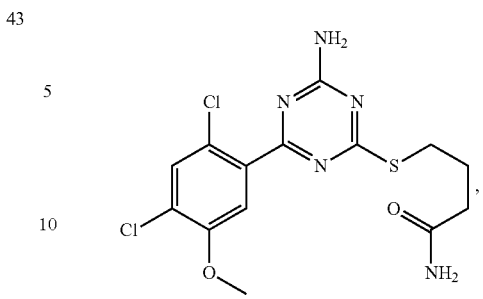
48
or a pharmaceutically acceptable salt thereof.
In some embodiments, a compound of the invention has the formula:
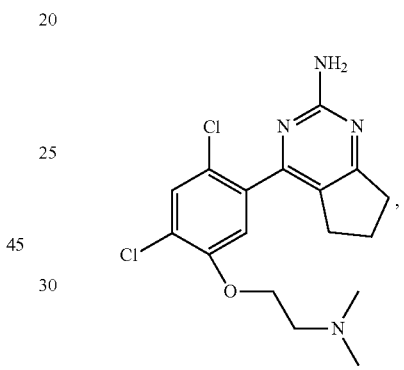
14
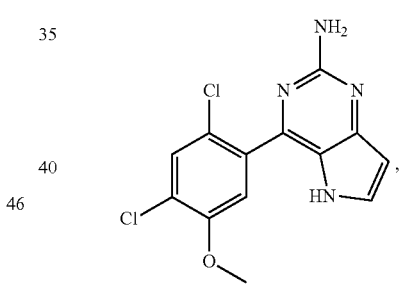
19
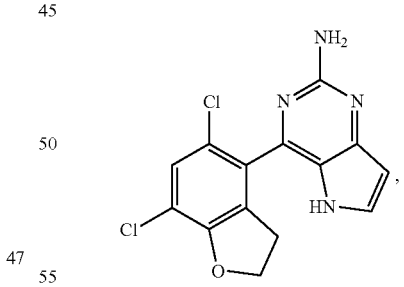
20
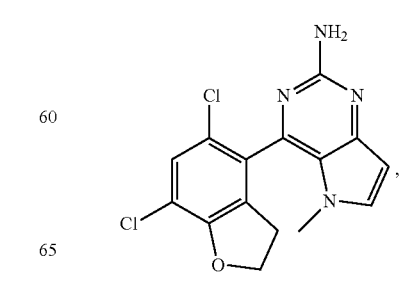
21

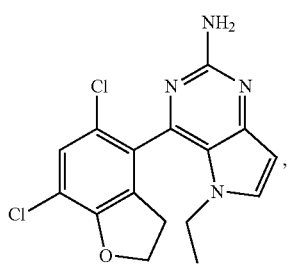
22
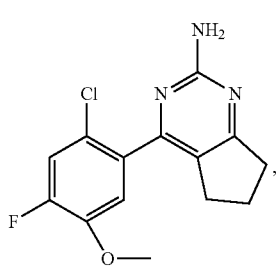
11
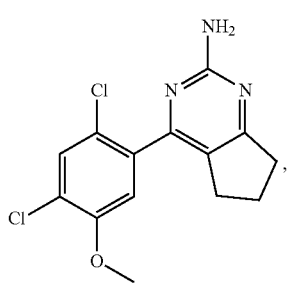
12
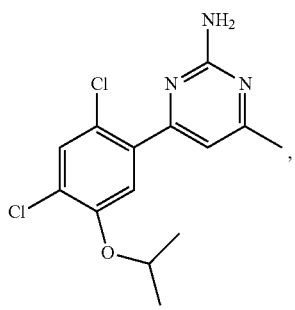
2
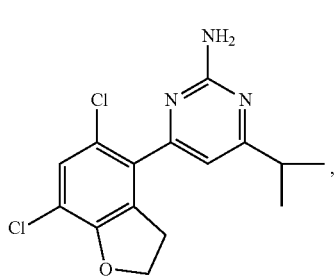
7
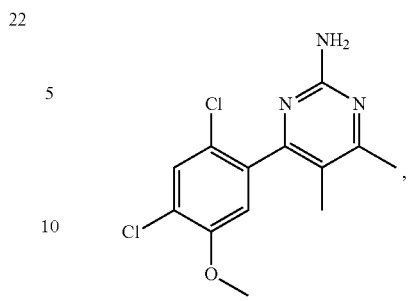
9
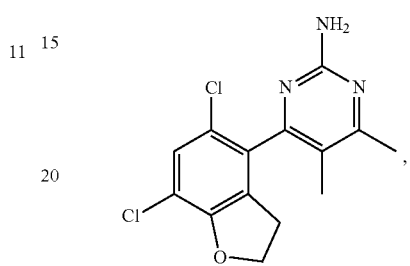
10
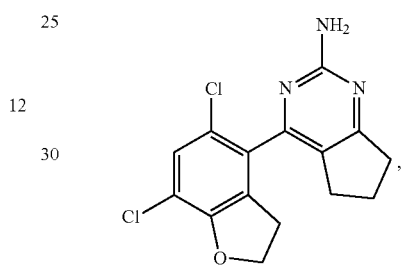
13
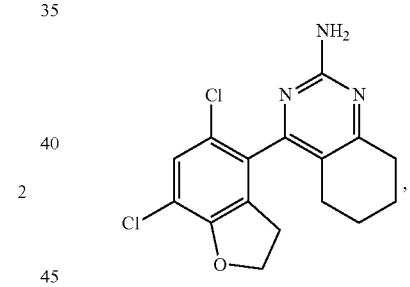
15
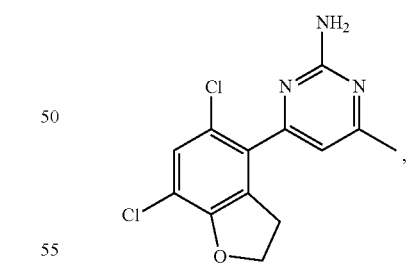
5
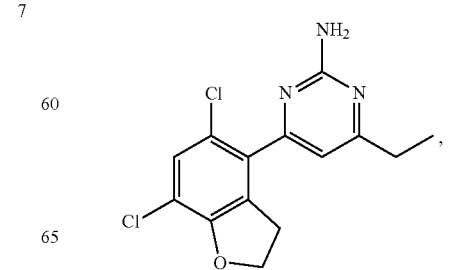
6

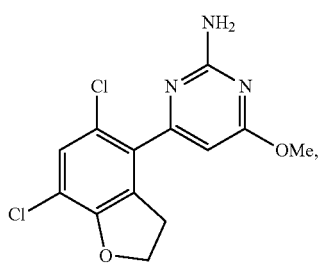
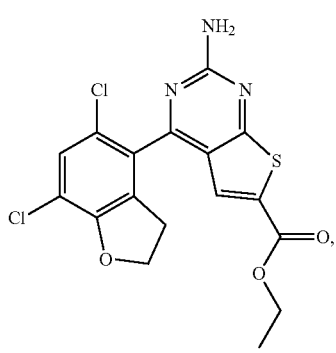
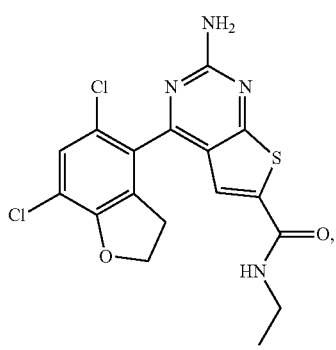
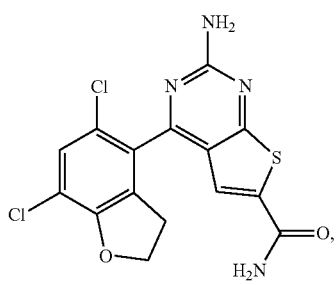
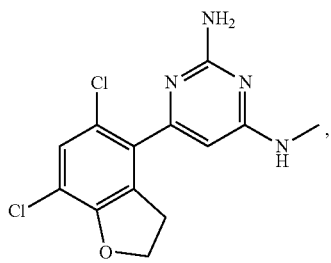

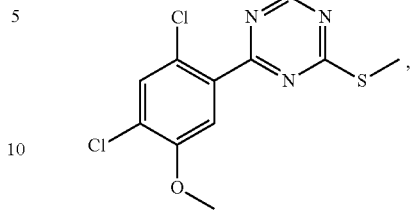
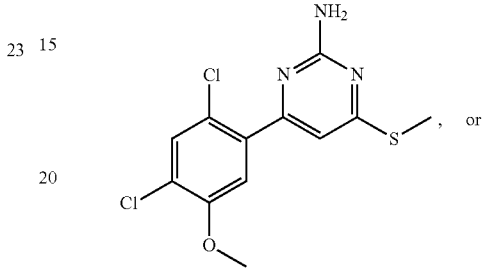

or a pharmaceutically acceptable salt thereof.

In further embodiments, the compound is not compound 38 or compound 39.

In certain embodiments of any formula described herein, each of $R^1$ and $R^2$ is H, $R^5$ is Cl, and $R^6$ is F or Cl.

In other embodiments of formula (I), (Ia), or (Ib), $R^3$ is H, halogen, optionally substituted $C_{1-3}$ alkyl, or optionally substituted $C_{1-3}$ alkoxy, and $R^4$ is halogen, optionally substituted $C_{1-3}$ alkyl, optionally substituted $C_{1-3}$ alkoxy, optionally substituted amino, or optionally substituted $C_{1-6}$ thioalkoxy, or $R^3$ and $R^4$, together with the atoms to which each is attached, join to form an optionally substituted five- or six-membered ring optionally comprising one nitrogen, one oxygen, or one sulfur, where the nitrogen is optionally substituted with $R^9$.

In yet other embodiments of formula (I), (Ia), or (Ib), $R^3$ is H, optionally substituted $C_1$ alkyl, or optionally substituted $C_{1-3}$ alkoxy, and $R^4$ is halogen, optionally substituted $C_{1-3}$ alkyl, optionally substituted $C_{1-3}$ alkoxy, optionally substituted amino, or optionally substituted $C_{1-6}$ thioalkoxy, or $R^3$ and $R^4$, together with the atoms to which each is attached, join to form an optionally substituted five- or six-membered ring optionally comprising one nitrogen, one oxygen, or one sulfur, where the nitrogen is optionally substituted with $R^9$.

In still other embodiments of formula (I), (Ia), or (Ib), $R^3$ is H, optionally substituted $C_1$ alkyl, or optionally substituted $C_{1-3}$ alkoxy, and $R^4$ is halogen, optionally substituted $C_{1-3}$ alkyl, optionally substituted $C_{1-3}$ alkoxy, optionally substituted amino, or optionally substituted $C_{1-6}$ thioalkoxy, or $R^3$ and $R^4$ join to form one of the following groups:

—N(R$^9$)—CH═CH—, —CH$_2$CH$_2$CH$_2$—, —CH$_2$CH$_2$CH$_2$CH$_2$—, and —C(R$^{13A}$)═C(R$^{13B}$)—S—, where N is proximal to position 5, and R$^9$ is H or C$_{1-3}$ alkyl.

In certain embodiments of formula (I), Z$^2$ is N, and R$^4$ is halogen, optionally substituted C$_{1-3}$ alkyl, optionally substituted C$_{1-3}$ alkoxy, optionally substituted amino, or optionally substituted C$_{1-6}$ thioalkoxy.

In particular embodiments of formula (I), Z$^2$ is N, and R$^4$ is optionally substituted C$_{1-3}$ alkoxy or optionally substituted C$_{1-6}$ thioalkoxy.

In other embodiments, X$^1$ is —N(R$^9$)—, —(CR$^{14}$R$^{15}$)—, —C(R$^{16}$)═, H, or optionally substituted C$_1$ alkyl. In yet other embodiments, X$^2$ is absent, —(CR$^{17}$R$^{18}$)$_n$—, —C(R$^{19}$)═, or ═C(R$^{20}$)—. In still other embodiments, X$^3$ is —(CR$^{14}$R$^{15}$)—, —S—, ═C(R$^{23}$)—, halogen, optionally substituted C$_{1-3}$ alkyl, optionally substituted C$_{1-6}$ thioalkoxy, or optionally substituted C$_{1-3}$ alkoxy. In certain embodiments, R$^9$ is H or C$_{1-3}$ alkyl.

In some embodiments, the compound of the invention has a molecular weight of less than about 500 g/mol (e.g., less than about 450 g/mol, or less than about 400 g/mol). In other embodiments, the compound of the invention exhibits apical to basal (A→B) permeability in MDR1-MDCK assay of greater than about 1×10$^{-7}$ cm/sec (e.g., greater than about 5×10$^{-7}$ cm/sec, greater than about 1×10$^{-6}$ cm/sec, or greater than about 3×10$^{-6}$ cm/sec). In particular embodiments, the compound of the invention exhibits the (B→A)/(A→B) ratio of less than about 30 (e.g., less than about 10, less than about 5, or less than about 3).

In another aspect, the invention features a pharmaceutical composition comprising a compound of the invention, or a pharmaceutically acceptable salt thereof, and one or more of pharmaceutically acceptable carriers or excipients. In certain embodiments, the composition is formulated for administration orally, intradermally, intramuscularly, parenterally, intravenously, intra-arterially, intracranially, subcutaneously, intraorbitally, intraventricularly, intraspinally, intraperitoneally, or intranasally. Preferably, the composition is formulated for oral administration.

In yet another aspect, the invention features a method of treating a disorder in a mammal (e.g., a human) caused by the action of heat shock protein 90 (Hsp90). The method involves administering to the mammal an effective amount of a compound according to formula (I):

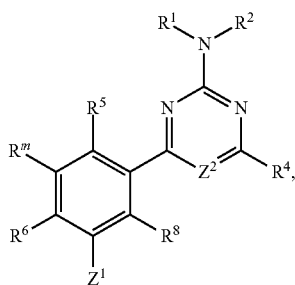

(I)

or a pharmaceutically acceptable salt thereof,
where
Z$^1$ is —OR$^7$, —N(R$^{10}$)R$^7$, —SR$^7$, or —C(R$^{10}$)(R$^{11}$)R$^7$;
Z$^2$ is —N═ or —C(R$^3$)═;
each R$^1$ and R$^2$ is, independently, H or optionally substituted C$_{1-3}$ alkyl;

R$^3$ is H, halogen, cyano, optionally substituted C$_{1-6}$ alkyl, optionally substituted C$_{1-3}$ alkoxy, or optionally substituted amino, and R$^4$ is halogen, cyano, optionally substituted C$_{1-6}$ alkyl, optionally substituted C$_{1-3}$ alkoxy, optionally substituted amino, optionally substituted C$_{1-6}$ thioalkoxy, or optionally substituted C$_{6-10}$ aryl, or R$^3$ and R$^4$, together with the atoms to which each is attached, join to form an optionally substituted five- or six-membered ring optionally comprising one nitrogen, one oxygen, or one sulfur, where the nitrogen is optionally substituted with R$^9$;

each R$^5$ and R$^6$ is, independently, optionally substituted C$_{1-3}$ alkyl, optionally substituted C$_{1-3}$ alkoxy, halogen, or CN;

R$^7$ is optionally substituted C$_{1-3}$ alkyl, optionally substituted C$_{1-3}$ alkcycloalkyl, optionally substituted C$_{1-3}$ alkheterocyclyl, or optionally substituted C$_{1-3}$ alkaryl, and R$^8$ is H; or R$^7$ and R$^8$, together with the atoms to which each is attached, join to form an optionally substituted five- or six-membered ring optionally comprising one or two heteroatoms selected from nitrogen, oxygen, and sulfur;

R$^9$ is H, optionally substituted C$_{1-3}$ alkyl, optionally substituted C$_{3-8}$ cycloalkyl, optionally substituted C$_{6-10}$ aryl, optionally substituted C$_{2-9}$ heteroaryl, optionally substituted C$_{2-9}$ heterocyclyl, optionally substituted C$_{1-3}$ alkcycloalkyl, optionally substituted C$_{1-3}$ alkheterocyclyl, or optionally substituted C$_{1-3}$ alkaryl;

R$^{10}$ is H, optionally substituted C$_{1-3}$ alkyl, optionally substituted C$_{3-8}$ cycloalkyl, optionally substituted C$_{6-10}$ aryl, optionally substituted C$_{2-9}$ heteroaryl, optionally substituted C$_{2-9}$ heterocyclyl, optionally substituted C$_{1-3}$ alkcycloalkyl, optionally substituted C$_{1-3}$ alkheterocyclyl, or optionally substituted C$_{1-3}$ alkaryl, and R$^{11}$ is H, optionally substituted C$_{1-3}$ alkyl, or R$^{10}$ and R$^{11}$ combine to form ═O or ═S and R$^m$ is H, halogen, optionally substituted C$_{1-4}$ alkyl, or optionally substituted C$_{1-3}$ alkoxy.

In certain embodiments of formula (I), when Z$^2$ is CR$^3$, each of R$^1$ and R$^2$ is H, R$^3$ is H, R$^4$ is methyl or halogen (e.g., chloro), and each of R$^5$ and R$^6$ is halogen (e.g., chloro),
Z$^1$ is not methoxy.

In certain embodiments of formula (I), when Z$^2$ is CR$^3$, R$^3$ is H, R$^4$ is methyl or halogen (e.g., chloro), each of R$^5$ and R$^6$ is halogen (e.g., chloro),
Z$^2$ is not unsubstituted C$_{1-3}$ alkoxy.

In particular embodiments of formula (I), when Z$^2$ is N, R$^3$ is H, R$^4$ is optionally substituted C$_{1-6}$ thioalkoxy, and each of R$^5$ and R$^6$ is halogen (e.g., chloro),
Z is not cyanomethoxy or aminomethoxy.

In other embodiments of formula (I), when Z$^2$ is N, R$^3$ is H, each of R$^5$ and R$^6$ is halogen (e.g., chloro), R$^4$ is substituted C$_{1-6}$ thioalkoxy,
Z$^1$ is not cyanomethoxy or aminomethoxy.

In some embodiments of formula (I), when Z$^2$ is N, R$^3$ is H, R$^4$ is optionally substituted C$_{1-6}$ thioalkoxy,
Z$^1$ is not cyanomethoxy or aminomethoxy.

In certain embodiments of formula (I), when Z$^2$ is N, R$^3$ is H, R$^4$ is substituted C$_{1-6}$ thioalkoxy,
Z$^1$ is not cyanomethoxy or aminomethoxy.

In further embodiments of formula (I), when Z$^2$ is N, R$^3$ is H, R$^4$ is substituted C$_{1-6}$ thioalkoxy,
Z$^1$ is not substituted C$_1$ alkoxy.

In particular embodiments of formula (I), when Z$^2$ is N, R$^3$ is H, R$^4$ is substituted C$_{1-6}$ thioalkoxy,
Z$^1$ is —OR$^7$, —N(R$^7$)R$^{10}$, —SR$^7$, or —C(R$^7$)(R$^{10}$)R$^{11}$, in which R$^7$ is methyl, dialkylaminoethyl, optionally substituted $C_{1-3}$ alkcycloalkyl, optionally substituted $C_{1-3}$ alkheterocyclyl, or optionally substituted $C_{1-3}$ alkaryl, or $R^7$ and $R^8$, together with the atoms to which each is attached, join to form an optionally substituted five- or six-membered ring optionally comprising one or two heteroatoms selected from nitrogen, oxygen, and sulfur.

In other embodiments of formula (I), when $Z^2$ is $CR^3$, each of $R^5$ and $R^6$ is chloro, $R^3$ is H, and $R^4$ is halogen (e.g., chloro), $Z^1$ is not 2-amino-2oxoethoxy, 2-(N,N-diethylamino)ethoxy, methoxy, or benzyloxy.

In yet other embodiments of formula (I), when $Z^2$ is $CR^3$, $R^3$ is H, and $R^4$ is halogen (e.g., chloro), $Z^1$ is not 2-amino-2oxoethoxy, 2-(N,N-diethylamino)ethoxy, methoxy, or benzyloxy.

In still other embodiments of formula (I), when $Z^2$ is $CR^3$, each of $R^5$ and $R^6$ is chloro, $R^3$ is H, and $R^4$ is halogen (e.g., chloro), $Z^1$ is —$OR^7$, —$N(R^7)R^{10}$, —$SR^7$, or —$C(R^7)(R^{10})R^{11}$, in which $R^7$ is dimethylaminoethyl, optionally substituted $C_{1-3}$ alkcycloalkyl, or optionally substituted $C_{1-3}$ alkheterocyclyl, or $R^7$ and $R^8$, together with the atoms to which each is attached, join to form an optionally substituted five- or six-membered ring optionally comprising one or two heteroatoms selected from nitrogen, oxygen, and sulfur.

In further embodiments of formula (I), when $Z^2$ is $CR^3$, each of $R^5$ and $R^6$ is chloro, $R^3$ is H, and $R^4$ is halogen (e.g., chloro), $Z^1$ is —$OR^7$, —$N(R^7)R^{10}$, —$SR^7$, or —$C(R^7)(R^{10})R^{11}$, in which $R^7$ is optionally substituted $C_{1-3}$ alkcycloalkyl, or optionally substituted $C_{1-3}$ alkheterocyclyl, or $R^7$ and $R^8$, together with the atoms to which each is attached, join to form an optionally substituted five- or six-membered ring optionally comprising one or two heteroatoms selected from nitrogen, oxygen, and sulfur.

In particular embodiments of formula (I), when $Z^2$ is $CR^3$, $R^3$ is H, and $R^4$ is halogen (e.g., chloro), $Z^1$ is —$OR^7$, —$N(R^7)R^{10}$, —$SR^7$, or —$C(R^7)(R^{10})R^{11}$, in which $R^7$ is optionally substituted $C_{1-3}$ alkcycloalkyl, or optionally substituted $C_{1-3}$ alkheterocyclyl, or $R^7$ and $R^8$, together with the atoms to which each is attached, join to form an optionally substituted five- or six-membered ring optionally comprising one or two heteroatoms selected from nitrogen, oxygen, and sulfur.

In some embodiments of formula (I), when $R^5$ is chloro, $R^6$ is bromo, $Z^1$ is —$OR^7$, $Z^2$ is $CR^3$, and $R^3$ and $R^4$ combine to form a group according to formula (IIa):

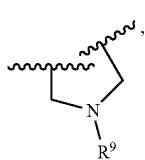

(IIa)

$R^7$ is not methyl, ethyl, n-propyl, 2-(N-pyrazolyl)ethyl, 2-(N-imidazolyl)ethyl, 3-hydroxypropyl, cyanomethyl, 2-chloroethyl, 2-hydroxyethyl, 2-oxo-propyl, 2-(N,N-dimethylamino)ethyl, difluoromethyl, or 2-(t-butylamino)ethyl.

In certain embodiments of formula (I), when $R^5$ is chloro, $R^6$ is bromo, $Z^1$ is —$OR^7$, $Z^2$ is $CR^3$, and $R^3$ and $R^4$ combine to form a group according to formula (IIa), $R^7$ is not substituted alkyl, unsubstituted alkyl, or unsubstituted $C_2$ alkheteroaryl.

In some embodiments of formula (I), when $R^5$ is chloro, $R^6$ is bromo, $Z^1$ is —$OR^7$, $Z^2$ is $CR^3$, and $R^3$ and $R^4$ combine to form a group according to formula (IIa), $R^7$ is not alkyl or unsubstituted $C_2$ alkheteroaryl.

In particular embodiments of formula (I), when $R^5$ is chloro, $R^6$ is bromo, $Z^1$ is —$OR^7$, $Z^2$ is $CR^3$, and $R^3$ and $R^4$ combine to form a group according to formula (IIa), $R^7$ is not substituted alkyl, unsubstituted alkyl, or unsubstituted $C_2$ alkheterocyclyl.

In other embodiments of formula (I), when $R^5$ is chloro, $R^6$ is bromo, $Z^1$ is —$OR^7$, $Z^2$ is $CR^3$, and $R^3$ and $R^4$ combine to form a group according to formula (IIa), $R^7$ is not alkyl or $C_2$ alkheterocyclyl.

In still other embodiments of formula (I), when $R^5$ is chloro, $R^6$ is bromo, $Z^1$ is —$OR^7$, $Z^2$ is $CR^3$, and $R^3$ and $R^4$ combine to form a group according to formula (IIa), $R^7$ and $R^8$, together with the atoms to which each is attached, join to form an optionally substituted five- or six-membered ring optionally comprising one or two heteroatoms selected from nitrogen, oxygen, and sulfur.

In yet other embodiments of formula (I), when $R^5$ is chloro, $R^6$ is bromo, $Z^2$ is $CR^3$, and $R^3$ and $R^4$ combine to form a group according to formula (IIa), Z is —$OR^7$, and $R^7$ and $R^8$ combine to form —$CH_2$—$CH_2$—.

In some embodiments of formula (I), when each $R^5$ and $R^6$ is bromo, $Z^1$ is —$OR^7$, $Z^2$ is $CR^3$, and $R^3$ and $R^4$ combine to form a group according to formula (IIa), $R^7$ is not methyl.

In particular embodiments of formula (I), when each $R^5$ and $R^6$ is chloro, $Z^1$ is —$OR^7$, $Z^2$ is $CR^3$, and $R^3$ and $R^4$ combine to form a group according to formula (IIa), $R^7$ is not methyl, 2-(N-imidazolyl)ethyl, methoxymethyl, 2-(N-pyrazolyl)ethyl, 2-(3-methylpyrazol-1-yl)ethyl, 2-pyridyl-methyl, 1,3-dimethyl-1H-1,2,4-triazol-5-yl-methyl, 2-pyrimidinylmethyl, imidazol-2-yl-methyl, 5-methyl-isoxazol-3-yl-methyl, 4-methyl-imidazol-5-yl-methyl, or 3-methyl-1,2,4-oxadiazol-5-yl-methyl.

In other embodiments of formula (I), when each $R^5$ and $R^6$ is chloro, $Z^1$ is —$OR^7$, $Z^2$ is $CR^3$, and $R^3$ and $R^4$ combine to form a group according to formula (IIa), $R^7$ is not unsubstituted alkyl, substituted alkyl, unsubstituted alkheteroaryl, or substituted alkheteroaryl.

In other embodiments of formula (I), when each $R^5$ and $R^6$ is chloro, $Z^1$ is —$OR^7$, $Z^2$ is $CR^3$, and $R^3$ and $R^4$ combine to form a group according to formula (IIa), $R^7$ is not unsubstituted alkyl, substituted alkyl, unsubstituted alkheterocyclyl, or substituted alkheterocyclyl.

In certain embodiments of formula (I), when each $R^5$ and $R^6$ is chloro, $Z^1$ is —$OR^7$, $R^7$ and $R^8$ combine to form —$CH_2$—$CH_2$—, $Z^2$ is $CR^3$, and $R^3$ and $R^4$ combine to form a group according to formula (IIa), $R^9$ is not ethoxycarbonyl, cyclobutylaminocarbonyl, or cyclobutadienylaminocarbonyl.

In other embodiments of formula (I), when each $R^5$ and $R^6$ is chloro, $Z^1$ is —$OR^7$, $R^7$ and $R^8$ combine to form —$CH_2$—$CH_2$—, $Z^2$ is $CR^3$, and $R^3$ and $R^4$ combine to form a group according to formula (IIa), $R^9$ is H or —C(O)—N(H)-(linear $C_{1-3}$ alkyl).

In particular embodiments of formula (I), when each $R^5$ and $R^6$ is halo, $Z^2$ is $CR^3$, and $R^3$ and $R^4$ combine to form a group according to formula (IIa), Z is —$OR^7$, $R^7$ is not methyl or 2-chloroethyl, and $R^9$ is H or —C(O)—N(H)-(linear $C_{1-3}$ alkyl).

In some embodiments of formula (I), when $R^5$ is methoxy, $R^6$ is methyl, $Z^1$ is —$OR^7$, $Z^2$ is $CR^3$, and $R^3$ and $R^4$ combine to form a group according to formula (IIa), $R^7$ is not methyl.

In certain embodiments of formula (I), when $R^5$ is chloro, $R^6$ is ethyl, $Z^1$ is —$OR^7$, $Z^2$ is $CR^3$, and $R^3$ and $R^4$ combine to form a group according to formula (IIa), $R^7$ is not methyl.

In some embodiments of formula (I), when each $R^5$ and $R^6$ is chloro, $Z^1$ is —$OR^7$, $Z^2$ is $CR^3$, and $R^3$ and $R^4$ combine to form a group according to formula (IIb) or (IIc),

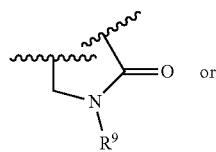

(IIb)

or

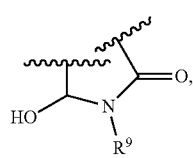

(IIc)

$R^7$ is not methyl or 2-(N,N-diethylamino)ethyl.

In other embodiments of formula (I), when each $R^5$ and $R^6$ is chloro, $Z^1$ is —$OR^7$, $Z^2$ is $CR^3$, and $R^3$ and $R^4$ combine to form a group according to formula (IIb) or (IIc), $R^7$ and $R^8$, together with the atoms to which each is attached, join to form an optionally substituted five- or six-membered ring optionally comprising one or two heteroatoms selected from nitrogen, oxygen, and sulfur.

In certain embodiments of formula (I), when each $R^5$ and $R^6$ is chloro, $Z^2$ is $CR^3$, and $R^3$ and $R^4$ combine to form a group according to formula (IIb) or (IIc), $Z^1$ is —$OR^7$, and $R^7$ and $R^8$ combine to form —$CH_2$—$CH_2$—.

In some embodiments of formula (I), when $R^7$ is methyl, $R^5$ is chloro, $Z^1$ is —$OR^7$, $Z^2$ is $CR^3$, and $R^3$ and $R^4$ combine to form a group according to formula (IIIa).

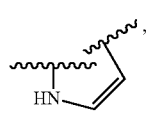

(IIIa)

$R^6$ is not bromo.

In particular embodiments of formula (I), when each $R^5$ and $R^6$ is chloro, $Z^1$ is —$OR^7$, $Z^2$ is $CR^3$, and $R^3$ and $R^4$ combine to form a group according to formula (IIIa), $R^7$ is not isopropyl, 3,3,3-trifluoropropyl, or 2-(N,N-dimethylamino)ethyl.

In certain embodiments of formula (I), when each $R^5$ and $R^6$ is chloro, $Z^1$ is —$OR^7$, $Z^2$ is $CR^3$, and $R^3$ and $R^4$ combine to form a group according to formula (IIIa), $R^8$ is not H.

In some embodiments of formula (I), when $Z^2$ is $CR^3$, and $R^3$ and $R^4$ combine to form a group according to formula (IIIa), each $R^5$ and $R^6$ is chloro, and $R^7$ is methyl and $R^8$ is H, or $R^7$ and $R^8$, together with the atoms to which each is attached, join to form an optionally substituted five- or six-membered ring optionally comprising one or two heteroatoms selected from nitrogen, oxygen, and sulfur.

In other embodiments of formula (I), when $R^5$ is chloro, $R^6$ is methoxy, $Z^1$ is —$OR^7$, $Z^2$ is $CR^3$, and $R^3$ and $R^4$ combine to form a group according to formula (IIIb):

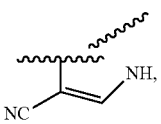

(IIIb)

neither $R^1$ nor $R^2$ is 2-(N,N-diethylamino)ethyl.

In certain embodiments of formula (I), when $R^5$ is chloro, $R^6$ is methoxy, $Z^1$ is —$OR^7$, $Z^2$ is $CR^3$, and $R^3$ and $R^4$ combine to form a group according to formula (IIIb), each $R^1$ and $R^2$ is H.

In some embodiments of formula (I), when each $R^5$ and $R^6$ is chloro, $Z^1$ is —$OR^7$, $Z^2$ is $CR^3$, and $R^3$ and $R^4$ combine to form a group according to formula (IVa):

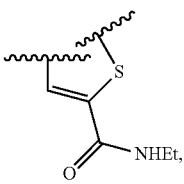

(IVa)

$R^7$ is not 3-(N-morpholinyl)propyl, benzyl, 1-ethyl-pyrrolydin-3-yl, 1-methyl-piperidin-4-yl, 2-(1-methyl-pyrrolidin-2-yl)ethyl, or 3-(N,N-diethylamino)propyl.

In particular embodiments of formula (I), when each $R^5$ and $R^6$ is chloro, $Z^1$ is —$OR^7$, $Z^2$ is $CR^3$, and $R^3$ and $R^4$ combine to form a group according to formula (IVa), $R^7$ is not substituted alkyl, heterocyclyl, alkheterocyclyl, or alkaryl.

In some embodiments of formula (I), when each $R^5$ and $R^6$ is chloro, $Z^1$ is —$OR^7$, $Z^2$ is $CR^3$, and $R^3$ and $R^4$ combine to form a group according to formula (IVb):

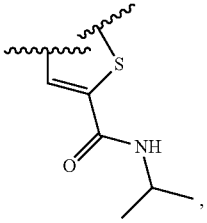

(IVb)

$R^7$ is not 2-methoxyethyl or benzyl.

In certain embodiments of formula (I), when each $R^5$ and $R^6$ is chloro, $Z^1$ is —$OR^7$, $Z^2$ is $CR^3$, and $R^3$ and $R^4$ combine to form a group according to formula (IVb), $R^7$ is not substituted alkyl or alkaryl.

In some embodiments of formula (I), when each $R^5$ and $R^6$ is chloro, $Z^1$ is —$OR^7$, $Z^2$ is $CR^3$, and $R^3$ and $R^4$ combine to form a group according to formula (IVc):

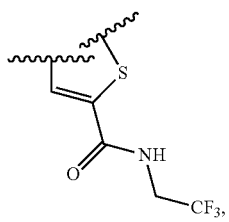
(IVc)

$R^7$ is not 2-(N,N-diethylamino)ethyl or 3-(N,N-dimethylamino)propyl.

In other embodiments of formula (I), when each $R^5$ and $R^6$ is chloro, $Z^1$ is —$OR^7$, $Z^2$ is $CR^3$, and $R^3$ and $R^4$ combine to form a group according to formula (IVc), $R^7$ is not substituted alkyl.

In particular embodiments of formula (I), when each $R^5$ and $R^6$ is chloro, $Z^1$ is —$OR^7$, $Z^2$ is $CR^3$, and $R^3$ and $R^4$ combine to form a group according to formula (IVd):

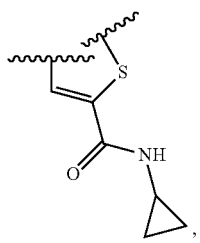
(IVd)

$R^7$ is not 2-(pyrrolidin-1-yl)ethyl or 2-hydroxyethyl.

In certain embodiments of formula (I), when each $R^5$ and $R^6$ is chloro, $Z^1$ is —$OR^7$, $Z^2$ is $CR^3$, and $R^3$ and $R^4$ combine to form a group according to formula (IVd), $R^7$ is not substituted alkyl or alkheterocyclyl.

In some embodiments of formula (I), when each $R^5$ and $R^6$ is chloro, $Z^1$ is —$OR^7$, $Z^2$ is $CR^3$, and $R^3$ and $R^4$ combine to form a group according to formula (IVe) or (IVf):

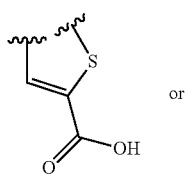
(IVe)

or

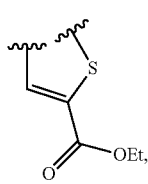
(IVf)

$R^7$ is not benzyl.

In other embodiments of formula (I), when each $R^5$ and $R^6$ is chloro, $Z^1$ is —$OR^7$, $Z^2$ is $CR^3$, and $R^3$ and $R^4$ combine to form a group according to formula (IVe) or (IVf), $R^7$ is not alkaryl.

In certain embodiments of formula (I), when $R^5$ is chloro, $R^6$ is bromo, $Z^1$ is —$OR^7$, $Z^2$ is $CR^3$, and $R^3$ and $R^4$ combine to form a group according to formula (IVg), (IVh), (IVi), (IVj), or (IVk):

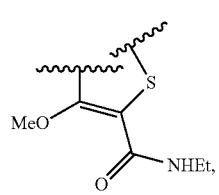
(IVg)

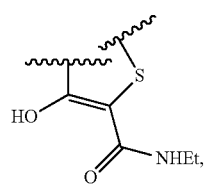
(IVh)

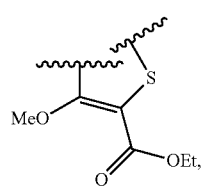
(IVi)

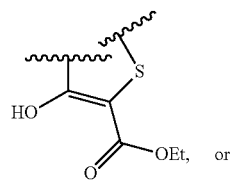
(IVj)

or

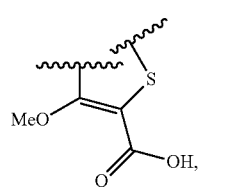
(IVk)

$R^7$ is not methyl.

In certain embodiments of formula (I), when $R^5$ is chloro, $R^6$ is bromo, $Z^1$ is —$OR^7$, $Z^2$ is $CR^3$, and $R^3$ and $R^4$ combine to form a group according to formula (IVg), (IVh), (IVi), (IVj), or (IVk), $R^7$ is not alkyl.

In some embodiments of formula (I), when $R^5$ is chloro, $R^6$ is bromo, $Z^1$ is —$OR^7$, $Z^2$ is $CR^3$, and $R^3$ and $R^4$ combine to form a group according to formula (IVg), (IVh), (IVi), (IVj), or (IVk), $R^7$ and $R^8$, together with the atoms to which each is attached, join to form an optionally substituted five- or six-membered ring optionally comprising one or two heteroatoms selected from nitrogen, oxygen, and sulfur.

In particular embodiments of formula (I), when $R^5$ is chloro, $R^6$ is bromo, $Z^1$ is —$OR^7$, and $Z^2$ is $CR^3$, $R^3$ and $R^4$ do not combine to form a group according to formula (IVg), (IVh), (IVi), (IVj), or (IVk).

In particular embodiments of formula (I), when $R^6$ is methyl, each $R^1$ and $R^2$ is H.

In certain embodiments of formula (I), when $R^3$ is H, and each $R^5$ and $R^6$ is chloro, $R^7$ is not methyl.

In particular embodiments of formula (I), $R'''$ is H (e.g., the compound of formula (I) has the following structure:

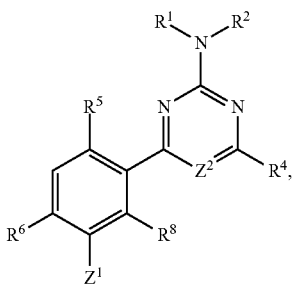

(I)

or a pharmaceutically acceptable salt thereof.

In certain embodiments of formula (I),

In some embodiments of the methods of the invention, the substituents are defined as described herein. In particular embodiments of the methods of the invention, the method involves administering to the mammal an effective amount of a compound according to formula (I). In certain embodiments of the methods of the invention, the method involves administering to the mammal an effective amount of a compound according to formula (Ib). In other embodiments, the method involves administering to the mammal an effective amount of a compound according to formula (Va). In certain embodiments, the method involves administering to the mammal an effective amount of a compound according to formula (Vb). In particular embodiments, the compound may be selected from Table 2, (e.g., any one of compounds 2, 5-16, 18-27, 29, 33-36, 40-48, and 58-77, or a or a pharmaceutically acceptable salt thereof). In further embodiments, the method involves administering to the mammal an effective amount of compound 38 or 39 or a pharmaceutically acceptable salt thereof.

In certain embodiments of the methods of the invention, the method involves treating a mammal having a neurodegenerative disorder by administering to the mammal the compound of formula (I) (e.g., formula (Ia), (Ib), (Va), or (Vb)).

In some embodiments, the disorder is a neurodegenerative disorder (e.g., a tauopathy). The neurodegenerative disorder may be Alzheimer's disease, Huntington's disease, progressive supranuclear palsy, Parkinson's syndrome, Pick's disease, corticobasal degeneration, chronic traumatic encephalopathy, traumatic brain injury, or frontotemporal dementia. Preferably, the neurodegenerative disorder is Alzheimer's disease. In other embodiments, the disorder is a proliferative disorder (e.g., a cancer, e.g., acute myeloid leukemia, gastrointestinal stromal tumor, gastric cancer, glioblastoma, lung cancer, lymphoma, melanoma, myeloma, non-small cell lung cancer, renal cancer, small cell lung cancer, blast-phase chronic myelogenous leukemia, leukemia, lymphoproliferative disorder, metastatic melanoma, relapsed multiple myeloma, refractory multiple myeloma, myeloproliferative disorders, pancreatic cancer, small intestine cancer, or solid tumor).

In particular embodiments, the disorder is an inflammatory or autoimmune disease (e.g., rheumatoid arthritis, systemic lupus erythermatosus, or asthma). In certain embodiments, the disorder is a cardiovascular disease (e.g., atherosclerosis or cardiomyoapthy). In other embodiments, the disorder is an allergy.

In yet another aspect, the invention features a method of treating an infectious disease in a mammal by administering an effective amount of the compound of the invention (e.g., compounds of the aspects described above), or a pharmaceutically acceptable salt thereof to the mammal.

In some embodiments, the infectious disease is a viral infection. In certain embodiments, the viral infection is a virus of Herpesviridae family (e.g., herpes simplex virus-1, herpes simplex virus-2, herpes herpesvirus-5, Kaposi's sarcoma-associated herpesvirus, varicella zoster virus, or Epstein-Barr virus), Polyomaviridae family (e.g., SV40), Poxviridae family (e.g., vaccinia virus), Reoviridae family (e.g., rotavirus), Birnaviridae family (e.g., infectious bursal disease virus), Picornaviridae family (e.g., poliovirus, rhinovirus, or coxsackievirus), Flaviviridae family (e.g., hepatitis C virus or dengue virus), Arenaviridae family (e.g., lymphocytic choriomeningitis virus), Hepeviridae family (e.g., Hepatitis E virus), Rhabdoviridae family (e.g., vesicular stomatitis virus), Paramoxyviridae family (e.g., human parainfluenza virus 2, human parainfluenza virus 3, SV5, SV41, measles virus, or Sendai virus), Bunyaviridae family (e.g., La Crosse virus), Orthomoxyviridae family (e.g., influenza A virus), Filoviridae family (e.g., Ebola virus), Retroviridae family (e.g., HTLV1 or HIV1), or Hepadnaviridae family (e.g., hepatitis B virus).

In particular embodiments, the infectious disease is a fungal infection (e.g., *Candida albicans, Aspergillus fumigates,* or *Pneumocystis jiroveci*).

In other embodiments, the infectious disease is a bacterial infection (e.g., mycobacteria, anthrax, or bacterial pneumonia).

In some embodiments of any aspect of the methods of the invention, the compound is administered orally, sublingually, buccally, transdermally, intradermally, intramuscularly, parenterally, intravenously, intra-arterially, intracranially, subcutaneously, intraorbitally, intraventricularly, intraspinally, intraperitoneally, intranasally, by inhalation, and topically. Preferably, the compound is administered orally.

In certain embodiments of any aspect of the methods of the invention, the mammal is human.

In a further aspect, the invention features a method of inhibiting Hsp90 by contacting a cell with the compound of the invention, or a pharmaceutically acceptable salt thereof. In some embodiments, the method is carried out in vitro. In other embodiments, the method is carried out in vivo.

In another aspect, the invention features a kit containing:
(i) the pharmaceutical composition of the invention; and
(ii) instructions for use of the pharmaceutical compositions of (i) to treat a disorder in a mammal (e.g., a human) caused by the action of Hsp90.

In yet another aspect, the invention features the compounds of the invention for use in treating a disorder caused by the action of heat shock protein 90 (Hsp90). In some embodiments of this aspect, the disorder is any one of the disorders described in the aspect featuring methods of the invention. In a related aspect, the invention features the compounds of the invention for use in treating an infectious disease. In certain embodiments of this aspect, the infectious disease is any one of the infectious diseases described in the aspect featuring methods of the invention.

In still another aspect, the invention features uses of a compound of the invention in treating a disorder caused by the action of heat shock protein 90 (Hsp90). In some embodiments of this aspect, the disorder can be any one of the disorders described in the aspect featuring methods of the invention. In a related aspect, the invention features uses of a compound of the invention in treating an infectious disease. In certain embodiments of this aspect, the infectious disease is any one of the infectious diseases described in the aspect featuring methods of the invention.

In a further aspect, the invention features uses of a compound of the invention in the manufacture of a medicament for treating a disorder caused by the action of heat shock protein 90 (Hsp90). In some embodiments of this aspect, the disorder can be any one of the disorders described in the aspect featuring methods of the invention. In a related aspect, the invention features uses of a compound of the invention in the manufacture of a medicament for treating an infectious disease. In certain embodiments of this aspect, the infectious disease is any one of the infectious diseases described in the aspect featuring methods of the invention.

Definitions

Chemical Substituents

The term "about," as used herein, represents a value that is ±10% of the recited value.

The term "acyl" or "alkanoyl," as used interchangeably herein, represent an alkyl group, as defined herein, or hydrogen attached to the parent molecular group through a carbonyl group, as defined herein, and is exemplified by formyl, acetyl, propionyl, butanoyl, and the like. Exemplary unsubstituted acyl groups include from 2 to 7 carbons. Acyl can be unsubstituted or substituted in the same as defined for alkyl.

The term "alkaryl," as defined herein, represents a chemical substituent of formula -(alkylene)-(aryl), where each group is as defined herein and may be substituted or unsubstituted according to each respective definition.

The term "alkheterocyclyl," as defined herein, represents a chemical substituent of formula -(alkylene)-(heterocyclyl), where each group is as defined herein and may be substituted or unsubstituted according to each respective definition.

The term "alkoxy," as used herein, represents a chemical substituent of formula —OR, where R is a $C_{1-6}$ alkyl group, unless otherwise specified (e.g., R is $C_{1-3}$ alkyl). Alkoxy may be unsubstituted or substituted with one, two, or three substituents independently selected from the group consisting of: (1) alkoxy of one to six carbons; (2) hydroxyl; (3) amino; (4) alkylamino of one to six carbons; (5) dialkylamino, where each of alkyl groups is, independently, one to six carbons; (6) cycloalkyl of three to eight carbons; (7) oxo; (8) hal; (9) alkylsulfonyl of one to six carbon atoms; (10) thioalkoxy of one to six carbon atoms; (11) aryl; (12) —$CO_2R^A$, where $R^A$ is selected from the group consisting of (a) hydrogen, (b) alkyl, (c) cycloalkyl, (d) alkcycloalkyl, and (e) alkaryl, where the alkylene group is of one to six carbon atoms; or (13) —$C(O)NR^BR^C$, where each of $R^B$ and $R^C$ is, independently, selected from the group consisting of (a) hydrogen, (b) alkyl, (c) cycloalkyl, (d) alkcycloalkyl, and (e) alkaryl, where the alkylene group is of one to six carbon atoms; with the proviso that no more than one substituent (2)-(5) may be attached to a single carbon atom of the alkyl group, and none of the substituents (2)-(5) may be attached to the carbon connected to the oxygen atom of the alkoxy group. No more than one oxo substituent may be attached to a single carbon of the alkoxy group, and no more than two oxo substituents may be found in any of the alkoxy group as defined herein.

The term "alkoxyalkyl," as used herein, represents an alkyl group that is substituted with an alkoxy group. Exemplary unsubstituted alkoxyalkyl groups include from 2 to 9 carbons. In some embodiments, the alkyl and the alkoxy each can be further substituted with 1, 2, 3, 4, or 5 substituent groups as defined herein for each respective group.

The terms "alkyl," as used herein, are inclusive of both straight chain and branched chain saturated groups of from 1 to 6 carbons, unless otherwise specified (e.g., from 1 to 3 carbons). Alkyl groups are exemplified by methyl, ethyl, n- and iso-propyl, and may be optionally substituted with one, two, three, or, in the case of alkyl groups of two carbons or more, four substituents, unless otherwise specified, independently selected from the group consisting of: (1) alkoxy of one to six carbons; (2) hydroxyl; (3) amino; (4) alkylamino of one to six carbons; (5) dialkylamino, where each of alkyl groups is, independently, one to six carbons; (6) cycloalkyl of three to eight carbons; (7) oxo; (8) hal; (9) alkylsulfonyl of one to six carbon atoms; (10) thioalkoxy of one to six carbon atoms; (11) aryl; (12) —$CO_2R^A$, where $R^A$ is selected from the group consisting of (a) hydrogen, (b) alkyl, (c) cycloalkyl, (d) alkcycloalkyl, and (e) alkaryl, where the alkylene group is of one to six carbon atoms; (13) —$C(O)NR^BR^C$, where each of $R^B$ and $R^C$ is, independently, selected from the group consisting of (a) hydrogen, (b) alkyl, (c) cycloalkyl, (d) alkcycloalkyl, and (e) alkaryl, where the alkylene group is of one to six carbon atoms, or $R^B$ and $R^C$ combine to form $C_{2-9}$ heterocyclyl; and (14) cyano; with the proviso that no more than one substituent (2)-(5) may be attached to a single carbon atom of the alkyl group. No more than one oxo substituent may be attached to a single carbon of the alkyl group, and no more than two oxo substituents may be found in any of the alkyl group as defined herein.

The term "alkylene" and the prefix "alk-," as used herein, represent a saturated divalent $C_{1-10}$ hydrocarbon group derived from a straight or branched chain saturated hydrocarbon by the removal of two hydrogen atoms, and is exemplified by methylene, ethylene, propylene, isopropylene, and the like. The term "$C_{x-y}$ alkylene" and the prefix "$C_{x-y}$ alk-" represent alkylene groups having between x and y carbons. Exemplary values for x are 1, 2, 3, 4, 5, and 6, and exemplary values for y are 2, 3, 4, 5, 6, 7, 8, 9, or 10. In some embodiments, the alkylene can be further substituted with 1, 2, 3, or 4 substituent groups as defined herein for the alkyl group.

The term "alkylsulfonyl," as used herein, represents an alkyl group attached to the parent molecular group through an —$S(O)_2$— group. Exemplary unsubstituted alkylsulfonyl groups are of from 1 to 6 carbons. In some embodiments, the alkyl group can be further substituted with 1, 2, 3, or 4 substituent groups as defined herein.

The term "amino," as used herein, represents a chemical substituent of formula —$NH_2$. Amino group may be singly substituted with, e.g., an alkyl, alkanoyl, aryl, aryloyl, cycloalkyl, heterocyclyl, or alkheterocyclyl group (e.g., "alkylamino" having formula —NH-(optionally substituted $C_{1-6}$ alkyl), e.g., —NH-(unsubstituted $C_{1-6}$ alkyl)), or doubly substituted with, e.g., alkyl, alkanoyl, aryl, aryloyl, cycloalkyl, heterocyclyl, or alkheterocyclyl group (e.g., "dialkylamino" having formula —NR'R", where each of R' and R" is, independently, optionally substituted $C_{1-6}$ alkyl, e.g., —NR'R", where each of R' and R" is, independently, unsubstituted $C_{1-6}$ alkyl). Optionally substituted $C_{1-6}$ alkyl group may be a $C_{1-6}$ haloalkyl, e.g., a $C_{1-6}$ fluoroalkyl.

The term "aminoalkyl," as used herein, represents an alkyl group that is substituted with an amino group. Each of the alkyl and amino groups may be, independently, substituted or unsubstituted as defined herein for each respective group.

The term "aryl," as used herein, represents a mono-, bicyclic, or multicyclic carbocyclic ring system having between three and twelve carbons and having one or two aromatic rings. Non-limiting examples of aryl groups include phenyl, naphthyl, 1,2-dihydronaphthyl, 1,2,3,4-tetrahydronaphthyl, fluorenyl, indanyl, indenyl, and the like. An aryl group may be optionally substituted with one, two, three, four, or five substituents independently selected from the group consisting of: (1) alkyl of one to six carbons; (2) alkoxy of one to six carbons; (3) hydroxyl; (4) amino; (5) alkylamino of one to six carbons; (6) dialkylamino, where each of alkyl groups is, independently, one to six carbons; (7) cycloalkyl of three to eight carbons; (8) oxo; (9) hal; (10) alkylsulfonyl of one to six carbon atoms; (11) thioalkoxy of one to six carbon atoms; (12) aryl; (13) alkaryl, where alkylene group is one to six carbon atoms; (14) —$CO_2R^A$, where $R^A$ is selected from the group consisting of (a) alkyl, (b) cycloalkyl, (c) alkcycloalkyl, (d) alkaryl, and (e) hydrogen, where the alkylene group is of one to six carbon atoms; and (15) —$C(O)NR^BR^C$, where each of $R^B$ and $R^C$ is, independently, selected from the group consisting of (a) alkyl, (b) cycloalkyl, (c) alkcycloalkyl, (d) alkaryl, and (e) hydrogen, where the alkylene group is of one to six carbon atoms.

The term "aryloyl," as used herein, represents an aryl group attached to the oarent molecular group through an alkyl group.

The term "carbonyl," as used herein, represents a C(O) group, which can also be represented as C=O, and results from the combination of a tetravalent carbon atom and an oxo substituent.

The term "cyano," as used herein represents —CN group.

The term "cyanoalkyl," as used herein represents an alkyl group that is substituted with cyano.

Exemplary unsubstituted cyanoalkyl groups include from 2 to 9 carbons. In some embodiments, the alkyl group can be further substituted with 1, 2, 3, 4, or 5 substituent groups as defined herein for each respective group.

The term "cycloalkyl," as used herein represents a monovalent saturated or unsaturated non-aromatic cyclic hydrocarbon group of from three to eight carbons, unless otherwise specified, and is exemplified by cyclopropyl, cyclobutyl, cyclopentyl, cyclohexyl, cycloheptyl, bicyclo [2.2.1.]heptyl, and the like. Cycloalkyl groups may be optionally substituted with, for example, one, two, three, or four substituents, independently, selected from the group consisting of: (1) alkyl of one to six carbons; (2) alkoxy of one to six carbons; (3) hydroxyl; (4) amino; (5) alkylamino of one to six carbons; (6) dialkylamino, where each of alkyl groups is, independently, one to six carbons; (7) cycloalkyl of three to eight carbons; (8) oxo; (9) halo; (10) alkylsulfonyl of one to six carbon atoms; (11) thioalkoxy of one to six carbon atoms; (12) aryl; (13) alkaryl, where alkylene group is one to six carbon atoms; (14) —$CO_2R^A$, where $R^A$ is selected from the group consisting of (a) alkyl, (b) cycloalkyl, (c) alkcycloalkyl, (d) alkaryl, and (e) hydrogen, where the alkylene group is of one to six carbon atoms; or (15) —$C(O)NR^BR^C$, where each of $R^B$ and $R^C$ is, independently, selected from the group consisting of (a) alkyl, (b) cycloalkyl, (c) alkcycloalkyl, (d) alkaryl, and (e) hydrogen, where the alkylene group is of one to six carbon atoms, or $R^B$ and $R^C$ combine to form $C_{2-9}$ heterocyclyl.

The term "five-membered ring," as used herein, represent a saturated or unsaturated aromatic or non-aromatic group having five atoms in a cyclic array, where, unless otherwise specified, four atoms are carbons and the remaining atom is selected from the group consisting of carbon, nitrogen, sulfur, and oxygen. A five-membered ring may be fused to another cyclic group selected from heterocyclyl, heteroaryl, cycloalkyl, and aryl. A five-membered ring may be unsubstituted or substituted with, for example, one, two, three, or four substituents, independently selected from the group consisting of: (1) alkoxy of one to six carbons; (2) hydroxyl; (3) amino; (4) alkylamino of one to six carbons; (5) dialkylamino, where each of alkyl groups is, independently, one to six carbons; (6) cycloalkyl of three to eight carbons; (7) oxo; (8) alkylsulfonyl of one to six carbon atoms; (9) thioalkoxy of one to six carbon atoms; (10) aryl; (11) alkaryl, where alkylene group is one to six carbon atoms; (12) optionally substituted alkyl of one to six carbons (e.g., unsubstituted alkyl, alkoxyalkyl, hydroxyalkyl, haloalkyl, or cyanoalkyl); (13) —$CO_2R^A$, where $R^A$ is selected from the group consisting of (a) alkyl, (b) cycloalkyl, (c) alkcycloalkyl, (d) alkaryl, and (e) hydrogen, where the alkylene group is of one to six carbon atoms; (14) —$C(O)NR^BR^C$, where each of $R^B$ and $R^C$ is, independently, selected from the group consisting of (a) optionally substituted alkyl (e.g., unsubstituted alkyl, alkoxyalkyl, hydroxyalkyl, haloalkyl, or cyanoalkyl), (b) cycloalkyl, (c) alkcycloalkyl, (d) alkaryl, (e) heterocyclyl, (f) alkheterocyclyl, (g) alkoxy, and (h) hydrogen, where the alkylene group is of one to six carbon atoms, or $R^B$ and $R^C$ combine to form $C_{2-9}$ heterocyclyl; and (15) cyano.

The term "fluoroalkyl," as used herein, represents an alkyl group, as defined herein, where one or more hydrogen radicals (e.g., 1, 2, 3, 4, or 5, or more hydrogen radicals) bound to the alkyl group have been replaced by a fluorine radical. In some embodiments, fluoroalkyl group may be perfluoroalkyl. Prefix "fluoro" indicates that the group in question is substituted by one or more (e.g., 1, 2, 3, 4, or 5, or more) fluorine radicals.

The term "haloalkyl," as used herein, represents an alkyl group, as defined herein, substituted by a halogen group (i.e., F, Cl, Br, or I). A $C_{1-6}$ haloalkyl may be substituted with one two, three, or in the case of alkyl groups of two carbons or more, four or five halogens. Haloalkyl groups include perfluoroalkyls. In certain embodiments, haloalkyl is fluoroalkyl. In some embodiments, the $C_{1-6}$ haloalkyl group may be further substituted with 1, 2, 3, or 4 substituent groups as described herein for alkyl groups.

The terms "halogen," "hal," or "halo," as used interchangeably herein, represent a group selected from fluorine (—F), chlorine (—Cl), bromine (—Br), and iodine (—I). Prefix "halo" indicates that the group in question is substituted by a halogen group (i.e., F, Cl, Br, or I).

The term "heterocyclyl," as used herein represents a 5-, 6- or 7-membered ring, unless otherwise specified, containing one, two, three, or four heteroatoms independently selected from the group consisting of nitrogen, oxygen, and sulfur. The 5-membered ring has zero to two double bonds, and the 6- and 7-membered rings have zero to three double bonds. The term "heterocyclyl" also represents a heterocyclic compound having a bridged multicyclic structure in which one or more carbons and/or heteroatoms bridges two non-adjacent members of a monocyclic ring, e.g., a quinuclidinyl group. The term "heterocyclyl" also includes bicyclic, tricyclic, and tetracyclic groups in which any of the above heterocyclic rings is fused to one, two, or three carbocyclic rings, e.g., an aryl ring, a cyclohexane ring, a cyclohexene ring, a cyclopentane ring, a cyclopentene ring, or another monocyclic heterocyclic ring, e.g., indolyl, quinolyl, isoquinolyl, tetrahydroquinolyl, benzofuryl, benzothienyl and the like. Examples of fused heterocyclyls include tropanes and 1,2,3,5,8,8a-hexahydroindolizine. Heterocyclics include pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidiniyl, morpholinyl, thiomorpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, thiazolidinyl, isothiazolyl, isoindazolyl, triazolyl, tetrazolyl, oxadiazolyl, uricyl, thiadiazolyl, tetrahydrofuranyl, dihydrofuranyl, tetrahydrothienyl, dihydrothienyl, dihydroindolyl, tetrahydroquinolyl, tetrahydroisoquinolyl, pyranyl, dihydropyranyl, dithiazolyl, benzofuranyl, benzothienyl and the like. The heterocyclyl group may be optionally substituted with one, two, three, four, or five substituents independently selected from the group consisting of: (1) alkyl of one to six carbons; (2) alkoxy of one to six carbons; (3) hydroxyl; (4) amino; (5) alkylamino of one to six carbons; (6) dialkylamino, where each of alkyl groups is, independently, one to six carbons; (7) cycloalkyl of three to eight carbons; (8) oxo; (9) hal; (10) alkylsulfonyl of one to six carbon atoms; (11) thioalkoxy of one to six carbon atoms; (12) aryl; (13) alkaryl; (14) —$CO_2R^A$, where $R^A$ is selected from the group consisting of (a) alkyl, (b) cycloalkyl, (c) alkcycloalkyl, (d) alkaryl, and (e) hydrogen, where the alkylene group is of one to six carbon atoms; or (15) —$C(O)NR^BR^C$, where each of $R^B$ and $R^C$ is, independently, selected from the group consisting of (a) alkyl, (b) cycloalkyl, (c) alkcycloalkyl, (d) alkaryl, and (e) hydrogen, where the alkylene group is of one to six carbon atoms, or $R^B$ and $R^C$ combine to form $C_{2-9}$ heterocyclyl.

The term "heteroaryl," as used herein, represents that subset of heterocyclyls, as defined herein, which are aromatic: i.e., they contain 4n+2 pi electrons within the mono- or multicyclic ring system. In some embodiments, the heteroaryl is substituted with, e.g., 1, 2, 3, or 4 substituent groups independently selected from the group consisting of: (1) alkyl of one to six carbons; (2) alkoxy of one to six carbons; (3) hydroxyl; (4) amino; (5) alkylamino of one to six carbons; (6) dialkylamino, where each of alkyl groups is, independently, one to six carbons; (7) cycloalkyl of three to eight carbons; (8) oxo; (9) hal; (10) alkylsulfonyl of one to six carbon atoms; (11) thioalkoxy of one to six carbon atoms; (12) aryl; (13) alkaryl; (14) —$CO_2R^A$, where $R^A$ is selected from the group consisting of (a) alkyl, (b) cycloalkyl, (c) alkcycloalkyl, (d) alkaryl, and (e) hydrogen, where the alkylene group is of one to six carbon atoms; or (15) —$C(O)NR^BR^C$, where each of $R^B$ and $R^C$ is, independently, selected from the group consisting of (a) alkyl, (b) cycloalkyl, (c) alkcycloalkyl, (d) alkaryl, and (e) hydrogen, where the alkylene group is of one to six carbon atoms.

The term "hydroxy," as used herein, represents an —OH group.

The term "hydroxyalkyl," as used herein, represents an alkyl group, as defined herein, substituted by one or two hydroxy groups, with the proviso that no more than one hydroxy group may be attached to a single carbon atom of the alkyl group and is exemplified by hydroxymethyl, dihydroxypropyl, and the like.

The term "N-protected amino," as used herein, refers to an amino group, as defined herein, to which is attached an N-protecting group, as defined herein.

The term "N-protecting group," as used herein, represents those groups intended to protect an amino group against undesirable reactions during synthetic procedures. Commonly used N-protecting groups are disclosed in Greene, *Protective Groups in Organic Synthesis*, 3$^{rd}$ Edition (John Wiley & Sons, New York, 1999), which is incorporated herein by reference. N-protecting groups include acyl, aroyl, or carbamyl groups, e.g., formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and chiral auxiliaries, e.g., protected or unprotected D, L or D, L-amino acids, e.g., alanine, leucine, phenylalanine, and the like; sulfonyl groups, e.g., benzenesulfonyl, p-toluenesulfonyl, and the like; carbamate forming groups, e.g., benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyl oxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, phenylthiocarbonyl, and the like, arylalkyl groups, e.g., benzyl, triphenylmethyl, benzyloxymethyl, and the like and silyl groups, e.g., trimethylsilyl, and the like. Preferred N-protecting groups are formyl, acetyl, benzoyl, pivaloyl, t-butylacetyl, alanyl, phenylsulfonyl, benzyl, t-butyloxycarbonyl (Boc), and benzyloxycarbonyl (Cbz).

The term "six-membered ring," as used herein, represent a saturated or unsaturated aromatic or non-aromatic group having six atoms in a cyclic array, where, unless otherwise specified, five atoms are carbons and the remaining atom is selected from the group consisting of carbon, nitrogen, sulfur, and oxygen. A six-membered ring may be fused to another cyclic group selected from heterocyclyl, heteroaryl, cycloalkyl, and aryl. A six-membered ring may be unsubstituted or substituted with, for example, one, two, three, or four substituents, independently selected from the group consisting of: (1) alkyl of one to six carbons; (2) alkoxy of one to six carbons; (3) hydroxyl; (4) amino; (5) alkylamino of one to six carbons; (6) dialkylamino, where each of alkyl groups is, independently, one to six carbons; (7) cycloalkyl of six to eight carbons; (8) oxo; (9) alkylsulfonyl of one to six carbon atoms; (10) thioalkoxy of one to six carbon atoms; (11) aryl; (12) alkaryl, where alkylene group is one to six carbon atoms; (13) —$CO_2R^A$, where $R^A$ is selected from the group consisting of (a) alkyl, (b) cycloalkyl, (c) alkcycloalkyl, (d) alkaryl, and (e) hydrogen, where the alkylene group is of one to six carbon atoms; (14) —$C(O)NR^BR^C$, where each of $R^B$ and $R^C$ is, independently, selected from the group consisting of (a) alkyl, (b) cycloalkyl, (c) alkcycloalkyl, (d) alkaryl, and (e) hydrogen, where the alkylene group is of one to six carbon atoms, or $R^B$ and $R^C$ combine to form $C_{2-9}$ heterocyclyl; and (15) cyano.

The term "thioalkoxy," as used herein, represents a chemical substituent of formula —SR, where R is an alkyl group. In some embodiments, the alkyl group can be further substituted with 1, 2, 3, or 4 substituent groups as described herein for alkyl groups.

The term "thiol," as used herein, represents a chemical substituent of formula —SH.

When referring to numbered position within the compounds of the invention, the following numbering system is employed:

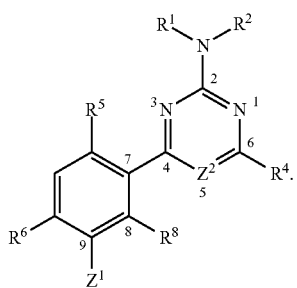

For example, the statement "$R^3$ and $R^4$ combine to form —N($R^9$)—CH=CH—" indicates that the nitrogen atom of —N($R^9$)—CH=CH— may be proximal to either $C^5$ carbon or $C^6$ carbon. The statement "$R^3$ and $R^4$ combine to form —N($R^9$)—CH=CH—" in combination with "the nitrogen atom of —N($R^9$)—CH=CH— is proximal to $C^5$" indicates the following compound:

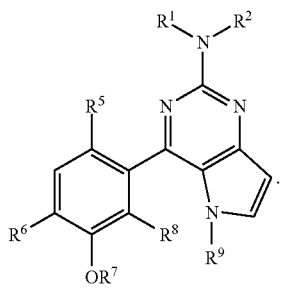

Asymmetric or chiral centers may exist in any of the compounds of the present invention. The present invention contemplates the various stereoisomers and mixtures thereof. Individual stereoisomers of compounds of the present invention are prepared synthetically from commercially available starting materials that contain asymmetric or chiral centers or by preparation of mixtures of enantiomeric compounds followed by resolution well known to those of ordinary skill in the art. These methods of resolution are exemplified by (1) attachment of a racemic mixture of enantiomers, designated (+/−), to a chiral auxiliary, separation of the resulting diastereomers by recrystallization or chromatography and liberation of the optically pure product from the auxiliary or (2) direct separation of the mixture of optical enantiomers on chiral chromatographic columns or by chiral HPLC methods. Methods of chiral separations have been described previously (G. B. Cox (ed.) in *Preparative Enantioselective Chromatography*, 2005, Blackwell Publishing). Alternatively, chiral compounds can be prepared by an asymmetric synthesis that favors the preparation of one enantiomer over the other. Alternatively a chiral pool synthesis (starting with an enantiomerically pure building block) can be used where the chiral group or center is retained in the intermediate or final product. Enantiomers are designated herein by the symbols "R," or "S," depending on the configuration of substituents around the chiral atom. Alternatively, enantiomers are designated as (+) or (−) depending on whether a solution of the enantiomer rotates the plane of polarized light clockwise or counterclockwise, respectively.

Geometric isomers may also exist in the compounds of the present invention. The present invention contemplates the various geometric isomers and mixtures thereof resulting from the arrangement of substituents around a carbon-carbon double bond and designates such isomers as of the Z or E configuration, where the term "Z" represents substituents on the same side of the carbon-carbon double bond and the term "E" represents substituents on opposite sides of the carbon-carbon double bond. It is also recognized that for structures in which tautomeric forms are possible, the description of one tautomeric form is equivalent to the description of both, unless otherwise specified.

Each position in the compounds of the invention may include elements in their natural isotopic abundance. Alternatively, one or more positions in the compound of the invention may include an element enriched in a naturally occurring or a synthetic isotope. For example, one or more positions of the compound of the invention including hydrogen may be enriched with, e.g., deuterium or tritium. In some embodiments, one or more positions of the compound of the invention including carbon may be enriched with, e.g., $^{14}C$ or $^{13}C$. In other embodiments, one or more positions of the compound of the invention including nitrogen may be enriched with, e.g., $^{15}N$. In certain embodiments, one or more positions of the compound of the invention including oxygen may be enriched with, e.g., $^{18}O$, $^{17}O$, or $^{15}O$. In particular embodiments, one or more positions of the compound of the invention including fluorine may be enriched with, e.g., $^{18}F$. In other embodiments, one or more positions of the compound of the invention including carbon may be enriched with, e.g., $^{32}S$, $^{33}S$, $^{34}S$, $^{35}S$, or $^{36}S$. In yet other embodiments, one or more positions of the compound of the invention including chlorine may be enriched with, e.g., $^{35}Cl$, $^{36}Cl$, or $^{37}Cl$.

Some abbreviations used herein:
BINAP—2,2'-bis(diphenylphosphino)-1,1'-binaphthyl;
t-Bu—tert-butyl or 1,1-dimethylethyl;
cat—catecholato;
dppb—bis(diphenylphosphino)butane;
dppf—bis(diphenylphosphino)ferrocene;
Et—ethyl;
Me—methyl;
OAc—acetate;
OMs—mesylate or methanesulfunoate;
ONf—nonaflate or nonafluoro-n-butylsulfonate;
OTf—triflate or trifluoromethanesulfonate;
pin—pinacolato;
i-Pr—isopropyl or 1-methylethyl; and
n-Pr—n-propyl;
SIMes—1,3-bis(2,4,6-trimethylphenyl)imidazolin-2-ylidene;
SIPr—1,3,-bis(2,6-diisopropylphenyl)imidazolin-2-ylidene; and
THF—tetrahydrofuran.

Other Terms

The term "about" is used herein to mean a value that is ±10% of the recited value.

The terms "effective amount" or "amount effective to" or "therapeutically effective amount" mean an amount of a compound of the invention sufficient to produce a desired result, for example, one or more of a decrease in Hsp90 activity (e.g., inhibition of Hsp90), an increase in expression of Hsp70, a decrease in aggregation of Aβ peptide (e.g., inhibition of aggregation of Aβ peptide), an increase in degradation of Aβ peptide, and a decrease in phosphorylation of tau protein, and/or a decrease in, or amelioration of symptoms of, a neurodegenerative disease (e.g., Alzheimer's disease) in a subject upon administration of a composition containing the compound of the invention. The increases and decreases related to administration an effective amount of a compound are relative to levels or symptoms, as applicable, in a subject that has not been administered a compound of the invention or relative to the subject prior to administration of a compound of the invention.

The term "element," as used herein, refers to a substance consisting of a single type of atoms, that is, each nucleus of each atom of a single element contains the same number of protons.

The term "neurodegeneration," as used herein, refers to the progressive loss of structure or function of neurons, including death of neurons. The term "neurodegenerative disease" refers to diseases in which neurodegeneration is, at least in part, a cause, symptom, or phenotype.

The terms "patient" and "subject," as used interchangeably herein, refer to any animal (e.g., a mammal, e.g., a human). A subject to be treated according to the methods described herein may be one who has been diagnosed with a neurodegenerative disease, e.g., tauopathy (e.g., Alzheimer's disease), or a proliferative disease as having such a condition or one at risk of developing the condition. Diagnosis may be performed by any method or technique known in the art. One skilled in the art will understand that a subject to be treated according to the present invention may have been subjected to standard tests or may have been identified, without examination, as one at high risk due to the presence of one or more risk factors, e.g., increased total level of tau protein or an increased level of phosphorylated tau protein in a sample (e.g., cerebrospinal fluid) from the subject in comparison to the levels in a sample from a healthy subject.

The term "pharmaceutical composition," as used herein, represents a composition containing a compound described herein, formulated with a pharmaceutically acceptable excipient, and manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein.

The term "pharmaceutically acceptable excipient" or "pharmaceutically acceptable carrier," as used interchangeably herein, refers to any ingredient other than the compounds described herein (e.g., a vehicle capable of suspending or dissolving the active compound) and having the properties of being nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, or waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

The term "pharmaceutically acceptable prodrugs" as used herein, represents those prodrugs of the compounds of the present invention which are, within the scope of sound medical judgment, suitable for use in contact with the tissues of humans and animals with undue toxicity, irritation, allergic response, and the like, commensurate with a reasonable benefit/risk ratio, and effective for their intended use.

The term "pharmaceutically acceptable salt," as use herein, represents those salts which are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. For example, pharmaceutically acceptable salts are described in: Berge et al., *J. Pharmaceutical Sciences* 66:1-19, 1977 and in *Pharmaceutical Salts: Properties, Selection, and Use*, (Eds. P. H. Stahl and C. G. Wermuth), Wiley-VCH, 2008. The salts can be prepared in situ during the final isolation and purification of the compounds described herein or separately by reacting the free base group with a suitable organic acid. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

The term "pharmaceutically acceptable solvate" as used herein means a compound as described herein wherein molecules of a suitable solvent are incorporated in the crystal lattice. A suitable solvent is physiologically tolerable at the dosage administered. For example, solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the molecule is referred to as a "hydrate."

The abbreviation "PSA" and the term "polar surface area" of a molecule, as used interchangeably herein, are defined as the surface sum over all polar atoms. The units of PSA are $Å^2$ (angstrom squared).

The term "prevent," as used herein, refers to prophylactic treatment or treatment that prevents one or more symptoms or conditions of a disease, disorder, or conditions described herein. Preventive treatment that includes administration of a compound described herein, or a pharmaceutically acceptable salt thereof, or a pharmaceutical composition thereof, can be acute, short-term, or chronic. The doses administered may be varied during the course of preventative treatment.

The term "prodrug," as used herein, represents compounds that are rapidly transformed in vivo to the parent compound of the above formula, for example, by hydrolysis in blood. Prodrugs of the compounds described herein may be conventional esters. Some common esters that have been utilized as prodrugs are phenyl esters, aliphatic ($C_1$-$C_8$ or $C_8$-$C_{24}$) esters, cholesterol esters, acyloxymethyl esters, carbamates, and amino acid esters. For example, a compound that contains an OH group may be acylated at this position in its prodrug form. A thorough discussion is provided in Higuchi and Stella, *Pro-drugs as Novel Delivery Systems*, Vol. 14 of the A.C.S. Symposium Series, Edward B. Roche, ed., *Bioreversible Carriers in Drug Design*, American Pharmaceutical Association and Pergamon Press, 1987, and Judkins et al., *Synthetic Communications* 26(23): 4351-4367, 1996, each of which is incorporated herein by reference. Preferably, prodrugs of the compounds of the present invention are suitable for use in contact with the tissues of humans and animals with undue toxicity, irritation, allergic response, and the like, commensurate with a reasonable benefit/risk ratio, and effective for their intended use.

The term "proliferative disease," as used herein, refers to both cancer and non-cancer disease. The proliferative disease is one characterized by unregulated proliferation of cells of a certain type (e.g., astrocytes). Preferably, the tumor cells associated with a proliferative disease (e.g., cancer) respond to the inhibition of Hsp90 by apoptosis. Proliferative diseases to be treated using compounds of the invention and according to the methods of the invention may include glioma, meningioma, pituitary adenoma, nerve sheath tumor (e.g., schwannoma or neurofibroma). Proliferative diseases within the scope of the present invention may be a cancer, e.g., acute myeloid leukemia, gastrointestinal stromal tumor, gastric cancer, lung cancer, lymphoma, melanoma, myeloma, non-small cell lung cancer, renal cancer, small cell lung cancer, blast-phase chronic myelogenous leukemia, leukemia, lymphoproliferative disorder, metastatic melanoma, relapsed multiple myeloma, refractory multiple myeloma, myeloproliferative disorders, pancreatic cancer, small intestine cancer, or solid tumor. Preferably, a proliferative disease to be treated using compounds of the invention according to the methods of the invention may include brain tumors (e.g., malignant brain tumors). For example, the brain tumors that may be treated with blood-brain-barrier penetrant compounds of the invention can be glioma or meningioma, in particular, glioma (e.g., glioblastoma), or a malignant version thereof. The cancers that may be treated according to the present invention may also be a cancer that has metastasized to the brain (e.g., lung cancer, breast cancer, melanoma, colon cancer, renal cancer, and thyroid cancer).

As used herein, and as well understood in the art, "treatment" is an approach for obtaining beneficial or desired results, e.g., clinical results. Beneficial or desired results can include, but are not limited to, alleviation or amelioration of one or more symptoms or conditions; diminishment of extent of disease, disorder, or condition; stabilized (i.e., not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment.

BRIEF DESCRIPTION OF DRAWINGS

FIG. 5B shows that expression of Hsp90 remains unchanged relative to variation in the concentration of compound 20.

DETAILED DESCRIPTION

Figure 1:
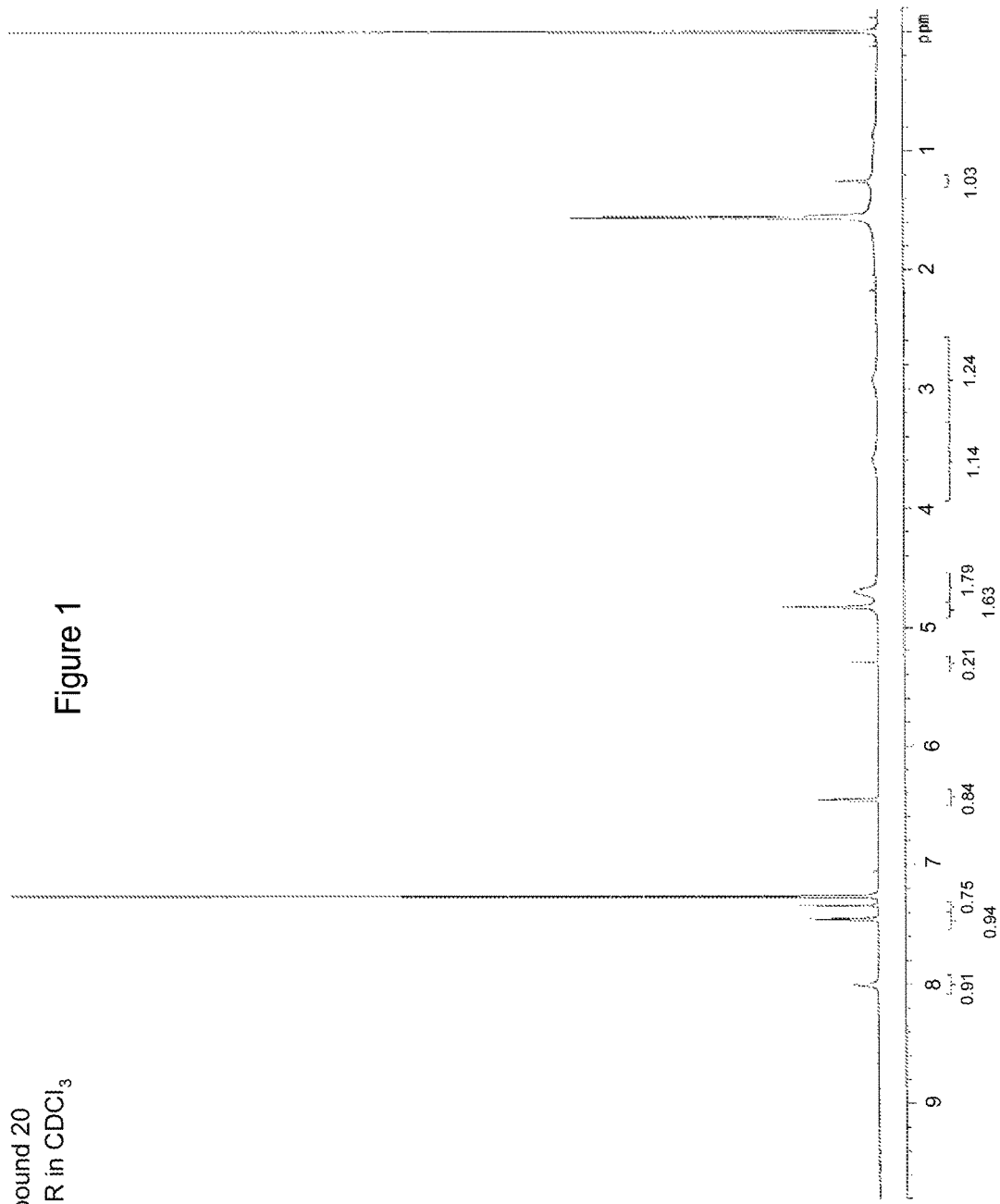
FIG. 1 shows a 500 MHz $^1$H NMR spectrum of compound 20 in $CDCl_3$.

The invention features novel aminopyrimidines and related compounds having Hsp90 inhibitory activity, pharmaceutical compositions containing them, and their medical use (e.g., treatment of a proliferative disease (e.g., cancer) or a neurodegenerative disease (e.g., a tauopathy)). In particular, the compounds of the invention are capable to penetrate blood-brain-barrier. Therefore, medical use of these compounds encompasses diseases and conditions afflicting mammalian (e.g., human) brain.

Compounds of the Invention

Exemplary compounds of the invention are shown in Table 2.

TABLE 2
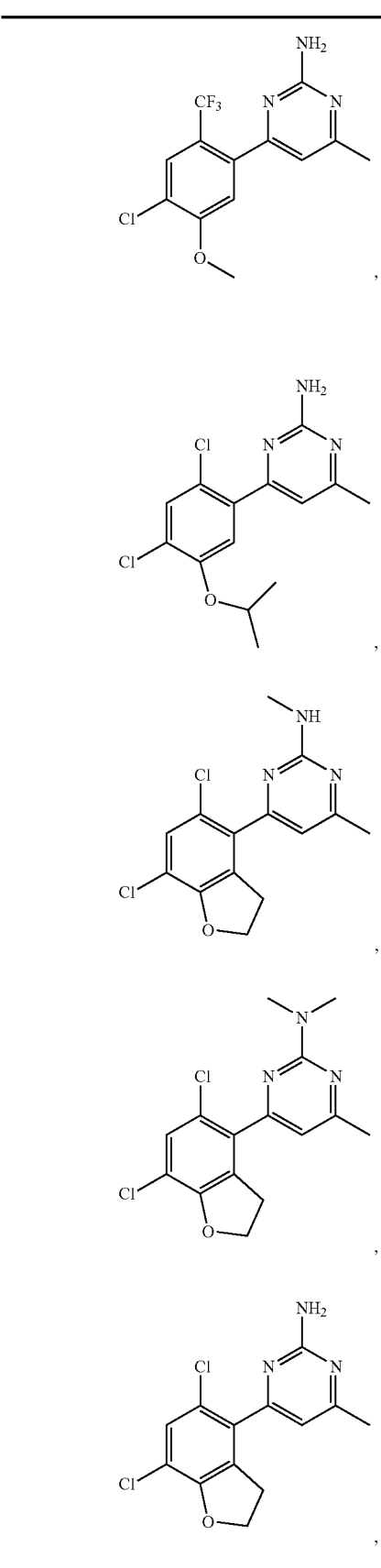
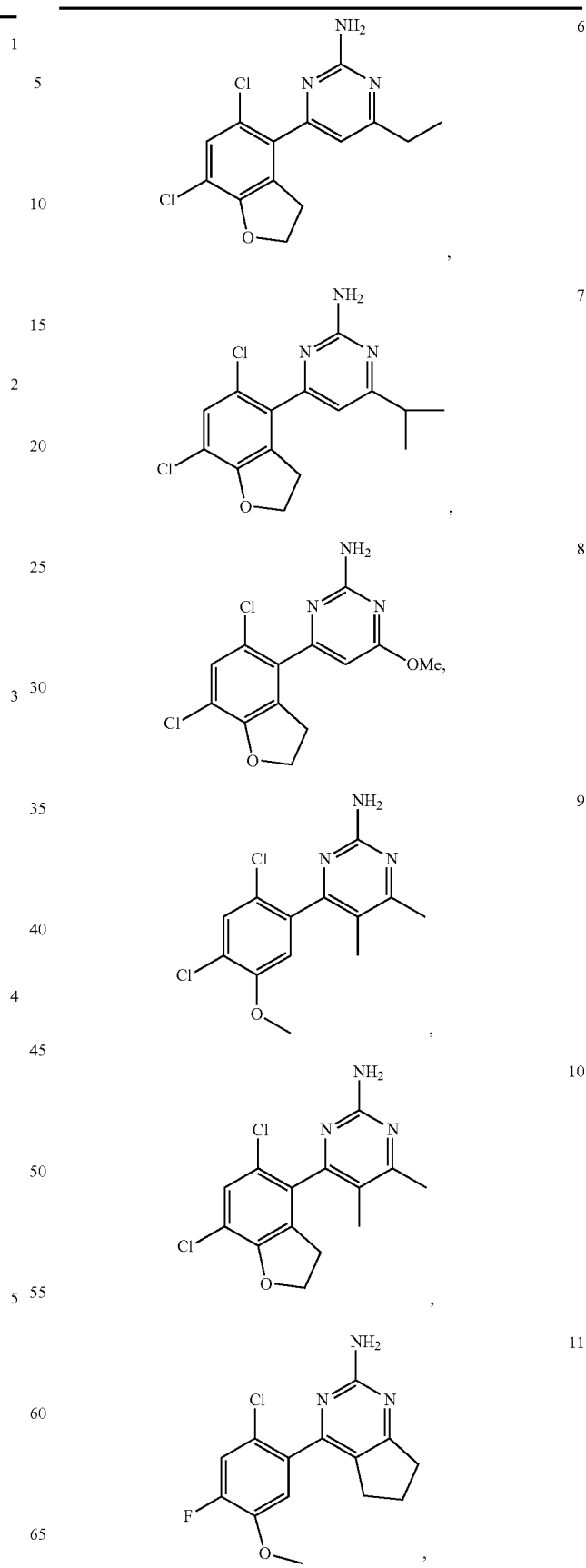

TABLE 2-continued
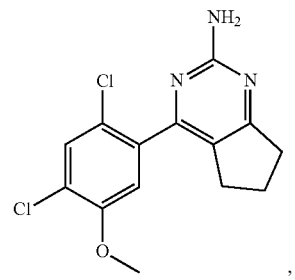 [SMILES: COc1cc(-c2nc(N)nc3c2CCC3)c(Cl)cc1Cl] 12
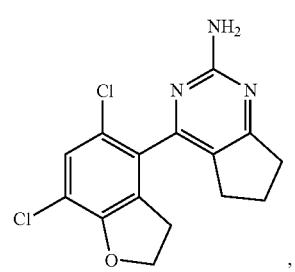 [SMILES: Nc1nc2c(c(-c3c(Cl)cc(Cl)c4c3CCO4)n1)CCC2] 13
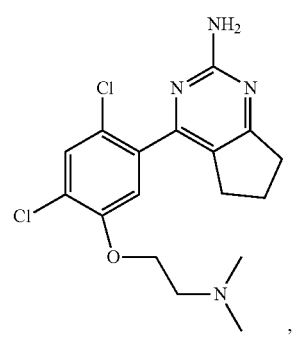 [SMILES: CN(C)CCOc1cc(-c2nc(N)nc3c2CCC3)c(Cl)cc1Cl] 14
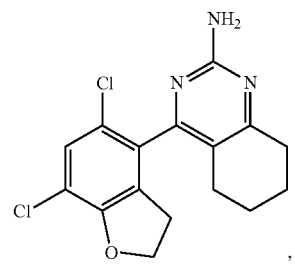 [SMILES: Nc1nc2c(c(-c3c(Cl)cc(Cl)c4c3CCO4)n1)CCCC2] 15
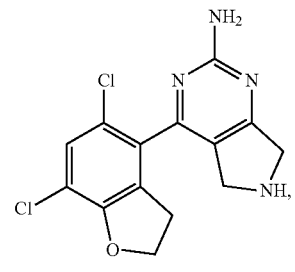 [SMILES: Nc1nc2c(c(-c3c(Cl)cc(Cl)c4c3CCO4)n1)CNC2] 16
TABLE 2-continued
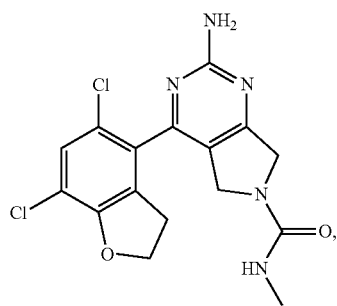 [SMILES: CNC(=O)N1Cc2nc(N)nc(-c3c(Cl)cc(Cl)c4c3CCO4)c2C1] 17
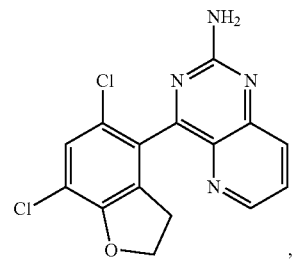 [SMILES: Nc1nc(-c2c(Cl)cc(Cl)c3c2CCO3)c2ncccc2n1] 18
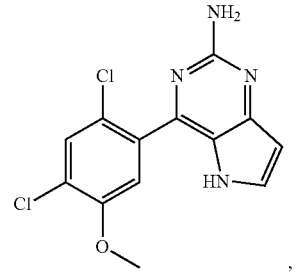 [SMILES: COc1cc(-c2nc(N)nc3cc[nH]c23)c(Cl)cc1Cl] 19
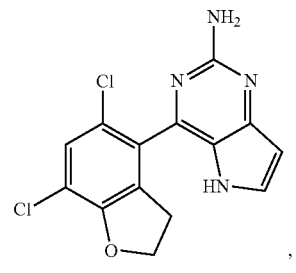 [SMILES: Nc1nc(-c2c(Cl)cc(Cl)c3c2CCO3)c2[nH]ccc2n1] 20
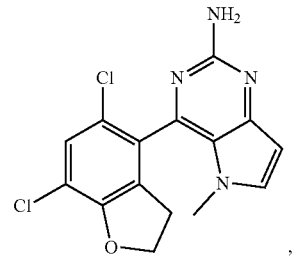 [SMILES: Cn1ccc2nc(N)nc(-c3c(Cl)cc(Cl)c4c3CCO4)c21] 21

TABLE 2-continued
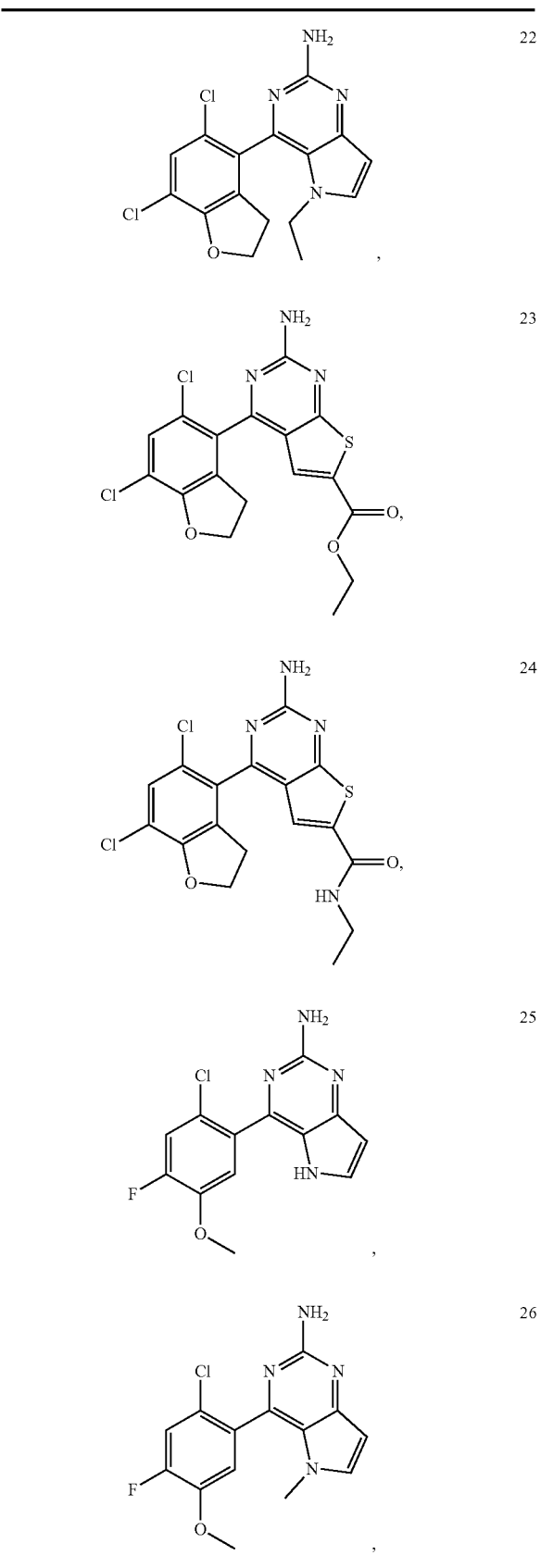
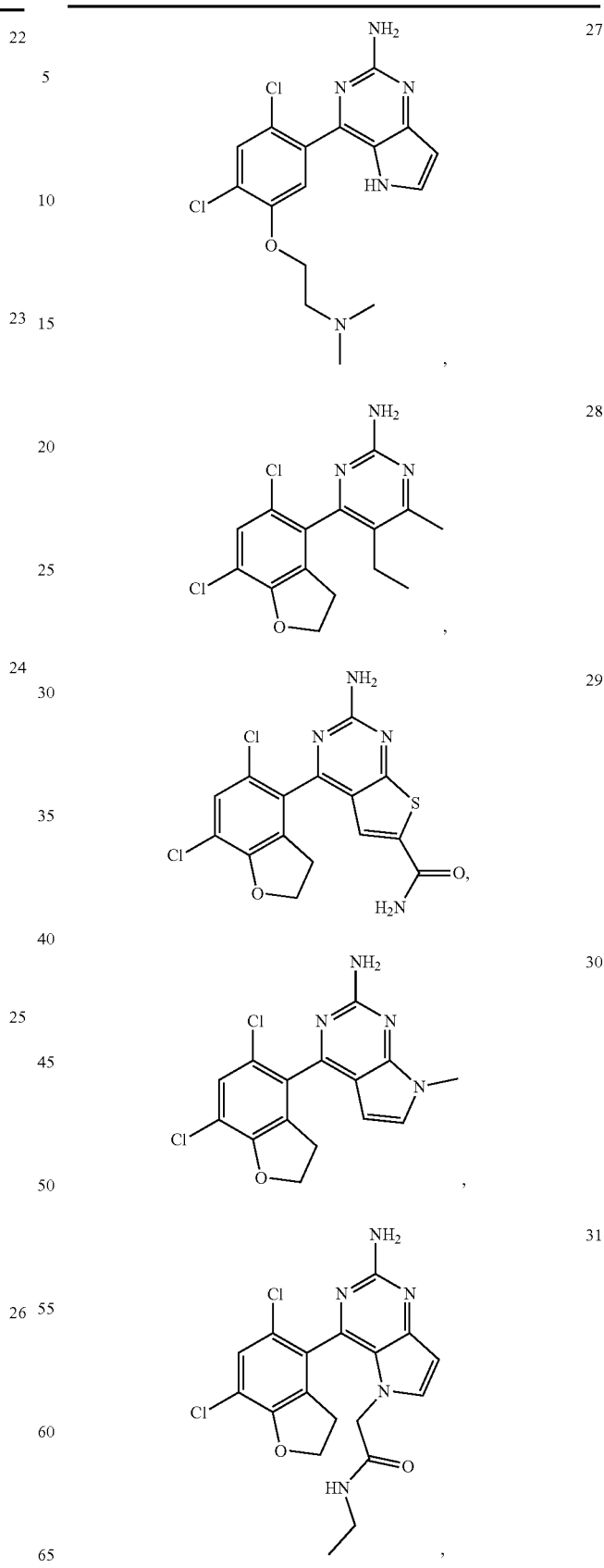

TABLE 2-continued
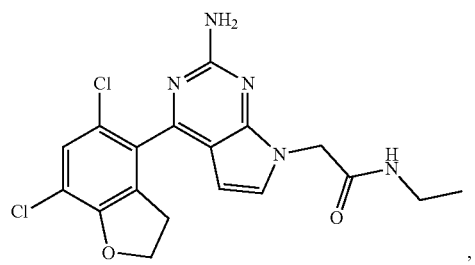 [SMILES: CCNC(=O)Cn1ccc2c(-c3c(Cl)cc(Cl)c4c3CCO4)nc(N)nc21] 32
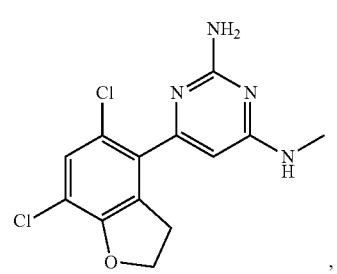 [SMILES: CNc1cc(-c2c(Cl)cc(Cl)c3c2CCO3)nc(N)n1] 33
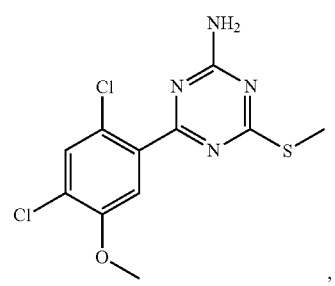 34
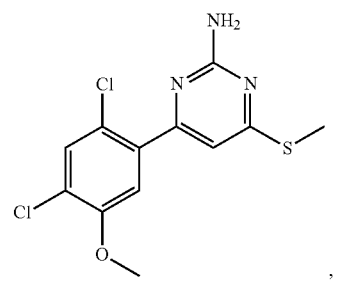 35
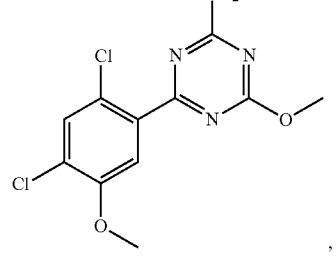 36
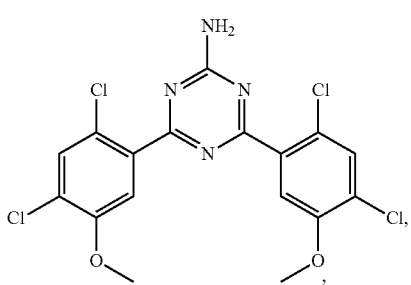 [SMILES: COc1cc(-c2nc(N)nc(-c3cc(OC)c(Cl)cc3Cl)n2)c(Cl)cc1Cl] 37
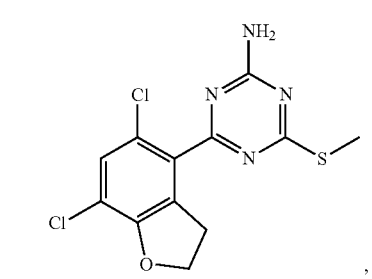 40
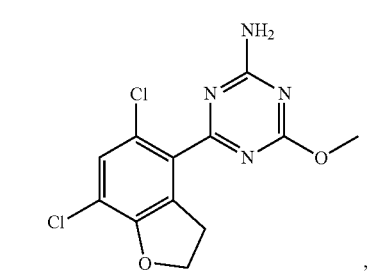 [SMILES: COc1nc(N)nc(-c2c(Cl)cc(Cl)c3c2CCO3)n1] 41
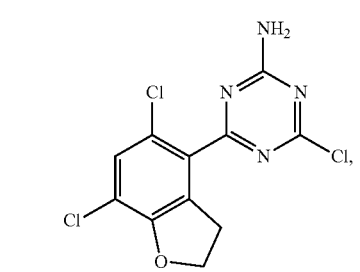 42
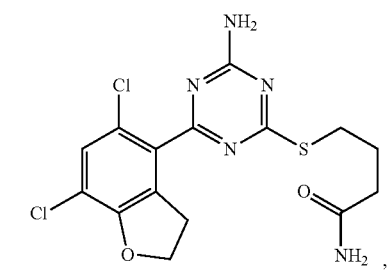 [SMILES: NC(=O)CCCSc1nc(N)nc(-c2c(Cl)cc(Cl)c3c2CCO3)n1] 43

TABLE 2-continued
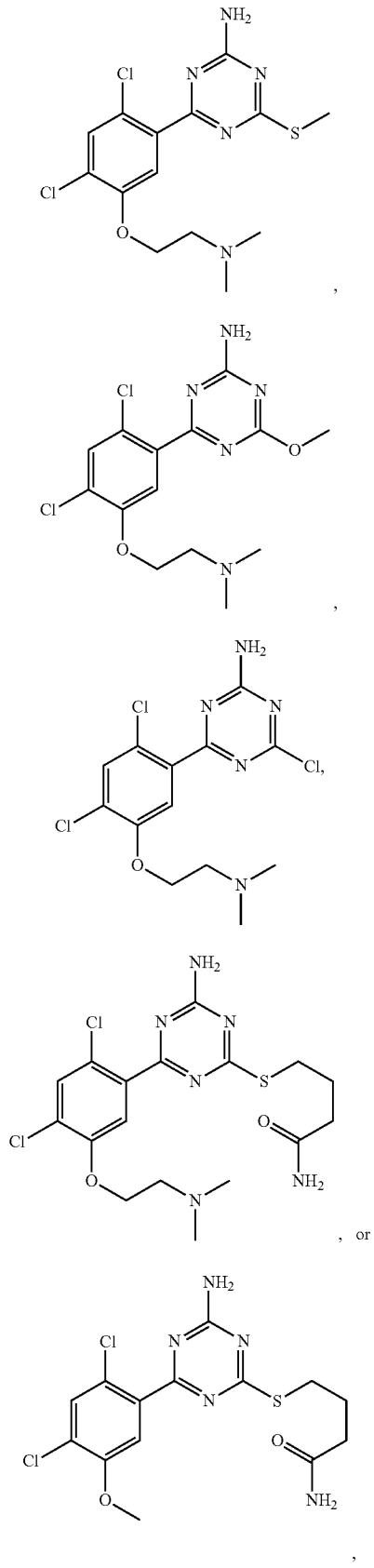
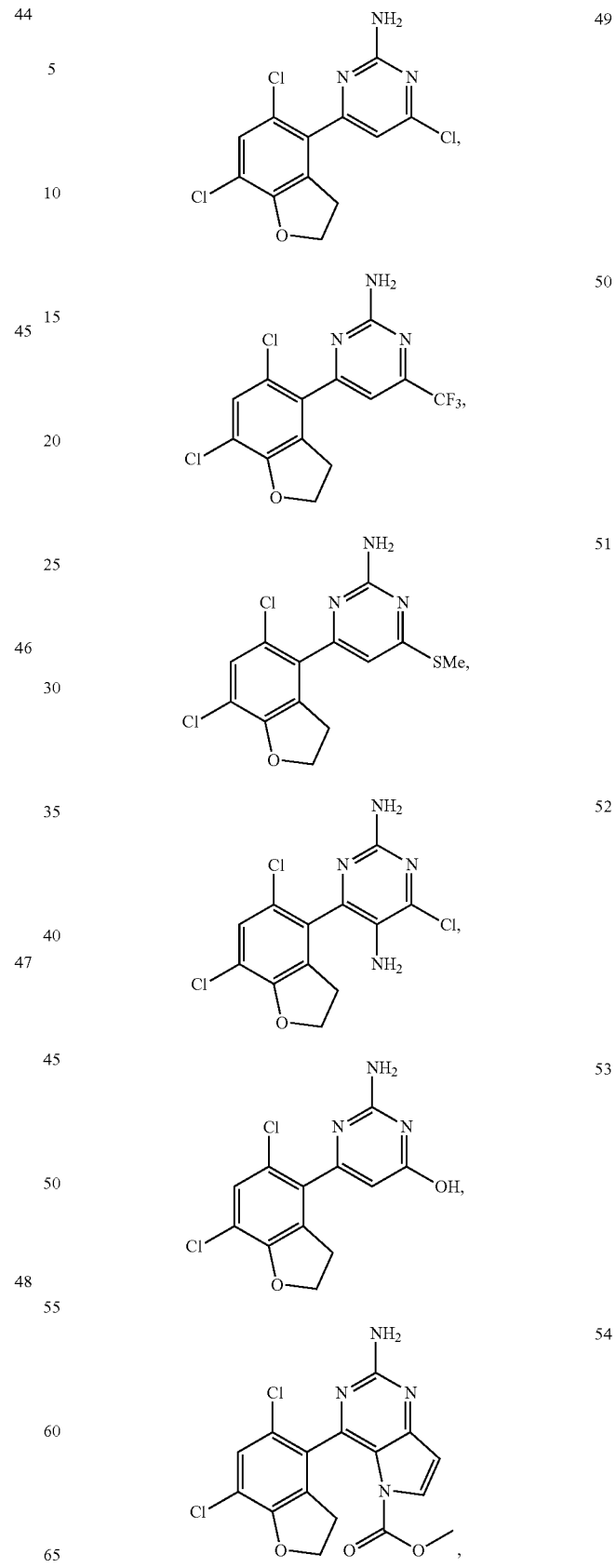

TABLE 2-continued
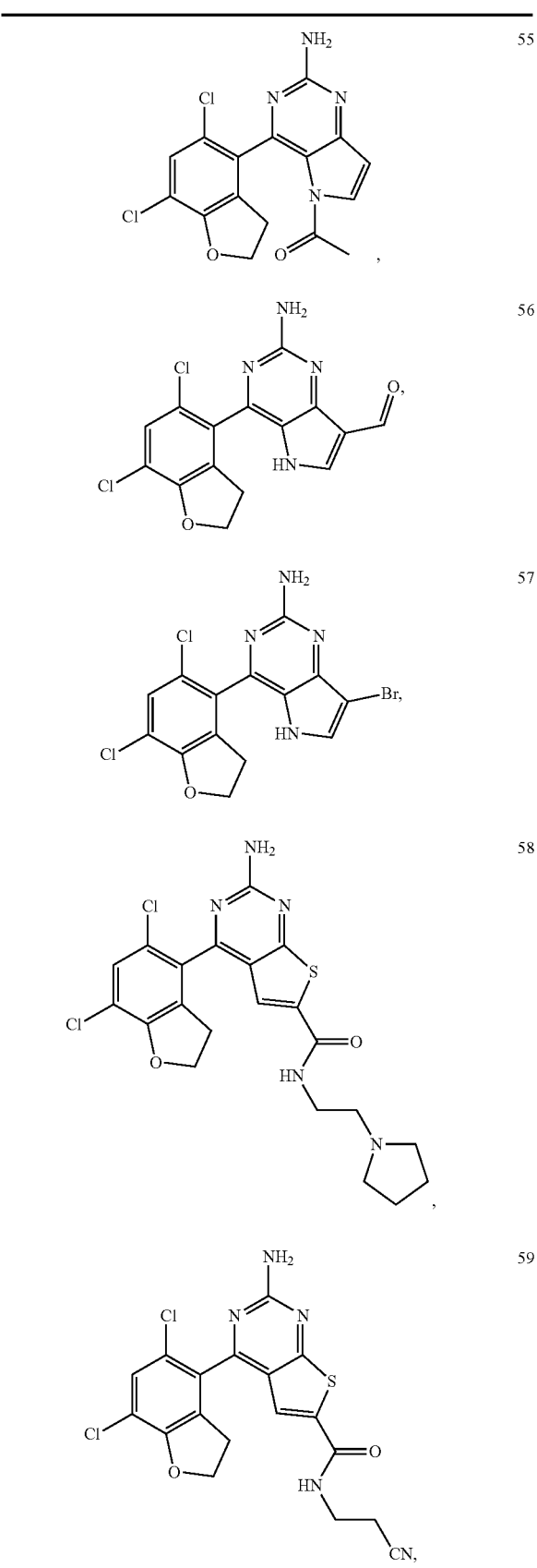
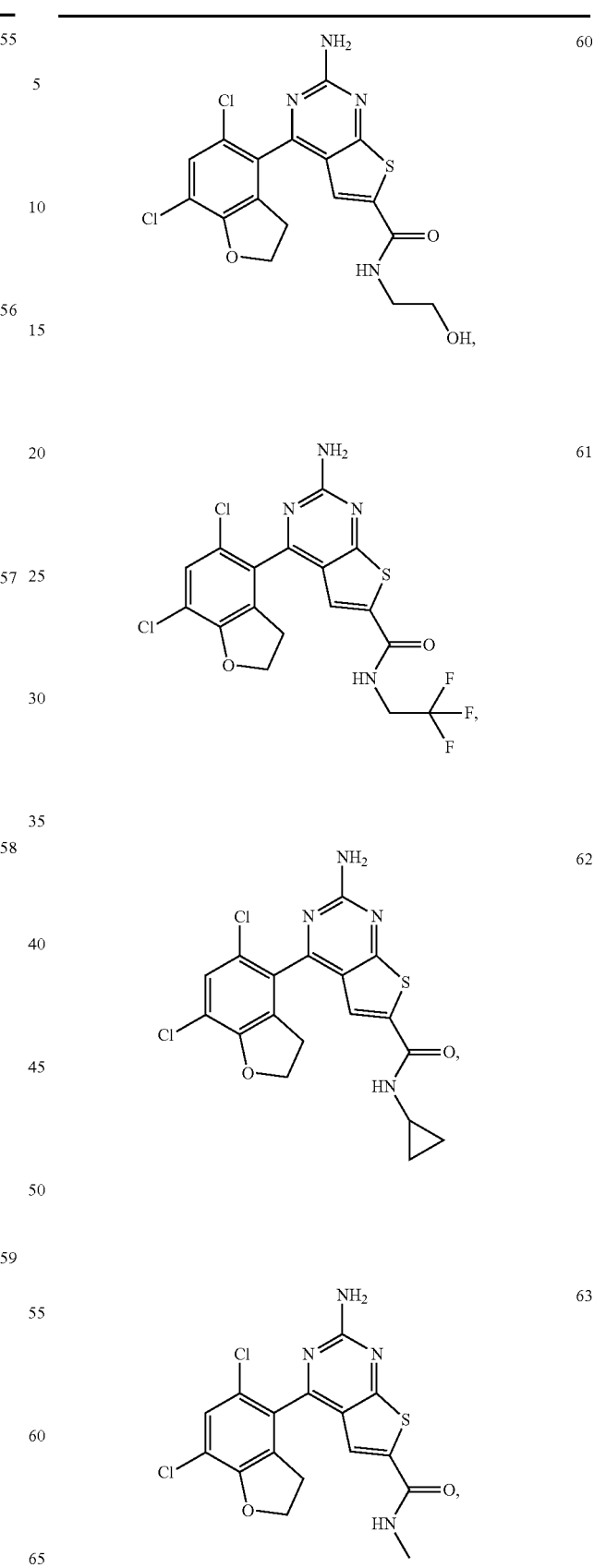

TABLE 2-continued
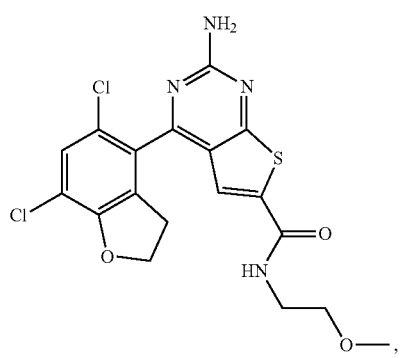
64
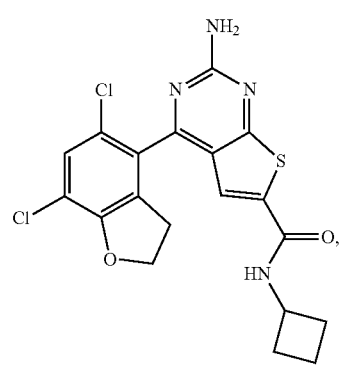
65
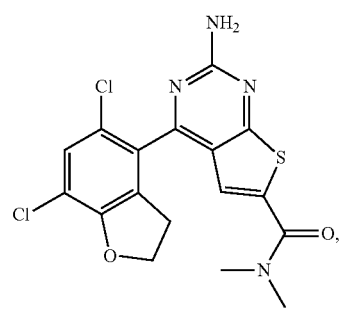 [SMILES: CN(C)C(=O)c1cc2c(-c3c(Cl)cc(Cl)c4c3CCO4)nc(N)nc2s1]
66
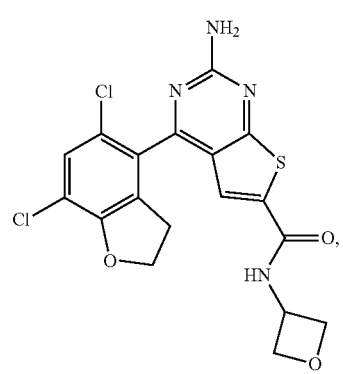 [SMILES: Nc1nc(-c2c(Cl)cc(Cl)c3c2CCO3)c2cc(C(=O)NC3COC3)sc2n1]
67
TABLE 2-continued
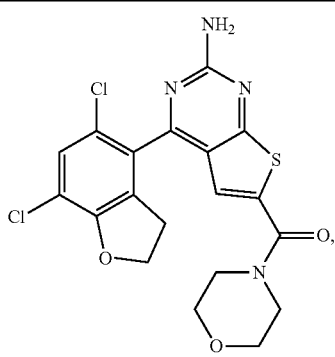
68
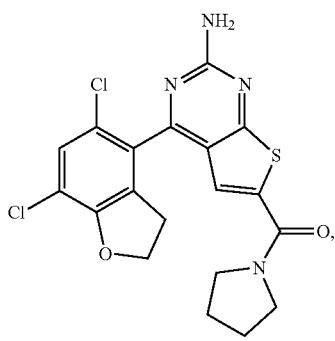 [SMILES: Nc1nc(-c2c(Cl)cc(Cl)c3c2CCO3)c2cc(C(=O)N3CCCC3)sc2n1]
69
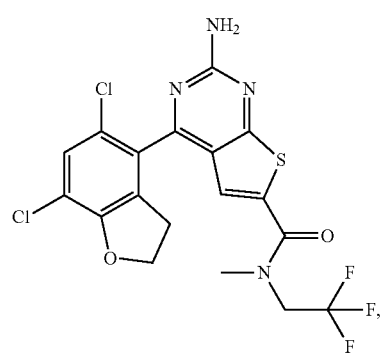 [SMILES: CN(CC(F)(F)F)C(=O)c1cc2c(-c3c(Cl)cc(Cl)c4c3CCO4)nc(N)nc2s1]
70
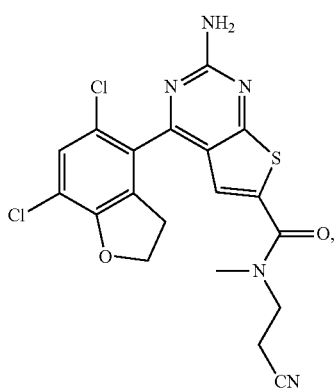 [SMILES: CN(CCC#N)C(=O)c1cc2c(-c3c(Cl)cc(Cl)c4c3CCO4)nc(N)nc2s1]
71

TABLE 2-continued
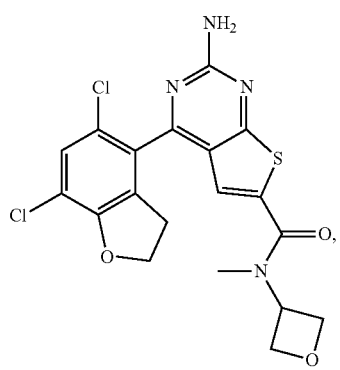
72
73
74
75
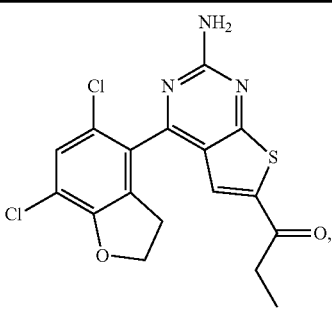
76
77
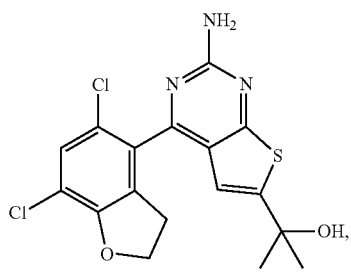 [SMILES: CC(C)(O)c1cc2c(-c3c(Cl)cc(Cl)c4c3CCO4)nc(N)nc2s1]
78
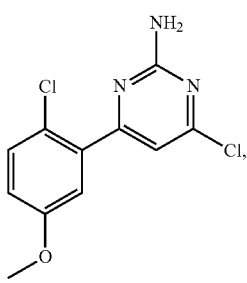 [SMILES: COc1ccc(Cl)c(-c2cc(Cl)nc(N)n2)c1]
79
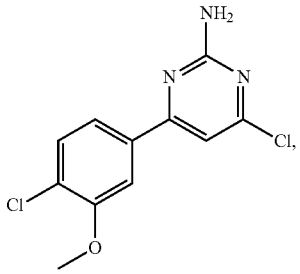 [SMILES: COc1cc(-c2cc(Cl)nc(N)n2)ccc1Cl]
or a pharmaceutically acceptable salt thereof.
A non-limiting example of a pharmaceutically acceptable salt of a compound of the invention is:
16-HCl
Exemplary methods for synthesizing compounds of the invention are described herein.

Methods of Preparing Compounds of the Invention

The compounds of the invention can be prepared by processes analogous to those established in the art, for example, by the reaction sequence shown in Scheme 1. The numbering system used for the general schemes does not necessarily correspond to that employed elsewhere in the description or in the claims.

As shown in Scheme 1, one strategy to access compounds of the invention (C) is to utilize standard cross-coupling reactions (e.g., Suzuki coupling, Hiyama coupling, Stille coupling, Negishi coupling, Tamao-Kumada coupling, or Murahashi coupling), where a nucleophile A and an electrophile B are coupled in the presence of a metal salt, e.g., a palladium, copper, iron, or nickel salt (e.g., $PdCl_2$, $Pd(OAc)_2$, CuBr, CuI, $(CuOTf)_2$.toluene complex, $Fe(OTf)_3$, $FeCl_3$, $FeBr_3$, $NiCl_2$, or $NiBr_2$). Optionally ligands, e.g., a phosphine (e.g., $PPh_3$, $P(2\text{-furyl})_3$, $P(t\text{-Bu})_3$, dppf, dppb, or BINAP), an N-heterocyclic carbene (e.g., SIMes or SIPr), or di-pyridine (e.g., 2,2'-bipyridyl or 1,10-phenanthroline), may be added to promote the reaction. Alternatively, an organometallic complex, e.g., $Pd(PPh_3)_4$ or $(dppf)PdCl_2$, may be employed directly with or without additional ligands. Additives, e.g., tetrabutylammonium fluoride, LiCl, KOAc, or AgOTf, may be added to minimize dehalogenation or to facilitate the cross-coupling reaction. One of skill in the art would be able to determine an appropriate solvent for the reaction through standard screening. Non-limiting examples of solvents used in cross-coupling reactions are water, ethanol, acetone, tetrahydrofuran, toluene, 1,4-dioxane, and mixtures thereof. For non-limiting examples of conditions and catalysts that can be used to prepare a compound of the invention according to formula C using cross-coupling chemistry, see Miyaura et al., "Cross-Coupling Reactions: A Practical Guide" in *Topics in Current Chemistry*, Springer, 2002, and Nicolaou et al., *Angew. Chem. Int. Ed.*, 44:4442-4489, 2005, which are incorporated herein by reference. Alternatively, a compound of formula A may be an electrophile and have a leaving group X instead of M, while compound of formula B may be a nucleophile and have a metal or metalloid group M instead of X.

Scheme 1.

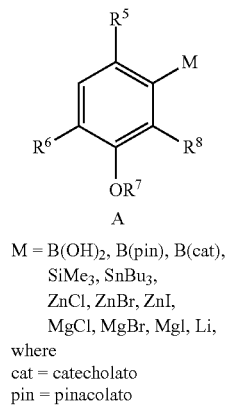

M = $B(OH)_2$, B(pin), B(cat),
SiMe₃, SnBu₃,
ZnCl, ZnBr, ZnI,
MgCl, MgBr, MgI, Li,
where
cat = catecholato
pin = pinacolato

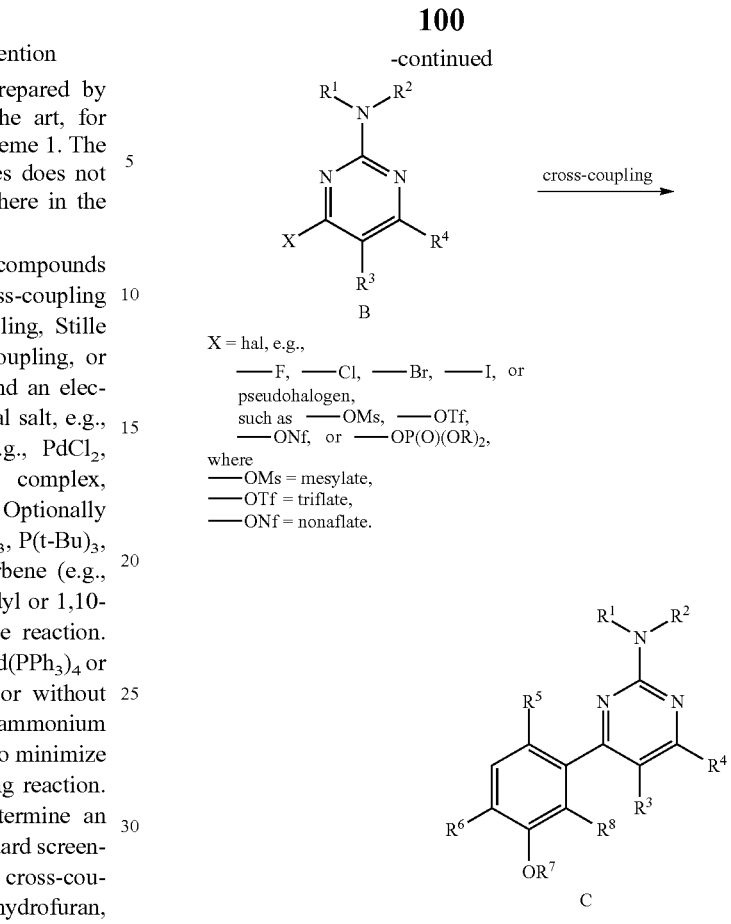

X = hal, e.g.,
—F, —Cl, —Br, —I, or pseudohalogen,
such as —OMs, —OTf,
—ONf, or —OP(O)(OR)₂,
where
—OMs = mesylate,
—OTf = triflate,
—ONf = nonaflate.

A compound of formula A may be prepared according any method known in the art, e.g., metal-halogen (e.g., lithium-halogen) exchange (with or without a subsequent addition of boron-based, silicon-based, tin-based, zinc-based, or magnesium-based agents), preparation of Grignard reagent, Sandmeyer reaction, or cross-coupling with di-metalloid agent (e.g., Miyaura borylation reaction). Non-limiting examples of preparation of A (Sandmeyer reaction and lithium halogen exchange to prepare E, and Miyaura borylation reaction to prepare G) are shown in Scheme 2.

Scheme 2. Preparation of nucleophile A, e.g., E or G

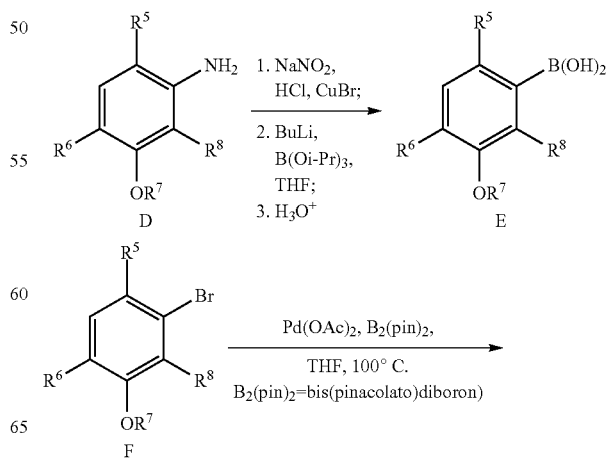

-continued

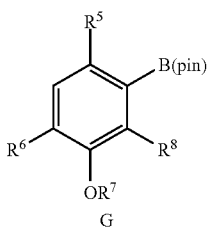

A compound of formula B may be prepared according to any method known in the art, e.g., Biginelli reaction followed by oxidation of the resulting 2-aminodihydropyrimidine derivative. Alternatively, a synthetic approach outlines in Scheme 3 can be used to access a compound of formula B.

Scheme 3. Preparation of electrophile B, e.g., an N-protected B, i.e. L

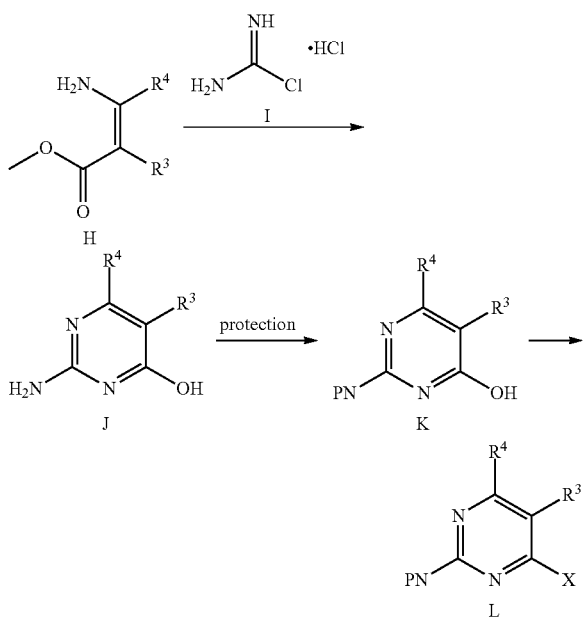

As shown in Scheme 3, a compound of formula H may undergo condensation with a compound of formula I to give a compound of formula J. The amino group of 2-aminopyrimidine derivative J may then be protected (P=a divalent N-protecting group, two monovalent N-protecting groups, or one monovalent N-protecting group and one hydrogen) to furnish a compound of formula K. The hydroxyl group in the compound of formula K may then be converted to a halogen in the compound of formula L according to any method known in the art, e.g., using dehydrating-halogenating reagents (e.g., $POCl_3$, $PCl_5$, $SOCl_2$, $SO_2Cl_2$, and brominating or iodinating variants thereof). Alternatively, the hydroxyl group of the compound of formula K may be converted into a pseudohalogen in the compound of formula L using reagents, e.g., $Tf_2O$, $PhNTf_2$, $PhNNf_2$, or $P(O)(OR)_2Cl$, and, optionally, a base (e.g., $Et_3N$, $(iPr)_2NEt$, or pyridine) and/or catalyst (e.g., 4-dimethylaminopyridine). N-protecting group P may be removed from the compound L before or after the cross coupling shown in Scheme 1 according to methods known in the art (see, e.g., Greene, *Protective Groups in Organic Synthesis*, 3$^{rd}$ Edition (John Wiley & Sons, New York, 1999)).

In the reactions described above, it may be necessary to protect reactive functional groups (e.g., hydroxy, amino, thio, or carboxy groups) to avoid their unwanted participation in the reactions. The incorporation of such groups, and the methods required to introduce and remove them are known to those skilled in the art (for example, Greene, supra). The deprotection step may be the final step in the synthesis such that the removal of protecting groups affords compounds of formula (Ia) as disclosed herein. Starting materials used in any of the schemes above can be purchased or prepared by methods described in the chemical literature, or by adaptations thereof, using methods known by those skilled in the art. The order in which the steps are performed can vary depending on the groups introduced and the reagents used, but would be apparent to those skilled in the art.

Compounds of any of formula (I), (Ia), (Ib), (Va), or (Vb), or any of the intermediates described in the schemes above, can be further derivatized by using one or more standard synthetic methods known to those skilled in the art. Such methods can involve substitution, oxidation or reduction reactions. These methods can also be used to obtain or modify compounds of formula (I), (Ia), (Ib), (Va), or (Vb), or any preceding intermediates by modifying, introducing or removing appropriate functional groups. Particular substitution approaches include alkylation, arylation, heteroarylation, acylation, thioacylation, halogenation, sulphonylation, nitration, formylation, hydrolysis, and coupling procedures. These procedures can be used to introduce a functional group onto the parent molecule (e.g., the nitration or sulphonylation of aromatic rings) or to couple two molecules together (for example to couple an amine to a carboxylic acid to afford an amide; or to form a carbon-carbon bond between two heterocycles). For example, alcohol or phenol groups can be converted to ether groups by coupling a phenol with an alcohol in a solvent, e.g., tetrahydrofuran in the presence of a phosphine (e.g., triphenylphosphine) and a dehydrating agent (e.g., diethyl-, diisopropyl-, or dimethylazodicarboxylate). Alternatively, ether groups can be prepared by deprotonation of an alcohol, using a suitable base (e.g., sodium hydride) followed by the addition of an alkylating agent (e.g., an alkyl halide or an alkylsulphonate).

In another example, a primary or secondary amine can be alkylated using a reductive alkylation process. For example, the amine can be treated with an aldehyde and a borohydride (e.g., sodium triacetoxyborohydride, or sodium cyanoborohydride) in a solvent (e.g., a halogenated hydrocarbon, for example, dichloromethane, or an alcohol, for example, ethanol) and, where necessary, in the presence of an acid (e.g., acetic acid).

In another example, —OH groups may be generated from the corresponding ester, acid, acid chloride or aldehyde by reduction with a suitable reducing agent, e.g., a complex metal hydride, e.g., lithium aluminium hydride in a solvent (e.g., tetrahydrofuran).

In another example, hydroxy groups (including phenolic OH groups) can be converted into leaving groups, e.g., halogen atoms or sulphonyloxy groups (e.g., alkylsulphonyloxy, e.g., trifluoromethylsulphonyloxy, or arylsuphonyl, e.g., p-toluenesulphonyloxy) using conditions known to those skilled in the art. For example, an aliphatic alcohol can be reacted with thionyl chloride in a halogenated hydrocarbon (e.g., dichloromethane) to afford the corresponding alkylchloride. A base (e.g., triethylamine) can also be used in the reaction.

In another example, ester groups can be converted to the corresponding carboxylic acid by acid- or base-catalysed hydrolysis depending on the nature of the ester group. Acid catalysed hydrolysis can be achieved by treatment with an organic or inorganic acid (e.g., trifluoroacetic acid in an aqueous solvent, or a mineral acid, e.g., hydrochloric acid in a solvent, e.g., dioxan). Base catalysed hydrolysis can be achieved by treatment with an alkali metal hydroxide (e.g., lithium hydroxide in an aqueous alcohol, e.g., methanol).

In another example, aromatic halogen substituents in the compounds may be subjected to halogen-metal exchange by treatment with a base (e.g., a lithium base, e.g., n-butyl or t-butyl lithium) optionally at a low temperature (e.g., −78° C.) in a solvent (e.g., tetrahydrofuran) and the mixture may then quenched with an electrophile to introduce a desired substituent. Thus, for example, a formyl group can be introduced by using dimethylformamide as the electrophile. Aromatic halogen substituents can also be subjected to palladium catalysed reactions to introduce groups, e.g., carboxylic acids, esters, cyano, or amino substituents.

In another example, aromatic halogen substituents in the compounds may participate in a range of metal catalysed reactions to introduce alternative functional groups, e.g., amines, amides, ethers, thiols, aryl groups, or heteroaryl groups.

Particular oxidation approaches include dehydrogenations and aromatisation, and the addition of oxygen to certain functional groups. For example, aldehyde groups can be prepared by oxidation of the corresponding alcohol using conditions well known to those skilled in the art. For example, an alcohol can be treated with an oxidising agent (e.g., the Dess-Martin reagent) in a solvent (e.g., a halogenated hydrocarbon, for example dichloromethane). Alternative oxidising conditions can be used, e.g., treatment with oxalyl chloride and an activating amount of dimethylsulphoxide and subsequent quenching by the addition of an amine (e.g., triethylamine). Such a reaction can be carried out in an appropriate solvent (e.g., a halogenated hydrocarbon, for example dichloromethane) and under appropriate conditions (e.g., cooling below room temperature, e.g., to −78° C. followed by warming to room temperature). In another example, sulphur atoms can be oxidised to the corresponding sulphoxide or sulphone using an oxidising agent (e.g., a peroxy acid, e.g., 3-chloroperoxybenzoic acid) in an inert solvent (e.g., a halogenated hydrocarbon, e.g., dichloromethane) at around ambient temperature.

Particular reduction approaches include the removal of oxygen atoms from particular functional groups, saturation (or partial saturation) of unsaturated compounds including aromatic rings. For example, primary alcohols can be generated from the corresponding ester or aldehyde by reduction, using a metal hydride (e.g., lithium aluminium hydride or sodium borohydride in a solvent, e.g., methanol). Alternatively, —OH groups can be generated from the corresponding carboxylic acid by reduction, using a metal hydride (e.g., lithium aluminium hydride in a solvent, e.g., tetrahydrofuran). In another example, a nitro group may be reduced to an amine by catalytic hydrogenation in the presence of a metal catalyst (e.g., palladium on a solid support, e.g., carbon) in a solvent (e.g., an ether, e.g., tetrahydrofuran, or an alcohol, e.g., methanol), or by chemical reduction using a metal (e.g., tin or iron) in the presence of an acid (e.g., hydrochloric acid). In a further example an amine can be obtained by reduction of a nitrile, e.g., by catalytic hydrogenation in the presence of a metal catalyst (e.g., palladium on a solid support, e.g., carbon), or Raney nickel in a solvent (e.g., tetrahydrofuran) and under suitable conditions (e.g., cooling to below room temperature, e.g., to −78° C., or heating, e.g., to reflux).

Pharmaceutical Compositions

The compounds used in the methods described herein are preferably formulated into pharmaceutical compositions for administration to human subjects in a biologically compatible form suitable for administration in vivo. Pharmaceutical compositions typically include a compound as described herein and a pharmaceutically acceptable excipient.

The compounds described herein can also be used in the form of the free base, in the form of salts, zwitterions, solvates, or as prodrugs, or pharmaceutical compositions thereof. All forms are within the scope of the invention. The compounds, salts, zwitterions, solvates, prodrugs, or pharmaceutical compositions thereof, may be administered to a patient in a variety of forms depending on the selected route of administration, as will be understood by those skilled in the art. The compounds used in the methods described herein may be administered, for example, by oral, parenteral, buccal, sublingual, nasal, rectal, patch, pump, or transdermal administration, and the pharmaceutical compositions formulated accordingly. Parenteral administration includes intravenous, intraperitoneal, subcutaneous, intramuscular, transepithelial, nasal, intrapulmonary, intrathecal, rectal, and topical modes of administration. Parenteral administration may be by continuous infusion over a selected period of time.

For human use, a compound of the invention can be administered alone or in admixture with a pharmaceutical carrier selected with regard to the intended route of administration and standard pharmaceutical practice. Pharmaceutical compositions for use in accordance with the present invention thus can be formulated in a conventional manner using one or more physiologically acceptable carriers comprising excipients and auxiliaries that facilitate processing of compounds of Formula (I), (Ia), (Ib), (Va), or (Vb) into preparations which can be used pharmaceutically.

This invention also includes pharmaceutical compositions which can contain one or more pharmaceutically acceptable carriers. In making the pharmaceutical compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semisolid, or liquid material (e.g., normal saline), which acts as a vehicle, carrier or medium for the active ingredient. Thus, the compositions can be in the form of tablets, powders, lozenges, sachets, cachets, elixirs, suspensions, emulsions, solutions, syrups, and soft and hard gelatin capsules. As is known in the art, the type of diluent can vary depending upon the intended route of administration. The resulting compositions can include additional agents, e.g., preservatives.

The excipient or carrier is selected on the basis of the mode and route of administration. Suitable pharmaceutical carriers, as well as pharmaceutical necessities for use in pharmaceutical formulations, are described in *Remington: The Science and Practice of Pharmacy,* 21$^{st}$ Ed., Gennaro, Ed., Lippencott Williams & Wilkins (2005), a well-known reference text in this field, and in the USP/NF (United States Pharmacopeia and the National Formulary). Examples of suitable excipients are lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents, e.g., talc, magnesium stearate, and mineral oil; wetting agents; emulsifying and suspending agents; preserving agents, e.g., methyl- and propylhydroxy-benzoates; sweetening agents; and flavoring agents. Other exemplary excipients are described in *Handbook of Pharmaceutical Excipients*, $6^{th}$ Edition, Rowe et al., Eds., Pharmaceutical Press (2009).

These pharmaceutical compositions can be manufactured in a conventional manner, e.g., by conventional mixing, dissolving, granulating, dragee-making, levigating, emulsifying, encapsulating, entrapping, or lyophilizing processes. Methods well known in the art for making formulations are found, for example, in *Remington: The Science and Practice of Pharmacy*, $21^{st}$ Ed., Gennaro, Ed., Lippencott Williams & Wilkins (2005), and Encyclopedia of Pharmaceutical Technology, eds. J. Swarbrick and J. C. Boylan, 1988-1999, Marcel Dekker, New York. Proper formulation is dependent upon the route of administration chosen. The formulation and preparation of such compositions is well-known to those skilled in the art of pharmaceutical formulation. In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

Dosages

The dosage of the compound used in the methods described herein, or pharmaceutically acceptable salts or prodrugs thereof, or pharmaceutical compositions thereof, can vary depending on many factors, e.g., the pharmacodynamic properties of the compound; the mode of administration; the age, health, and weight of the recipient; the nature and extent of the symptoms; the frequency of the treatment, and the type of concurrent treatment, if any; and the clearance rate of the compound in the animal to be treated. One of skill in the art can determine the appropriate dosage based on the above factors. The compounds used in the methods described herein may be administered initially in a suitable dosage that may be adjusted as required, depending on the clinical response. In general, a suitable daily dose of a compound of the invention will be that amount of the compound that is the lowest dose effective to produce a therapeutic effect. Such an effective dose will generally depend upon the factors described above.

A compound of the invention may be administered to the patient in a single dose or in multiple doses. When multiple doses are administered, the doses may be separated from one another by, for example, 1-24 hours, 1-7 days, 1-4 weeks, or 1-12 months. The compound may be administered according to a schedule or the compound may be administered without a predetermined schedule. An active compound may be administered, for example, 1, 2, 3, 4, 5, 6, 7, 8, 9, 10, 11, or 12 times per day, every $2^{nd}$, $3^{rd}$, $4^{th}$, $5^{th}$, or $6^{th}$ day, 1, 2, 3, 4, 5, 6, or 7 times per week, 1, 2, 3, 4, 5, or 6 times per month, or 1, 2, 3, 4, 5, 6, 7, 8, 9, 10, 11, or 12 times per year. It is to be understood that, for any particular subject, specific dosage regimes should be adjusted over time according to the individual need and the professional judgment of the person administering or supervising the administration of the compositions.

While the attending physician ultimately will decide the appropriate amount and dosage regimen, an effective amount of a compound of the invention may be, for example, a total daily dosage of, e.g., between 0.05 mg and 3000 mg of any of the compounds described herein. Alternatively, the dosage amount can be calculated using the body weight of the patient. Such dose ranges may include, for example, between 10-1000 mg (e.g., 50-800 mg). In some embodiments, 50, 100, 150, 200, 250, 300, 350, 400, 450, 500, 550, 600, 650, 700, 750, 800, 850, 900, 950, or 1000 mg of the compound is administered.

In the methods of the invention, the time period during which multiple doses of a compound of the invention are administered to a patient can vary. For example, in some embodiments doses of the compounds of the invention are administered to a patient over a time period that is 1-7 days; 1-12 weeks; or 1-3 months. In other embodiments, the compounds are administered to the patient over a time period that is, for example, 4-11 months or 1-30 years. In other embodiments, the compounds are administered to a patient at the onset of symptoms. In any of these embodiments, the amount of compound that is administered may vary during the time period of administration. When a compound is administered daily, administration may occur, for example, 1, 2, 3, 4, 5, 6, 7, 8, 9, 10, 11, or 12 times per day.

Formulations

A compound identified as capable of treating any of the conditions described herein, using any of the methods described herein, may be administered to patients or animals with a pharmaceutically-acceptable diluent, carrier, or excipient, in unit dosage form. The chemical compounds for use in such therapies may be produced and isolated by any standard technique known to those in the field of medicinal chemistry. Conventional pharmaceutical practice may be employed to provide suitable formulations or compositions to administer the identified compound to patients suffering from a disease in which necrosis occurs. Administration may begin before the patient is symptomatic.

Exemplary routes of administration of the compounds (e.g., the compounds having Formula (I), (Ia), (Ib), (Va) or (Vb)), or pharmaceutical compositions thereof, used in the present invention include oral, sublingual, buccal, transdermal, intradermal, intramuscular, parenteral, intravenous, intra-arterial, intracranial, subcutaneous, intraorbital, intraventricular, intraspinal, intraperitoneal, intranasal, inhalation, and topical administration. The compounds desirably are administered with a pharmaceutically acceptable carrier. Pharmaceutical formulations of the compounds described herein formulated for treatment of the disorders described herein are also part of the present invention.

Formulations for Oral Administration

The pharmaceutical compositions contemplated by the invention include those formulated for oral administration ("oral dosage forms"). Oral dosage forms can be, for example, in the form of tablets, capsules, a liquid solution or suspension, a powder, or liquid or solid crystals, which contain the active ingredient(s) in a mixture with non-toxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

Formulations for oral administration may also be presented as chewable tablets, as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders, granulates, and pellets may be prepared using the ingredients mentioned above under tablets and capsules in a conventional manner using, e.g., a mixer, a fluid bed apparatus or a spray drying equipment.

Controlled release compositions for oral use may be constructed to release the active drug by controlling the dissolution and/or the diffusion of the active drug substance. Any of a number of strategies can be pursued in order to obtain controlled release and the targeted plasma concentration versus time profile. In one example, controlled release is obtained by appropriate selection of various formulation parameters and ingredients, including, e.g., various types of controlled release compositions and coatings. Examples include single or multiple unit tablet or capsule compositions, oil solutions, suspensions, emulsions, microcapsules, microspheres, nanoparticles, patches, and liposomes. In certain embodiments, compositions include biodegradable, pH, and/or temperature-sensitive polymer coatings.

Dissolution or diffusion controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

The liquid forms in which the compounds and compositions of the present invention can be incorporated for administration orally include aqueous solutions, suitably flavored syrups, aqueous or oil suspensions, and flavored emulsions with edible oils, e.g., cottonseed oil, sesame oil, coconut oil, or peanut oil, as well as elixirs and similar pharmaceutical vehicles.

Formulations for Buccal Administration

Dosages for buccal or sublingual administration typically are 0.1 to 500 mg per single dose as required. In practice, the physician determines the actual dosing regimen which is most suitable for an individual patient, and the dosage varies with the age, weight, and response of the particular patient. The above dosages are exemplary of the average case, but individual instances exist wherein higher or lower dosages are merited, and such are within the scope of this invention.

For buccal administration, the compositions may take the form of tablets, lozenges, etc. formulated in a conventional manner. Liquid drug formulations suitable for use with nebulizers and liquid spray devices and electrohydrodynamic (EHD) aerosol devices will typically include a compound of the invention with a pharmaceutically acceptable carrier. Preferably, the pharmaceutically acceptable carrier is a liquid, e.g., alcohol, water, polyethylene glycol, or a perfluorocarbon. Optionally, another material may be added to alter the aerosol properties of the solution or suspension of compounds of the invention. Desirably, this material is liquid, e.g., an alcohol, glycol, polyglycol, or a fatty acid. Other methods of formulating liquid drug solutions or suspension suitable for use in aerosol devices are known to those of skill in the art (see, e.g., Biesalski, U.S. Pat. No. 5,112,598 and Biesalski, U.S. Pat. No. 5,556,611, each of which is herein incorporated by reference).

Formulations for Nasal or Inhalation Administration

The compounds may also be formulated for nasal administration. Compositions for nasal administration also may conveniently be formulated as aerosols, drops, gels, and powders. The formulations may be provided in a single or multidose form. In the case of a dropper or pipette, dosing may be achieved by the patient administering an appropriate, predetermined volume of the solution or suspension. In the case of a spray, this may be achieved, for example, by means of a metering atomizing spray pump.

The compounds may further be formulated for aerosol administration, particularly to the respiratory tract by inhalation and including intranasal administration. The compound will generally have a small particle size for example on the order of five (5) microns or less. Such a particle size may be obtained by means known in the art, for example by micronization. The active ingredient is provided in a pressurized pack with a suitable propellant, e.g., a chlorofluorocarbon (CFC), for example, dichlorodifluoromethane, trichlorofluoromethane, or dichlorotetrafluoroethane, or carbon dioxide, or other suitable gas. The aerosol may conveniently also contain a surfactant, e.g., lecithin. The dose of drug may be controlled by a metered valve. Alternatively, the active ingredients may be provided in a form of a dry powder, e.g., a powder mix of the compound in a suitable powder base, e.g., lactose, starch, and starch derivatives, e.g., hydroxypropylmethyl cellulose, and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

Aerosol formulations typically include a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device, e.g., a single dose nasal inhaler or an aerosol dispenser fitted with a metering valve which is intended for disposal after use. Where the dosage form comprises an aerosol dispenser, it will contain a propellant, which can be a compressed gas, e.g., compressed air or an organic propellant, e.g., fluorochlorohydrocarbon. The aerosol dosage forms can also take the form of a pump-atomizer.

Formulations for Parenteral Administration

The compounds described herein for use in the methods of the invention can be administered in a pharmaceutically acceptable parenteral (e.g., intravenous or intramuscular)

formulation as described herein. The pharmaceutical formulation may also be administered parenterally (intravenous, intramuscular, subcutaneous or the like) in dosage forms or formulations containing conventional, non-toxic pharmaceutically acceptable carriers and adjuvants. In particular, formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. For example, to prepare such a composition, the compounds of the invention may be dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution and isotonic sodium chloride solution. The aqueous formulation may also contain one or more preservatives, for example, methyl, ethyl or n-propyl p-hydroxybenzoate. Additional information regarding parenteral formulations can be found, for example, in the United States Pharmacopeia-National Formulary (USP-NF), herein incorporated by reference.

The parenteral formulation can be any of the five general types of preparations identified by the USP-NF as suitable for parenteral administration:

(1) "Drug Injection:" a liquid preparation that is a drug substance (e.g., a compound of Formula (I), (Ia), (Ib), (Va) or (Vb)), or a solution thereof;

(2) "Drug for Injection:" the drug substance (e.g., a compound of Formula (I), (Ia), (Ib), (Va) or (Vb)) as a dry solid that will be combined with the appropriate sterile vehicle for parenteral administration as a drug injection;

(3) "Drug Injectable Emulsion:" a liquid preparation of the drug substance (e.g., a compound of Formula (I), (Ia), (Ib), (Va) or (Vb)) that is dissolved or dispersed in a suitable emulsion medium;

(4) "Drug Injectable Suspension:" a liquid preparation of the drug substance (e.g., a compound of Formula (I), (Ia), (Ib), (Va) or (Vb)) suspended in a suitable liquid medium; and (5) "Drug for Injectable Suspension:" the drug substance (e.g., a compound of Formula (I), (Ia), (Ib), (Va) or (Vb)) as a dry solid that will be combined with the appropriate sterile vehicle for parenteral administration as a drug injectable suspension.

Exemplary formulations for parenteral administration include solutions of the compound prepared in water suitably mixed with a surfactant, e.g., hydroxypropylcellulose. Dispersions can also be prepared in glycerol, liquid polyethylene glycols, DMSO and mixtures thereof with or without alcohol, and in oils. Under ordinary conditions of storage and use, these preparations may contain a preservative to prevent the growth of microorganisms. Conventional procedures and ingredients for the selection and preparation of suitable formulations are described, for example, in *Remington: The Science and Practice of Pharmacy*, 21$^{st}$ Ed., Gennaro, Ed., Lippencott Williams & Wilkins (2005) and in The United States Pharmacopeia: The National Formulary (USP 36 NF31), published in 2013.

Formulations for parenteral administration may, for example, contain excipients, sterile water, or saline, polyalkylene glycols, e.g., polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

The parenteral formulation can be formulated for prompt release or for sustained/extended release of the compound. Exemplary formulations for parenteral release of the compound include: aqueous solutions, powders for reconstitution, cosolvent solutions, oil/water emulsions, suspensions, oil-based solutions, liposomes, microspheres, and polymeric gels.

Methods of Treatment

The compounds and compositions described herein can be used in the treatment of conditions and disorders in which Hsp90 has been implicated, e.g., cell proliferative disorders, e.g., cancers, neurodegenerative diseases, e.g., tauopathies (e.g., Alzheimer's disease), and infectious diseases.

Cell Proliferative Disorders

Hsp90 has emerged as a key therapeutic target for cancer therapy due to the involvement of this multichaperone complex in various pathogenic cellular processes. Hsp90 client proteins include those implicated in: acute myeloid leukemia (Flt-3), breast cancer (HER2), chronic lymphoid leukemia (Zap70), chronic myeloid leukemia (Bcr-Abl or mBcr-Abl), gastrointestinal stromal tumor (c-Kit), gastric cancer (c-Met), glioblastoma (mutant EGFR or c-Met), lung cancer (c-Met), lymphoma (NMP-ALK), melanoma (Raf-1/mutant BRAF), myeloma (IGF-1R/Akt), non-small cell lung cancer (mutant EGFR), renal cancer, (HIF-la), and small cell lung cancer (Akt). The compounds of the invention are particularly useful in the treatment of brain tumors due to their blood-brain-barrier penetrant properties. Brain tumors that may be treated using compounds of the invention include glioma or meningioma, in particular, glioma (e.g., glioblastoma) or neuroblastoma. The brain tumors (e.g., brain cancers) that may be treated using compounds of the invention according to the methods of the invention may include primary tumors (those tumors that originated in the brain) and metastatic tumors (those tumors that originated in tissues other than brain tissues and spread to the brain). Still other cell proliferative disorders that may be treated by the inhibition of Hsp90 include: blast-phase chronic myelogenous leukemia, leukemia, lymphoproliferative disorder, metastatic melanoma, multiple myeloma (e.g., relapsed or refractory multiple myeloma), myeloproliferative disorders, pancreatic cancer, small intestine cancer, and solid tumor. Moreover, cancer cells have been shown to be more sensitive to Hsp90 inhibition than non-pathogenic cells. Accordingly, the compounds described herein may be useful treatments for cell proliferative disorders.

Neurodegenerative Diseases

Increased levels of Hsp90 have been implicated in neurodegenerative disorders. For example, aberrant Hsp90 activity has been shown in tauopathies, which are conditions characterized by accumulation of abnormal Tauproteins (e.g., hyperphosphorylated and aggregated Tau). Accordingly, compounds and compositions described herein can be useful for the treatment of neurodegenerative diseases and tauopathies that include Alzheimer's disease (AD), argyrophilic grain disease, amyotrophic lateral sclerosis, corticobasal degeneration, dementia pugislistica, Down's syndrome, familial British dementia, frontal lobe degeneration (dementia lacking distinctive histopathological features), chronic traumatic encephalopathy, traumatic brain injury, frontotemporal dementia (FTD; e.g., fronto-temporal dementia with parkinsonism linked to chromosome 17 (FTDP-17)), hippocampal tauopathy in cerebral aging, myotonic dystrophy of type I, Niemann-Pick disease of type C, Parkinson's disease (e.g., parkinsonism-dementia complex of Guam, Parkinsonism with dementia of Guadeloupe, or postencephalitic parkinsonism), Pick's disease (PiD), and progressive supranuclear palsy. Accordingly, the compounds described herein may be useful in treating a neurodegenerative disorder, e.g., tauopathy (e.g., Alzheimer's disease).

Infectious Diseases

Hsp90 has emerged as a therapeutic target for treating infectious diseases, e.g., viral infections, fungal infections, and bacterial infections. Many pathogens (e.g., viruses, fungi, and bacteria) rely on Hsp90-dependent processes (see, e.g., Geller et al., *Biochim. Biophys. Acta—Mol. Cell Res.*, 1823:698-706, 2012; the disclosure of which is incorporate herein in its entirety). Thus, inhibition of Hsp90 provides a therapeutic benefit to a patient afflicted with an infection that relies on the activity of Hsp90. For example, an Hsp90 inhibitor (geldanamycin) was shown to delay the growth of influenza virus in cell culture. Other viruses that rely on Hsp90 dependent processes include those belonging to the families: Herpesviridae (e.g., herpes simplex virus-1, herpes simplex virus-2, herpes herpesvirus-5, Kaposi's sarcoma-associated herpesvirus, varicella zoster virus, or Epstein-Barr virus), Polyomaviridae (e.g., SV40), Poxviridae (e.g., vaccinia virus), Reoviridae (e.g., rotavirus), Birnaviridae (e.g., infectious bursal disease virus), Picornaviridae (e.g., poliovirus, rhinovirus, or coxsackievirus), Flaviviridae (e.g., hepatitis C virus or dengue virus), Arenaviridae (e.g., lymphocytic choriomeningitis virus), Hepeviridae (e.g., Hepatitis E virus), Rhabdoviridae (e.g., vesicular stomatitis virus), Paramoxyviridae (e.g., human parainfluenza virus 2, human parainfluenza virus 3, SV5, SV41, measles virus, or Sendai virus), Bunyaviridae (e.g., La Crosse virus), Orthomoxyviridae (e.g., influenza A virus), Filoviridae (e.g., Ebola virus), Retroviridae (e.g., HTLV1 or HIV1), and Hepadnaviridae (e.g., hepatitis B virus). Hsp90 inhibitors have also been used in vivo for the treatment of fungal infectious diseases, e.g., treatment of *Candida albicans, Aspergillus fumigates*, or *Pneumocystis jiroveci*. Moreover, Hsp90 inhibitors are also useful in the treatment of bacterial infections, e.g., mycobacteria, anthrax, or bacterial pneumonia. A discussion of the diseases that may be treated with Hsp90 inhibitors is provided in the U.S. Patent Application Publication 2011/0201587, the disclosure of which is incorporated herein by reference in its entirety. Therefore, the compounds of the invention may be used according to the method of the invention to treat infectious diseases, e.g., viral infections, fungal infections, or bacterial infections.

Inflammatory and Autoimmune Diseases, Allergy

Hsp90 has been shown to play a role in antigen presentation, activation of lymphocytes, macrophages, maturation of dendritic cells, and in the enhanceosome mediated induction of inflammation. Hsp90 inhibition is associated with blockage of components of inflammation, e.g., reduction of cytokine and NO production, as well as blockage of NFκB nuclear translocation. Further, considerable body of work indicates that chaperones, such as Hsp90, may be capable of inducing the production of proinflammatory cytokines by the monocyte-macrophage system and the activation and maturation of dendritic cells via the TLR2- and 4-signal transduction pathways. Thus, Hsp90 apparently can function as a potent activator of the innate immune system. Indeed, elevated levels of Hsp90 were detected in the serum of systemic lupus erythematosus patients. Autoantibodies and cells reactive to Hsp have been detected in patients with rheumatoid arthritis. Antiinflammatory effect of inhibiting Hsp90 was also observed to reduce airway inflammation in murine model of asthma. The compounds of the invention may be applicable to the treatment of inflammatory or autoimmune diseases in a patient. Moreover, anti-inflammatory effect of Hsp90 inhibition can have therapeutic application in the treatment of allergies. Thus, the compounds of the invention may be used in the treatment of allergy.

Cardiovascular Diseases

Hsp90 has recently been implicated in etiology of cardiovascular disorders, such as atherosclerosis and cardiomyopathy. Thus, the compounds of the present invention may be applicable to the treatment of cardiovascular diseases (e.g., atherosclerosis or cardiomyopathy).

Kits of the Invention

The present invention also provides kits containing (i) a pharmaceutical composition of the invention, and (ii) instructions for use of the pharmaceutical composition to treat a disorder in a mammal caused by the action of Hsp90, e.g., a neurodegenerative disorder, a proliferative disorder, or an infectious disease, as described herein. Kits of the invention may include instructions explaining how a practitioner (e.g., a physician, a nurse, a care-giver, or a patient) may administer the composition contained therein. The pharmaceutical composition within the kit of the invention may be provided in a container (e.g., a bottle, an ampule, a tube, or a blister pack). Furthermore, the kits may also include additional components, e.g., instructions or administration schedules for a patient suffering from a neurodegenerative disease or a proliferative disease, and optionally, a device(s) for administering the pharmaceutical composition (e.g., a syringe).

The following examples are meant to illustrate the invention. They are not meant to limit the invention in any way.

EXAMPLES

Example 1. Synthesis of the Compounds of the Invention

Scheme 1. Reagents and conditions: (a) Pd(PPh$_3$)$_4$, Na$_2$CO$_3$, dioxane/H$_2$O (9/5), 90° C., 72%

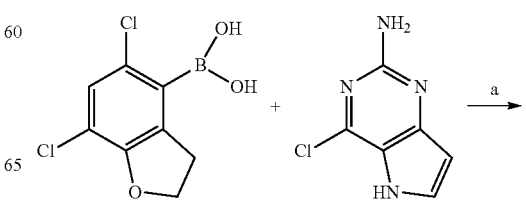

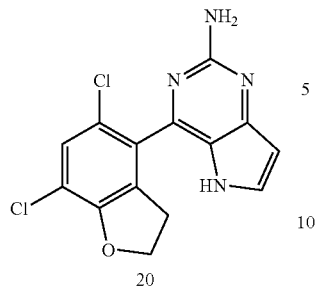

4-(5,7-Dichloro-2,3-dihydrobenzofuran-4-yl)-5H-pyrrolo[3,2-d]pyrimidin-2-amine (20)

A mixture of 5,7-dichloro-2,3-dihydro-1-benzofuran-4-yl boronic acid (233 mg, 1.0 mmol), 4-chloro-5H-pyrrolo[3,2-d]pyrimidin-2-amine (219 mg, 1.3 mmol), sodium carbonate (318 mg, 3.0 mmol), palladium tetrakis(triphenylphosphine), and dioxane/water (9/5, 14 ml) was stirred at 90° C. under argon for 20 h, then cooled down to room temperature, quenched with brine (25 ml), and extracted with ethyl acetate (30 ml×2). The combined organic layers were dried over sodium sulfate and concentrated. The residue was purified by chromatography on silica gel using cyclohexane/ethyl acetate (100/0 to 30/70, 15 min) to give a product as a white solid (230 mg, 72%). $^1$H NMR (500 MHz, CDCl$_3$): δ 8.01 (s, 1H), 7.45 (t, J=3 Hz, 1H), 7.34 (s, 1H), 6.46 (m, 1H), 4.83 (s, 2H), 4.71 (m, 2H), 3.60 (m, 1H), 2.94 (m, 1H); LCMS [M+H]+: 321.0 (calcd for [C$_{14}$H$_{10}$Cl$_2$N$_4$O+H]$^+$: 321.0).

The following compounds of the invention have been prepared according to the procedure described herein.

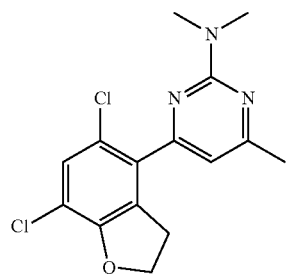 [SMILES: Cc1cc(-c2c(Cl)cc(Cl)c3c2CCO3)nc(N(C)C)n1]

4-(5,7-Dichloro-2,3-dihydrobenzofuran-4-yl)-N,N,6-trimethylpyrimidin-2-amine(4)

$^1$H NMR (500 MHz, CDCl$_3$): δ 7.25 (s, 1H), 6.51 (s, 1H), 4.67 (t, J=9 Hz, 2H), 3.30 (t, J=9 Hz, 2H), 3.20 (s, 6H), 2.40 (s, 3H).

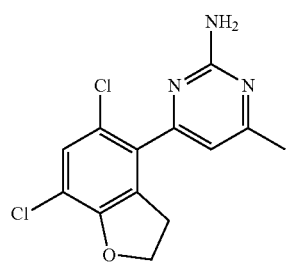 [SMILES: Cc1cc(-c2c(Cl)cc(Cl)c3c2CCO3)nc(N)n1]

4-(5,7-Dichloro-2,3-dihydrobenzofuran-4-yl)-6-methylpyrimidin-2-amine(5)

$^1$H NMR (500 MHz, CDCl$_3$): δ 7.27 (s, 1H), 6.64 (s, 1H), 5.04 (s, 2H), 4.68 (t, J=9 Hz, 2H), 3.25 (t, J=9 Hz, 2H), 2.42 (s, 3H).

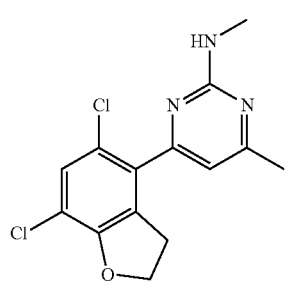

4-(5,7-Dichloro-2,3-dihydrobenzofuran-4-yl)-N,6-dimethylpyrimidin-2-amine(3)

$^1$H NMR (500 MHz, CDCl$_3$): b 7.25 (s, 1H), 6.57 (s, 1H), 5.07 (d, J=10 Hz, 1H), 4.68 (t, J=9 Hz, 2H), 3.29 (t, J=9 Hz, 2H), 3.02 (d, J=10 Hz, 3H), 2.40 (s, 3H).

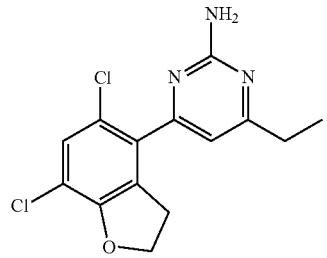 [SMILES: CCc1cc(-c2c(Cl)cc(Cl)c3c2CCO3)nc(N)n1]

4-(5,7-dichloro-2,3-dihydrobenzofuran-4-yl)-6-ethylpyrimidin-2-amine (6)

$^1$H NMR (500 MHz, CDCl$_3$): δ 7.27 (s, 1H), 6.65 (s, 1H), 5.05 (s, 2H), 4.68 (t, J=9 Hz, 2H), 3.26 (t, J=8.5 Hz, 2H), 2.68 (q, J=8 Hz, 2H), 1.29 (t, J=7.5 Hz, 3H); LCMS [M+H]$^+$: 310.1 (calcd for [C14H13Cl2N3O+H]$^+$: 310.04).

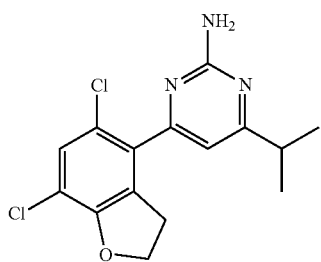 [SMILES: CC(C)c1cc(-c2c(Cl)cc(Cl)c3c2CCO3)nc(N)n1]

4-(5,7-dichloro-2,3-dihydrobenzofuran-4-yl)-6-isopropylpyrimidin-2-amine (7)

$^1$H NMR (500 MHz, CDCl$_3$): δ 7.28 (s, 1H), 6.66 (s, 1H), 5.04 (s, 2H), 4.69 (t, J=9 Hz, 2H), 3.27 (t, J=9 Hz, 2H), 2.87 (m, 1H), 1.28 (d, J=7 Hz, 6H); LCMS [M+H]$^+$: 324.02 (calcd for [C15H15Cl2N3O+H]$^+$: 324.06).

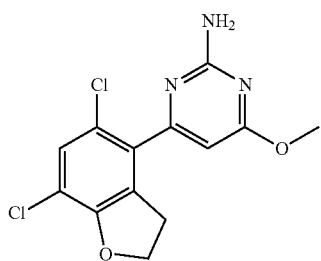

4-(5,7-dichloro-2,3-dihydrobenzofuran-4-yl)-6-methoxypyrimidin-2-amine (8)

$^1$H NMR (500 MHz, CDCl$_3$): δ 7.28 (s, 1H), 6.19 (s, 1H), 4.98 (s, 2H), 4.68 (t, J=8.5 Hz, 2H), 3.94 (s, 3H), 3.25 (t, J=9 Hz, 2H); LCMS [M+H]$^+$: 311.87 (calcd for [C13H11Cl12N3O2+H]$^+$: 312.02).

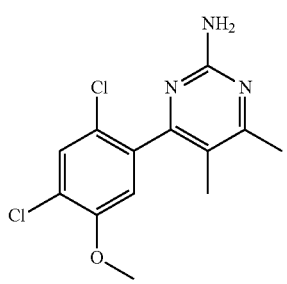 [SMILES: COc1cc(-c2nc(N)nc(C)c2C)c(Cl)cc1Cl]

4-(2,4-Dichloro-5-methoxyphenyl)-5,6-dimethylpyrimidin-2-amine(9)

$^1$H NMR (500 MHz, CDCl$_3$): δ 7.47 (s, 1H), 6.83 (s, 1H), 4.88 (s, 2H), 3.90 (s, 3H), 2.42 (s, 3H), 1.95 (s, 3H).

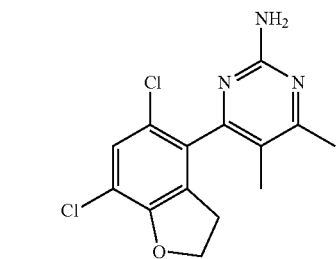 [SMILES: Cc1nc(N)nc(-c2c(Cl)cc(Cl)c3c2CCO3)c1C]

4-(5,7-Dichloro-2,3-dihydrobenzofuran-4-yl)-5,6-dimethylpyrimidin-2-amine(10)

$^1$H NMR (500 MHz, CDCl$_3$): δ 7.25 (s, 1H), 4.89 (s, 2H), 4.69 (t, J=9 Hz, 2H), 3.25 (m, 1H), 2.88 (m, 1H), 2.42 (s, 3H), 1.93 (s, 3H).

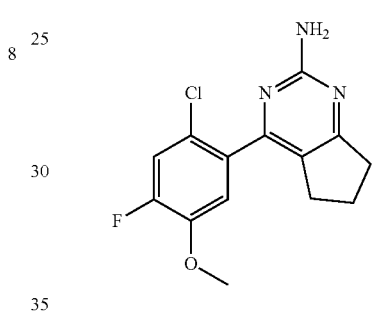

4-(2-chloro-4-fluoro-5-methoxyphenyl)-6,7-dihydro-5H-cyclopenta[d]pyrimidin-2-amine (11)

$^1$H NMR (500 MHz, CDCl$_3$): δ 7.20 (d, J=10.5 Hz, 1H), 6.94 (d, J=9 Hz, 1H), 4.99 (s, 2H), 3.90 (s, 3H), 2.91 (t, J=8 Hz, 2H), 2.72 (t, J=7.5 Hz, 2H), 2.08 (m, 2H); LCMS [M+H]$^+$: 294.2 (calcd for [C14H13ClFN3O+H]$^+$: 294.07).

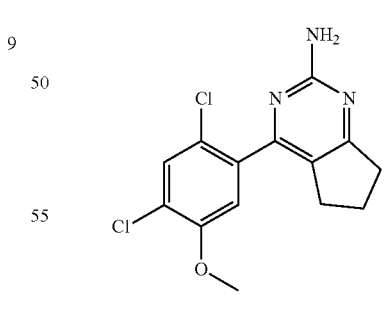

4-(2,4-Dichloro-5-methoxyphenyl)-6,7-dihydro-5H-cyclopenta[d]pyrimidin-2-amine(12)

$^1$H NMR (500 MHz, CDCl$_3$): δ 7.47 (s, 1H), 6.90 (s, 1H), 4.98 (s, 2H), 3.91 (s, 3H), 2.92 (t, J=7.5 Hz, 2H), 2.72 (t, J=7.5 Hz, 2H), 2.08 (m, 2H).

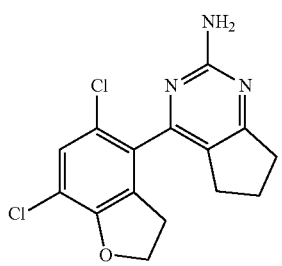 [SMILES: Nc1nc2c(c(-c3c(Cl)cc(Cl)c4c3CCO4)n1)CCC2]

4-(5,7-Dichloro-2,3-dihydrobenzofuran-4-yl)-6,7-dihydro-5H-cyclopenta[d]pyrimidin-2-amine (13)

$^1$H NMR (500 MHz, CDCl$_3$): δ 7.25 (s, 1H), 4.69 (m, 2H), 3.38 (m, 1H), 2.99-2.81 (m, 4H), 2.49 (m, 1H), 2.17-2.00 (m, 2H).

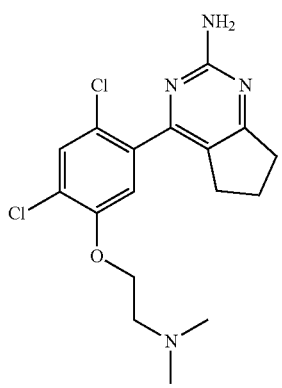

4-(2,4-dichloro-5-(2-(dimethylamino)ethoxy)phenyl)-6,7-dihydro-5H-cyclopenta[d]pyrimidin-2-amine (14)

$^1$H NMR (500 MHz, CDCl$_3$): δ 7.46 (s, 1H), 6.90 (s, 1H), 4.97 (s, 2H), 4.13 (t, J=6 Hz, 2H), 2.91 (t, J=8 Hz, 2H), 2.80 (t, J=6 Hz, 2H), 2.71 (t, J=7.5 Hz, 2H), 2.36 (s, 6H), 2.08 (m, 2H); LCMS [M+H]$^+$: 367.1 (calcd for [C17H20Cl2N4O+H]$^+$: 367.10).

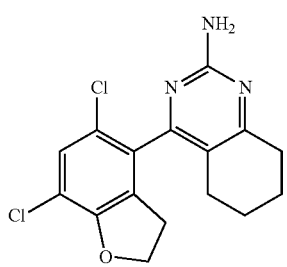 [SMILES: Nc1nc2c(c(-c3c(Cl)cc(Cl)c4c3CCO4)n1)CCCC2]

4-(5,7-dichloro-2,3-dihydrobenzofuran-4-yl)-5,6,7,8-tetrahydroquinazolin-2-amine (15)

$^1$H NMR (500 MHz, CDCl$_3$): δ 7.28 (s, 1H), 4.88 (s, 2H), 4.69 (t, J=9 Hz, 2H), 3.21 (m, 1H), 2.89 (m, 1H), 2.78 (m, 2H), 2.44 (m, 1H), 2.15 (m, 1H), 1.86 (m, 2H), 1.72 (m, 2H); LCMS [M+H]$^+$: 336.1 (calcd for [C16H15Cl2N3O+H]$^+$: 336.06).

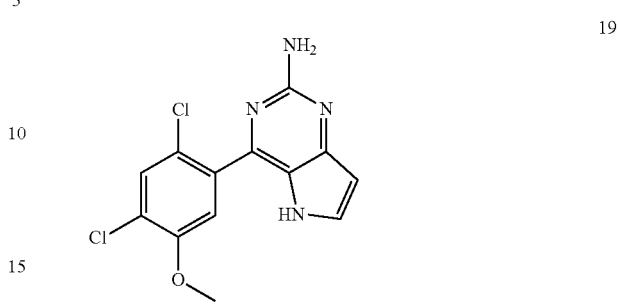

4-(2,4-Dichloro-5-methoxyphenyl)-5H-pyrrolo[3,2-d]pyrimidin-2-amine (19)

$^1$H NMR (500 MHz, CDCl$_3$): δ 8.15 (s, 1H), 7.54 (s, 1H), 7.46 (m, 1H), 7.15 (s, 1H), 6.45 (m, 1H), 4.86 (s, 2H), 3.94 (s, 3H).

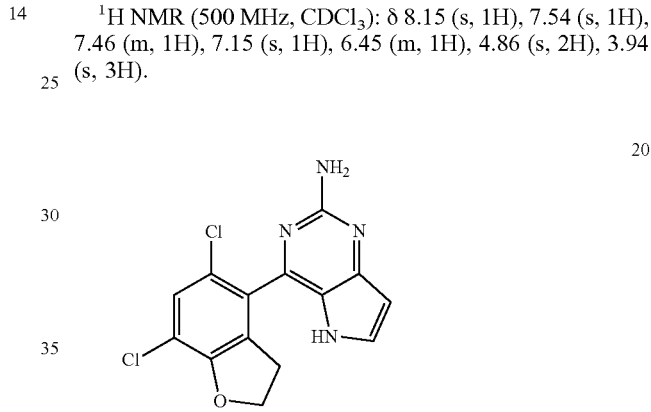

4-(5,7-Dichloro-2,3-dihydrobenzofuran-4-yl)-5H-pyrrolo[3,2-d]pyrimidin-2-amine (20)

$^1$H NMR (500 MHz, CDCl$_3$): δ 8.01 (s, 1H), 7.45 (t, J=3 Hz, 1H), 7.34 (s, 1H), 6.46 (m, 1H), 4.83 (s, 2H), 4.71 (m, 2H), 3.60 (m, 1H), 2.94 (m, 1H); LCMS [M+H]$^+$: 321.0 (calcd for [C14H10Cl2N4O+H]$^+$: 321.0). The $^1$H NMR spectrum is shown in FIG. 1.

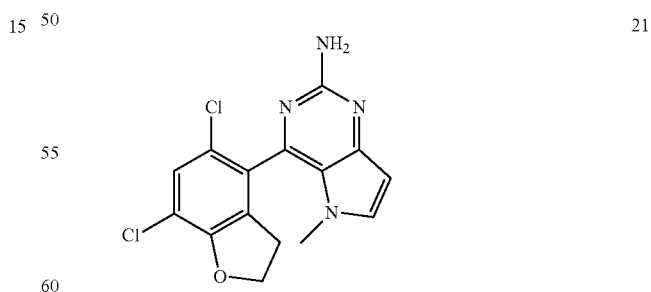

4-(5,7-dichloro-2,3-dihydrobenzofuran-4-yl)-5-methyl-5H-pyrrolo[3,2-d]pyrimidin-2-amine (21)

$^1$H NMR (500 MHz, CDCl$_3$): δ 7.32 (s, 1H), 7.22 (d, J=3 Hz, 1H), 6.36 (d, J=3 Hz, 1H), 4.81 (s, 2H), 4.72 (m, 2H), 3.40 (s, 3H), 3.34 (m, 1H), 2.91 (m, 1H); LCMS [M+H]⁺: 335.0 (calcd for [C15H12Cl2N4O+H]⁺: 335.04).

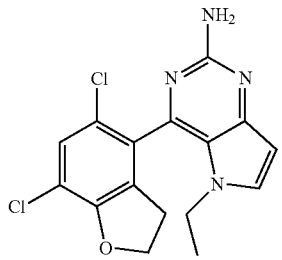

4-(5,7-dichloro-2,3-dihydrobenzofuran-4-yl)-5-ethyl-5H-pyrrolo[3,2-d]pyrimidin-2-amine (22)

¹H NMR (500 MHz, CDCl₃): δ 7.33 (m, 2H), 6.40 (d, J=2.5 Hz, 1H), 4.80 (s, 2H), 4.70 (m, 2H), 3.72 (d, J=7 Hz, 2H), 3.33 (m, 1H), 2.91 (m, 1H), 1.14 (t, J=7.5 Hz, 3H); LCMS [M+H]⁺: 349.1 (calcd for [C16H14Cl2N4O+H]⁺: 349.05).

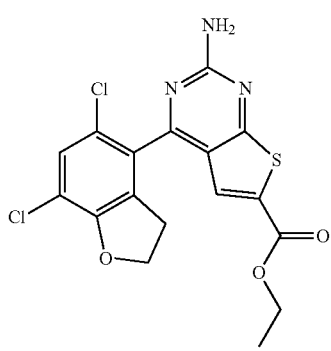 [SMILES: CCOC(=O)c1cc2c(-c3c(Cl)cc(Cl)c4c3CCO4)nc(N)nc2s1]

Ethyl-2-amino-4-(5,7-dichloro-2,3-dihydrobenzofuran-4-yl)thieno[2,3-d]pyrimidine-6-carboxylate (23)

¹H NMR (500 MHz, CDCl₃): δ 7.54 (s, 1H), 7.35 (s, 1H), 5.32 (s, 2H), 4.70 (m, 2H), 4.37 (m, 2H), 3.35 (m, 1H), 2.92 (m, 1H), 1.38 (t, J=7 Hz, 3H); LCMS [M+H]⁺: 410.0 (calcd for [C17H13Cl2N3O3S+H]⁺: 410.01).

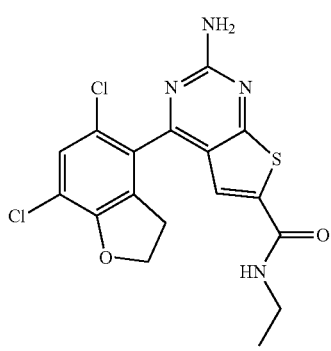 [SMILES: CCNC(=O)c1cc2c(-c3c(Cl)cc(Cl)c4c3CCO4)nc(N)nc2s1]

2-amino-4-(5,7-dichloro-2,3-dihydrobenzofuran-4-yl)-N-ethylthieno[2,3-d]pyrimidine-6-carboxamide (24)

¹H NMR (500 MHz, CDCl₃): δ 7.34 (s, 1H), 7.21 (s, 1H), 5.91 (s, 1H), 5.28 (s, 2H), 4.70 (m, 2H), 4.48 (m, 2H), 3.36 (m, 1H), 2.91 (m, 1H), 1.26 (t, J=3.5 Hz, 3H); LCMS [M+H]⁺: 409.0 (calcd for [C17H14Cl2N4O2S+H]⁺: 409.02).

Figure 2:
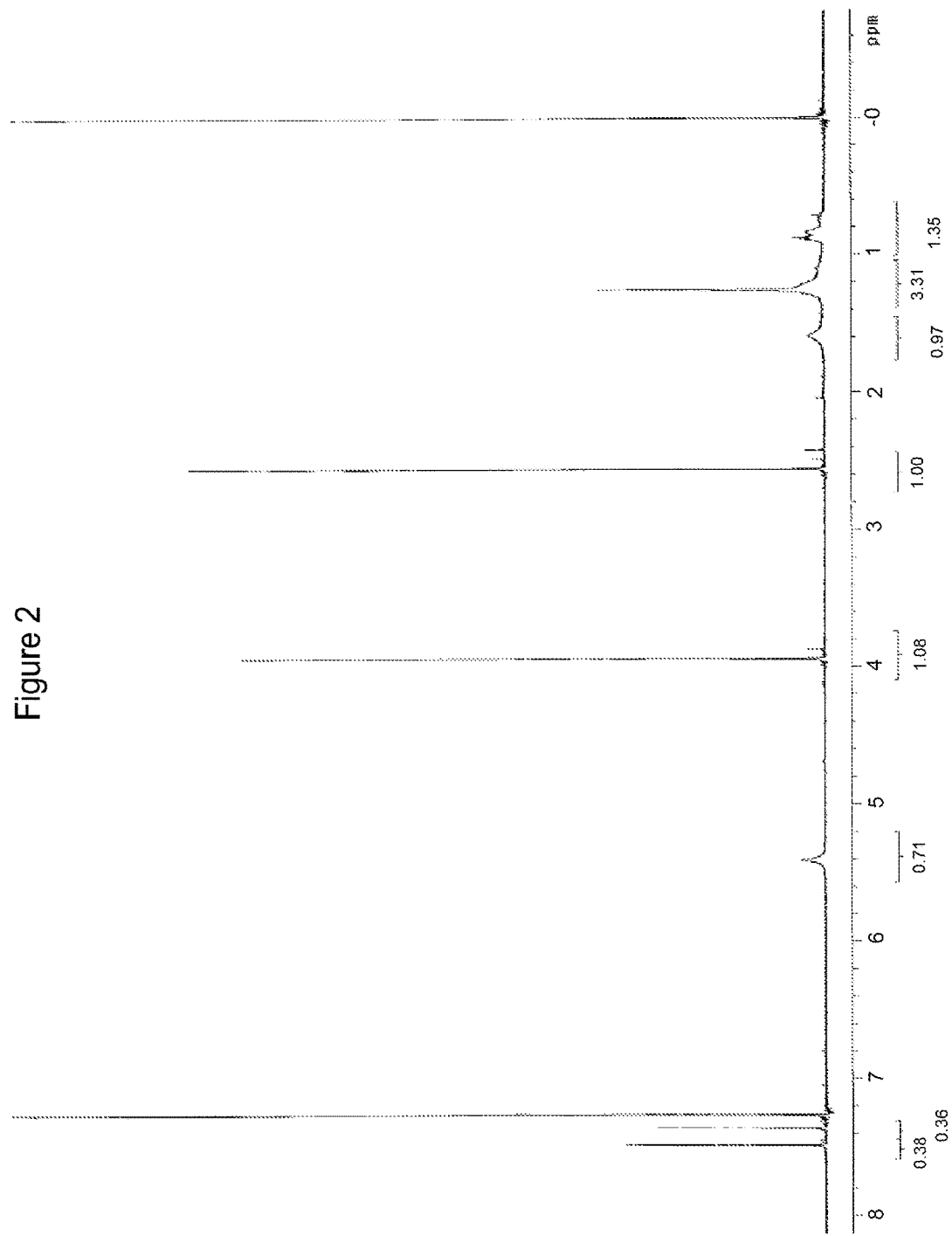
FIG. 2 shows a 500 MHz $^1$H NMR spectrum of compound 34 in $CDCl_3$.
Figure 3:
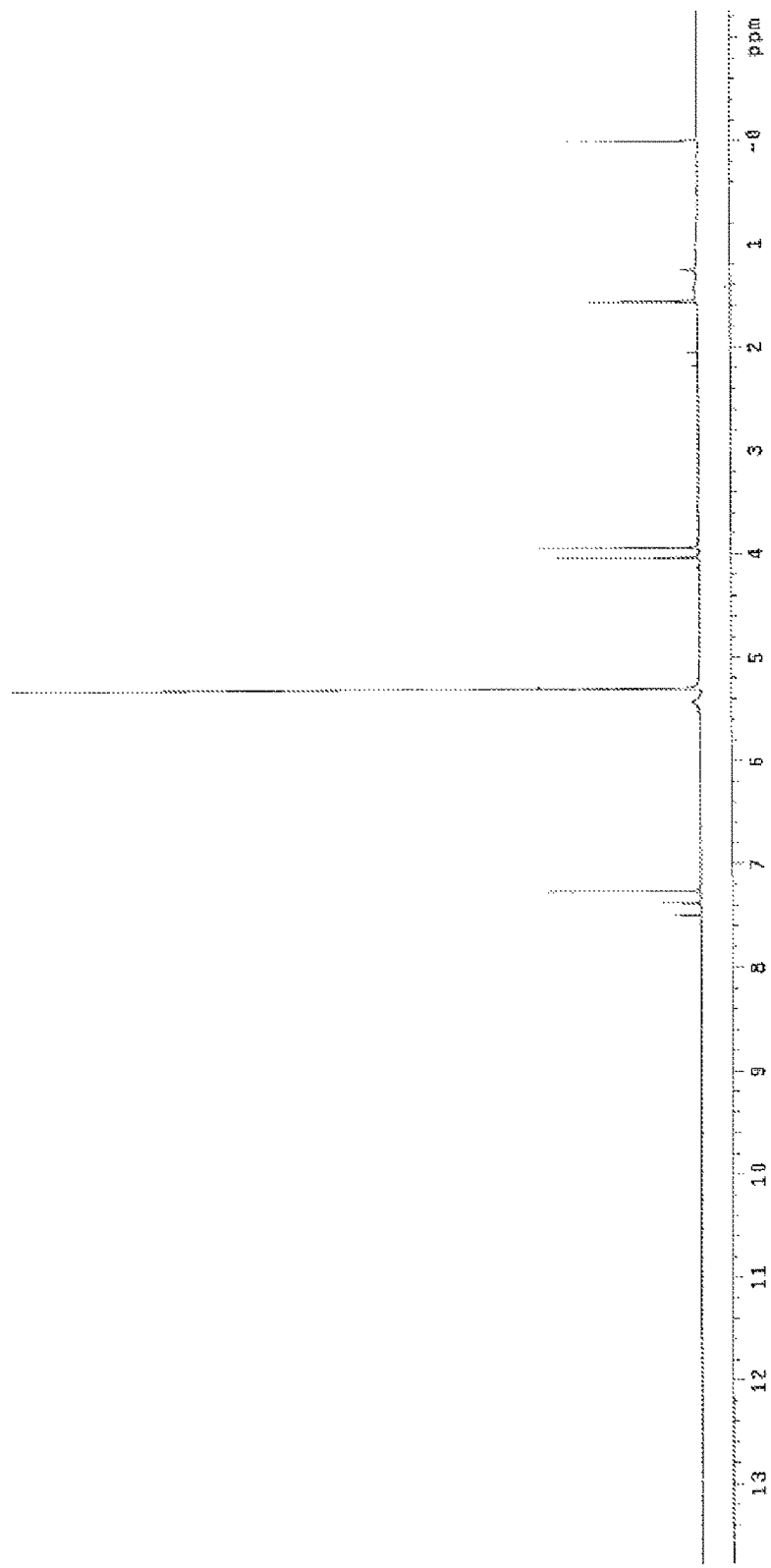
FIG. 3 shows a 500 MHz $^1$H NMR spectrum of compound 36 in $CDCl_3$.

Compounds 34 and 36 were prepared according to methods known in the art, e.g., those described herein. The ¹H NMR spectra (CDCl₃) for compounds 34 and 36 are provided in FIGS. 2 and 3, respectively.

Compounds 40-48 can be prepared according to methods known in the art, e.g., those described herein.

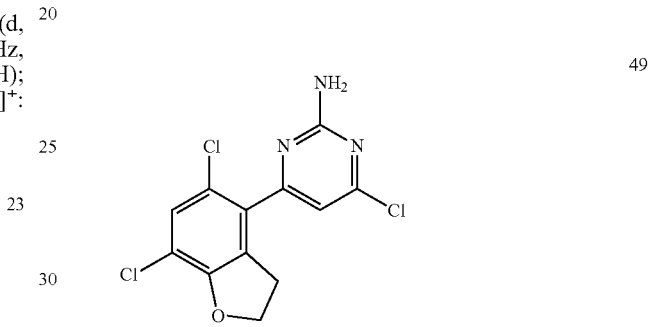

4-chloro-6-(5,7-dichloro-2,3-dihydrobenzofuran-4-yl)pyrimidin-2-amine (49)

¹H NMR (400 MHz, DMSO-d6): δ=7.48 (s, 1H), 7.30 (s, 2H), 6.78 (s, 1H), 4.64 (t, J=8.8 Hz, 2H), 3.20 (t, J=8.8 Hz, 2H). LCMS: m/z calcd for C₁₂H₈Cl₃N₃O [M+H]⁺: 316.0; found: 316.0.

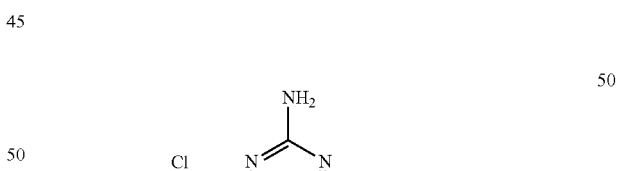

4-trifluoromethyl-6-(5,7-dichloro-2,3-dihydrobenzofuran-4-yl)pyrimidin-2-amine (50)

¹H NMR (400 MHz, DMSO-d6): δ 7.520 (br s, 2H, NH₂), 7.093 (s, 1H), 4.655 (t, 2H, J=8.8 Hz), 3.547 (s, 1H), 3.221 (t, 2H, J=8.8 Hz). LCMS: m/z calcd for C₁₃H₈Cl₂F₃N₃O [M+H]⁺: 350.1; found: 350.0.

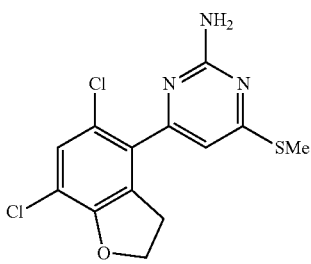 [SMILES: CSc1cc(-c2c(Cl)cc(Cl)c3c2CCO3)nc(N)n1]

4-thiomethyl-6-(5,7-dichloro-2,3-dihydrobenzo-furan-4-yl)pyrimidin-2-amine (51)

$^1$H NMR (400 MHz, DMSO-d6): δ 7.438 (s, 1H), 6.815 (br s, 2H, NH$_2$), 6.549 (s, 1H), 4.633 (t, 2H, J=8.8 Hz), 3.178 (t, 2H, J=8.8 Hz), 2.453 (s, 3H). LCMS: m/z calcd for C$_{13}$H$_{11}$Cl$_2$N$_3$OS [M+H]$^+$: 328.2; found: 328.1.

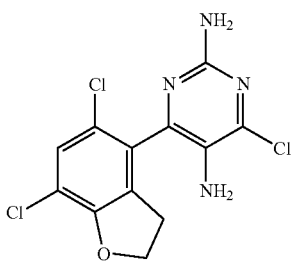

4-chloro-6-(5,7-dichloro-2,3-dihydrobenzofuran-4-yl)pyrimidine-2,5-diamine (52)

$^1$H NMR (400 MHz, DMSO-d6): δ=7.46 (s, 1H), 6.25 (s, 2H), 4.67 (t, J=8.8 Hz, 2H), 4.30 (s, 2H), 3.15-3.07 m, 2H). HPLC/MS: m/z calcd for C$_{12}$H$_9$Cl$_3$N$_4$O [M+H]$^+$: 331.0; found: 331.1.

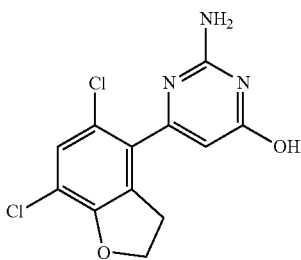

2-amino-6-(5,7-dichloro-2,3-dihydrobenzofuran-4-yl)pyrimidin-4-ol (53)

To a flask containing dioxane:1 N NaOH aq. (50:50; 1 mL:1 mL) were added 4-chloro-6-(5,7-dichloro-2,3-dihydrobenzofuran-4-yl)pyrimidin-2-amine (49) (20 mg, 0.063 mmol), and DABCO (8 mg, 0.069 mmol), at rt. The reaction was subsequently heated at 80° C. The reaction was cooled down, acidified by addition of 1 N HCl aq. (2 mL), taken up in ethyl acetate (5 mL) and washed with brine (3×5 mL). The organic layer was dried over Na$_2$SO$_4$, filtered, and volatiles were evaporated. The residue was purified by silica gel chromatography using a gradient of DCM:MeOH (100:0 to 90:10). The product was obtained in 77% yield as a white solid. $^1$H NMR (400 MHz, DMSO-d6): δ=7.39 (s, 1H), 5.57 (s, 1H), 4.62 (t, J=8.8 Hz, 2H), 3.20 (t, J=8.8 Hz, 2H). HPLC/MS: m/z calcd for C$_{12}$H$_9$Cl$_2$N$_3$O$_2$ [M+H]$^+$: 298.0; found: 298.1.

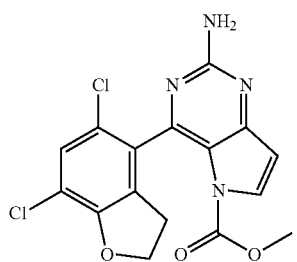

Methyl 2-amino-4-(5,7-dichloro-2,3-dihydrobenzofuran-4-yl)-5H-pyrrolo[3,2-d]pyrimidine-5-carboxylate (54)

To a flask containing 4-(5,7-dichloro-2,3-dihydrobenzofuran-4-yl)-5H-pyrrolo[3,2-d]pyrimidin-2-amine (20) (20 mg, 0.062 mmol) in DCM (1 mL) were added dry K$_2$CO$_3$ (30 mg, 0.22 mmol), and methyl chloroformate (0.014 mL, 0.186 mmol), at 0° C. The reaction was allowed to stir for 8 h at rt. Afterwards, the reaction was quenched by addition of 1 N NaOH aq. (1 mL) and stirred at rt for 1 h. The reaction was taken up in DCM (10 mL) and washed with sat. NaHCO$_3$ aq. (10 mL). The organic layer was dried over Na$_2$SO$_4$, filtered, and volatiles were evaporated. The residue was purified by silica gel chromatography using a gradient of DCM:MeOH (100:0 to 90:10). The product was obtained in 66% yield as a yellow solid.

$^1$H NMR (400 MHz, CDCl3): δ=7.61 (s, 1H), 7.23 (s, 1H), 6.51 (s, 1H), 4.63 (br s, 2H), 3.77 (s, 3H), 3.65 (br s, 1H), 2.85 (br s, 1H). HPLC/MS: m/z calcd for C$_{16}$H$_{12}$Cl$_2$N$_4$O$_3$ [M+H]$^+$: 379.0; found: 379.1.

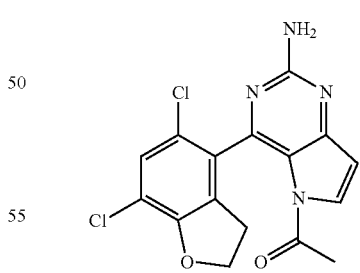

1-(2-amino-4-(5,7-dichloro-2,3-dihydrobenzofuran-4-yl)-5H-pyrrolo[3,2-d]pyrimidin-5-yl)ethan-1-one (55)

To a flask containing 4-(5,7-dichloro-2,3-dihydrobenzofuran-4-yl)-5H-pyrrolo[3,2-d]pyrimidin-2-amine (20 mg, 0.062 mmol) in DCM (1 mL) were added dry K$_2$CO$_3$ (30 mg, 0.22 mmol), and acetyl chloride (0.006 mL, 0.074 mmol), at 0° C. The reaction was allowed to stir for 8 h at rt. Afterwards, the reaction was quenched by addition of 1 N NaOH aq. (1 mL) and stirred at rt for 1 h. The reaction was taken up in DCM (10 mL) and washed with sat. NaHCO$_3$ aq. (10 mL). The organic layer was dried over Na$_2$SO$_4$, filtered, and volatiles were evaporated. The residue was purified by silica gel chromatography using a gradient of DCM:MeOH (100:0 to 90:10). The product was obtained in 81% yield as a yellow solid.

$^1$H NMR (400 MHz, CDCl3): δ=7.57 (s, 1H), 7.23 (s, 1H), 6.55 (s, 1H), 4.63 (br s, 2H), 3.45 (br s, 1H), 3.35 (s, 3H), 2.85 (br s, 1H). HPLC/MS: m/z calcd for C$_{16}$H$_{12}$Cl$_2$N$_4$O$_2$ [M+H]$^+$: 363.0; found: 363.1.

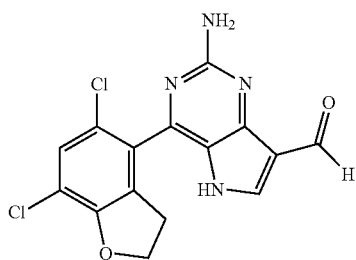

56

2-amino-4-(5,7-dichloro-2,3-dihydrobenzofuran-4-yl)-5H-pyrrolo[3,2-d]pyrimidine-7-carbaldehyde (56)

To a flask containing dry THF (2 mL), were added dry DMF (0.1 mL) and POCl$_3$ (0.015 mL, 0.16 mmol), at 0° C. Reaction was stirred at 0° C. for 30 min, under argon, upon which 4-(5,7-dichloro-2,3-dihydrobenzofuran-4-yl)-5H-pyrrolo[3,2-d]pyrimidin-2-amine (20 mg, 0.062 mmol) in THF (1 mL) was added dropwise. The reaction was allowed to stir for 8 h warming to rt. To the reaction was then added 1 N NaOH aq. (2 mL) and heated to 80° C. for 1 h. The reaction was cooled to rt and taken up in EtOAc (20 mL) and washed with sat. NaHCO$_3$ aq. (20 mL). The organic layer was dried over Na$_2$SO$_4$, filtered, and volatiles were evaporated. The residue was purified by silica gel chromatography using a gradient of DCM:MeOH (100:0 to 90:10). The product was obtained in 58% yield as a white solid.

$^1$H NMR (400 MHz, CDCl3): δ=10.05 (s, 1H), 7.96 (s, 1H), 7.24 (s, 1H), 4.63 (br s, 2H), 3.31 (br s, 1H), 2.85 (br s, 1H). HPLC/MS: m/z calcd for C$_{15}$H$_{10}$Cl$_2$N$_4$O$_2$ [M+H]$^+$: 349.0; found: 349.1.

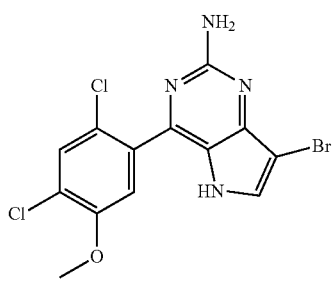 [SMILES: COc1cc(-c2nc(N)nc3c(Br)c[nH]c23)c(Cl)cc1Cl]

57

7-bromo-4-(2,4-dichloro-5-methoxyphenyl)-5H-pyrrolo[3,2-d]pyrimidin-2-amine (57)

To a flask containing 4-(2,4-dichloro-5-methoxyphenyl)-5H-pyrrolo[3,2-d]pyrimidin-2-amine (20 mg, 0.065 mmol) in AcOH:tBuOH (50:50, 0.5 mL:0.5 mL) were added LiBr (18 mg, 0.22 mmol), and Br$_2$ (0.011 mL, 0.22 mmol), at 0° C. The reaction was allowed to stir for 8 h at rt. Afterwards, the reaction was taken up in EtOAc (20 mL) and washed with sat. NaHCO$_3$ aq. (3×20 mL), and Na$_2$S$_2$O$_3$ (10% wt. aq., 20 mL). The organic layer was dried over Na$_2$SO$_4$, filtered, and volatiles were evaporated. The residue was purified by silica gel chromatography using a gradient of DCM:MeOH (100:0 to 90:10). The product was obtained in 56% yield as a yellow solid.

$^1$H NMR (400 MHz, DMSO-d6): δ=7.75 (s, 1H), 7.72 (s, 1H), 7.26 (s, 1H), 6.24 (s, 2H), 3.86 (s, 3H). HPLC/MS: m/z calcd for C$_{13}$H$_9$BrCl$_2$N$_4$O [M+H]$^+$: 386.9; found: 387.0.

General procedure for synthesis of 2-amino-4-(5,7-dichloro-2,3-dihydrobenzofuran-4-yl)thieno[2,3-d]pyrimidine-6-carboxamides

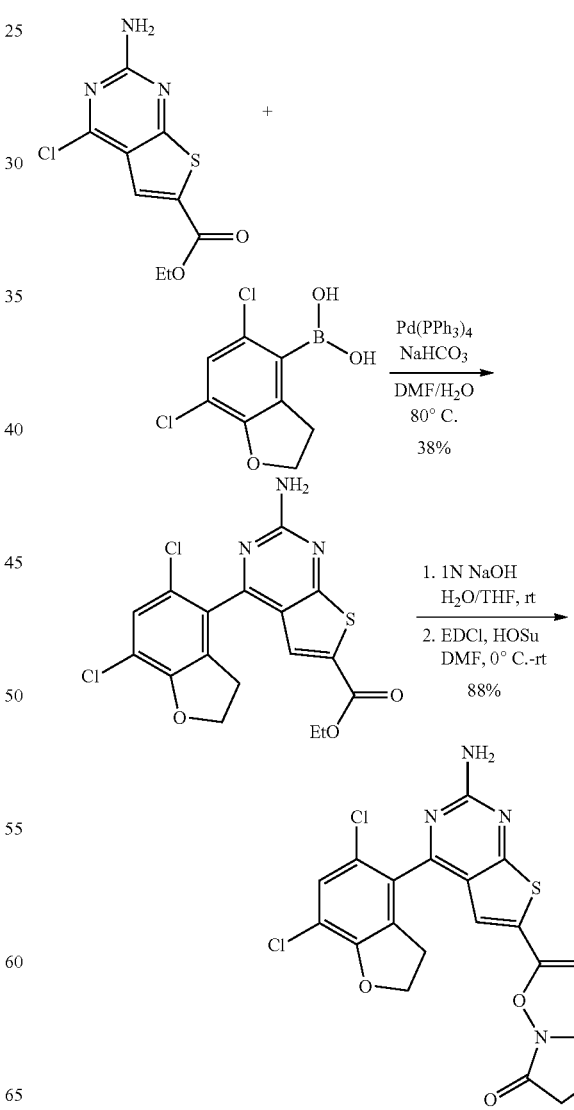

Step 1: Synthesis of precursor 2,5-dioxopyrrolidin-1-yl 2-amino-4-(5,7-dichloro-2,3-dihydrobenzofuran-4-yl)thieno[2,3-d]pyrimidine-6-carboxylate To a flask containing degassed DMF:H₂O (50:50; 2 mL:2 mL) were added ethyl 2-amino-4-chlorothieno[2,3-d]pyrimidine-6-carboxylate (100 mg, 0.39 mmol), (5,7-dichloro-2,3-dihydrobenzofuran-4-yl)boronic acid (91 mg, 0.39 mmol), NaHCO₃ (82 mg, 0.98 mmol), and Pd(PPh₃)₄ (22 mg, 0.02 mmol), at rt. The reaction was subsequently heated at 80° C. for 8 h under argon. The reaction was cooled down, taken up in ethyl acetate (20 mL) and washed with brine (3×20 mL). The organic layer was dried over Na₂SO₄, filtered, and volatiles were evaporated. The residue was purified by silica gel chromatography using a gradient of DCM:MeOH (100:0 to 90:10). The product ethyl 2-amino-4-(5,7-dichloro-2,3-dihydrobenzofuran-4-yl)thieno[2,3-d]pyrimidine-6-carboxylate was obtained in 38% yield as a yellow solid.

Ethyl 2-amino-4-(5,7-dichloro-2,3-dihydrobenzofuran-4-yl)thieno[2,3-d]pyrimidine-6-carboxylate (60 mg, 0.15 mmol) was dissolved in THF (1 mL) and to the flask was added 1 N NaOH aq. (1 mL). The reaction was stirred for 8 h at rt. Subsequently, the solution was cooled to 0° C. and acidified by addition of 1 N HCl aq. (2 mL), resulting in formation of white precipitate, which was filtered and dried, affording 2-amino-4-(5,7-dichloro-2,3-dihydrobenzofuran-4-yl)thieno[2,3-d]pyrimidine-6-carboxylic acid in quantitative yield, without further purification. The filtrand (57 mg, 0.15 mmol) was dissolved in dry DMF (1 mL), cooled to 0° C., and to the reaction vessel were added N-hydroxysuccinimide (23 mg, 0.2 mmol) and 1-ethyl-3-(3-dimethylaminopropyl)carbodiimide HCl (38 mg, 0.2 mmol). The solution was left to stir warming to rt over 8 h. The solution was taken up into DCM (20 mL) and washed with sat. NH₄Cl aq. (3×20 mL). The organic layer was dried over Na₂SO₄, filtered, and volatiles were evaporated. The residue was purified by silica gel chromatography using a gradient of DCM:MeOH (100:0 to 90:10). The product 2,5-dioxopyrrolidin-1-yl 2-amino-4-(5,7-dichloro-2,3-dihydrobenzofuran-4-yl)thieno[2,3-d]pyrimidine-6-carboxylate was obtained as a white solid in 88% yield.

Step 2: General Procedure for Formation of Amides

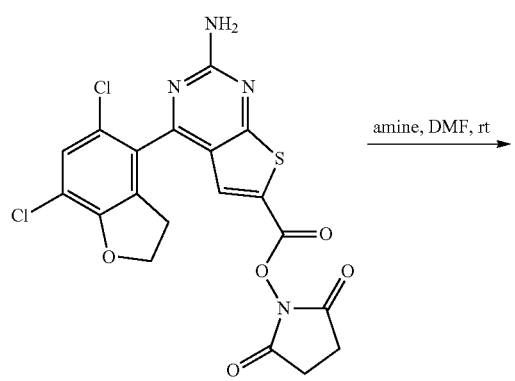

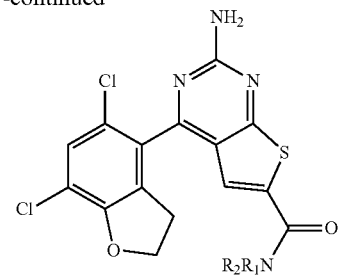

$R_1$ = H, or alkyl chain
$R_2$ = H, OMe, or alkyl chain

To a flask containing the 2,5-dioxopyrrolidin-1-yl 2-amino-4-(5,7-dichloro-2,3-dihydrobenzofuran-4-yl)thieno[2,3-d]pyrimidine-6-carboxylate (10 mg, 0.02 mmol) was added dry DMF (0.5 mL), followed by addition of an amine (3 eq., 0.06 mmol), (e.g. ammonia, primary amine, or secondary amine). The reaction was allowed to stir at rt for 12 h, upon which it was taken up in DCM (5 mL) and washed with sat. NH₄Cl aq. (3×5 mL). The organic layer was dried over Na₂SO₄, filtered, and volatiles were evaporated. The residue was purified by silica gel chromatography using a gradient of DCM:MeOH (100:0 to 90:10). The resulting amides were obtained in good to excellent yields.

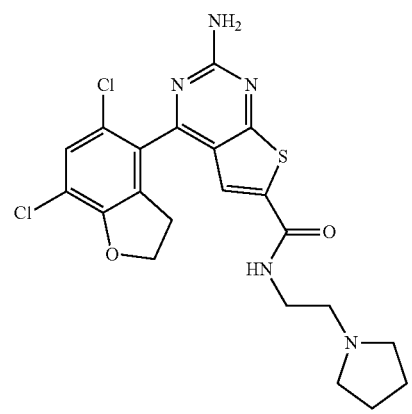

58

2-amino-4-(5,7-dichloro-2,3-dihydrobenzofuran-4-yl)-N-(2-(pyrrolidin-1-yl)ethyl)thieno[2,3-d]pyrimidine-6-carboxamide (58)

¹H NMR (400 MHz, DMSO-d6): δ=8.79 (s, 1H), 7.61 (s, 1H), 7.58 (s, 1H), 7.28 (s, 2H), 4.67 (t, J=8.8 Hz, 2H), 3.44-3.11 (m, 6H), 2.90-2.75 (m, 4H), 1.77-1.73 (m, 4H). HPLC/MS: m/z calcd for $C_{21}H_{21}Cl_2N_5O_2S$ [M+H]⁺: 478.1; found: 478.1.

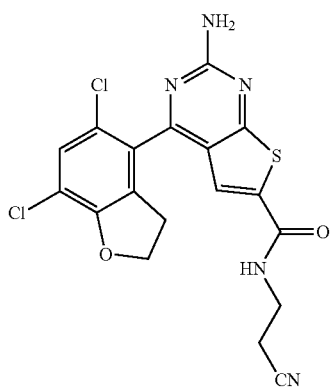 [SMILES: N#CCCNC(=O)c1cc2c(-c3c(Cl)cc(Cl)c4c3CCO4)nc(N)nc2s1]

2-amino-N-(2-cyanoethyl)-4-(5,7-dichloro-2,3-dihydrobenzofuran-4-yl)thieno[2,3-d]pyrimidine-6-carboxamide (59)

$^1$H NMR (400 MHz, DMSO-d6): δ=8.94 (t, J=5.6 Hz, 1H), 7.63 (s, 1H), 7.60 (s, 1H), 7.34 (s, 2H), 4.69 (t, J=8.8 Hz, 2H), 3.46-3.41 (m, 2H), 3.23-3.15 (m, 1H), 3.03-2.97 (m, 1H), 2.76 (t, J=6.4 Hz, 2H). HPLC/MS: m/z calcd for $C_{18}H_{13}Cl_2N_5O_2S$ [M+H]$^+$: 434.0; found: 434.1.

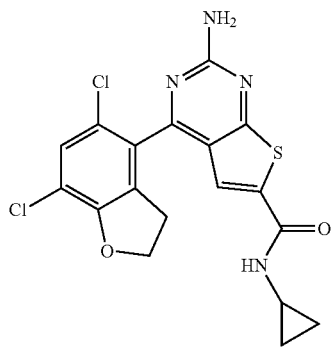 [SMILES: Nc1nc(-c2c(Cl)cc(Cl)c3c2CCO3)c2cc(C(=O)NC3CC3)sc2n1]

2-amino-4-(5,7-dichloro-2,3-dihydrobenzofuran-4-yl)-N-(2-hydroxyethyl)thieno[2,3-d]pyrimidine-6-carboxamide (60)

$^1$H NMR (400 MHz, DMSO-d6): δ=8.57 (t, J=5.6 Hz, 1H), 7.59 (s, 2H), 7.26 (s, 2H), 4.73 (t, J=5.6 Hz, 1H), 4.67 (t, J=8.8 Hz, 2H), 3.46-3.41 (m, 2H), 3.26-3.12 (m, 3H), 3.03-2.94 (m, 1H). HPLC/MS: m/z calcd for $C_{17}H_{14}Cl_2N_4O_3S$ [M+H]$^+$: 425.0; found: 425.1.

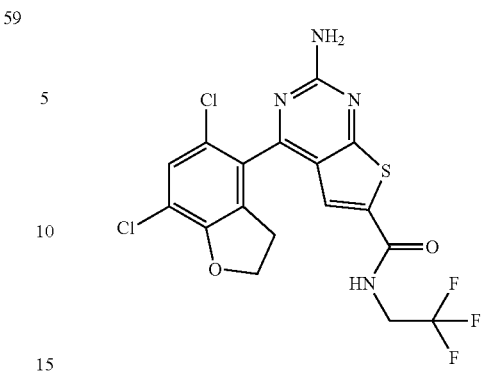

2-amino-4-(5,7-dichloro-2,3-dihydrobenzofuran-4-yl)-N-(2,2,2-trifluoroethyl)thieno[2,3-d]pyrimidine-6-carboxamide (61)

$^1$H NMR (400 MHz, DMSO-d6): δ=9.18 (t, J=6.0 Hz, 1H), 7.72 (s, 1H), 7.63 (s, 1H), 7.38 (s, 2H), 4.69 (t, J=8.8 Hz, 2H), 4.12-4.03 (m, 2H), 3.26-3.18 (m, 1H), 3.03-2.94 (m, 1H). HPLC/MS: m/z calcd for $C_{17}H_{11}Cl_2F_3N_4O_2S$ [M+H]$^+$: 463.0; found: 463.1.

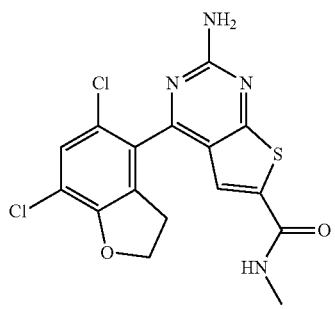

2-amino-N-cyclopropyl-4-(5,7-dichloro-2,3-dihydrobenzofuran-4-yl)thieno[2,3-d]pyrimidine-6-carboxamide (62)

$^1$H NMR (400 MHz, DMSO-d6): δ=8.54 (s, 1H), 7.61 (s, 1H), 7.53 (s, 1H), 7.29 (s, 2H), 4.68 (t, J=8.8 Hz, 2H), 3.26-3.18 (m, 1H), 3.03-2.94 (m, 1H), 2.81-2.71 (m, 1H), 0.75-0.61 (m, 2H), 0.55-0.40 (m, 2H). HPLC/MS: m/z calcd for $C_{18}H_{14}Cl_2N_4O_2S$ [M+H]$^+$: 421.0; found: 421.1.

2-amino-4-(5,7-dichloro-2,3-dihydrobenzofuran-4-yl)-N-methylthieno[2,3-d]pyrimidine-6-carboxamide (63)

$^1$H NMR (400 MHz, DMSO-d6): δ=8.62-8.59 (m, 1H), 7.61 (s, 2H), 7.27 (s, 2H), 4.64 (t, J=8.8 Hz, 2H), 3.24 (s, 3H), 3.23-3.18 (m, 1H), 3.03-2.91 (m, 1H). HPLC/MS: m/z calcd for $C_{16}H_{12}Cl_2N_4O_2S$ [M+H]$^+$: 395.0; found: 395.1.

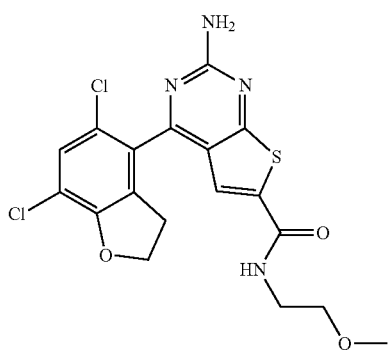

2-amino-4-(5,7-dichloro-2,3-dihydrobenzofuran-4-yl)-N-(2-methoxyethyl)thieno[2,3-d]pyrimidine-6-carboxamide (64)

$^1$H NMR (400 MHz, DMSO-d6): δ=8.51-8.41 (m, 1H), 7.59 (s, 1H), 7.50 (s, 1H), 7.26 (s, 2H), 4.67 (t, J=8.8 Hz, 2H), 3.23-3.10 (m, 4H), 3.03-2.91 (m, 2H), 2.72-2.67 (m, 3H). HPLC/MS: m/z calcd for $C_{18}H_{16}Cl_2N_4O_3S$ [M+H]$^+$: 439.0; found: 439.1.

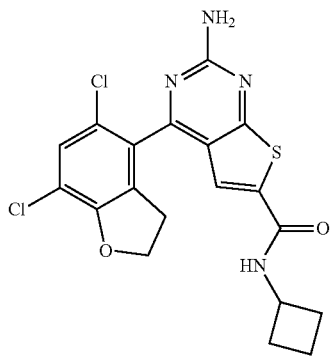 [SMILES: Nc1nc(-c2c(Cl)cc(Cl)c3c2CCO3)c2cc(C(=O)NC3CCC3)sc2n1]

2-amino-N-cyclobutyl-4-(5,7-dichloro-2,3-dihydrobenzofuran-4-yl)thieno[2,3-d]pyrimidine-6-carboxamide (65)

$^1$H NMR (400 MHz, DMSO-d6): δ=8.68 (d, J=6.8 Hz, 1H), 7.61 (s, 1H), 7.56 (s, 1H), 7.26 (s, 2H), 4.67 (t, J=8.8 Hz, 2H), 4.33-4.26 (m, 1H), 3.23-3.18 (m, 1H), 3.03-2.91 (m, 1H), 2.16-1.92 (m, 2H), 1.70-1.60 (m, 1H), 1.33-1.20 (m, 2H), 0.90-0.78 (m, 1H). HPLC/MS: m/z calcd for $C_{19}H_{16}Cl_2N_4O_2S$ [M+H]$^+$: 435.0; found: 435.1.

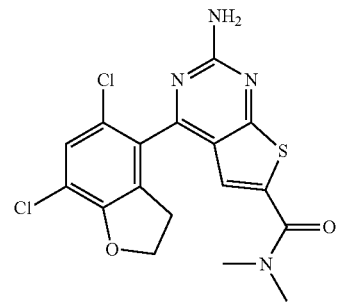

2-amino-4-(5,7-dichloro-2,3-dihydrobenzofuran-4-yl)-N,N-dimethylthieno[2,3-d]pyrimidine-6-carboxamide (66)

$^1$H NMR (400 MHz, DMSO-d6): δ=7.54 (s, 1H), 7.23 (s, 2H), 7.15 (s, 1H), 4.66 (t, J=8.8 Hz, 2H), 3.31 (s, 3H), 3.23-2.90 (m, 5H). HPLC/MS: m/z calcd for $C_{17}H_{14}Cl_2N_4O_2S$ [M+H]$^+$: 409.0; found: 409.1.

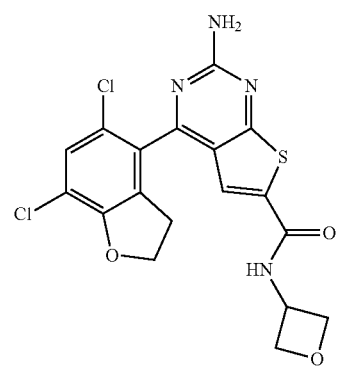 [SMILES: Nc1nc(-c2c(Cl)cc(Cl)c3c2CCO3)c2cc(C(=O)NC3COC3)sc2n1]

2-amino-4-(5,7-dichloro-2,3-dihydrobenzofuran-4-yl)-N-(oxetan-3-yl)thieno[2,3-d]pyrimidine-6-carboxamide (67)

$^1$H NMR (400 MHz, DMSO-d6): δ=9.17 (d, J=6.8 Hz, 1H), 7.64 (s, 1H), 7.62 (s, 1H), 7.31 (s, 2H), 4.97-4.90 (m, 1H), 4.75-4.65 (m, 4H), 4.55-4.45 (m, 2H), 3.20-3.11 (m, 1H), 3.02-2.92 (m, 1H). HPLC/MS: m/z calcd for $C_{18}H_{14}Cl_2N_4O_3S$ [M+H]$^+$: 437.0; found: 437.1.

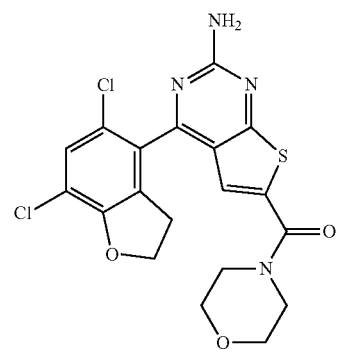 [SMILES: Nc1nc(-c2c(Cl)cc(Cl)c3c2CCO3)c2cc(C(=O)N3CCOCC3)sc2n1]

(2-amino-4-(5,7-dichloro-2,3-dihydrobenzofuran-4-yl)thieno[2,3-d]pyrimidin-6-yl)(morpholino)methanone (68)

$^1$H NMR (400 MHz, DMSO-d6): δ=7.54 (s, 1H), 7.23 (s, 2H), 7.12 (s, 1H), 4.66 (t, J=8.8 Hz, 2H), 3.59 (br s, 8H), 3.26-3.21 (m, 1H), 3.02-2.92 (m, 1H). HPLC/MS: m/z calcd for $C_{19}H_{16}Cl_2N_4O_3S$ [M+H]$^+$: 451.0; found: 451.1.

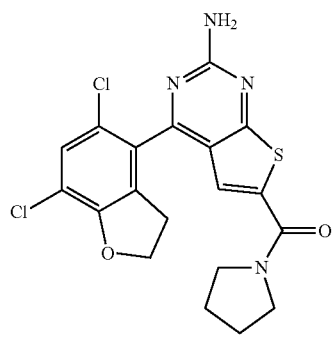 [SMILES: Nc1nc(-c2c(Cl)cc(Cl)c3c2CCO3)c2cc(C(=O)N3CCCC3)sc2n1]

69

(2-amino-4-(5,7-dichloro-2,3-dihydrobenzofuran-4-yl)thieno[2,3-d]pyrimidin-6-yl)(pyrrolidin-1-yl)methanone (69)

$^1$H NMR (400 MHz, DMSO-d6): δ=7.54 (s, 1H), 7.23 (s, 2H), 7.21 (s, 1H), 4.66 (t, J=8.8 Hz, 2H), 3.68-3.64 (m, 2H), 3.44 (br s, 2H), 3.26-3.16 (m, 1H), 3.02-2.92 (m, 1H), 1.91-1.76 (m, 4H). HPLC/MS: m/z calcd for $C_{19}H_{16}Cl_2N_4O_2S$ [M+H]: 435.0; found: 435.1.

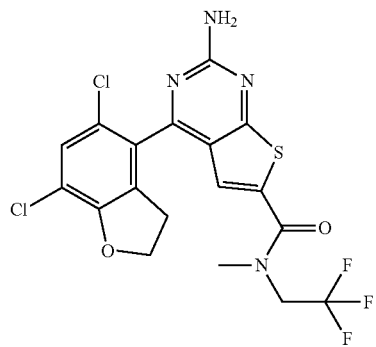 [SMILES: CN(CC(F)(F)F)C(=O)c1cc2c(-c3c(Cl)cc(Cl)c4c3CCO4)nc(N)nc2s1]

70

2-amino-4-(5,7-dichloro-2,3-dihydrobenzofuran-4-yl)-N-methyl-N-(2,2,2-trifluoroethyl)thieno[2,3-d]pyrimidine-6-carboxamide (70)

$^1$H NMR (400 MHz, DMSO-d6): δ=7.54 (s, 1H), 7.33 (s, 3H), 4.66 (t, J=8.8 Hz, 2H), 4.41-4.28 (m, 2H), 3.27 (s, 3H), 3.26-3.16 (m, 1H), 3.02-2.92 (m, 1H). HPLC/MS: m/z calcd for $C_{18}H_{13}Cl_2F_3N_4O_2S$ [M+H]$^+$: 477.0; found: 477.1.

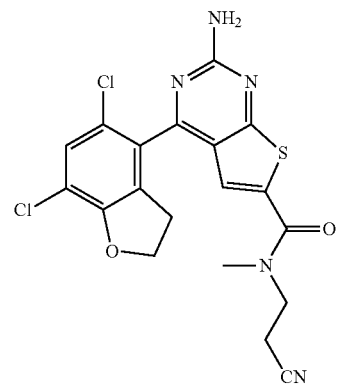 [SMILES: CN(CCC#N)C(=O)c1cc2c(-c3c(Cl)cc(Cl)c4c3CCO4)nc(N)nc2s1]

71

2-amino-N-(2-cyanoethyl)-4-(5,7-dichloro-2,3-dihydrobenzofuran-4-yl)-N-methylthieno[2,3-d]pyrimidine-6-carboxamide (71)

$^1$H NMR (400 MHz, DMSO-d6): δ=7.54 (s, 1H), 7.28 (s, 2H), 7.20 (s, 1H), 4.66 (t, J=8.8 Hz, 2H), 3.69 (br s, 2H), 3.26-3.16 (m, 4H), 3.02-2.92 (m, 1H), 2.82-2.70 (m, 2H). HPLC/MS: m/z calcd for $C_{19}H_{15}Cl_2N_5O_2S$ [M+H]$^+$: 448.0; found: 448.1.

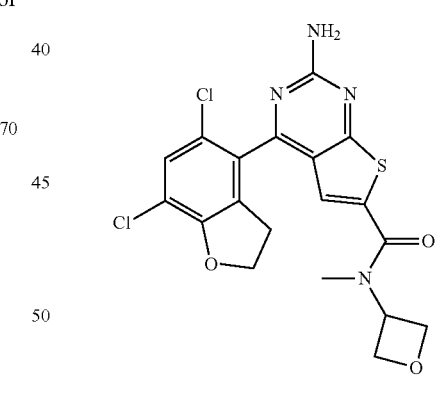

72

2-amino-4-(5,7-dichloro-2,3-dihydrobenzofuran-4-yl)-N-methyl-N-(oxetan-3-yl)thieno[2,3-d]pyrimidine-6-carboxamide (72)

$^1$H NMR (400 MHz, DMSO-d6): δ=7.55 (s, 1H), 7.26 (s, 2H), 7.16 (s, 1H), 5.21-5.16 (m, 1H), 4.69-4.60 (m, 6H), 3.26-3.14 (m, 4H), 3.02-2.92 (m, 1H). HPLC/MS: m/z calcd for $C_{19}H_{16}C_2N_4O_3S$ [M+H]$^+$: 451.0; found: 451.1.

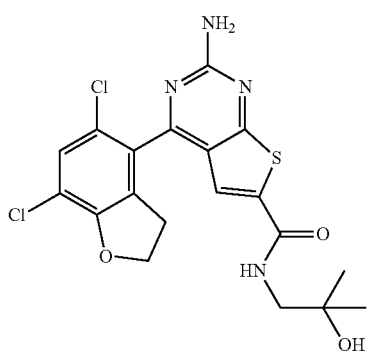 [SMILES: CN(CC(C)(C)O)C(=O)c1cc2c(-c3c(Cl)cc(Cl)c4c3CCO4)nc(N)nc2s1]

2-amino-4-(5,7-dichloro-2,3-dihydrobenzofuran-4-yl)-N-(2-hydroxy-2-methylpropyl)thieno[2,3-d]pyrimidine-6-carboxamide (73)

$^1$H NMR (400 MHz, DMSO-d6): δ=8.44 (s, 1H), 7.69 (s, 1H), 7.59 (s, 1H), 7.23 (s, 2H), 4.67 (t, J=8.8 Hz, 2H), 4.45 (s, 1H), 3.21-3.12 (m, 3H), 3.02-2.92 (m, 1H), 1.04 (s, 6H). HPLC/MS: m/z calcd for $C_{19}H_{18}Cl_2N_4O_3S$ [M+H]$^+$: 453.0; found: 453.1.

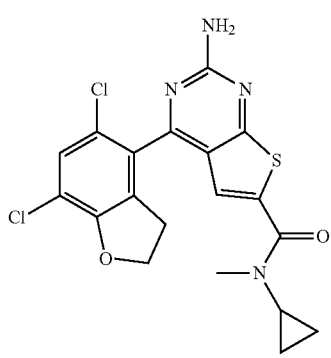 [SMILES: CN(C(=O)c1cc2c(-c3c(Cl)cc(Cl)c4c3CCO4)nc(N)nc2s1)C1CC1]

2-amino-N-cyclopropyl-4-(5,7-dichloro-2,3-dihydrobenzofuran-4-yl)-N-methylthieno[2,3-d]pyrimidine-6-carboxamide (74)

$^1$H NMR (400 MHz, DMSO-d6): δ=7.55 (s, 1H), 7.36 (s, 1H), 7.28 (s, 2H), 4.70-4.62 (m, 2H), 3.13-3.06 (m, 1H), 3.00-2.91 (m, 4H), 0.80-0.72 (m, 2H), 0.68-0.63 (m, 2H). HPLC/MS: m/z calcd for $C_{19}H_{16}Cl_2N_4O_2S$ [M+H]$^+$: 435.0; found: 435.1.

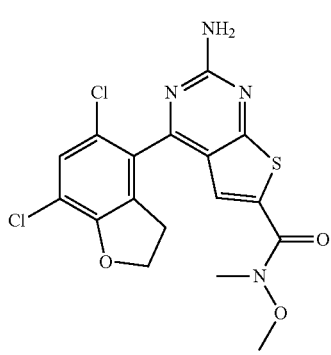 [SMILES: CON(C)C(=O)c1cc2c(-c3c(Cl)cc(Cl)c4c3CCO4)nc(N)nc2s1]

2-amino-4-(5,7-dichloro-2,3-dihydrobenzofuran-4-yl)-N-methoxy-N-methylthieno[2,3-d]pyrimidine-6-carboxamide (75)

$^1$H NMR (400 MHz, DMSO-d6): δ=7.57 (s, 1H), 7.47 (s, 1H), 7.37 (s, 2H), 4.70-4.62 (m, 2H), 3.74 (s, 3H), 3.27-3.19 (m, 4H), 3.00-2.91 (m, 1H). HPLC/MS: m/z calcd for $C_{17}H_{14}Cl_2N_4O_3S$ [M+H]$^+$: 425.0; found: 425.1.

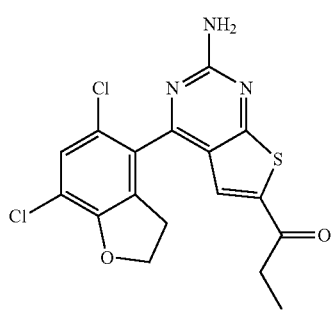 [SMILES: CCC(=O)c1cc2c(-c3c(Cl)cc(Cl)c4c3CCO4)nc(N)nc2s1]

1-(2-amino-4-(5,7-dichloro-2,3-dihydrobenzofuran-4-yl)thieno[2,3-d]pyrimidin-6-yl)propan-1-one (76)

To a flask containing 2-amino-4-(5,7-dichloro-2,3-dihydrobenzofuran-4-yl)-N-methoxy-N-methylthieno[2,3-d]pyrimidine-6-carboxamide (20 mg, 0.048 mmol) in dry THF (1 mL), was added EtMgBr (2.0 M in THF; 0.029 mL, 0.057 mmol), at 0° C. The reaction was stirred for 8 h, upon which it was quenched by addition of sat. NH$_4$Cl aq (1 mL). The aqueous layer was extracted with EtOAc (3×2 mL), dried over Na$_2$SO$_4$, filtered, and volatiles were evaporated. The residue was purified by silica gel chromatography using a gradient of DCM:MeOH (100:0 to 90:10). The product was obtained in 91% yield as a white solid.

$^1$H NMR (400 MHz, CDCl$_3$): δ=7.41 (s, 1H), 7.34 (s, 1H), 5.84 (br s, 2H), 4.74-4.64 (m, 2H), 3.87-3.76 (m, 1H), 3.30-3.10 (m, 3H), 1.50-1.41 (m, 3H). HPLC/MS: m/z calcd for $C_{17}H_{13}Cl_2N_3O_2S$ [M+H]$^+$: 394.0; found: 394.1.

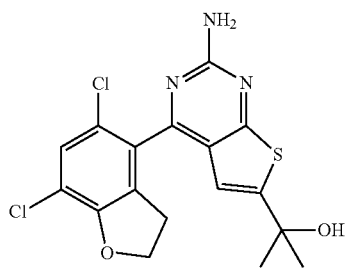 [SMILES: CC(C)(O)c1cc2c(-c3c(Cl)cc(Cl)c4c3CCO4)nc(N)nc2s1]

2-(2-amino-4-(5,7-dichloro-2,3-dihydrobenzofuran-4-yl)thieno[2,3-d]pyrimidin-6-yl)propan-2-ol (77)

To a flask containing ethyl 2-amino-4-(5,7-dichloro-2,3-dihydrobenzofuran-4-yl)thieno[2,3-d]pyrimidine-6-carboxylate (20 mg, 0.048 mmol) in dry THF (1 mL), was added MeMgBr (2.0 M in THF; 0.072 mL, 0.144 mmol), at 0° C. The reaction was stirred for 8 h, upon which it was quenched by addition of sat. NH$_4$Cl aq (1 mL). The aqueous layer was extracted with EtOAc (3×2 mL), dried over $Na_2SO_4$, filtered, and volatiles were evaporated. The residue was purified by silica gel chromatography using a gradient of DCM:MeOH (100:0 to 90:10). The product was obtained in 78% yield as a white solid.

$^1$H NMR (400 MHz, DMSO-d6): δ=7.53 (s, 1H), 6.85 (s, 2H), 6.54 (s, 1H), 5.95 (s, 1H), 4.64 (t, J=8.8 Hz, 2H), 3.20-3.12 (m, 1H), 3.00-2.90 (m, 1H), 1.46 (s, 3H), 1.44 (s, 3H). HPLC/MS: m/z calcd for $C_{17}H_{15}Cl_2N_3O_2S$ $[M+H]^+$: 396.0; found: 396.1.

Example 2. In Vitro Assays of the Compounds of the Invention

Hsp90 Biochemical Assay (Fluorescence Polarization)

Figure 4:
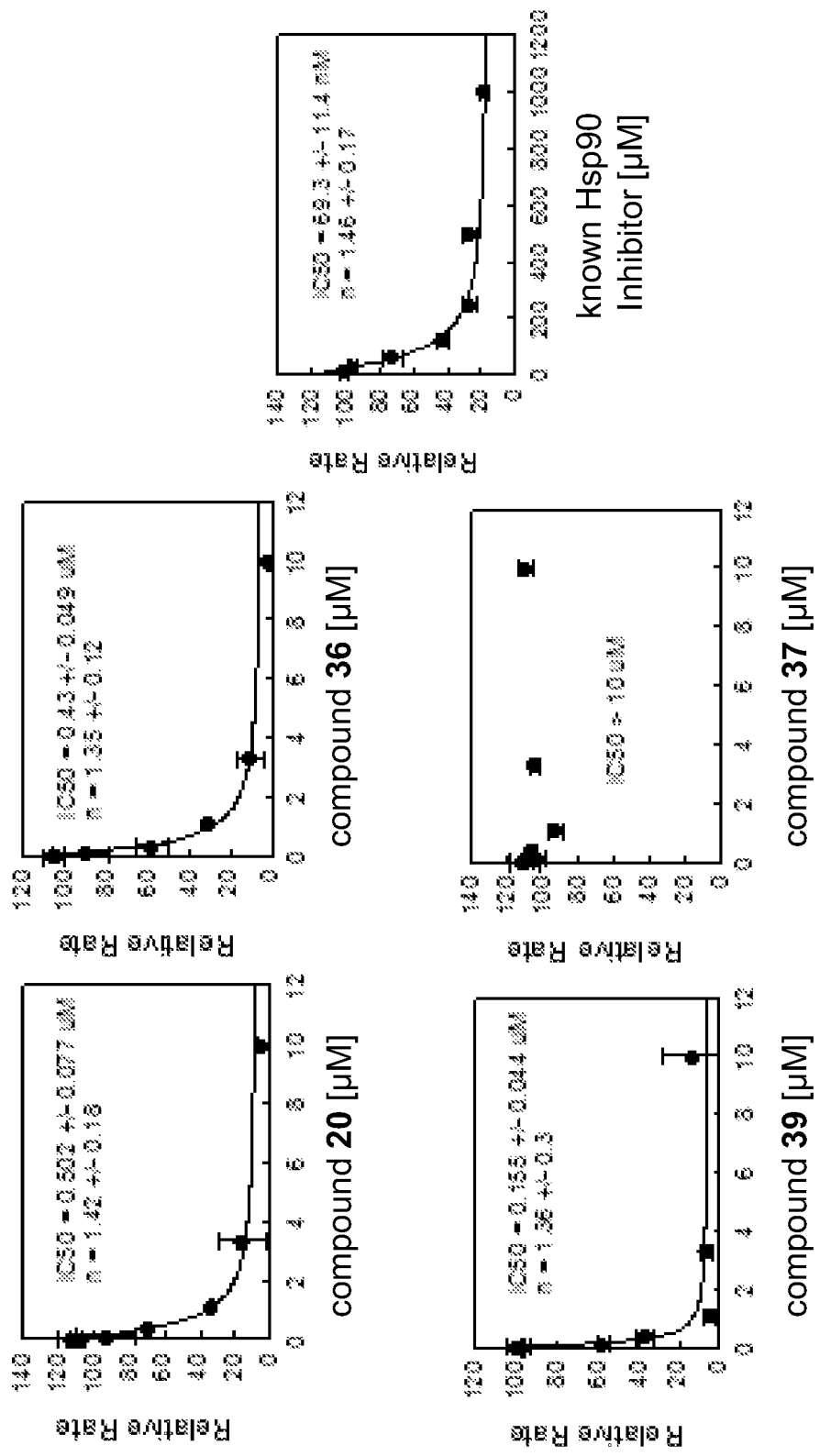
FIG. 4 shows five graphs providing $IC_{50}$ data for compounds 20, 36, 37, and 39 and for a known Hsp90 inhibitor, as measured using a fluorescence polarization assay described in Example 2.

Hsp90 inhibitory activity of the compounds of the invention was assessed using a fluorescence polarization (FP) assay using FITC-labeled geldanamycin and truncated alpha-Hsp90 protein. Measurement of binding activity was performed on BMG CLARIOstar® reader (BMG Labtech, Ortenberg, Germany). This assay is homogeneous and is performed in 384-well plates performing consistently with known standards. The assay was validated with known Hsp90 inhibitors, e.g., PU-H71 ($IC_{50}$=60 nM), which is in agreement with the reported $IC_{50}$ (Luo et al., supra). The results of this assay for compounds 20, 36, 37, and 39 and for the known Hsp90 inhibitor are shown in FIG. 4.

Hsp90 Biochemical Assay (AlphaLISA)

Figure 5:
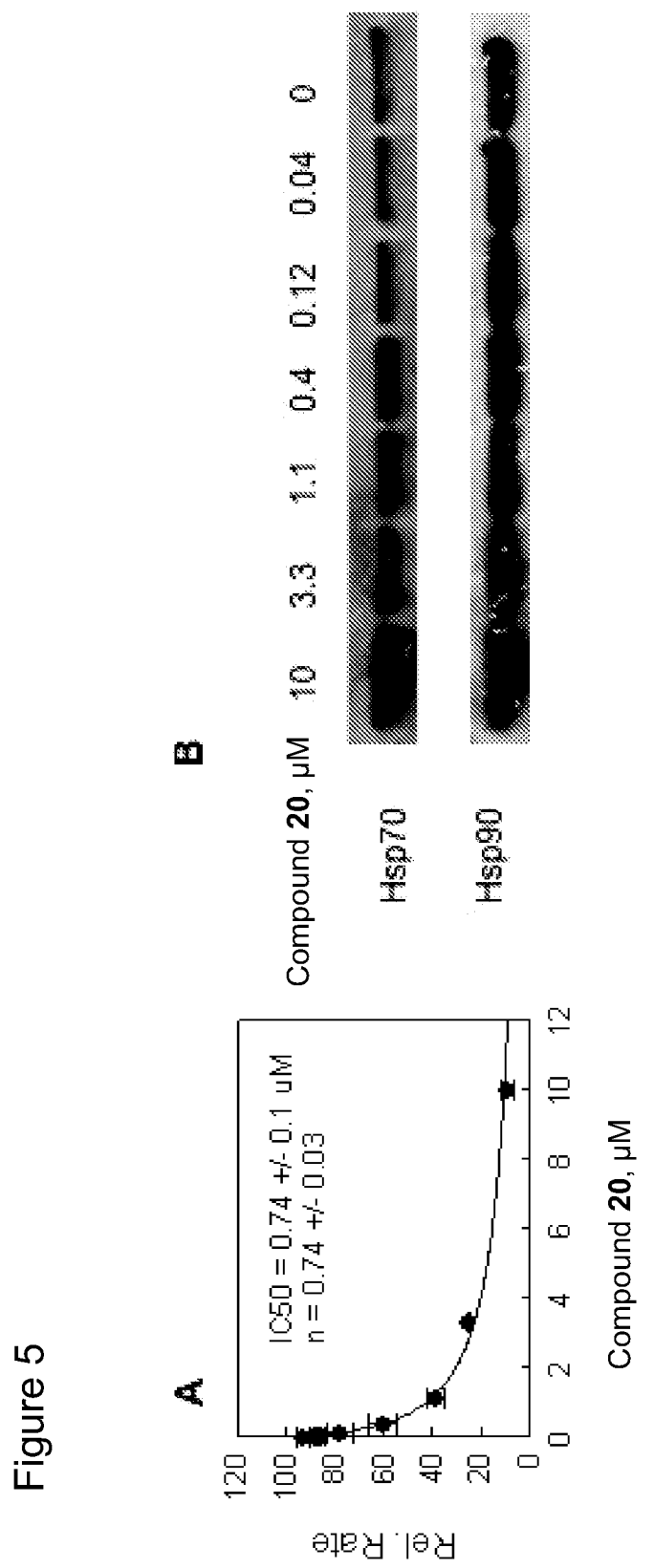
FIG. 5A shows a graph comparing relative association/dissociation rates to the concentration of compound 20.
FIG. 5B is a photograph of a gel demonstrating increase of the expression of Hsp70 at higher concentrations of compound 20 in a cell based functional assay. Further.

Hsp90 inhibitory activity of the compounds of the invention was assessed using a robust and reproducible assay based on the AlphaLISA format was developed (PerkinElmer, Inc., Waltham, Mass.; the format of the assay is described in, e.g., ELISA to AlphaLISA Conversion Guide, PerkinElmer, Inc., published in August, 2012). This assay employs biotinylated geldanamycin, His-tagged-Hsp90, and $Ni^{+2}$ coated beads. This assay is homogenous and miniaturized to 384-well plates. Measurement of binding activity was performed on an Envision reader. The assay was validated with known Hsp90 inhibitors, including PU-H71 ($IC_{50}$=60 nM) which is in agreement with the reported $IC_{50}$ (Luo et al., supra). This assay is the primary assay for evaluating compounds of the invention. In this assay, compound 20 showed Hsp90 inhibitory activity ($IC_{50}$ of 0.74±0.1 μM; see FIG. 5A).

Hsp90 Cell Based Functional Assays

Cells were treated with compounds of the invention for 24 h and then lysed in a buffer containing NP-40, orthovanadate, and protease inhibitors. Western blots were performed with antibodies specific to Hsp70, Hsp90, or actin (as control). Tau phosphorylation was assayed using, e.g., a method of Liu et al., Biochemistry, 49:4921-4929, 2010, with SHSY5Y-hTau441V337M/R406W cell line (Loeffler et al., *J. Mol. Neurosci.*, 47:192-203, 2012). This cell line represents stable transfected cell line that has been shown to have hyper-phosphorylated tau by over-express the longest human tau isoform, hTAU441 with two mutations: V337M and R406W. The functional assay described herein provides an in vitro model of tauopathy and can be used to evaluate the effect of Hsp90 inhibitors on phosphorylated tau protein (p-Tau). In these assays, compound 20 showed increase in the expression of Hsp70 (see FIG. 5B), significant decreases in the levels of pTau231 at 0.1 and 0.5 μM (see FIG. 6B), and significant decreases in the levels of pTau396 at 0.05, 0.1, and 0.5 μM (see FIG. 6C).

Cytotoxicity Assays

Figure 6:
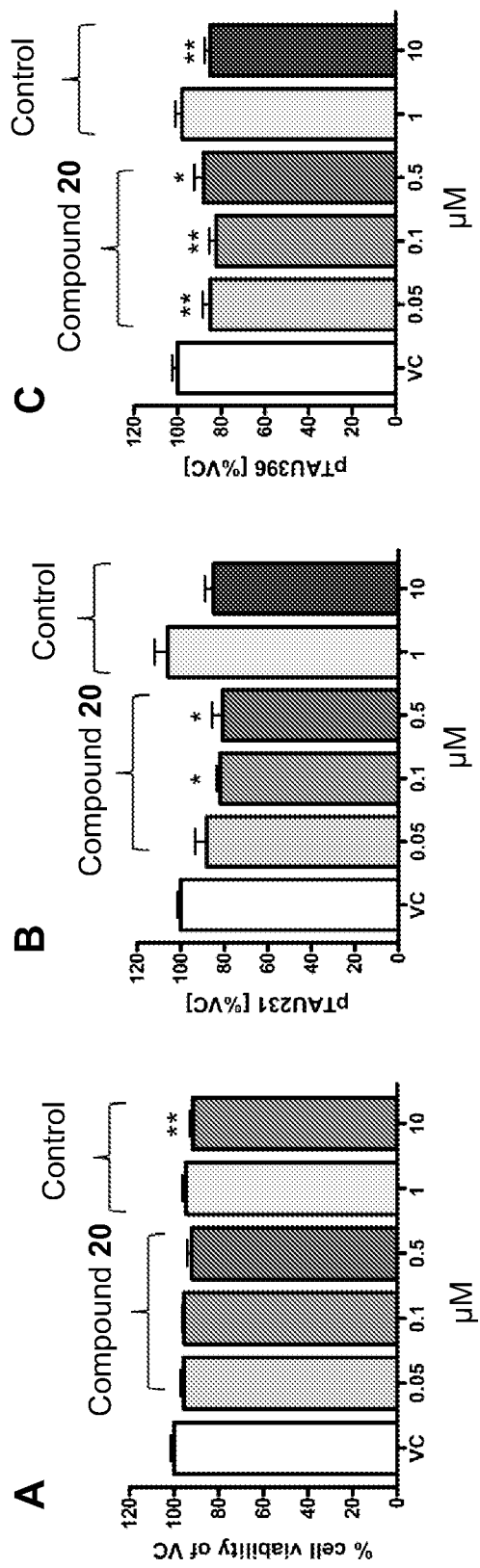
FIG. 6A shows a histogram comparing % cell viability in viable cells (VC), cells contacted with compound 20, and cells contacted with a control compound (JNK inhibitor).
FIG. 6B shows a graph comparing pTau231 levels in viable cells (VC), cells contacted with compound 20, and cells contacted with a control compound (JNK inhibitor).
FIG. 6C shows a graph comparing pTau396 levels in viable cells (VC), cells contacted with compound 20, and cells contacted with a control compound (JNK inhibitor).

SH-SY5Y-hTAU441 cell viability was determined using the MTT assay. As shown in FIG. 6A, compound 20 did not affect cell viability of SH-SY5Y-hTAU441 cells. SH-SY5Y cell viability may also be measured after 24 and 48 h with the CellTiter-Glo® assay that measures ATP-levels. In addition, cytotoxicity may be assessed using the Celigo® with live cell microscopic imaging and a GE InCell Analyzer 2000 to measure multiple outcomes including apoptosis markers, membrane permeability, and mitochondrial activity.

Mouse Liver Microsomal Stability

Metabolic stability of the compounds of the invention was assessed by monitoring their degradation in mouse liver microsomes. Compound 20 demonstrated good microsomal stability ($T_{1/2}$=26 min).

Solubility

Compound solubility was determined in pH 7.4 buffer. Aqueous solubility of greater than or equal to about 0.5 μM (e.g., greater than or equal to about 1 μM, greater than or equal to about 2 μM, greater than or equal to about 5 μM, greater than or equal to about 10 μM, greater than or equal to about 20 μM, or greater than or equal to about 30 μM) may indicate a compound having acceptable solubility for medical use, e.g., for treatment of a neurodegenerative disorder. At pH of 7.4, compound 20 exhibits an aqueous solubility of 30 μM.

Cell Permeability

Compounds may be assessed in MDR1-MDCK permeability assay or Caco-2 permeability assay to determine their permeability. Apical (A) to basal (B) permeability >3×10$^{-6}$ cm/sec and B→A/A→B asymmetry <3 for a compound are considered acceptable predictors of brain penetration, and compounds having such properties are unlikely to be P-glycoprotein (P-gp) substrates. Compound 20 has shown excellent permeability in MDR1-MDCK assay (A-B=28×10$^{-6}$ cm/s) with low asymmetry (B→A/A→B asymmetry=0.9).

Results of the above-described assays for certain compounds of the invention are summarized in Table 3.

TABLE 3

| Compound | | MW | cLogP | PSA | Hsp90 inhibitory activity | Hsp 70 agonist activity |
|---|---|---|---|---|---|---|
| (structure with $NH_2$, $CF_3$, Cl, pyrimidine, methoxy) | 1 | 317 | 4 | 60 | — | |

TABLE 3-continued

| Compound | | MW | cLogP | PSA | Hsp90 inhibitory activity | Hsp 70 agonist activity |
|---|---|---|---|---|---|---|
| (structure) | 2 | 311 | 4.3 | 60 | ++ | |
| (structure) | 3 | 309 | 3.9 | 46 | − | |
| (structure) | 4 | 323 | 4.7 | 37 | − | |
| (structure) | 5 | 295 | 3.6 | 60 | +++ | >2 fold at 0.4-1.0 μM |
| (structure) | 6 | 310 | 4.1 | 60 | +++ | ≥10 μM |

TABLE 3-continued
| Compound | | MW | cLogP | PSA | Hsp90 inhibitory activity | Hsp 70 agonist activity |
|---|---|---|---|---|---|---|
| 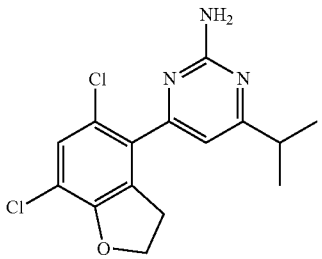 | 7 | 324 | 4.5 | 60 | +++ (1) | – |
| 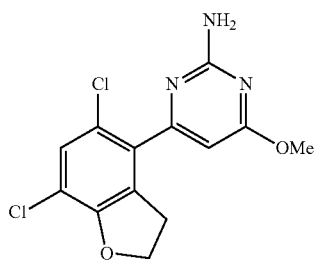 | 8 | 312 | 3.5 | 69 | +++ (2) | – |
| 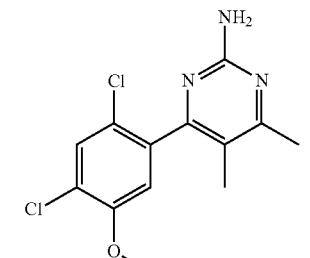 | 9 | 298 | 3.5 | 60 | +++ (3) | 1.5-fold at 1 μM |
| 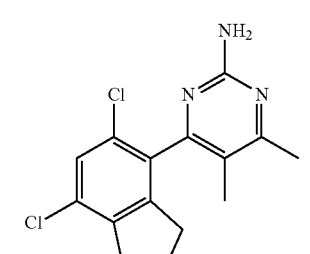 | 10 | 310 | 3.9 | 60 | +++ (4) | >2-fold at 0.4 μM |
| 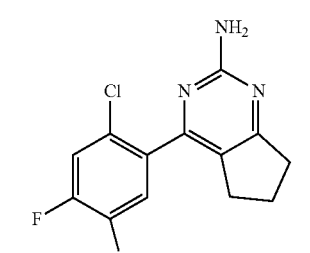 | 11 | 293 | 3.7 | 60 | + | |

TABLE 3-continued

| Compound | | MW | cLogP | PSA | Hsp90 inhibitory activity | Hsp 70 agonist activity |
|---|---|---|---|---|---|---|
| (structure) | 12 | 310 | 3.9 | 60 | +++ (5) | >2-fold at ≥10 μM |
| (structure) | 13 | 322 | 4.2 | 60 | +++ (6) | – |
| (structure) | 14 | 367 | 4.1 | 63 | +++ | >2-fold at 10 μM |
| (structure) | 15 | 336 | 4.5 | 60 | + | |
| (structure) | 16 | 323 | | | | |

TABLE 3-continued

| Compound | | MW | cLogP | PSA | Hsp90 inhibitory activity | Hsp 70 agonist activity |
|---|---|---|---|---|---|---|
| (structure) | 17 | 394 | | | – | |
| (structure) | 18 | 333 | | | | |
| (structure) | 19 | 309 | 3.8 | 72 | +++ | >2-fold at 0.4-1 μM |
| (structure) | 20 | 321 | 4.1 | 72 | +++ | – |
| (structure) | 21 | 335 | 3.1 | 63 | ++ | – |

TABLE 3-continued

| Compound | | MW | cLogP | PSA | Hsp90 inhibitory activity | Hsp 70 agonist activity |
|---|---|---|---|---|---|---|
| [structure: 5,7-dichloro-2,3-dihydrobenzofuran linked to 5-ethyl-pyrrolopyrimidine-2-amine] | 22 | 349 | 3.4 | 63 | + | − |
| [structure: 5,7-dichloro-2,3-dihydrobenzofuran linked to thienopyrimidine-2-amine with ethyl ester] | 23 | 410 | 4.8 | 86 | + (7) | 3.3 μM |
| [structure: 5,7-dichloro-2,3-dihydrobenzofuran linked to thienopyrimidine-2-amine with ethyl amide] | 24 | 409 | 4.1 | 89 | +++ | 0.4 μM |
| [structure: 2-chloro-4-fluoro-5-methoxyphenyl linked to pyrrolopyrimidine-2-amine] | 25 | 292.70 | 2.5 | 72 | + (8) | 1.5 fold, or no observable effect |
| [structure: 2-chloro-4-fluoro-5-methoxyphenyl linked to N-methyl-pyrrolopyrimidine-2-amine] | 26 | 306.73 | 2.7 | 63 | ++ (9) | 2 fold at 3.3 μM, or no observable effect |

TABLE 3-continued
| Compound | | MW | cLogP | PSA | Hsp90 inhibitory activity | Hsp 70 agonist activity |
|---|---|---|---|---|---|---|
| 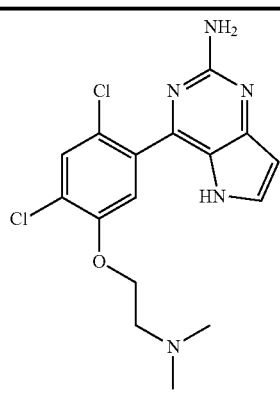 | 27 | 366.25 | 2.9 | 75 | ++ | 10 μM |
| 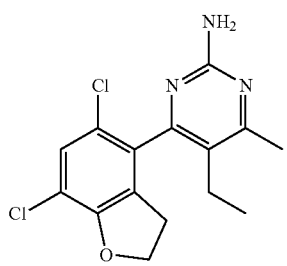 | 28 | 324.21 | 4.5 | 60 | -- | |
| 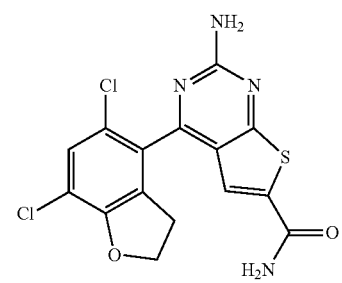 | 29 | 381.23 | 3.6 | 103 | +++ | 0.4 μM |
| 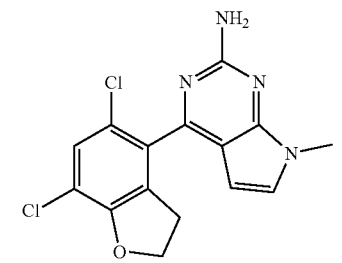 | 30 | 335.19 | 3.4 | 63 | − | |
| 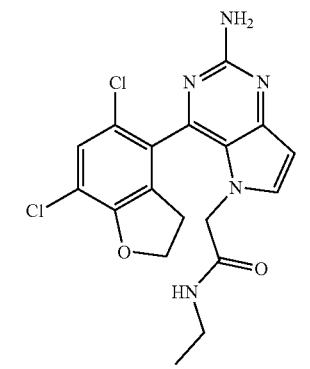 | 31 | 406.27 | 2.3 | 92 | − | |

TABLE 3-continued

| Compound | | MW | cLogP | PSA | Hsp90 inhibitory activity | Hsp 70 agonist activity |
|---|---|---|---|---|---|---|
| (structure) | 32 | 406.27 | 2.6 | 92 | − | |
| (structure) | 33 | 311.17 | 3.1 | 72 | + | |
| (structure) | 34 | 317.19 | 4.5 | 72 | +++ | 3.3 µM; 10 µM |
| (structure) | 35 | 316.20 | 4.0 | 60 | +++ | 3.3 µM; 10 µM |
| (structure) | 36 | 301.13 | 3.9 | 82 | +++ | >10 µM |

TABLE 3-continued

| Compound | | MW | cLogP | PSA | Hsp90 inhibitory activity | Hsp 70 agonist activity |
|---|---|---|---|---|---|---|
| (Structure with triazine, NH₂, two 2-Cl-4-Cl-5-OMe-phenyl groups) | 37 | 446.11 | 7.0 | 82 | − | |
| (Structure: 2-amino-4-methyl-6-(2,4-dichloro-5-methoxyphenyl)pyrimidine) | 38 | 284.14 | 3.6 | 60 | ++ | |
| (Structure: 2-amino-4-chloro-6-(2,4-dichloro-5-methoxyphenyl)pyrimidine) | 39 | 304.56 | 3.8 | 60 | +++ | 0.4 μM |
| (Structure: 2-amino-4-chloro-6-(5,7-dichloro-2,3-dihydrobenzofuran-4-yl)pyrimidine) | 49 | 316.6 | 3.8 | 60 | +++ | |
| (Structure: 2-amino-4-(trifluoromethyl)-6-(5,7-dichloro-2,3-dihydrobenzofuran-4-yl)pyrimidine) | 50 | 350.1 | 4.0 | 60 | ++ | |

TABLE 3-continued

| Compound | | MW | cLogP | PSA | Hsp90 inhibitory activity | Hsp 70 agonist activity |
|---|---|---|---|---|---|---|
| (structure) | 51 | 328.2 | 4.0 | 60 | +++ | |
| (structure) | 52 | 331.6 | 3.0 | 86 | +++ | |
| (structure) | 53 | 298.1 | 3.2 | 80 | − | |
| (structure) | 54 | 379.2 | 3.4 | 90 | − | |
| (structure) | 55 | 363.2 | 2.8 | 80 | − | |

TABLE 3-continued

| Compound | | MW | cLogP | PSA | Hsp90 inhibitory activity | Hsp 70 agonist activity |
|---|---|---|---|---|---|---|
| (structure) | 56 | 348.0 | 2.6 | 89 | – | |
| (structure) | 57 | 388.1 | 3.7 | 72 | – | |
| (structure) | 58 | 478.4 | 4.1 | 9.2 | +++ | |
| (structure) | 59 | 434.3 | 3.8 | 113 | +++ | |

TABLE 3-continued

| Compound | | MW | cLogP | PSA | Hsp90 inhibitory activity | Hsp 70 agonist activity |
|---|---|---|---|---|---|---|
| | 60 | 425.3 | 3.3 | 109 | +++ | |
| | 61 | 463.3 | 4.8 | 89 | +++ | |
| | 62 | 421.3 | 4.1 | 89 | +++ | |
| | 63 | 395.3 | 3.8 | 89 | +++ | |

TABLE 3-continued
| Compound | | MW | cLogP | PSA | Hsp90 inhibitory activity | Hsp 70 agonist activity |
|---|---|---|---|---|---|---|
| 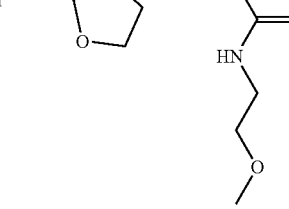 | 64 | 439.3 | 3.6 | 98 | +++ | |
| 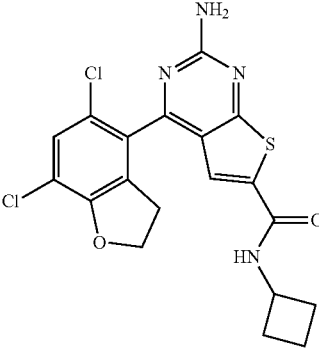 | 65 | 435.3 | 4.5 | 89 | +++ | |
| 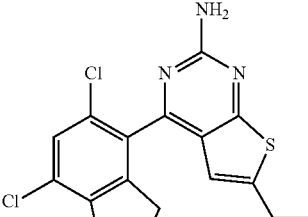 | 66 | 409.3 | 4.0 | 80 | +++ | |
| 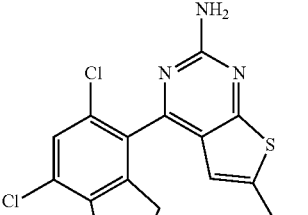 | 67 | 437.3 | 3.4 | 98 | +++ | |

TABLE 3-continued

| Compound | | MW | cLogP | PSA | Hsp90 inhibitory activity | Hsp 70 agonist activity |
|---|---|---|---|---|---|---|
| (structure) | 68 | 451.3 | 3.6 | 89 | ++ | |
| (structure) | 69 | 435.3 | 4.3 | 80 | ++ | |
| (structure) | 70 | 477.3 | 5.0 | 89 | + | |
| (structure) | 71 | 448.3 | 4.1 | 104 | +++ | |

TABLE 3-continued

| Compound | | MW | cLogP | PSA | Hsp90 inhibitory activity | Hsp 70 agonist activity |
|---|---|---|---|---|---|---|
| | 72 | 451.3 | 3.6 | 89 | ++ | |
| | 73 | 453.3 | 3.8 | 109 | +++ | |
| | 74 | 435.3 | 4.3 | 80 | ++ | |
| | 75 | 425.3 | | 89 | +++ | |

TABLE 3-continued

| Compound | | MW | cLogP | PSA | Hsp90 inhibitory activity | Hsp 70 agonist activity |
|---|---|---|---|---|---|---|
| [structure with NH2, Cl, Cl, dihydrobenzofuran, thienopyrimidine, propanoyl] | 76 | 394.3 | 4.6 | 77 | +++ | |
| [structure with NH2, Cl, Cl, dihydrobenzofuran, thienopyrimidine, C(CH3)2OH] | 77 | 396.3 | 4.6 | 80 | ++ | |
| [structure with NH2, Cl, chloropyrimidine, methoxyphenyl] | 78 | 269.01 | | | ++ | |
| [structure with NH2, Cl, chloropyrimidine, chloro-methoxyphenyl] | 79 | 269.01 | | | +++ | |

In Table 3, "Hsp90 inhibitory activity" provides an assessment of exemplary compounds for their ability to inhibit Hsp90. In particular, "-" indicates that the compound has IC$_{50}$ of greater than about 10 μM, "+" indicates that the compound has IC$_{50}$ in the range of about 4 μM to about 10 μM; "++" indicates that the compound has IC$_{50}$ in the range of about 1 μM to about 4 μM; "+++" indicates that the compound has IC$_{50}$ of less than about 1 μM. "Hsp 70 agonist activity" indicates EC$_{50}$ (μM) of the exemplary compound at which Hsp70 is increased two-fold unless otherwise noted; "-" designates lack of observable effect at concentrations exceeding 10 μM. (1) Data according to AlphaLISA assay, FP assay result: >10 μM. (2) Data according to AlphaLISA assay, FP assay result: 5.5 and 6.2 μM. (3) Data according to AlphaLISA assay, FP assay result: 1 and 1.4 μM. (4) Data according to AlphaLISA assay, FP assay result: 2.3 and 2.4 μM. (5) Data according to AlphaLISA assay, FP assay result: 1.7 μM. (6) Data according to AlphaLISA assay, FP assay result: 1.8 μM. (7) Data according to AlphaLISA assay, FP assay result: 11.1 μM. (8) Data according to AlphaLISA assay, FP assay result: 12.1 and 19.3 μM. (9) Data according to AlphaLISA assay, FP assay result: 8.5 and 11.2 μM.

Example 3. Pharmacokinetic Properties of the Compounds of the Invention

The pre-clinical study included 85 mice, distributed over 6 groups; a summary of treatment groups is given in Table 4.

TABLE 4

| Group | n | Sacrificed at | Sample reference |
|---|---|---|---|
| A | 5 | Pre-dose | A_0 |
| B | 3 | 15 minutes | B_0.25 |
| C | 3 | 30 minutes | C_0.5 |
| D | 3 | 1 hour | D_1 |
| E | 3 | 2 hours | E_2 |
| F | 3 | 8 hours | F_8 |

Plasma and brain samples were taken pre-dose and at post dose time points of pre-dose, 15 and 30 minutes, 1, 2, and 8 hours. The pre-dose group was represented by 5 animals, whereas the post-dose groups were represented by 3 animals.

Bioanalysis Methods

Bioanalysis of mouse plasma samples for compound 20 was conducted by protein precipitation and LC-MS/MS with compound 22 as the internal standard. The method was based on a 'generic assay' and some method development was conducted to tailor that assay to the particular compound and internal standard. The eventual non-GLP assay was first tested by analyzing a bioanalytical run with spiked mouse plasma samples. The qualification run passed by the run acceptance criteria (see below). Bioanalysis was then conducted of plasma sample extracts and of brain sample homogenate extracts, using a calibration and quality control samples spiked in mouse plasma. The assay is described below.

Assay of Mouse Plasma Levels of Compound 20

Sample Treatment

Compound 20 and compound 22 were extracted from the mouse plasma matrix by protein precipitation. To 20.0 µL of sample was added 10.0 µL of internal standard working solution (1000 ng/mL in MeOH) and 200 µL of MeCN. The mixture was vortexed (5 sec) and centrifuged (14000 rpm, 5 min). The supernatant was then recovered and evaporated to dryness. The residue was redissolved in 100 µL of redissolving solution (80:20 v:v of mobile phases A:B). For analysis, 20.0 µL was injected in to the LC-MS/MS system.

Chromatography

All chromatography was done with a type 1100 liquid chromatograph (Agilent), equipped with an auto-injector. The analytical column was an Xbridge C18 3.5 µm 2.1×50 mm (Waters), employed at 50° C. The mobile phase was a gradient, composed of solvent A:1 g/L ammonium acetate in Milli-Q water, and solvent B: MeCN. The gradient was as shown in Table 5.

TABLE 5

| Step | Total time (min) | Flow rate (µL/min) | A (%) | B (%) |
|---|---|---|---|---|
| 0 | 0.00 | 700 | 80 | 20 |
| 1 | 0.20 | 700 | 80 | 20 |
| 2 | 1.00 | 700 | 0 | 100 |
| 3 | 2.00 | 700 | 0 | 100 |
| 4 | 2.10 | 700 | 80 | 20 |
| 5 | 5.00 | 700 | 80 | 20 |

Mass Spectrometry

All experiments were done on an API 3000 triple quadrupole instrument (AB Sciex), operated in positive turbo-ionspray mode ('TIS+'). The instrument parameters had been optimized during method development. The MS/MS transitions employed were as shown in Table 6.

TABLE 6

| Compound | Q1, [M + H] + (35Cl2) (Da) | Q3 [M + H—HCl] + (35Cl2) (Da) |
|---|---|---|
| Compound 20 | 321.1 | 285.0 |
| Compound 22 | 349.2 | 318.9 |

Description of Bioanalytical Experiment and Acceptance Criteria

The calibration range for compound 20 was set up to cover concentrations between 0.988 and 20000 ng/mL. Two sets of calibration samples were used, one set placed before and the other placed after the study samples. In addition, QC samples at 5 levels (two samples at each level) were included in the run, as performance indicators and for run acceptance.

Acceptance criteria for calibration and QC samples were applied, as follows:

The absolute % RE (|% RE|) relative to the nominal concentration for individual calibration and QC samples should be within 20% (or 25% at LLOQ);

A calibration level was considered valid when at least one of the calibration samples at that concentration level was accepted by the above |% RE| criterion;

A QC level was considered valid when at least one of the QC samples at that concentration level was accepted by the above |% RE| criterion.

The lowest and highest accepted calibration concentration levels were adopted as the lower and upper limit of quantification, LLOQ and HLOQ, respectively.

Bioanalytical Results

For compound 20, the highest calibration level (STD L, 20000 ng/mL) did not pass acceptance criteria as both calibration samples displayed too high a bias (see Table 7). All other calibration levels of compound 20, STD A through STD K, were accepted with single samples at STD C and STD G displaying too high bias. As a consequence, the lowest level (STD A, 0.988 ng/mL) was adopted as the LLOQ and the next higher level (STD K, 8000 ng/mL) was adopted as the HLOQ. One of the QC LLOQ and one of the QC Med sample results had too high a bias. The overall method performance in the bioanalytical run was accepted for compound 20.

Calibration and QC concentration levels employed are shown in Table 7:

TABLE 7

| Sample indicator | Compound 20 concentration (ng/mL) |
|---|---|
| STD A | 0.988 |
| STD B | 2.37 |
| STD C | 5.93 |
| STD D | 14.8 |
| STD E | 35.6 |
| STD F | 88.9 |
| STD G | 222 |
| STD H | 533 |
| STD I | 1333 |
| STD J | 3333 |
| STD K | 8000 |
| STD L | 20000 |
| QCLLQ | 2.37 |
| QCLow | 14.8 |
| QCMed | 88.9 |
| QCHigh | 1333 |
| QCOC | 8000 |

The bioanalysis results for plasma and brain samples are presented in Tables 8 and 9.

TABLE 8

| Group | IRN | Concentration compound 20 (ng/mL) |
|---|---|---|
| A_0 | 2 | 0.00 [a] |
| A_0 | 4 | 2.16 |
| A_0 | 6 | 0.00 [a] |
| A_0 | 8 | 0.00 [a] |
| A_0 | 10 | 0.00 [a] |
| B_0.25 | 12 | 2.66 |
| B_0.25 | 14 | 17,900 [b] |
| B_0.25 | 16 | 12,000 [b] |
| C_0.5 | 18 | 11,500 [b] |
| C_0.5 | 20 | 10,500 [b] |
| C_0.5 | 22 | 11,100 [b] |
| D_1 | 24 | 6,890 |
| D_1 | 26 | 7,130 |
| D_1 | 28 | 7,470 |
| E_2 | 30 | 4,150 |
| E_2 | 32 | 4,180 |
| E_2 | 34 | 4,440 |
| F_8 | 36 | 99.3 |
| F_8 | 38 | 22.5 |
| F_8 | 40 | 21.9 |

[a] "0.00" represents 'below limit of quantification' (LLOQ; the LLOQ was 0.988 ng/mL).
[b] Value is out of range (0.988-8000 ng/mL); two calibrators at 20000 ng/mL were rejected but showed an average response of 14000 ng/mL.

TABLE 9

| Group | IRN | Homogenate concentration (ng/mL) | Brain weight (g) | Brain concentration of compound 20 (ng/g) |
|---|---|---|---|---|
| A_0 | 2 | 0.00 [a] | 0.453 | 0.00 [a] |
| A_0 | 4 | 0.00 [a] | 0.483 | 0.00 [a] |
| A_0 | 6 | 0.00 [a] | 0.451 | 0.00 [a] |
| A_0 | 8 | 0.00 [a] | 0.487 | 0.00 [a] |
| A_0 | 10 | 0.00 [a] | 0.472 | 0.00 [a] |
| B_0.25 | 12 | 0.00 [a] | 0.463 | 0.00 [a] |
| B_0.25 | 14 | 2300 | 0.445 | 20674 |
| B_0.25 | 16 | 1250 | 0.460 | 10870 |
| C_0.5 | 18 | 1400 | 0.482 | 11618 |
| C_0.5 | 20 | 844 | 0.458 | 7371 |
| C_0.5 | 22 | 1200 | 0.458 | 10480 |
| D_1 | 24 | 888 | 0.474 | 7494 |
| D_1 | 26 | 859 | 0.459 | 7486 |
| D_1 | 28 | 789 | 0.461 | 6846 |
| E_2 | 30 | 410 | 0.455 | 3604 |
| E_2 | 32 | 385 | 0.461 | 3341 |
| E_2 | 34 | 294 | 0.467 | 2518 |
| F_8 | 36 | 7.53 | 0.478 | 63.0 |
| F_8 | 38 | 1.83 | 0.489 | 15.0 |
| F_8 | 40 | 1.53 | 0.476 | 12.9 |

[a] "0.00" represents "below limit of quantification" (LLOQ; the LLOQ was 0.988 ng/mL).

In the plasma samples, the following observations were made:
  There was one minor response in a pre-dose sample (one A_0 sample; found at 2.16 ng/mL). This response may have come from a minor contamination or from assay interference. Although selectivity of LC-MS/MS methods is generally high, selectivity for compound 20 in plasma was not tested. Conclusions can only be drawn after more elaborate method qualification or even method validation. At less than 3 times LLOQ, this pre-dose response is considered negligible here.
  Results for most measurements in time point B_0.25 and all measurements in time point C_0.5 are above the upper limit of quantification (ULOQ, at 8000 ng/mL). For obtaining more reliable results, these samples would have to be diluted prior to analysis. It is noted that a highest calibrator at 20000 ng/mL was included in the run but failed on bias. The mean back-calculated concentration of 20000 ng/mL was 14000 ng/mL., indicating a bias of −30% at that level. The above ULOQ results were included in this Example as indicative values, in support of PK evaluation. However, the results from B_0.25 and C_0.5 time points should be treated with caution.

Results from the first subject in the time point B_0.25 (IRN 12) are unlikely to be near the observed 2.66 ng/mL, as that does not match with the relatively high concentrations observed in the other two subjects at this first post-dose time point (IRN 14 and 16). Provisionally, PK evaluation for this time point was conducted for both cases: (1) mean of 3 and (2) mean of two with exclusion of this BLOQ result.

In the brain (homogenate) samples one result appear different from expectation:
  results from the first subject in the time point B_0.25 (IRN 12) are unlikely to be below LLOQ, as that does not match with the relatively high concentrations observed in the other two subjects at this first post-dose time point (IRN 14 and 16). Please note that this parallels the findings for plasma from this subject (IRN 12). Provisionally, PK evaluation for this time point was conducted for both cases: (1) mean of 3 and (2) mean of two with exclusion of this BLOQ result.

Pharmacokinetic Evaluation

Evaluation of pharmacokinetic parameters was conducted by calculation from the mean concentration (n=5 pre-dose, n=3 post-dose) at each time point. The pharmacokinetic results are summarized below.

Mouse Plasma

Figure 7:
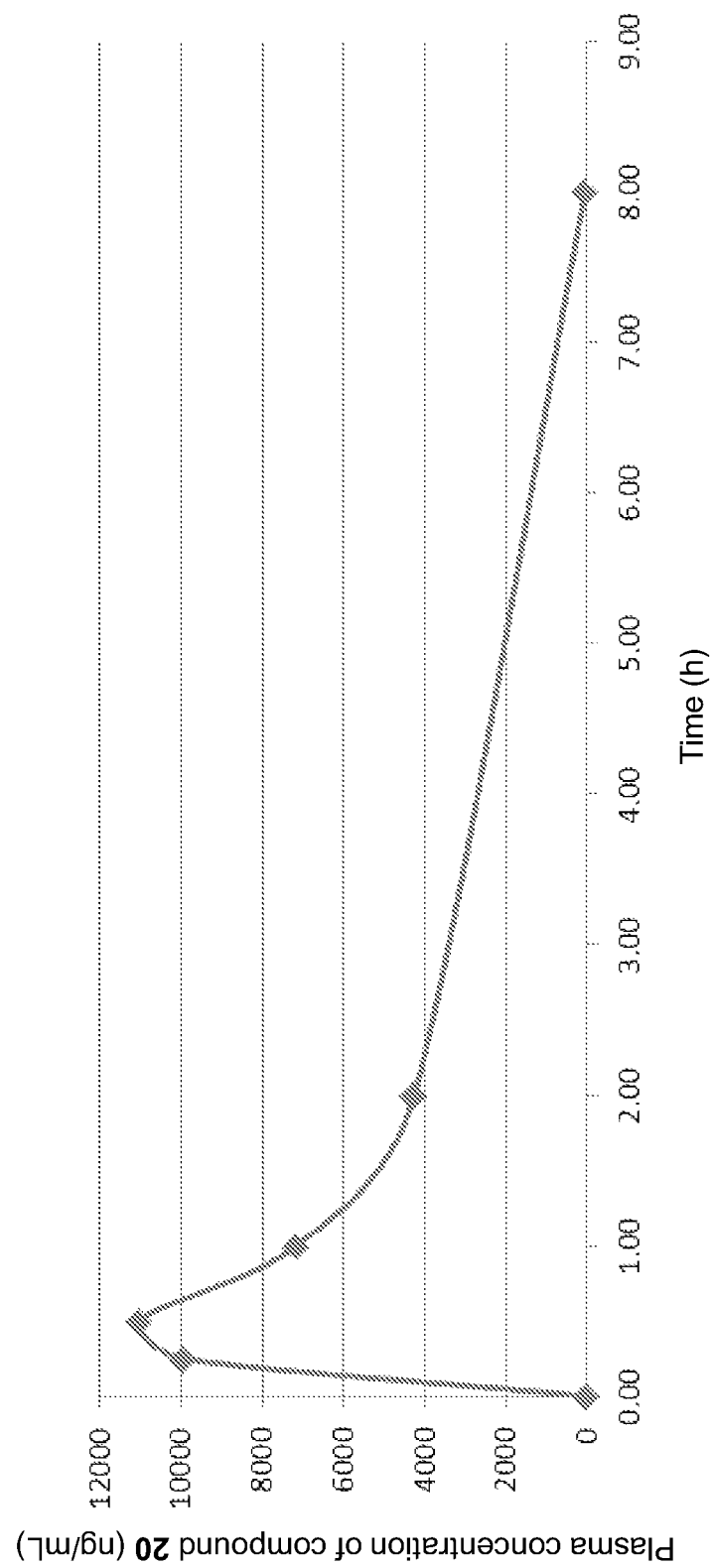
FIG. 7 shows a graph of the concentration of compound 20 in mouse plasma. The data in this graph excludes the plasma level of compound 20 in animal IRN 12.
Figure 8:
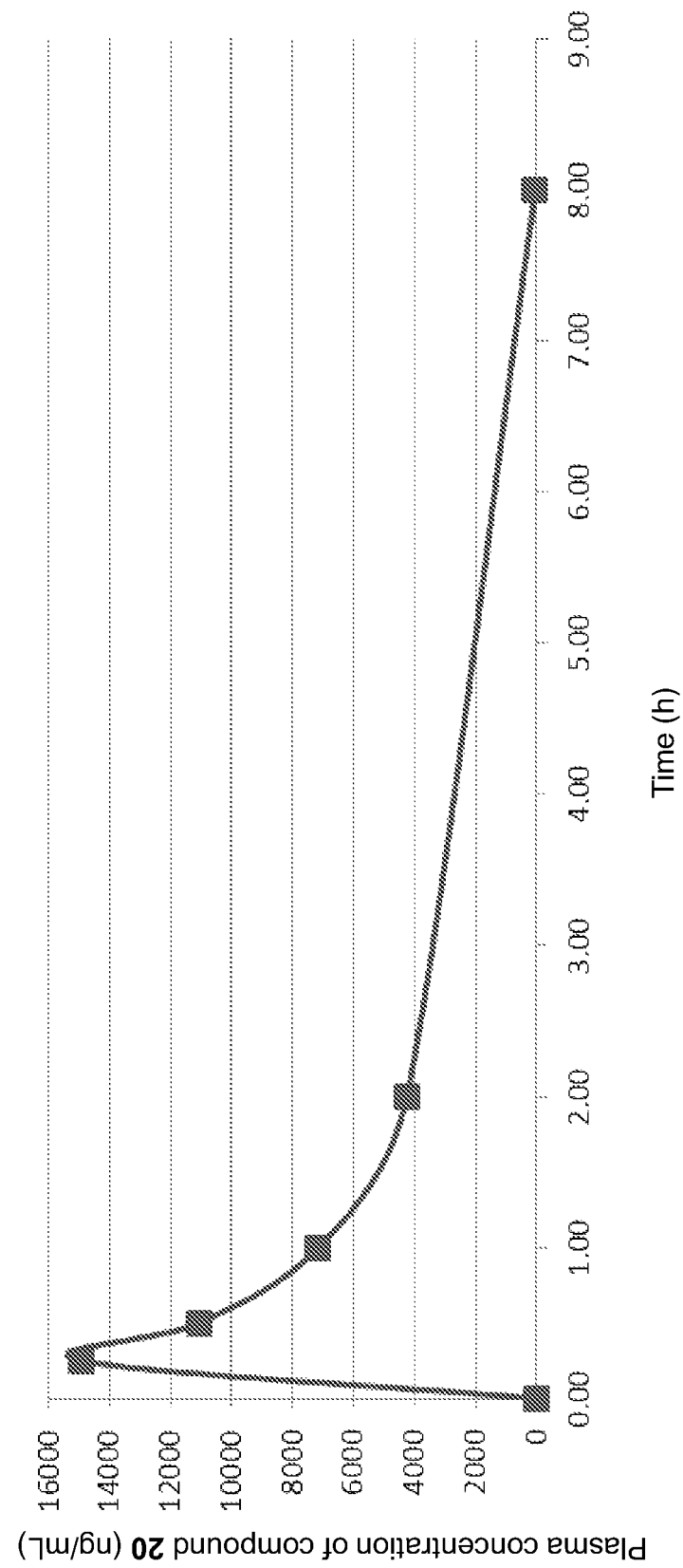
FIG. 8 shows a graph of the concentration of compound 20 in mouse plasma. The data in this graph includes all mouse plasma data points.

Results for pharmacokinetic evaluation are given in Tables 10-12 and FIGS. 7 and 8. No corrections were made for results above the ULOQ or for the inclusion of the result for animal IRN12 in group B_0.25.

TABLE 10

| Group | Time Point (h) | Mean Group Concentration (ng/mL) |
|---|---|---|
| A_0 | 0.00 | 0.432 |
| B_0.25 | 0.25 | 9968 [a] |
| C_0.5 | 0.50 | 11033 |
| D_1 | 1.00 | 7163 |
| E_2 | 2.00 | 4257 |
| F_8 | 8.00 | 47.9 |

[a] Excluding IRN 12 result: 14950 ng/mL

Tables 11 and 12 provide plasma pharmacokinetic profile of compound 20.

TABLE 11 [(a)]

| Parameter | Value | Unit |
|---|---|---|
| $C_{max}$ | 11033 | ng/mL |
| $T_{max}$ | 0.50 | hours (h) |
| $K_{elimination}$ | 0.725 | per hour (h$^{-1}$) |
| Half life ($t_{1/2}$) | 0.96 | hours (h) |
| AUC(0-8 h) | 27044 | ng/mL · h |
| AUC(0-inf) | 27055 | ng/mL · h |

[(a)] excluding IRN12 result.

TABLE 12 [a]{

| Parameter | Value | Unit |
|---|---|---|
| $C_{max}$ | 14950 | ng/mL |
| $T_{max}$ | 0.25 | hours (h) |
| $K_{elimination}$ | 0.730 | per hour (h$^{-1}$) |
| Half life ($t_{1/2}$) | 0.95 | hours (h) |
| AUC(0-8 h) | 28290 | ng/mL · h |
| AUC(0-inf) | 28301 | ng/mL · h |

[a]{ including IRN12 result.

Mouse Brain Tissue

Figure 9:
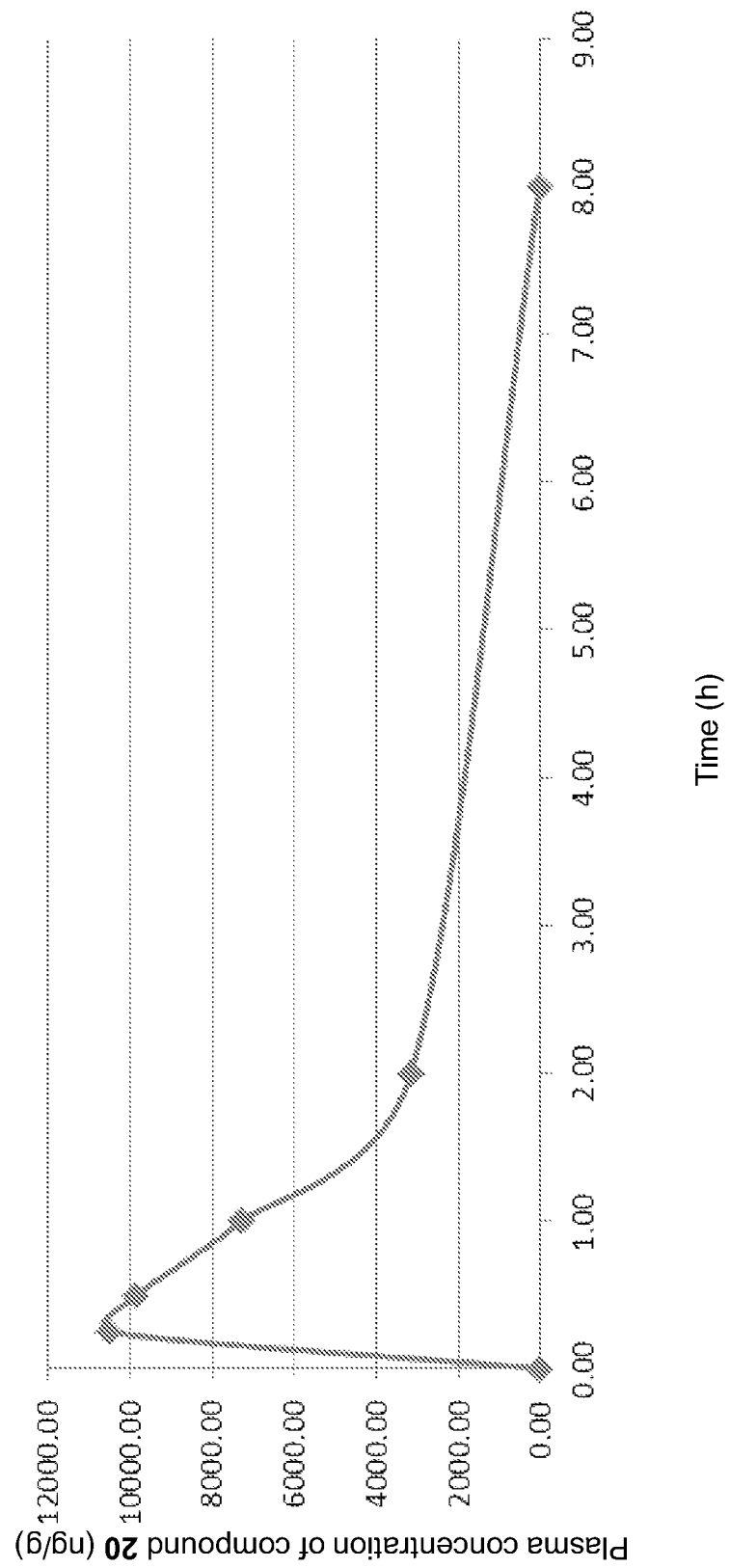
FIG. 9 shows a graph of the concentration of compound 20 in mouse brain tissue. The data in this graph excludes the plasma level of compound 20 in animal IRN 12.
Figure 10:
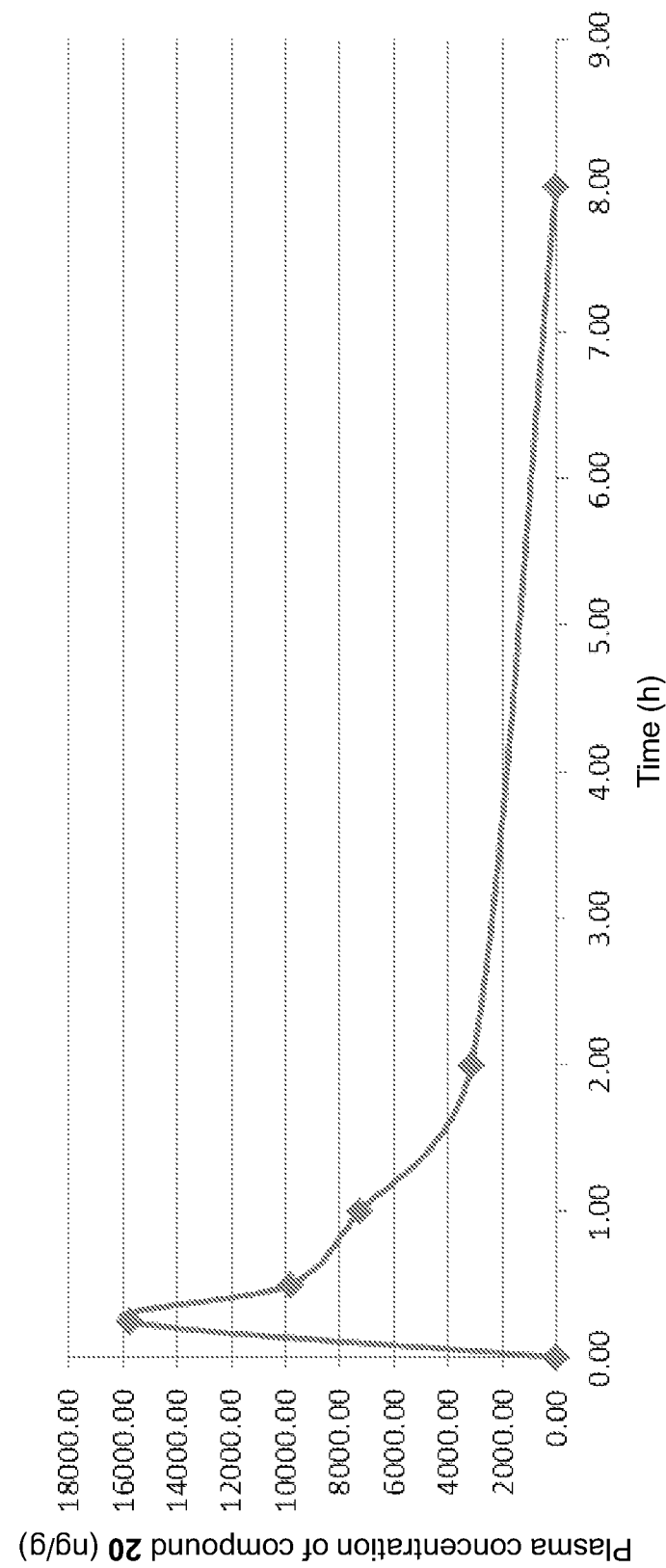
FIG. 10 shows a graph of the concentration of compound 20 in mouse brain tissue. The data in this graph includes all mouse brain tissue data points.

Results for brain tissue pharmacokinetic evaluation are given in FIGS. 9 and 10 and Tables 13-15. No corrections were made for the inclusion of the odd result for animal IRN 12 in group B_0.25.

TABLE 13

| | | Mean Group Concentration | |
|---|---|---|---|
| Group | Time Point (h) | Homogenate (ng/mL) | Tissue (ng/g) |
| A_0 | 0.00 | 0.00 | 0.00 |
| B_0.25 | 0.25 | 1183 | 10515 [a] |
| C_0.5 | 0.50 | 1148 | 9823 |
| D_1 | 1.00 | 845 | 7275 |
| E_2 | 2.00 | 363 | 3154 |
| F_8 | 8.00 | 3.63 | 30.0 |

[a] excluding IRN 12 result: 15772 ng/g.

Tables 14 and 15 provide brain tissue pharmacokinetic profile of compound 20.

TABLE 14 [a]

| Parameter | Value | Unit |
|---|---|---|
| $C_{max}$ | 10515 | ng/mL |
| $T_{max}$ | 0.25 | hours (h) |
| $K_{elimination}$ | 0.769 | per hour (h$^{-1}$) |
| Half life ($t_{1/2}$) | 0.90 | hours (h) |
| AUC(0-8 h) | 22898 | ng/mL · h |
| AUC(0-inf) | 22908 | ng/mL · h |

[a] excluding IRN 12 result.

TABLE 15 [a]

| Parameter | Value | Unit |
|---|---|---|
| $C_{max}$ | 15772 | ng/mL |
| $T_{max}$ | 0.25 | hours (h) |
| $K_{elimination}$ | 0.789 | per hour (h$^{-1}$) |
| Half life ($t_{1/2}$) | 0.88 | hours (h) |
| AUC(0-8 h) | 24212 | ng/mL · h |
| AUC(0-inf) | 22908 | ng/mL · h |

[a] including IRN 12 result.

Example 4. Effect of the Compounds of the Invention on the Total Level of Tau and Level of p-Tau in Cerebrospinal Fluid (CSF) and Brain in the Tau Transgenic Mouse Model (hTAU441)

To assess the effect of the compounds of the invention on p-tau accumulation, age-matched (e.g., 5 month old) transgenic mice humanized for the tau gene (hTAU mice) may be treated with low- or high-dose of a compound of the invention or vehicle by intraperitoneal administration for 7 days (N=6 per arm). Dose of the compound of the invention may be calculated based on the PK results. hTAU transgenic mice (C57BL/6 background) over-express TAU441 bearing the missense mutations V337M and R406W under the control of the brain specific murine Thy-1 promoter. This human mutated tau isoform is expressed in high levels and the tau pathology and is visible at an early age starting at four months. Severity of the brain pathology correlates with increasing age and behavioral deficits, whereas no motor deficits occur. All animals may be sacrificed and quantified for soluble and insoluble tau and p-tau brain (hippocampus and cortex) using MSD multiarray p-tau (ThR$^{21}$1) immunosorbent assay (Meso Scale Discovery, Rockville, Md.) to establish total tau and p-tau levels in CSF and Hsp70 levels in brain extracts. Specifically, the animals may be anaesthetized with ketamine/xylazin mix (note: isoflurane is known to influence p-tau levels), kept warm and in a horizontal position, prior to and during the collection of CSF followed by blood. The volume of CSF collected in hTAU441 is only 2-6 µL/mouse compared to some strains (2-15 µL/mouse). p-Tau (ThR$^{21}$ 1) and total tau levels may be assessed using phospho-PHF-Tau pThR$^{21}$1 (MSD duplex kit, Meso Scale Discovery, Rockville, Md.).

Administration of a compound of the invention may lead to a decrease in p-tau levels in mice treated with a compound of the invention relative to p-tau levels in mice administered a vehicle.

Example 5. Effect of the Compounds of the Invention on Memory and Learning in the hTAU441 Transgenic Mouse Model Five month old transgenic hTAU mice described in Example 3 may be administered intraperitoneally a low- or high-dose of a compound of the invention groups or a vehicle daily for 12 weeks (N=15 per arm). A corresponding untreated group of mice will be analyzed as baseline. Behavioral testing, e.g., Probe Trial, Nose Poke Curiosity and Activity Test, and the Morris Water Maze task may be performed. Upon completion of the study, CSF may be collected and brain tissue may be harvested from these animals. Total tau levels and p-tau levels may be assessed in the CSF and brain. Additionally, immunohistochemical determination of tau pathology may be conducted. Tau depositions may be determined using the monoclonal antibodies AT180 (Thermo Scientific Pierce Antibodies, Rockford, Ill.) and HT7 (Thermo Scientific Pierce Antibodies, Rockford, Ill.). Sodium selenate, a PP2A phosphatase activator that dephosphorylates tau and reverses memory deficits, is effective in the TMHT tau model (Corcoran et al., *J. Clin. Neuroscience*, 17:1025-1033, 2010).

If chronic treatment with a compound of the invention is associated with a general improvement in memory function as measured by the Morris Maze, reduced levels of p-tau in the brain may be observed.

Other Embodiments

The invention is also described by the following numbered embodiments:

1. A compound according to formula (I):

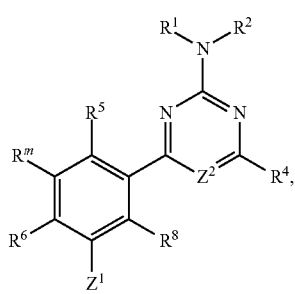

or a pharmaceutically acceptable salt thereof,
where
$Z^1$ is —$OR^7$, —$N(R^{10})R^7$, —$SR^7$, or —$C(R^{10})(R^{11})R^7$;
$Z^2$ is —N= or —$C(R^3)$=;
each $R^1$ and $R^2$ is, independently, H or optionally substituted $C_{1-3}$ alkyl;
$R^3$ is H, halogen, cyano, optionally substituted $C_{1-6}$ alkyl, optionally substituted $C_{1-3}$ alkoxy, or optionally substituted amino, and $R^4$ is halogen, cyano, optionally substituted $C_{1-6}$ alkyl, optionally substituted $C_{1-3}$ alkoxy, optionally substituted amino, optionally substituted $C_{1-6}$ thioalkoxy, or optionally substituted $C_{6-10}$ aryl, or $R^3$ and $R^4$, together with the atoms to which each is attached, join to form an optionally substituted five- or six-membered ring optionally including one nitrogen, one oxygen, or one sulfur, where the nitrogen is optionally substituted with $R^9$;
each $R^5$ and $R^6$ is, independently, H, optionally substituted $C_{1-3}$ alkyl, optionally substituted $C_{1-3}$ alkoxy, halogen, or CN;
$R^7$ is optionally substituted $C_{1-3}$ alkyl, optionally substituted $C_{1-3}$ alkcycloalkyl, optionally substituted $C_{1-3}$ alkheterocyclyl, or optionally substituted $C_{1-3}$ alkaryl, and $R^8$ is H; or $R^7$ and $R^8$, together with the atoms to which each is attached, join to form an optionally substituted five- or six-membered ring optionally including one or two heteroatoms selected from nitrogen, oxygen, and sulfur;
$R^9$ is H, optionally substituted $C_{1-3}$ alkyl, optionally substituted $C_{3-8}$ cycloalkyl, optionally substituted $C_{6-10}$ aryl, optionally substituted $C_{2-9}$ heteroaryl, optionally substituted $C_{2-9}$ heterocyclyl, optionally substituted $C_{1-3}$ alkcycloalkyl, optionally substituted $C_{1-3}$ alkheterocyclyl, or optionally substituted $C_{1-3}$ alkaryl;
$R^{10}$ is H, optionally substituted $C_{1-3}$ alkyl, optionally substituted $C_{3-8}$ cycloalkyl, optionally substituted $C_{6-10}$ aryl, optionally substituted $C_{2-9}$ heteroaryl, optionally substituted $C_{2-9}$ heterocyclyl, optionally substituted $C_{1-3}$ alkcycloalkyl, optionally substituted $C_{1-3}$ alkheterocyclyl, or optionally substituted $C_{1-3}$ alkaryl, and $R^{11}$ is H, optionally substituted $C_{1-3}$ alkyl, or $R^{10}$ and $R^{11}$ combine to form =O or =S;
$R^m$ is H, halogen, optionally substituted $C_{1-4}$ alkyl, or optionally substituted $C_{1-3}$ alkoxy; where,
when $Z^2$ is $CR^3$, each of $R^1$ and $R^2$ is H, $R^3$ is H, $R^4$ is methyl or chloro, and each of $R^5$ and $R^6$ is chloro, $Z^1$ is not methoxy;

when $Z^2$ is N, each of $R^5$ and $R^6$ is chloro, $R^3$ is H, $R^4$ is substituted $C_{1-6}$ thioalkoxy,
$Z^1$ is not cyanomethoxy or aminomethoxy;
when $Z^2$ is $CR^3$, each of $R^5$ and $R^6$ is chloro, $R^3$ is H, and $R^4$ is halogen,
$Z^1$ is not 2-amino-2-oxoethoxy, 2-(N,N-diethylamino)ethoxy, methoxy, or benzyloxy;
when $R^5$ is chloro, $R^6$ is bromo, $Z^1$ is —$OR^7$, and $R^3$ and $R^4$ combine to form a group according to formula (IIa):

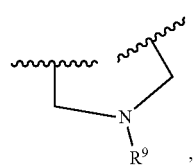

$R^7$ is not methyl, ethyl, n-propyl, 2-(N-pyrazolyl)ethyl, 2-(N-imidazolyl)ethyl, 3-hydroxypropyl, cyanomethyl, 2-chloroethyl, 2-hydroxyethyl, 2-oxo-propyl, 2-(N,N-dimethylamino)ethyl, difluoromethyl, or 2-(t-butylamino)ethyl;
when each $R^5$ and $R^6$ is bromo, $Z^1$ is —$OR^7$, and $R^3$ and $R^4$ combine to form a group according to formula (IIa),
$R^7$ is not methyl;
when each $R^5$ and $R^6$ is chloro, $Z^1$ is —$OR^7$, and $R^3$ and $R^4$ combine to form a group according to formula (IIa),
$R^7$ is not methyl, 2-(N-imidazolyl)ethyl, methoxymethyl, 2-(N-pyrazolyl)ethyl, 2-(3-methylpyrazol-1-yl)ethyl, 2-pyridyl-methyl, 1,3-dimethyl-1H-1,2,4-triazol-5-yl-methyl, 2-pyrimidinylmethyl, imidazol-2-yl-methyl, 5-methyl-isoxazol-3-yl-methyl, 4-methyl-imidazol-5-yl-methyl, or 3-methyl-1,2,4-oxadiazol-5-yl-methyl;
when each $R^5$ and $R^6$ is chloro, $Z^1$ is —$OR^7$, $R^7$ and $R^8$ combine to form —$CH_2$—$CH_2$—, and $R^3$ and $R^4$ combine to form a group according to formula (IIa),
$R^9$ is not ethoxycarbonyl, cyclobutylaminocarbonyl, or cyclobutadienylaminocarbonyl
when $R^5$ is methoxy, $R^6$ is methyl, $Z^1$ is —$OR^7$, and $R^3$ and $R^4$ combine to form a group according to formula (IIa),
$R^7$ is not methyl;
when $R^5$ is chloro, $R^6$ is ethyl, $Z^1$ is —$OR^7$, and $R^3$ and $R^4$ combine to form a group according to formula (IIa),
$R^7$ is not methyl;
when each $R^5$ and $R^6$ is chloro, $Z^1$ is —$OR^7$, and $R^3$ and $R^4$ combine to form a group according to formula (IIb) or (IIc),

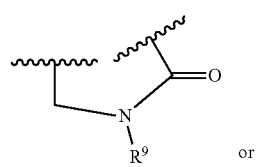

or

-continued

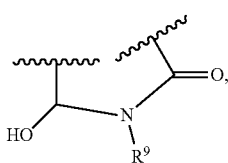 (IIc)

$R^7$ is not methyl or 2-(N,N-diethylamino)ethyl;
when $R^7$ is methyl, $R^5$ is chloro, $Z^1$ is —$OR^7$, and $R^3$ and $R^4$ combine to form a group according to formula (IIIa),

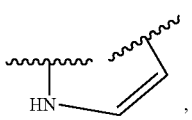 (IIIa)

$R^6$ is not bromo;
when $R^5$ is chloro, $R^6$ is methoxy, $Z^1$ is —$OR^7$, and $R^3$ and $R^4$ combine to form a group according to formula (IIIb):

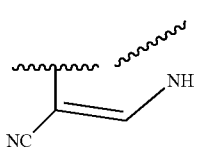 (IIIb)

neither $R^1$ nor $R^2$ is 2-(N,N-diethylamino)ethyl;
when each $R^5$ and $R^6$ is chloro, $Z^1$ is —$OR^7$, and $R^3$ and $R^4$ combine to form a group according to formula (IVa):

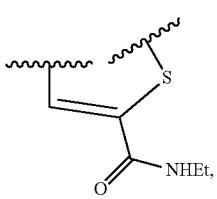 (IVa)

$R^7$ is not 3-(N-morpholinyl)propyl, benzyl, 1-ethyl-pyrrolydin-3-yl, 1-methyl-piperidin-4-yl, 2-(1-methyl-pyrrolidin-2-yl)ethyl, or 3-(N,N-diethylamino)propyl;
when each $R^5$ and $R^6$ is chloro, $Z^1$ is —$OR^7$, and $R^3$ and $R^4$ combine to form a group according to formula (IVb):

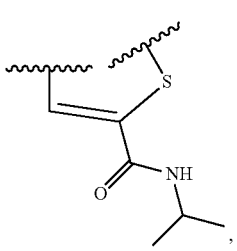 (IVb)

$R^7$ is not 2-methoxyethyl or benzyl;

when each $R^5$ and $R^6$ is chloro, $Z^1$ is —$OR^7$, and $R^3$ and $R^4$ combine to form a group according to formula (IVc):

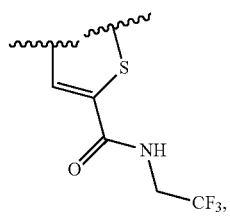 (IVc)

$R^7$ is not 2-(N,N-diethylamino)ethyl or 3-(N,N-dimethylamino)propyl;
when each $R^5$ and $R^6$ is chloro, $Z^1$ is —$OR^7$, and $R^3$ and $R^4$ combine to form a group according to formula (IVd):

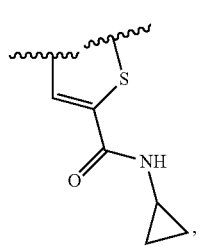 (IVd)

$R^7$ is not 2-(pyrrolidin-1-yl)ethyl or 2-hydroxyethyl;
when each $R^5$ and $R^6$ is chloro, $Z^1$ is —$OR^7$, and $R^3$ and $R^4$ combine to form a group according to formula (IVe) or (IVf):

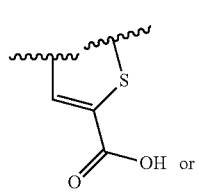 (IVe)

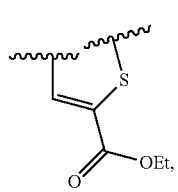 (IVf)

$R^7$ is not benzyl;
when $R^5$ is chloro, $R^6$ is bromo, $Z^1$ is —$OR^7$, and $R^3$ and $R^4$ combine to form a group according to formula (IVg), (IVh), (IVi), (IVj), or (IVk):

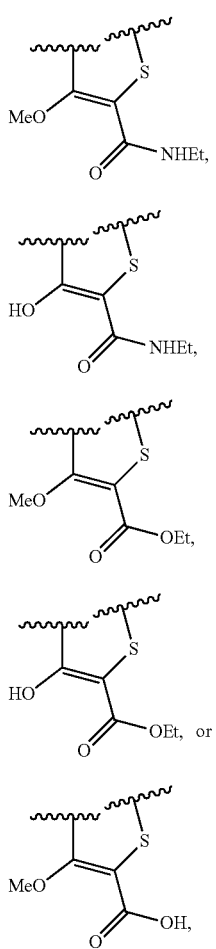

(IVg)

(IVh)

(IVi)

(IVj)

(IVk)

$R^7$ is not methyl;
when $R^6$ is methyl,
each $R^1$ and $R^2$ is H; and
when $R^3$ is H, $Z^1$ is —$OR^7$, and each $R^5$ and $R^6$ is chloro, $R^7$ is not methyl.

2. The compound of embodiment 1, where $R^m$ is H.

3. A compound according to formula (Ia):

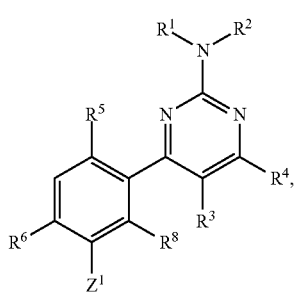

(Ia)

or a pharmaceutically acceptable salt thereof,
where
each $R^1$ and $R^2$ is, independently, H or optionally substituted $C_{1-3}$ alkyl;
$R^3$ is H, halogen, cyano, optionally substituted $C_{1-6}$ alkyl, optionally substituted $C_{1-3}$ alkoxy, or optionally substituted amino, and $R^4$ is halogen, cyano, optionally substituted $C_{1-6}$ alkyl, optionally substituted $C_{1-3}$ alkoxy, optionally substituted amino, optionally substituted $C_{1-6}$ thioalkyl, or optionally substituted $C_{6-10}$ aryl, or $R^3$ and $R^4$, together with the atoms to which each is attached, join to form an optionally substituted five- or six-membered ring optionally including one nitrogen, one oxygen, or one sulfur, where the nitrogen is optionally substituted with $R^9$;
each $R^5$ and $R^6$ is, independently, H, optionally substituted $C_{1-3}$ alkyl, optionally substituted $C_{1-3}$ alkoxy, halogen, or CN;
$R^7$ is optionally substituted $C_{1-3}$ alkyl, optionally substituted $C_{1-3}$ alkcycloalkyl, optionally substituted $C_{1-3}$ alkheterocyclyl, or optionally substituted $C_{1-3}$ alkaryl, and $R^8$ is H; or $R^7$ and $R^8$, together with the atoms to which each is attached, join to form an optionally substituted five- or six-membered ring optionally including one or two heteroatoms selected from nitrogen, oxygen, and sulfur;
$R^9$ is H, optionally substituted $C_{1-3}$ alkyl, optionally substituted $C_{3-8}$ cycloalkyl, optionally substituted $C_{6-10}$ aryl, optionally substituted $C_{2-9}$ heteroaryl, optionally substituted $C_{2-9}$ heterocyclyl, optionally substituted $C_{1-3}$ alkcycloalkyl, optionally substituted $C_{1-3}$ alkheterocyclyl, or optionally substituted $C_{1-3}$ alkaryl;
$Z^1$ is —$OR^7$, —$N(R^{10})R^7$, —$SR^7$, or —$C(R^{10})(R^1)R^7$; and
$R^{10}$ is H, optionally substituted $C_{1-3}$ alkyl, optionally substituted $C_{3-8}$ cycloalkyl, optionally substituted $C_{6-10}$ aryl, optionally substituted $C_{2-9}$ heteroaryl, optionally substituted $C_{2-9}$ heterocyclyl, optionally substituted $C_{1-3}$ alkcycloalkyl, optionally substituted $C_{1-3}$ alkheterocyclyl, or optionally substituted $C_{1-3}$ alkaryl, and $R^{11}$ is H, optionally substituted $C_{1-3}$ alkyl, or $R^{10}$ and $R^{11}$ combine to form =O or =S;
where,
when each of $R^1$ and $R^2$ is H, $R^3$ is H, $R^4$ is methyl or chloro, and each of $R^5$ and $R^6$ is chloro,
$Z^1$ is not methoxy;
when each of $R^5$ and $R^6$ is chloro, $R^3$ is H, and $R^4$ is halogen,
$Z^1$ is not 2-amino-2-oxoethoxy, 2-(N,N-diethylamino) ethoxy, methoxy, or benzyloxy;
when $R^5$ is chloro, $R^6$ is bromo, $Z^1$ is —$OR^7$, and $R^3$ and $R^4$ combine to form a group according to formula (IIa):

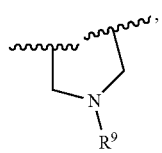

(IIa)

$R^7$ is not methyl, ethyl, n-propyl, 2-(N-pyrazolyl)ethyl, 2-(N-imidazolyl)ethyl, 3-hydroxypropyl, cyanomethyl, 2-chloroethyl, 2-hydroxyethyl, 2-oxo-propyl, 2-(N,N-dimethylamino)ethyl, difluoromethyl, or 2-(t-butylamino)ethyl;
when each $R^5$ and $R^6$ is bromo, $Z^1$ is —$OR^7$, and $R^3$ and $R^4$ combine to form a group according to formula (IIa), $R^7$ is not methyl;
when each $R^5$ and $R^6$ is chloro, $Z^1$ is —$OR^7$, and $R^3$ and $R^4$ combine to form a group according to formula (IIa), $R^7$ is not methyl, 2-(N-imidazolyl)ethyl, methoxymethyl, 2-(N-pyrazolyl)ethyl, 2-(3-methylpyrazol-1-yl)ethyl, 2-pyridyl-methyl, 1,3-dimethyl-1H-1,2,4-triazol-5-yl-methyl, 2-pyrimidinylmethyl, imidazol-2-yl-methyl, 5-methyl-isoxazol-3-yl-methyl, 4-methyl-imidazol-5-yl-methyl, or 3-methyl-1,2,4-oxadiazol-5-yl-methyl;

when each $R^5$ and $R^6$ is chloro, $Z^1$ is —$OR^7$, $R^7$ and $R^8$ combine to form —$CH_2$—$CH_2$—, and $R^3$ and $R^4$ combine to form a group according to formula (IIa), $R^9$ is not ethoxycarbonyl, cyclobutylaminocarbonyl, or cyclobutadienylaminocarbonyl when $R^5$ is methoxy, $R^6$ is methyl, $Z^1$ is —$OR^7$, and $R^3$ and $R^4$ combine to form a group according to formula (IIa), $R^7$ is not methyl;

when $R^5$ is chloro, $R^6$ is ethyl, $Z^1$ is —$OR^7$, and $R^3$ and $R^4$ combine to form a group according to formula (IIa), $R^7$ is not methyl;

when each $R^5$ and $R^6$ is chloro, $Z^1$ is —$OR^7$, and $R^3$ and $R^4$ combine to form a group according to formula (IIb) or (IIc),

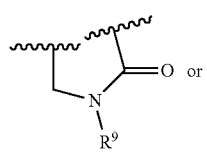
(IIb)

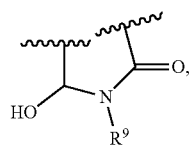
(IIc)

$R^7$ is not methyl or 2-(N,N-diethylamino)ethyl;

when $R^7$ is methyl, $R^5$ is chloro, $Z^1$ is —$OR^7$, and $R^3$ and $R^4$ combine to form a group according to formula (IIIa),

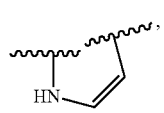
(IIIa)

$R^6$ is not bromo;

when $R^5$ is chloro, $R^6$ is methoxy, $Z^1$ is —$OR^7$, and $R^3$ and $R^4$ combine to form a group according to formula (IIIb):

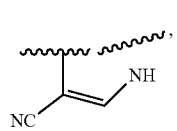
(IIIb)

neither $R^1$ nor $R^2$ is 2-(N,N-diethylamino)ethyl;

when each $R^5$ and $R^6$ is chloro, $Z^1$ is —$OR^7$, and $R^3$ and $R^4$ combine to form a group according to formula (IVa):

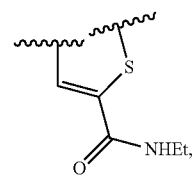
(IVa)

$R^7$ is not 3-(N-morpholinyl)propyl, benzyl, 1-ethyl-pyrrolydin-3-yl, 1-methyl-piperidin-4-yl, 2-(1-methyl-pyrrolidin-2-yl)ethyl, or 3-(N,N-diethylamino)propyl;

when each $R^5$ and $R^6$ is chloro, $Z^1$ is —$OR^7$, and $R^3$ and $R^4$ combine to form a group according to formula (IVb):

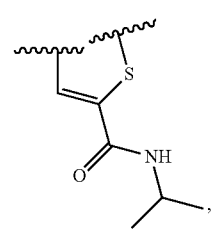
(IVb)

$R^7$ is not 2-methoxyethyl or benzyl;

when each $R^5$ and $R^6$ is chloro, $Z^1$ is —$OR^7$, and $R^3$ and $R^4$ combine to form a group according to formula (IVc):

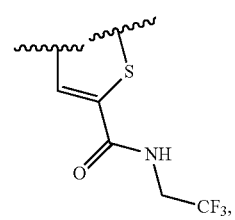
(IVc)

$R^7$ is not 2-(N,N-diethylamino)ethyl or 3-(N,N-dimethylamino)propyl;

when each $R^5$ and $R^6$ is chloro, $Z^1$ is —$OR^7$, and $R^3$ and $R^4$ combine to form a group according to formula (IVd):

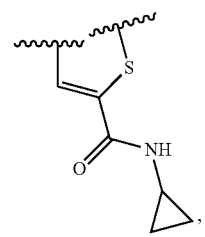
(IVd)

$R^7$ is not 2-(pyrrolidin-1-yl)ethyl or 2-hydroxyethyl;

when each $R^5$ and $R^6$ is chloro, $Z^1$ is —$OR^7$, and $R^3$ and $R^4$ combine to form a group according to formula (IVe) or (IVf):

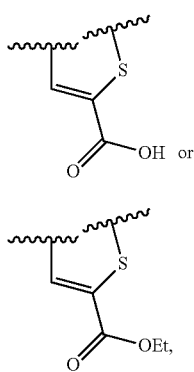

R⁷ is not benzyl;
when R⁵ is chloro, R⁶ is bromo, Z¹ is —OR⁷, and R³ and R⁴ combine to form a group according to formula (IVg), (IVh), (IVi), (IVj), or (IVk):

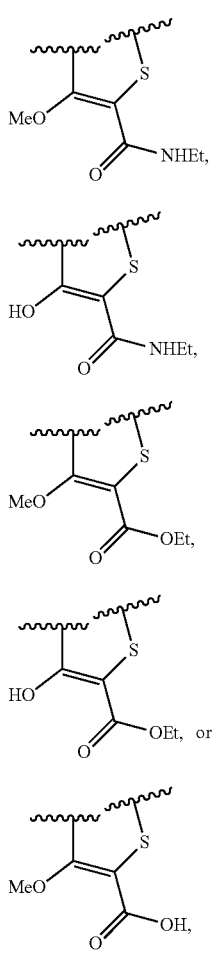

R⁷ is not methyl;
when R⁶ is methyl,
each R¹ and R² is H; and
when R³ is H, Z¹ is —OR⁷, and each R⁵ and R⁶ is chloro, R⁷ is not methyl.

4. A compound according to formula (Ib):

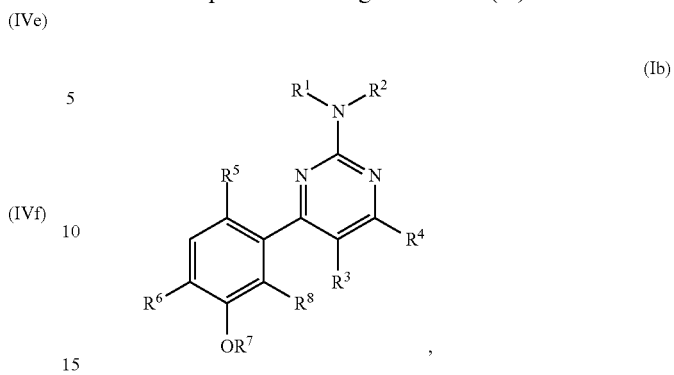

or a pharmaceutically acceptable salt thereof,
where
each of R¹ and R² is, independently, H or optionally substituted $C_{1-3}$ alkyl;
R³ is H, halogen, cyano, optionally substituted $C_{1-6}$ alkyl, optionally substituted $C_{1-3}$ alkoxy, or optionally substituted amino, and R⁴ is halogen, cyano, optionally substituted $C_{1-6}$ alkyl, optionally substituted $C_{1-3}$ alkoxy, optionally substituted amino, optionally substituted $C_{1-6}$ thioalkoxy, or optionally substituted $C_{6-10}$ aryl, or R³ and R⁴, together with the atoms to which each is attached, join to form an optionally substituted five- or six-membered ring optionally including one nitrogen, one sulfur, or one oxygen, where the nitrogen is optionally substituted with R⁹;
each of R⁵ and R⁶ is, independently, H, optionally substituted $C_{1-3}$ alkyl, optionally substituted $C_{1-3}$ alkoxy, halogen, or CN;
R⁷ is optionally substituted $C_{1-3}$ alkyl, optionally substituted $C_{1-3}$ alkcycloalkyl, optionally substituted $C_{1-3}$ alkheterocyclyl, or optionally substituted $C_{1-3}$ alkaryl, and R⁸ is H; or R⁷ and R⁸, together with the atoms to which each is attached, join to form an optionally substituted five- or six-membered ring; and
R⁹ is H, optionally substituted $C_{1-3}$ alkyl, optionally substituted $C_{3-8}$ cycloalkyl, optionally substituted $C_{6-10}$ aryl, optionally substituted $C_{2-9}$ heteroaryl, optionally substituted $C_{2-9}$ heterocyclyl, optionally substituted $C_{1-3}$ alkcycloalkyl, optionally substituted $C_{1-3}$ alkheterocyclyl, or optionally substituted $C_{1-3}$ alkaryl;
where,
when each of R¹ and R² is H, R³ is H, R⁴ is methyl or chloro, and each of R⁵ and R⁶ is chloro, R⁷ is not methyl;
when each of R⁵ and R⁶ is chloro, R³ is H, and R⁴ is halogen, R⁷ is not 2-amino-2-oxoethyl, 2-(N,N-diethylamino)ethyl, methyl, or benzyl;
when R⁵ is chloro, R⁶ is bromo, and R³ and R⁴ combine to form a group according to formula (IIa):

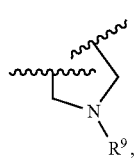

R⁷ is not methyl, ethyl, n-propyl, 2-(N-pyrazolyl)ethyl, 2-(N-imidazolyl)ethyl, 3-hydroxypropyl, cyanomethyl, 2-chloroethyl, 2-hydroxyethyl, 2-oxo-propyl, 2-(N,N-dimethylamino)-ethyl, difluoromethyl, or 2-(t-butylamino)ethyl;

when each $R^5$ and $R^6$ is bromo, and $R^3$ and $R^4$ combine to form a group according to formula (IIa), $R^7$ is not methyl;

when each $R^5$ and $R^6$ is chloro, $R^8$ is H, and $R^3$ and $R^4$ combine to form a group according to formula (IIa), $R^7$ is not methyl, 2-(N-imidazolyl)ethyl, methoxymethyl, 2-(N-pyrazolyl)ethyl, 2-(3-methylpyrazol-1-yl)ethyl, 2-pyridyl-methyl, 1,3-dimethyl-1H-1,2,4-triazol-5-yl-methyl, 2-pyrimidinylmethyl, imidazol-2-yl-methyl, 5-methyl-isoxazol-3-yl-methyl, 4-methyl-imidazol-5-yl-methyl, or 3-methyl-1,2,4-oxadiazol-5-yl-methyl;

when each $R^5$ and $R^6$ is chloro, $R^7$ and $R^8$ combine to form —CH$_2$—CH$_2$—, and $R^3$ and $R^4$ combine to form a group according to formula (IIa), $R^9$ is not ethoxycarbonyl, cyclobutylaminocarbonyl, or cyclobutadienylaminocarbonyl;

when $R^5$ is methoxy, $R^6$ is methyl, and $R^3$ and $R^4$ combine to form a group according to formula (IIa), $R^7$ is not methyl;

when $R^5$ is chloro, $R^6$ is ethyl, and $R^3$ and $R^4$ combine to form a group according to formula (IIa), $R^7$ is not methyl;

when each $R^5$ and $R^6$ is chloro, and $R^3$ and $R^4$ combine to form a group according to formula (IIb) or (IIc),

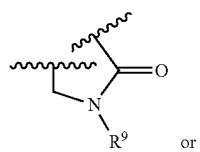
(IIb)

or

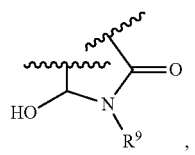
(IIc)

$R^7$ is not methyl or 2-(N,N-diethylamino)ethyl;

when $R^7$ is methyl, $R^5$ is chloro, and $R^3$ and $R^4$ combine to form a group according to formula (IIIa),

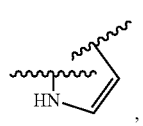
(IIIa)

$R^6$ is not bromo;

when $R^5$ is chloro, $R^6$ is methoxy, and $R^3$ and $R^4$ combine to form a group according to formula (IIIb):

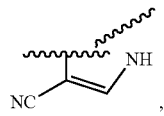
(IIIb)

neither $R^1$ nor $R^2$ is 2-(N,N-diethylamino)ethyl;

when each $R^5$ and $R^6$ is chloro, and $R^3$ and $R^4$ combine to form a group according to formula (IVa):

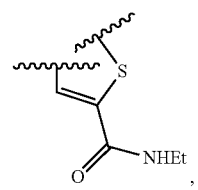
(IVa)

$R^7$ is not 3-(N-morpholinyl)propyl, benzyl, 1-ethyl-pyrrolydin-3-yl, 1-methyl-piperidin-4-yl, 2-(1-methyl-pyrrolidin-2-yl)ethyl, or 3-(N,N-diethylamino)propyl;

when each $R^5$ and $R^6$ is chloro, and $R^3$ and $R^4$ combine to form a group according to formula (IVb):

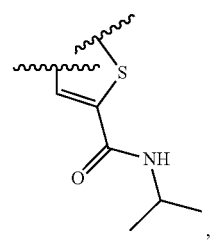
(IVb)

$R^7$ is not 2-methoxyethyl or benzyl;

when each $R^5$ and $R^6$ is chloro, and $R^3$ and $R^4$ combine to form a group according to formula (IVc):

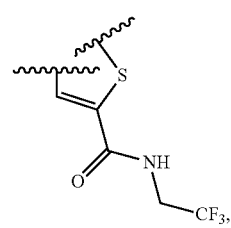
(IVc)

$R^7$ is not 2-(N,N-diethylamino)ethyl or 3-(N,N-dimethylamino)propyl;

when each $R^5$ and $R^6$ is chloro, and $R^3$ and $R^4$ combine to form a group according to formula (IVd):

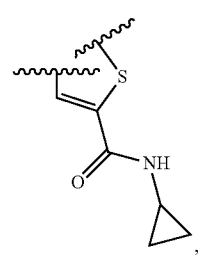
(IVd)

$R^7$ is not 2-(pyrrolidin-1-yl)ethyl or 2-hydroxyethyl;

when each $R^5$ and $R^6$ is chloro, and $R^3$ and $R^4$ combine to form a group according to formula (IVe) or (IVf):

(IVe)

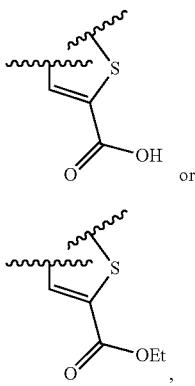

or (IVf)

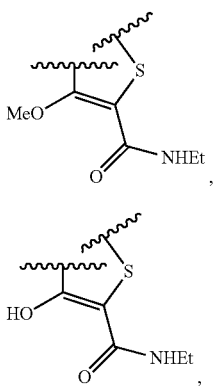

$R^7$ is not benzyl;
when $R^5$ is chloro, $R^6$ is bromo, and $R^3$ and $R^4$ combine to form a group according to formula (IVg), (IVh), (IVi), (IVj), or (IVk):

(IVg)

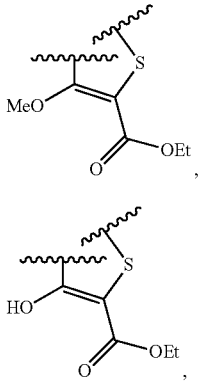

(IVh)

(IVi)

(IVj)

(IVk)

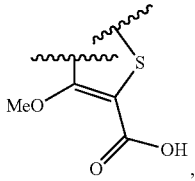

$R^7$ is not methyl;
when $R^6$ is methyl,
each $R^1$ and $R^2$ is H; and
when $R^3$ is H, and each $R^5$ and $R^6$ is chloro, $R^7$ is not methyl.

5. The compound of any one of embodiments 1 to 4, where $R^3$ is H, halogen, optionally substituted $C_{1-3}$ alkyl, or optionally substituted $C_{1-3}$ alkoxy, and $R^4$ is halogen, optionally substituted $C_{1-3}$ alkyl, optionally substituted $C_{1-3}$ alkoxy, optionally substituted amino, optionally substituted $C_{1-6}$ thioalkyl, or optionally substituted $C_{6-10}$ aryl, or $R^3$ and $R^4$, together with the atoms to which each is attached, join to form an optionally substituted five- or six-membered ring optionally including one nitrogen, one oxygen, or one sulfur, where the nitrogen is optionally substituted with $R^9$.

6. The compound of any one of embodiments 1 to 5, where $R^3$ and $R^4$, together with the atoms to which each is attached, join to form an optionally substituted five-membered ring.

7. The compound of any one of embodiments 1 to 5, where $R^3$ and $R^4$ combine to form —$CH_2CH_2CH_2$— group.

8. The compound of any one of embodiments 1 to 5, where $R^3$ and $R^4$, together with the atoms to which each is attached, join to form an optionally substituted five-membered ring including one nitrogen.

9. The compound of embodiment 8, where $R^3$ and $R^4$ combine to form —$N(R^9)$—$CH$=$CH$— group.

10. The compound of embodiment 9, where $R^9$ is H.

11. The compounds of any one of embodiments 1 to 5, where $R^3$ and $R^4$, together with the atoms to which each is attached, join to form an optionally substituted five-membered ring including one sulfur.

12. The compound of any one of embodiments 1 to 5, where $R^3$ and $R^4$ combine to form —$C(R^{13A})$=$C(R^{13B})$—$S$— group, where $R^{13A}$ is H, and $R^{13B}$ is H or optionally substituted $C_{1-3}$ alkyl.

13. The compound of embodiment 12, where $R^{13B}$ is optionally substituted $C_{1-3}$ alkyl.

14. The compound of embodiment 13, where $R^{13B}$ is —$C(O)$—$R^{13C}$, where $R^{13C}$ is optionally substituted $C_{1-3}$ alkoxy or optionally substituted amino.

15. The compound of any one of embodiments 1 to 5, where $R^3$ and $R^4$ combine to form —$C(R^{13A})$=$C(R^{13B})$—$S$— group, where $R^{13A}$ is H, and $R^{13B}$ is H or —$C(O)$—$R^{13C}$, where $R^{13C}$ is optionally substituted $C_{1-3}$ alkyl, optionally substituted $C_{1-3}$ alkoxy, optionally substituted amino, or optionally substituted $C_{2-9}$ heterocyclyl.

16. The compound of any one of embodiments 1 to 5, where $R^4$ is $C_{1-3}$ alkyl.

17. The compound of embodiment 16, where $R^4$ is methyl, ethyl, or isopropyl.

18. The compound of any one of embodiments 1 to 5, where $R^4$ is $C_{1-3}$ alkoxy.

19. The compound of embodiment 18, where $R^4$ is methoxy.

20. The compound of any one of embodiments 1 to 5, where $R^4$ is optionally substituted $C_{1-6}$ thioalkoxy.

21. The compound of embodiment 20, where $R^4$ is 4-amino-4-oxobutyl.

22. The compound of any one of embodiments 1 to 5, where $R^4$ is optionally substituted amino.

23. The compound of embodiment 22, where $R^4$ is methylamino.

24. The compound of any one of embodiments 1 to 5, where $R^4$ is halogen.

25. The compound of embodiment 24, where $R^4$ is chloro.

26. The compound of any one of embodiments 1-5 and 15-25, where $R^3$ is hydrogen or $C_{1-3}$ alkyl.

27. The compound of embodiment 26, where $R^3$ is hydrogen, methyl, or ethyl.

28. The compound of any one of embodiments 1 to 5, where $R^3$ and $R^4$ combine to form —$X^1$—$X^2$—$X^3$—, where
$X^1$ is —S—, —O—, —$(CR^{14}R^{15})$—, —$C(R^{16})$=, —$N(R^9)$—, —N=, H, or optionally substituted $C_{1-3}$ alkyl;
$X^2$ is absent, —$(CR^7R^8)_n$—, —S—, —O—, —N=, —$N(R^9)$—, —$C(R^{19})$=, =N—, =$C(R^{20})$—, or =$C(R^{21})$—$C(R^{22})$=;
$X^3$ is —$(CR^{14}R^{15})$—, —S—, —O—, —$N(R^9)$—, =N—, =$C(R^{23})$—, halogen, optionally substituted $C_{1-3}$ alkyl, optionally substituted $C_{1-6}$ thioalkoxy, optionally substituted $C_{1-3}$ alkoxy, or optionally substituted $C_{6-10}$ aryl;
each $R^{14}$ and $R^{15}$ is, independently, H or optionally substituted $C_{1-3}$ alkyl, or $R^{14}$ and $R^{15}$ combine to form =O or =S;
each $R^{17}$ and $R^{18}$ is, independently, H or optionally substituted $C_{1-3}$ alkyl, or $R^{17}$ and $R^{18}$ combine to form =O or =S;
each $R^{16}$, $R^{19}$, $R^{20}$, $R^{21}$, $R^{22}$, and $R^{23}$ is, independently, H, or optionally substituted $C_{1-3}$ alkyl; and
n is 1 or 2; and
where, when $X^2$ is not absent,
the chain of atoms —$X^1$—$X^2$—$X^3$— includes no more than one heteroatom, the heteroatom being selected from the group consisting of nitrogen, oxygen, and sulfur.

29. The compound of embodiment 28, where $X^1$ is —$(CR^{14}R^{15})$—, —$C(R^{16})$=, —$N(R^9)$—, —N=, or optionally substituted $C_{1-3}$ alkyl.

30. The compound of embodiment 29, where $X^1$ is —$(CR^{14}R^{15})$—.

31. The compound of embodiment 30, where each $R^{14}$ and $R^{15}$ is H.

32. The compound of embodiment 29, where $X^1$ is —$C(R^{16})$=.

33. The compound of embodiment 32, where $R^{16}$ is H.

34. The compound of embodiment 29, where $X^1$ is —$N(R^9)$—.

35. The compound of embodiment 34, where $R^9$ is H or optionally substituted $C_{1-3}$ alkyl.

36. The compound of embodiment 35, where $R^9$ is hydrogen, methyl, or ethyl.

37. The compound of embodiment 29, where $X^1$ is —N=.

38. The compound of embodiment 29, where $X^1$ is optionally substituted $C_{1-3}$ alkyl.

39. The compound of any one of embodiments 28 to 37, where $X^2$ is absent, —$(CH_2)_n$—, —$N(R^9)$—, —$C(H)$=, =$C(R^{20})$—, or =$C(H)$—$C(H)$=.

40. The compound of embodiment 39, where $X^2$ is —$C(H)$=.

41. The compound of embodiment 39, where $X^2$ is —$N(R^9)$—.

42. The compound of embodiment 41, where $R^9$ is H.

43. The compound of embodiment 41, where $R^9$ is optionally substituted $C_{1-3}$ alkyl.

44. The compound of embodiment 43, where $R^9$ is —C(O)—N(H)-Et.

45. The compound of embodiment 39, where $X^2$ is =$C(R^{20})$—.

46. The compound of embodiment 45, where $R^{20}$ is optionally substituted $C_{1-3}$ alkyl.

47. The compound of embodiment 39, where $X^2$ is absent.

48. The compound of any one of embodiments 28-37 and 39-47, where $X^3$ is —$CH_2$—, —S—, =$C(H)$—, —$N(R^9)$—, halogen, optionally substituted $C_{1-3}$ alkyl, optionally substituted $C_{1-3}$ alkoxy, optionally substituted $C_{1-6}$ thioalkoxy, optionally substituted $C_{6-10}$ aryl.

49. The compound of embodiment 48, where $X^3$ is —$CH_2$—.

50. The compound of embodiment 48, where $X^3$ is —S—.

51. The compound of embodiment 48, where $X^3$ is =$C(H)$—.

52. The compound of embodiment 48, where $X^3$ is —$N(R^9)$—.

53. The compound of embodiment 48, where $X^3$ is halogen, optionally substituted $C_{1-3}$ alkyl, optionally substituted $C_{1-3}$ alkoxy, optionally substituted $C_{1-6}$ thioalkoxy, or optionally substituted $C_{6-10}$ aryl.

54. The compound of any one of embodiments 1 to 53, where each $R^5$ and $R^6$ is, independently, halo or optionally substituted $C_{1-3}$ alkyl.

55. The compound of embodiment 54, where each $R^5$ and $R^6$ is halo.

56. The compound of embodiment 55, where each $R^5$ and $R^6$ is chloro.

57. The compound of any one of embodiments 1 to 56, where $R^7$ and $R^8$, together with the atoms to which each is attached, join to form an optionally substituted five- or six-membered ring optionally including one or two heteroatoms selected from nitrogen, oxygen, and sulfur.

58. The compound of any one of embodiments 1 to 56, where $R^7$ and $R^8$, together with the atoms to which each is attached, join to form an optionally substituted five- or six-membered saturated ring optionally including one or two heteroatoms selected from nitrogen, oxygen, and sulfur.

59. The compound of any one of embodiments 1 to 56, where $R^7$ and $R^8$, together with the atoms to which each is attached, join to form an optionally substituted five- of six-membered ring optionally including one or two heteroatoms selected from nitrogen and oxygen.

60. The compound of any one of embodiments 1 to 56, where $R^7$ and $R^8$, together with the atoms to which each is attached, join to form an optionally substituted five-membered ring.

61. The compound of any one of embodiments 1 to 56, where the $R^7$ and $R^8$, together with the atoms to which each is attached, join to form an optionally substituted saturated five-membered ring.

62. The compound of any one of embodiments 1 to 56, where the $R^7$ and $R^8$ combine to form a —$CH_2CH_2$— group.

63. The compound of any one of embodiments 1 to 56, where $R^7$ is optionally substituted $C_{1-3}$ alkyl.

64. The compound of embodiment 63, where $R^7$ is methyl.

65. The compound of embodiment 63, where $R^7$ is —$(CH_2)_k$—$N(R^{24})R^{25}$, where k is 2 or 3, and where each $R^{24}$ and $R^{25}$ is, independently, H or optionally substituted $C_{1-3}$ alkyl.

66. The compound of embodiment 65, where k is 2.

67. The compound of embodiment 65 or 66, where each $R^{24}$ and $R^{25}$ is, independently, optionally substituted $C_{1-3}$ alkyl.

68. The compound of any one of embodiments 65 to 67, where each $R^{24}$ and $R^{25}$ is methyl.

69. The compound of any one of embodiments 1 to 56, where $R^7$ and $R^8$ form a group —$Y^1$—$Y^2$—, where:
$Y^1$ is —$(CR^{26}R^{27})_m$— or optionally substituted $C_{1-3}$ alkyl, optionally substituted $C_{1-3}$ alkheterocyclyl, optionally substituted $C_{1-3}$ alkcycloalkyl, or optionally substituted $C_{1-3}$ alkaryl; and Y² is —(CR²⁶R²⁷)— or H; where
   each R²⁶ and R²⁷ is, independently, H or optionally substituted C₁₋₃ alkyl; and
m is 1 or 2.

70. The compound of any one of embodiments 1 to 5, where Z¹ and R⁸ combine to form —Z³—Y¹—Y²-, where
   Z³ is —O—, —N(R¹⁰)—, —N=, —S—, or —(CR¹⁴R¹⁵)—;
   Y¹ is —O—, —N(R¹⁰)—, —S—, —(CR²⁶R²⁷)ₘ—, —C(R²⁰)=, =C(R²⁰)—, =C(R²¹)—C(R²²)=, optionally substituted C₁₋₃ alkyl, optionally substituted C₁₋₃ alkheterocyclyl, optionally substituted C₁₋₃ alkcycloalkyl, or optionally substituted C₁₋₃ alkaryl; and
   Y² is —O—, —S—, —N(R¹⁰)—, —(CR²⁶R²⁷)—, =C(R²⁰)—, =N—, or H;
   where
   each R²⁰, R²¹, and R²² is, independently, H or optionally substituted C₁₋₃ alkyl; and
   each R²⁶ and R²⁷ is, independently, H or optionally substituted C₁₋₃ alkyl, or R²⁶ and R²⁷ combine to form =O or =S;
   m is 1 or 2; and
   where, when Y² is H,
      the chain of atoms —Z³—Y¹—Y²— includes no more than two heteroatoms, the heteroatom selected from nitrogen, oxygen, and sulfur.

71. The compound of embodiment 70, where Z³ is —O—.

72. The compound of embodiment 69 or 71, where Y¹ is —(CR²⁶R²⁷)ₘ— or optionally substituted C₁₋₃ alkyl, optionally substituted C₁₋₃ alkheterocyclyl, optionally substituted C₁₋₃ alkcycloalkyl, or optionally substituted C₁₋₃ alkaryl.

73. The compound of any one of embodiments 69 to 72, where Y¹ is —(CR²⁶R²⁷)ₘ— or optionally substituted C₁₋₃ alkyl.

74. The compound of any one of embodiments 69 to 73, where Y² is —(CR²⁶R²⁷)— or H.

75. The compound of any one of embodiments 69 to 74, where Y² is —(CR²⁶R²⁷)—.

76. The compound of any one of embodiments 69 to 75, where R²⁶ is H.

77. The compound of any one of embodiments 69 to 76, where R²⁷ is H.

78. The compound of any one of embodiments 69 to 77, where m is 1.

79. The compound of any one of embodiments 69 to 78, where Y¹ is optionally substituted C₁₋₃ alkyl.

80. The compound of embodiment 79, where Y¹ is methyl.

81. The compound of embodiment 80, where Y¹ is —(CH₂)ₖ—N(R²⁴)R²⁵, where k is 2 or 3, and where each R²⁴ and R²⁵ is, independently, H or optionally substituted C₁₋₃ alkyl.

82. The compound of embodiment 81, where k is 2.

83. The compound of embodiment 81 or 82, where each R²⁴ and R²⁵ is, independently, optionally substituted C₁₋₃ alkyl.

84. The compound of any one of embodiments 81 to 83, where each R²⁴ and R²⁵ is methyl.

85. The compound of any one of embodiments 1 to 84, where each R¹ and R² is H.

86. A compound:

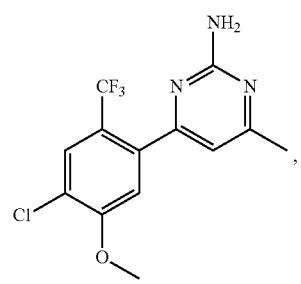
1,

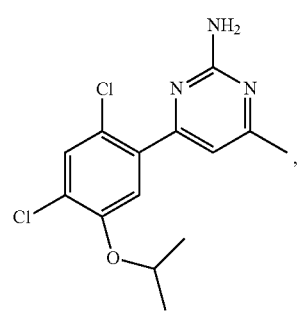
2,

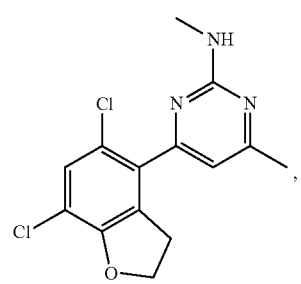
3,

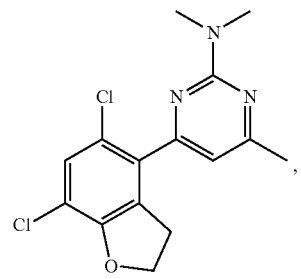
4,

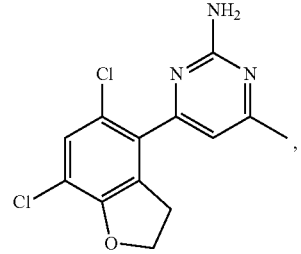
5,

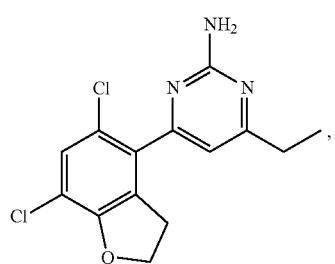
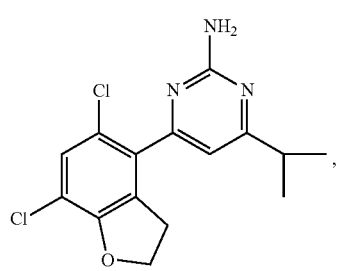
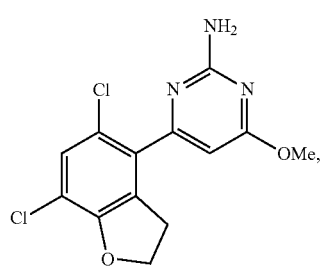
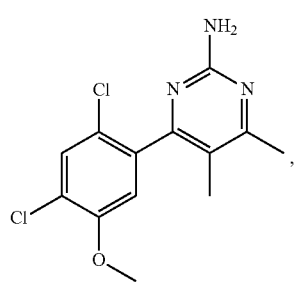
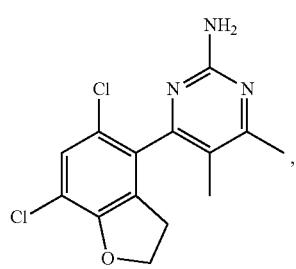
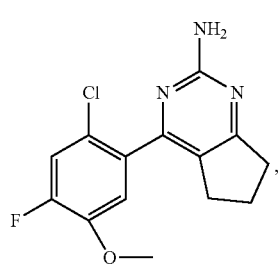
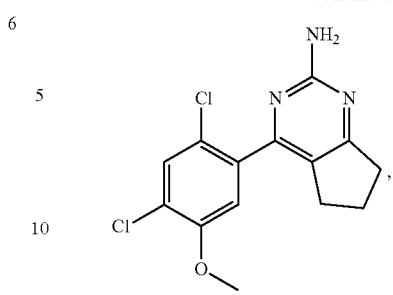
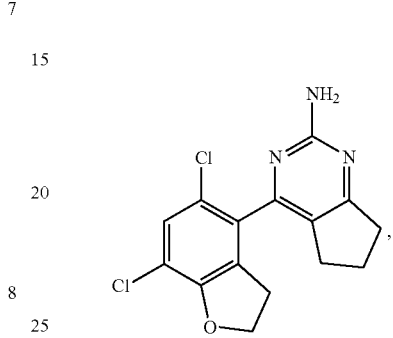
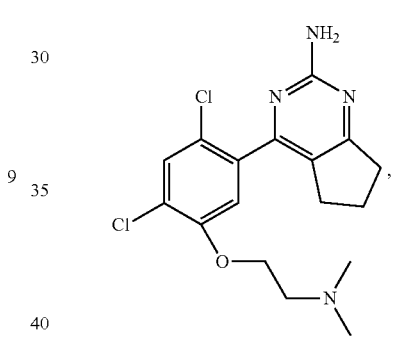
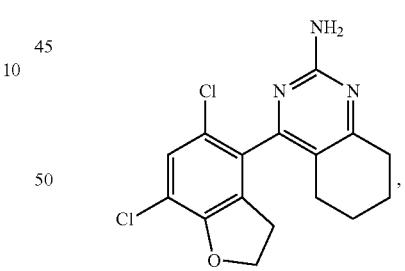
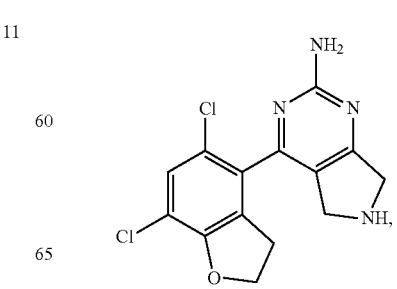

17
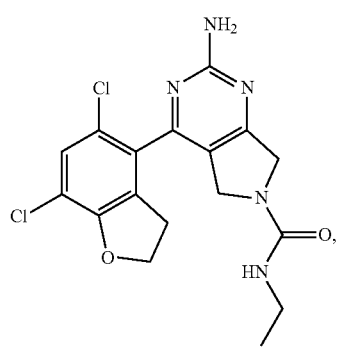
18
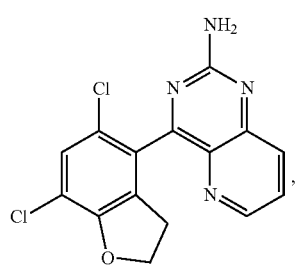
19
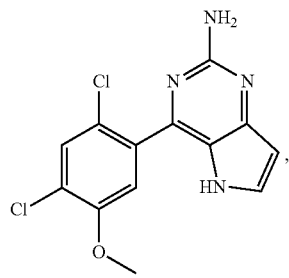
20
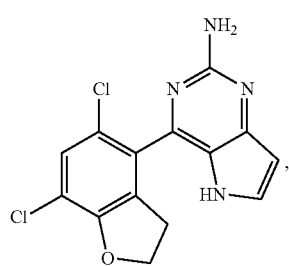
21
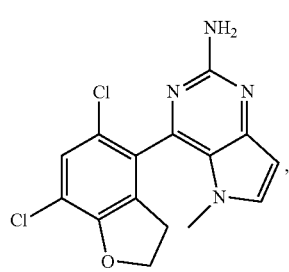
22
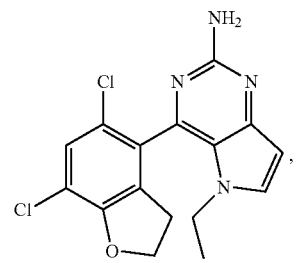
23
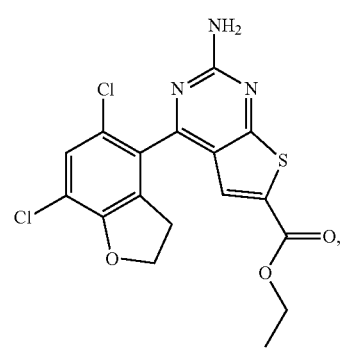
24
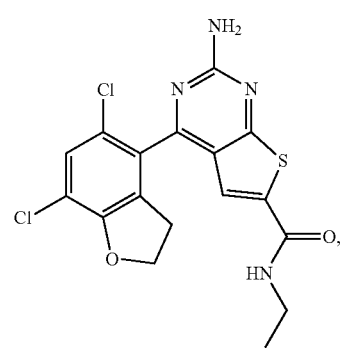
25
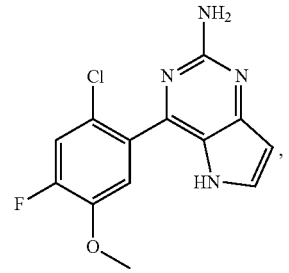
26
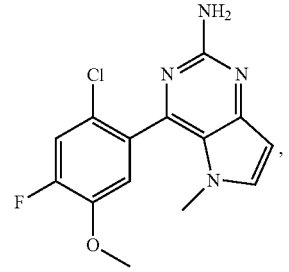

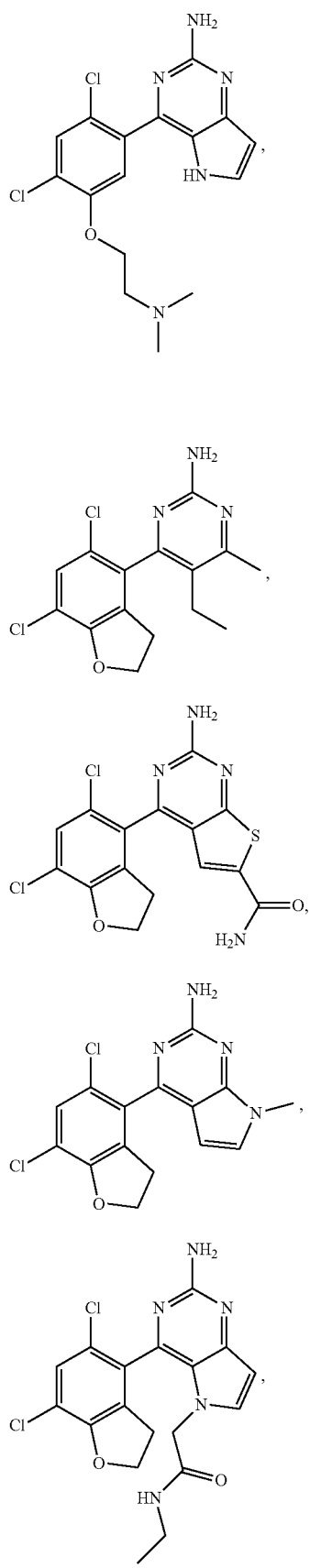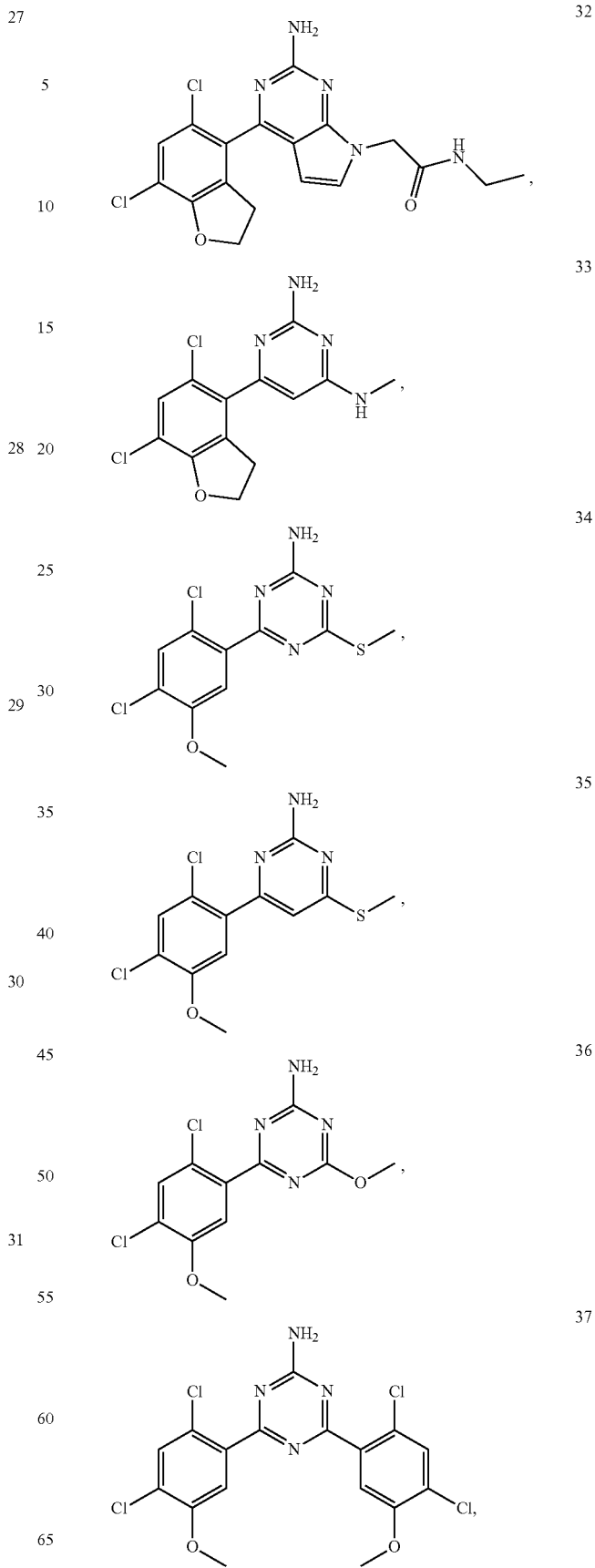

40
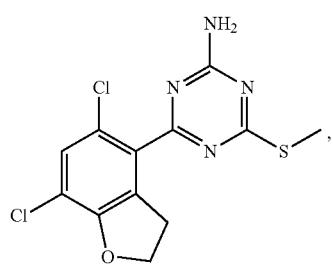
41
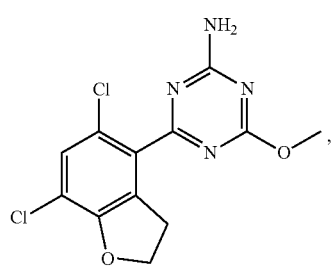
42
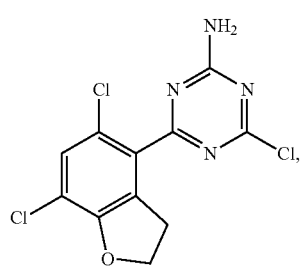
43
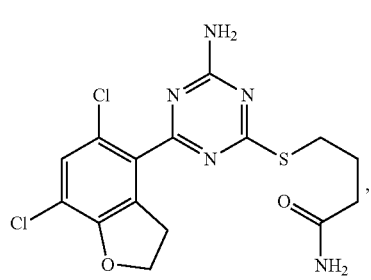
44
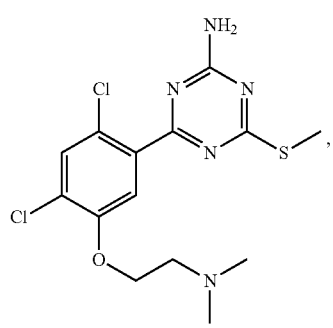
45
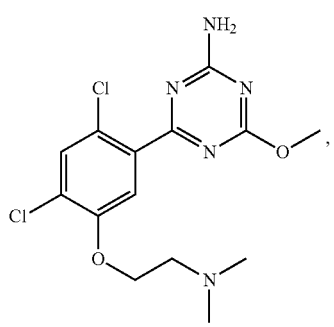
46
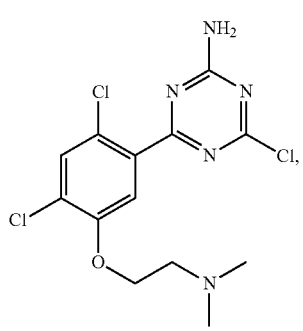
47
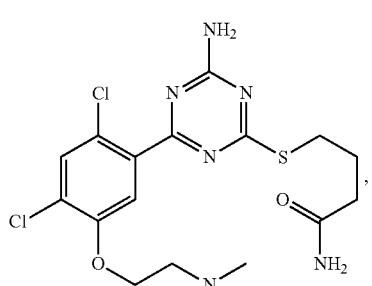
48
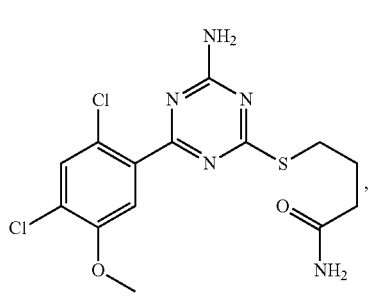
49
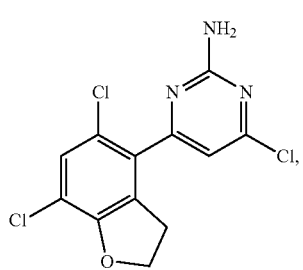

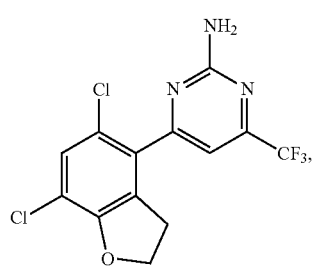
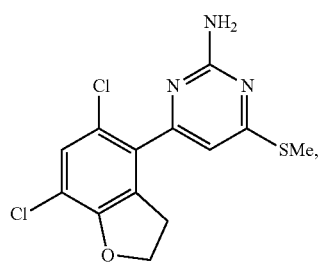
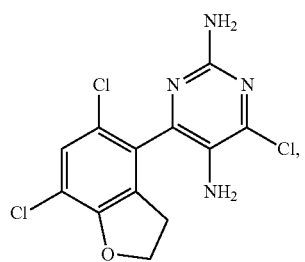
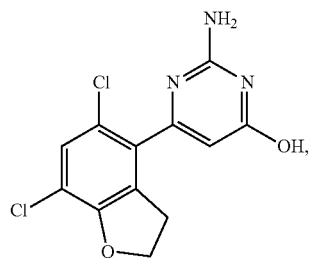
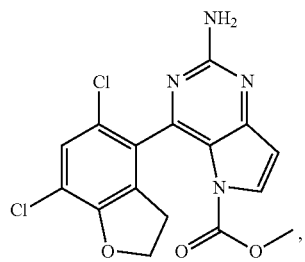
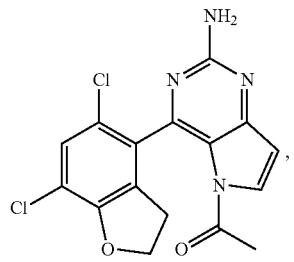
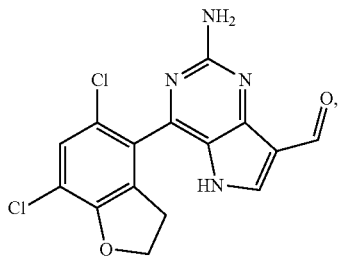
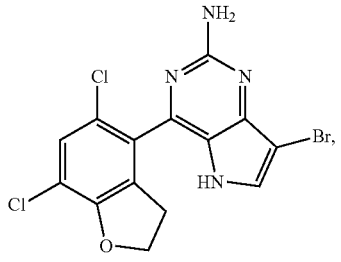
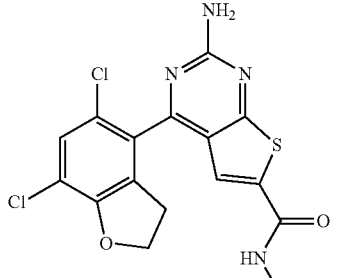
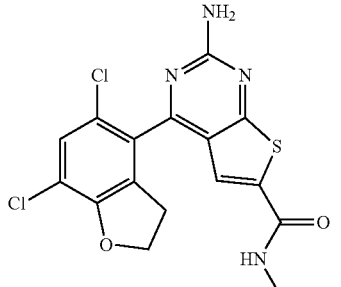
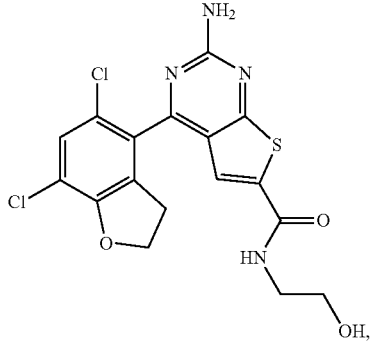

-continued
| | |
|---|---|
| 61 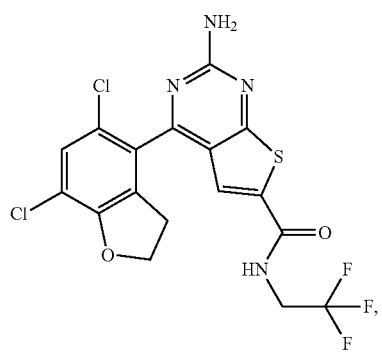 | 65 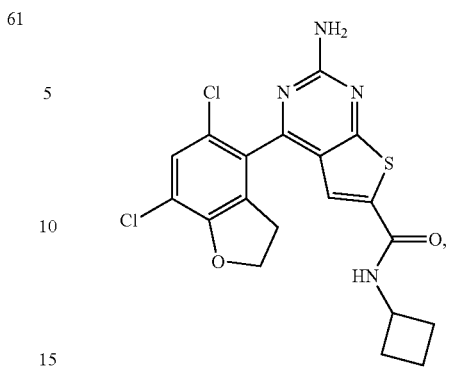 |
| 62 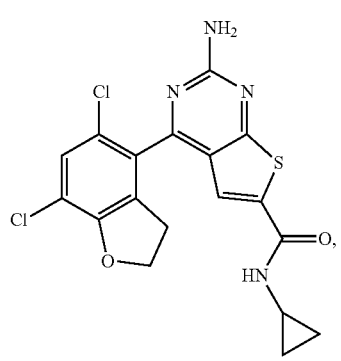 | 66 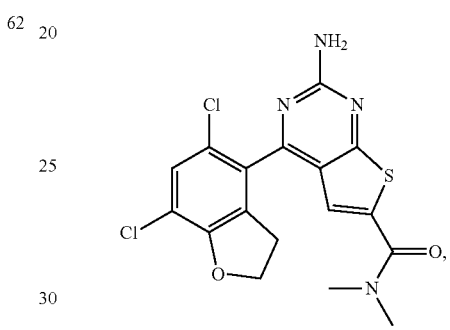 |
| 63 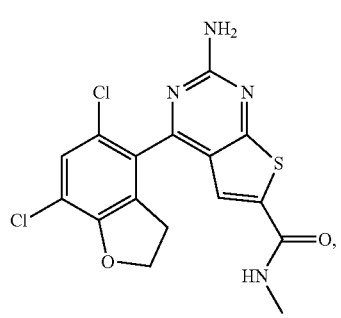 | 67 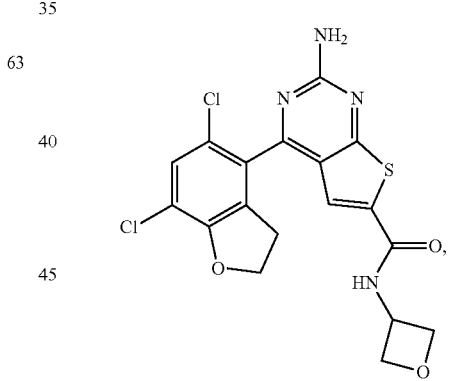 |
| 64 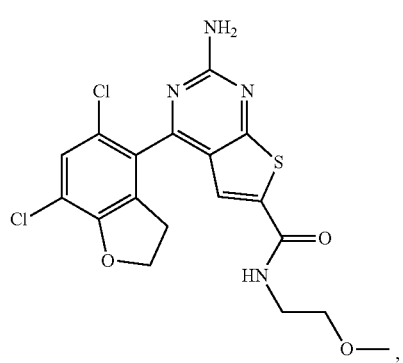 | 68 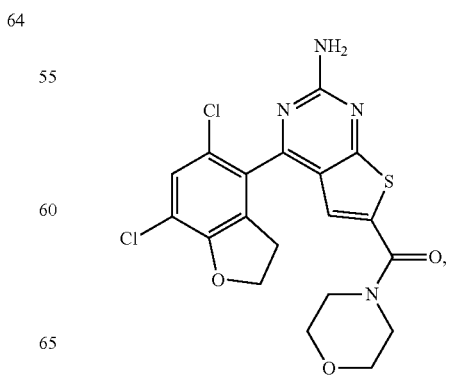 |

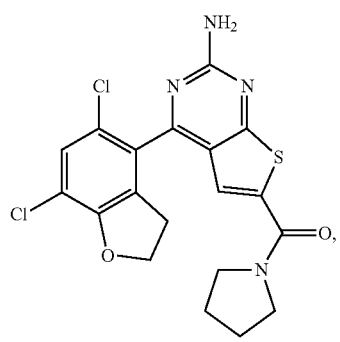
69
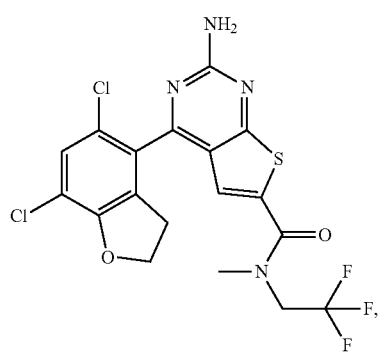
70
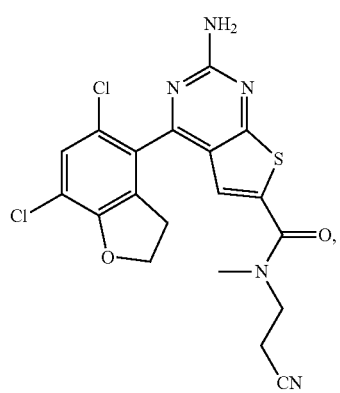
71
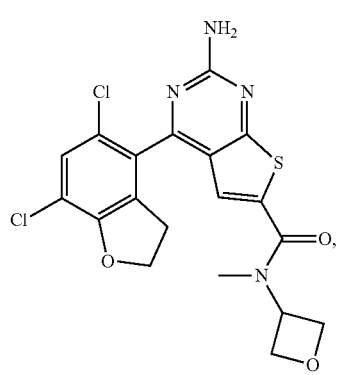
72
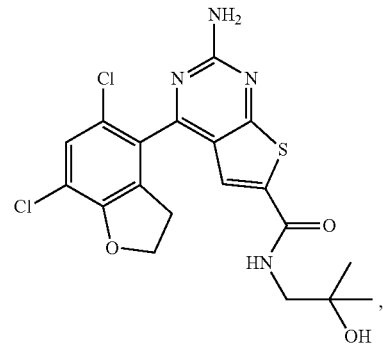
73
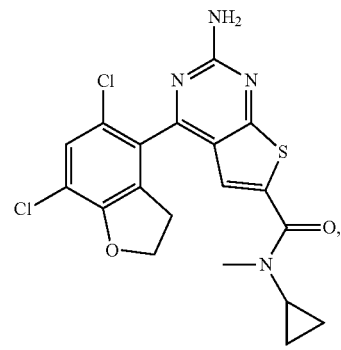
74
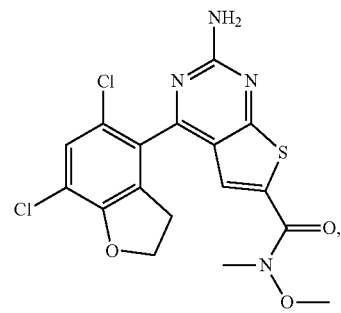
75
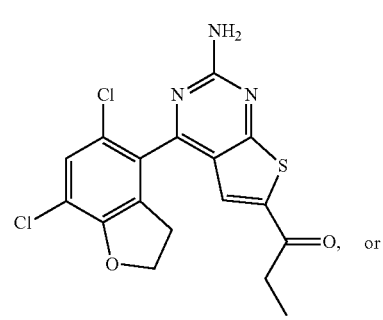
76
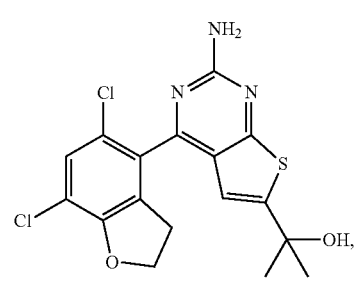
77
or a pharmaceutically acceptable salt thereof.

87. The compound of embodiment 84 having the formula:
14
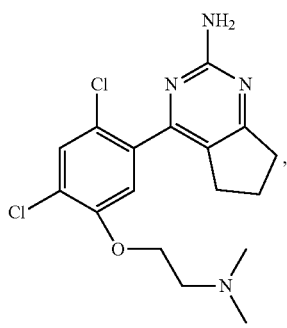
19
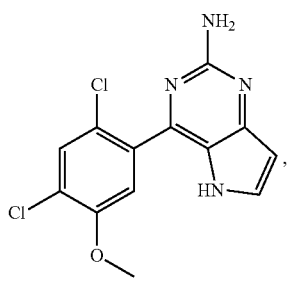
20
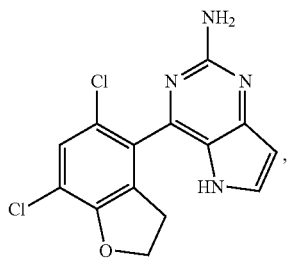
21
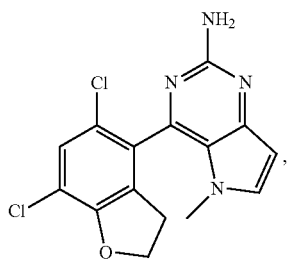
22
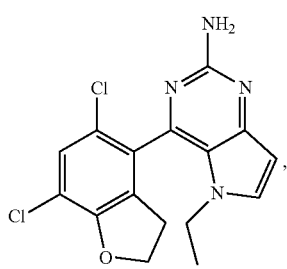
5
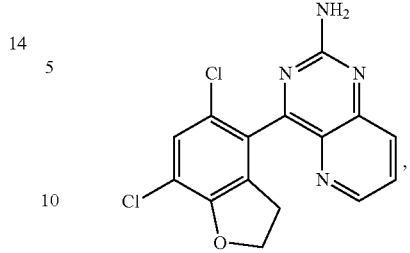
11
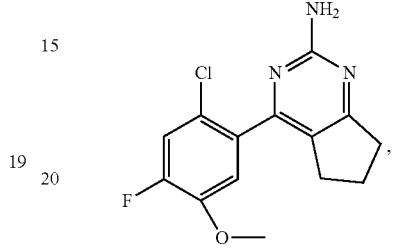
12
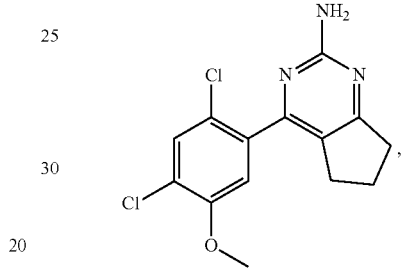
7
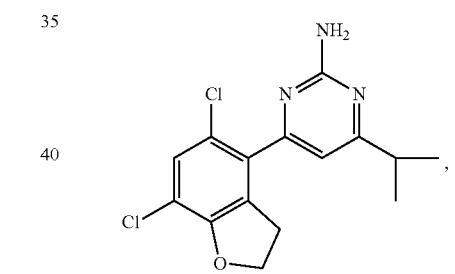
9
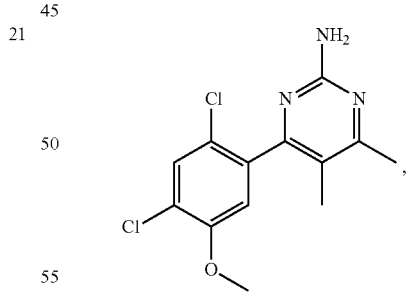
10
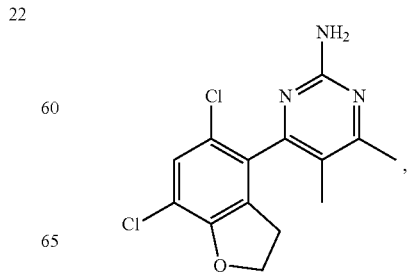

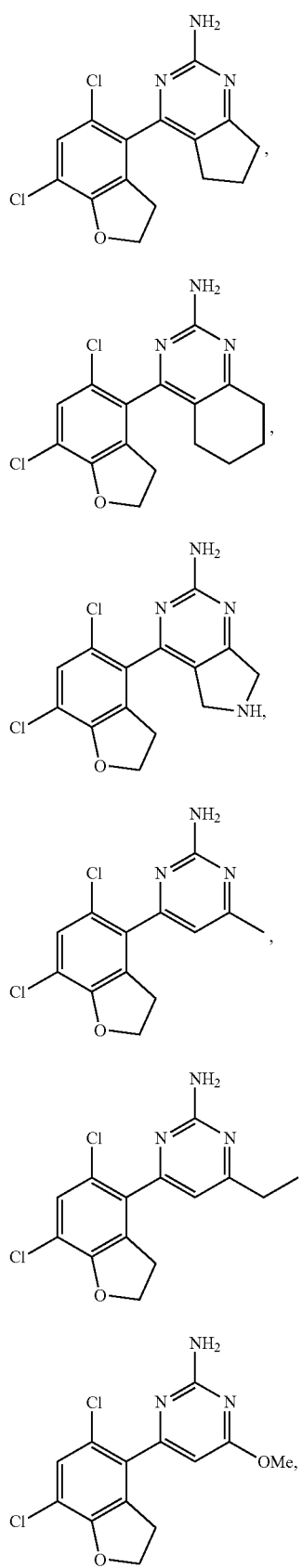
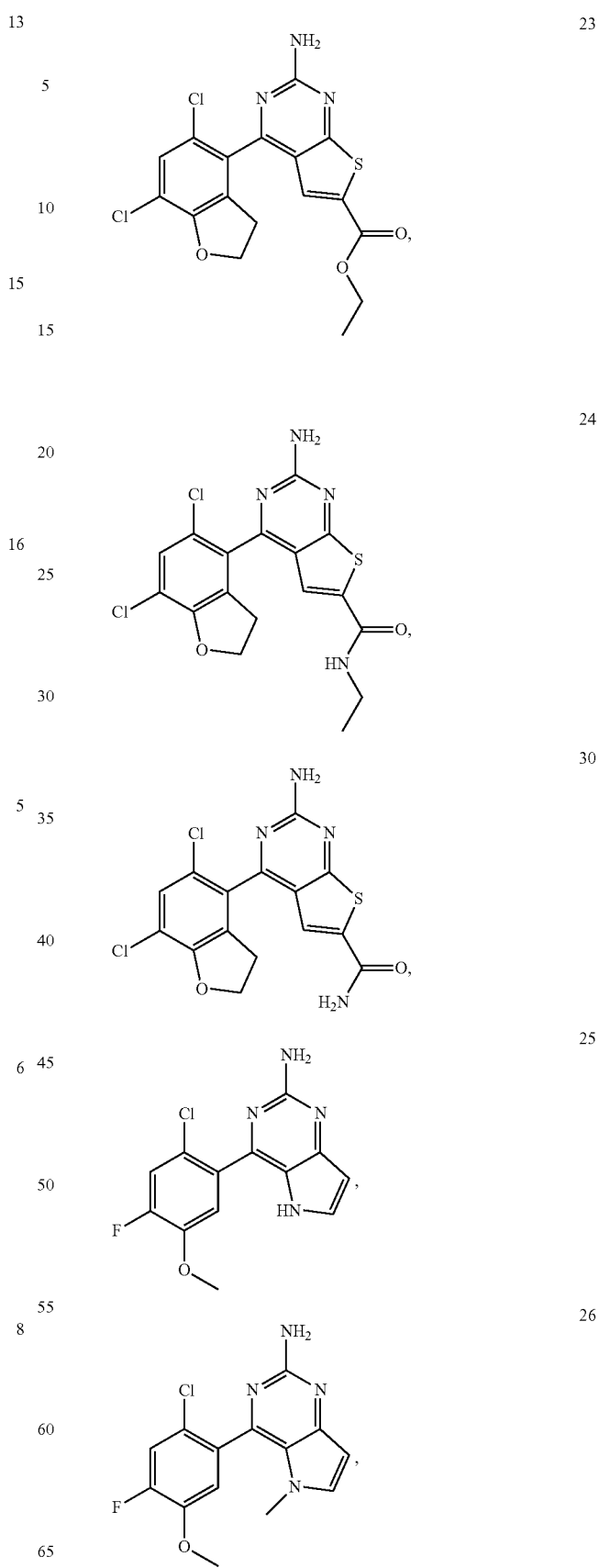

-continued
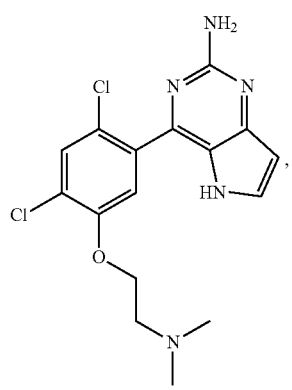
27
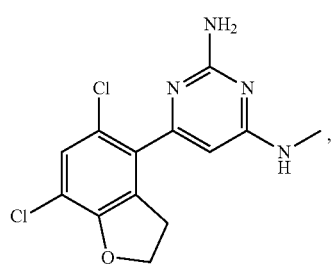
33
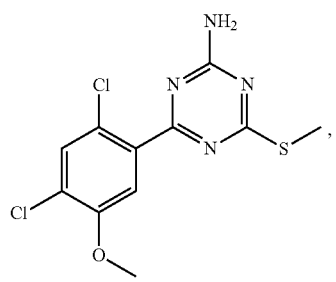
34
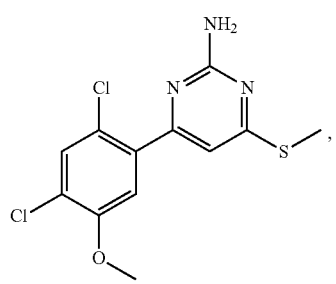
35
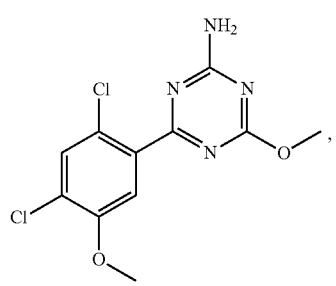
36
-continued
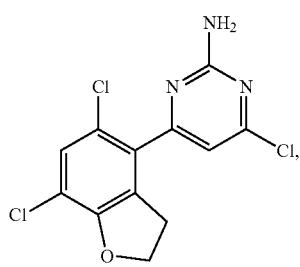
49
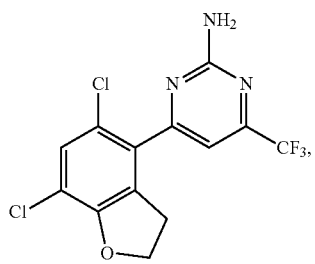
50
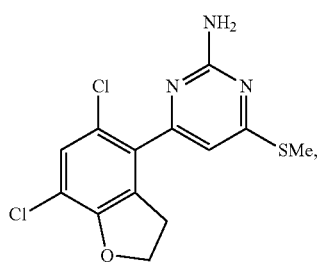
51
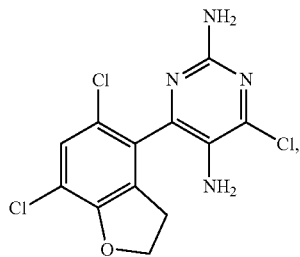
52
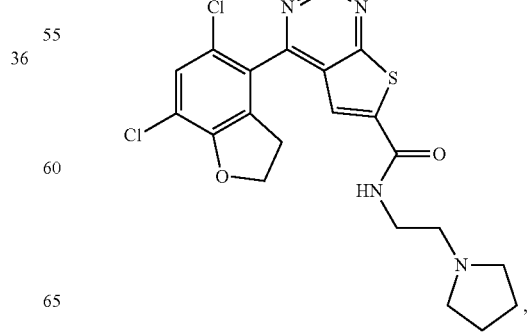
58

59
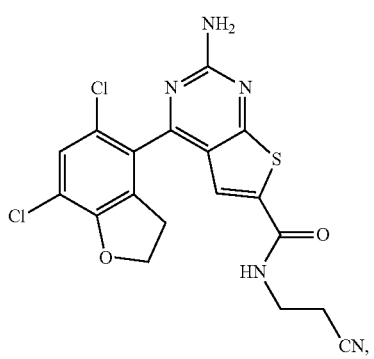
60
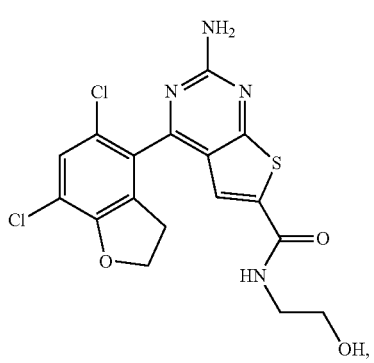
61
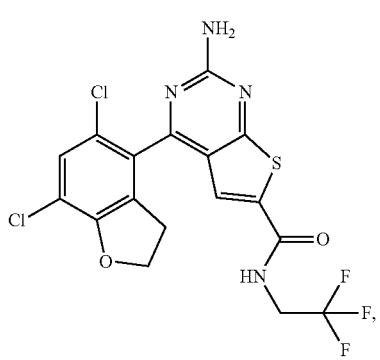
62
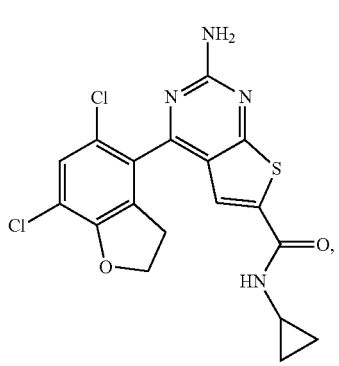
63
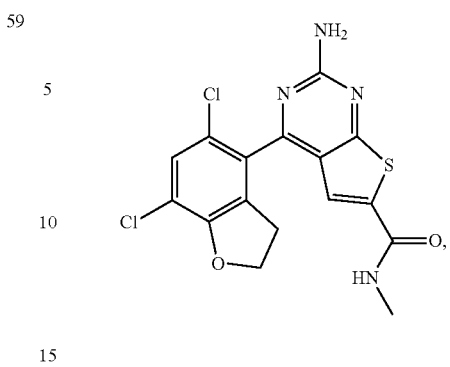
64
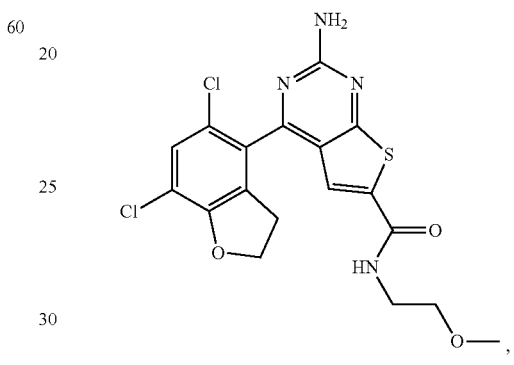
65
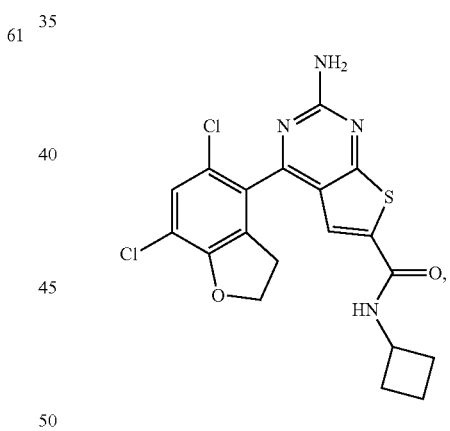
66
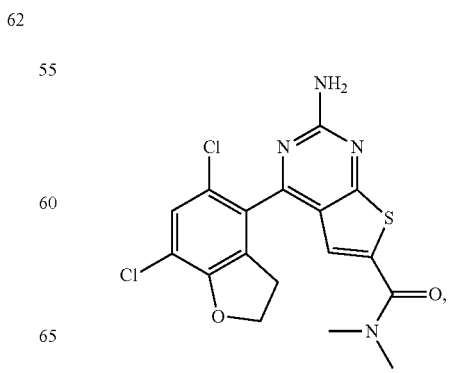

213
-continued
67
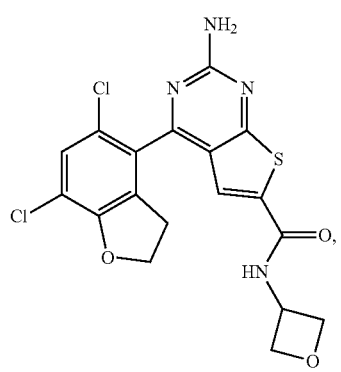
68
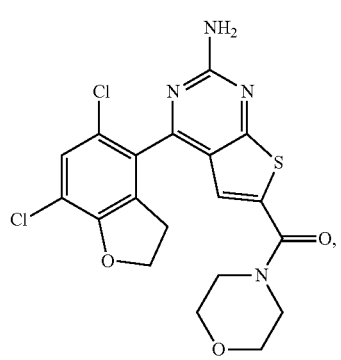
69
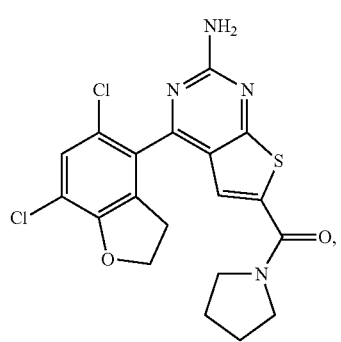
70
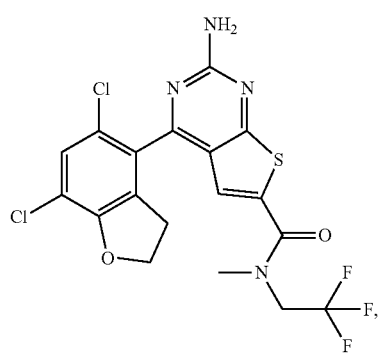
214
-continued
71
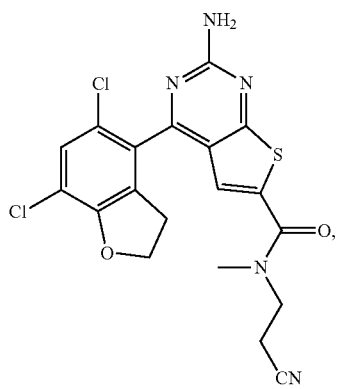
72
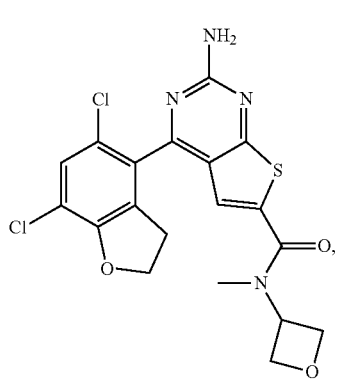
73
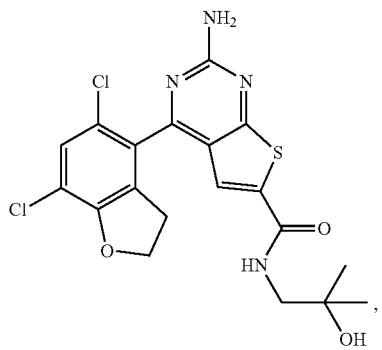
74
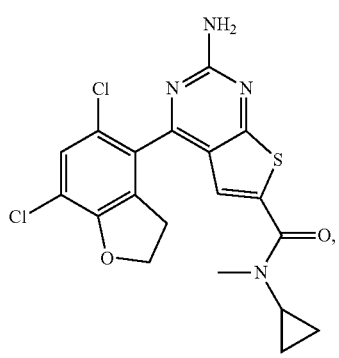

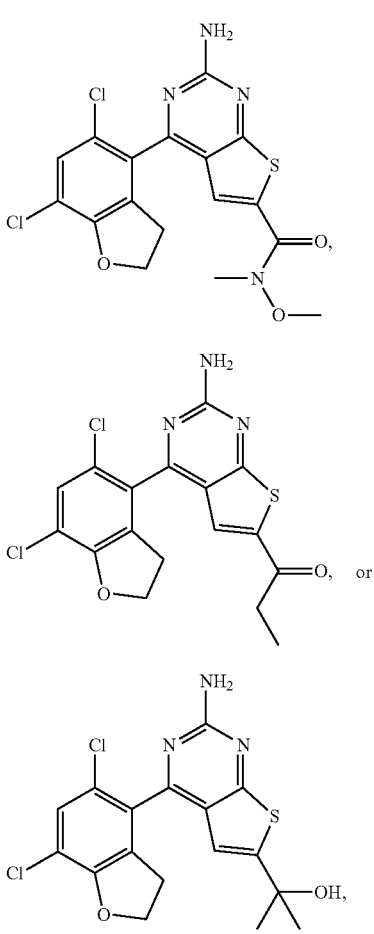

or a pharmaceutically acceptable salt thereof.

88. A pharmaceutical composition including the compound of any one of embodiments 1 to 87, or a pharmaceutically acceptable salt thereof, and one or more of pharmaceutically acceptable carriers or excipients.

89. The pharmaceutical composition of embodiment 88, where the composition is formulated for administration orally, sublingually, buccally, transdermally, intradermally, intramuscularly, parenterally, intravenously, intra-arterially, intracranially, subcutaneously, intraorbitally, intraventricularly, intraspinally, intraperitoneally, intranasally, by inhalation, and topically.

90. The pharmaceutical composition of embodiment 89, where the composition is formulated for oral administration.

91. A method of treating a disorder in a mammal caused by the action of heat shock protein 90 (Hsp90), the method including administering an effective amount of the compound of any one of embodiments 1 to 87 or a pharmaceutically acceptable salt thereof or the pharmaceutical composition of embodiment 88 to the mammal.

92. The method of embodiment 91, where the disorder is a neurodegenerative disorder.

93. The method of embodiment 92, where the neurodegenerative disorder is a tauopathy.

94. The method of embodiment 92 or 93, where the neurodegenerative disorder is Alzheimer's disease, Huntington's disease, progressive supranuclear palsy, Parkinson's disease, Pick's disease, corticobasal degeneration, chronic traumatic encephalopathy, traumatic brain injury, or frontotemporal dementia.

95. The method of embodiment 94, where the neurodegenerative disorder is Alzheimer's disease.

96. The method of embodiment 91, where the disorder is a proliferative disorder.

97. The method of embodiment 96, where the proliferative disorder is a cancer.

98. The method of embodiment 97, where the cancer is acute myeloid leukemia, gastrointestinal stromal tumor, gastric cancer, glioma, neuroblastoma, glioblastoma, lung cancer, lymphoma, melanoma, myeloma, non-small cell lung cancer, renal cancer, small cell lung cancer, blast-phase chronic myelogenous leukemia, leukemia, lymphoproliferative disorder, metastatic melanoma, relapsed multiple myeloma, refractory multiple myeloma, myeloproliferative disorders, pancreatic cancer, small intestine cancer, or solid tumor.

99. A method of treating an infectious disease in a mammal, the method including administering an effective amount of the compound of any one of embodiments 1 to 87 or a pharmaceutically acceptable salt or the pharmaceutical composition of embodiment 88 thereof to the mammal.

100. The method of embodiment 99, where the infectious disease is a viral infection.

101. The method of embodiment 100, where the viral infection is an infection by a virus of a family selected from the group consisting of Herpesviridae, Polyomaviridae, Poxviridae, Reoviridae, Birnaviridae, Picornaviridae, Flaviviridae, Arenaviridae, Hepeviridae, Rhabdoviridae, Paramoxyviridae, Bunyaviridae, Orthomoxyviridae, Filoviridae, Retroviridae, and Hepadnaviridae.

102. The method of embodiment 101, where the virus of a family Herpesviridae is herpes simplex virus-1, herpes simplex virus-2, herpes herpesvirus-5, Kaposi's sarcoma-associated herpesvirus, varicella zoster virus, or Epstein-Barr virus.

103. The method of embodiment 101, where the virus of Polyomaviridae family is SV40.

104. The method of embodiment 101, where the virus of Poxviridae family is vaccinia virus.

105. The method of embodiment 101, where the virus of Reoviridae family is rotavirus.

106. The method of embodiment 101, where the virus of Birnaviridae family is infectious bursal disease virus.

107. The method of embodiment 101, where the virus of Picornaviridae family is poliovirus, rhinovirus, or coxsackievirus.

108. The method of embodiment 101, where the virus of Flaviviridae family is hepatitis C virus or dengue virus.

109. The method of embodiment 101, where the virus of Arenaviridae family is lymphocytic choriomeningitis virus.

110. The method of embodiment 101, where the virus of Hepeviridae family is Hepatitis E virus.

111. The method of embodiment 101, where the virus of Rhabdoviridae family is vesicular stomatitis virus.

112. The method of embodiment 101, where the virus of Paramoxyviridae family is human parainfluenza virus 2, human parainfluenza virus 3, SV5, SV41, measles virus, or Sendai virus.

113. The method of embodiment 101, where the virus of Bunyaviridae family is La Crosse virus.

114. The method of embodiment 101, where the virus of Orthomoxyviridae family is influenza A virus.

115. The method of embodiment 101, where the virus of Filoviridae family is Ebola virus.

116. The method of embodiment 101, where the virus of Retroviridae family is HTLV1 or HIV1.

117. The method of embodiment 101, where the virus of Hepadnaviridae family is hepatitis B virus.

118. The method of embodiment 99, where the infectious disease is a fungal infection.

119. The method of embodiment 118, where the fungal infection is a *Candida albicans* infection, an *Aspergillus fumigates* infection, or *Pneumocystis jiroveci* infection.

120. The method of embodiment 99, where the infectious disease is a bacterial infection.

121. The method of embodiment 120, where the bacterial infection is a mycobacteria infection or anthrax infection.

122. The method of embodiment 120, where the bacterial infection is a bacterial pneumonia.

123. The method of embodiment 91, where the disorder an inflammatory or autoimmune disease.

124. The method of embodiment 123, where the inflammatory or autoimmune disease is rheumatoid arthritis, systemic lupus erythematosus, or asthma.

125. The method of embodiment 91, where the disorder is a cardiovascular disease.

126. The method of embodiment 125, where the cardiovascular disease is atherosclerosis or cardiomyopathy.

127. The method of embodiment 91, where the disorder is an allergy.

128. The method of any one of embodiments 91 to 127, where the compound is administered orally, sublingually, buccally, transdermally, intradermally, intramuscularly, parenterally, intravenously, intra-arterially, intracranially, subcutaneously, intraorbitally, intraventricularly, intraspinally, intraperitoneally, intranasally, by inhalation, and topically.

129. The method of embodiment 128, where the compound is administered orally.

130. The method of any one of embodiments 91 to 129, where the mammal is human.

131. The method of any one of embodiments 91 to 130, where the compound is administered orally, sublingually, buccally, transdermally, intradermally, intramuscularly, parenterally, intravenously, intra-arterially, intracranially, subcutaneously, intraorbitally, intraventricularly, intraspinally, intraperitoneally, intranasally, by inhalation, and topically.

132. The method of embodiment 131, where the compound is administered orally.

133. The method of any one of embodiments 91 to 132, where the mammal is human.

134. A compound for use in treating a disorder in a mammal caused by the action of heat shock protein 90 (Hsp90), where the compound is the compound of any one of embodiments 1 to 87 or a pharmaceutically acceptable salt thereof.

135. The compound of embodiment 134, where the disorder is a neurodegenerative disorder.

136. The compound of embodiment 135, where the neurodegenerative disorder is a tauopathy.

137. The compound of embodiment 134 or 135, where the neurodegenerative disorder is Alzheimer's disease, Huntington's disease, progressive supranuclear palsy, Parkinson's disease, Pick's disease, corticobasal degeneration, chronic traumatic encephalopathy, traumatic brain injury, or frontotemporal dementia.

138. The compound of embodiment 137, where the neurodegenerative disorder is Alzheimer's disease.

139. The compound of embodiment 134, where the disorder is a proliferative disorder.

140. The compound of embodiment 139, where the proliferative disorder is a cancer.

141. The compound of embodiment 140, where the cancer is acute myeloid leukemia, gastrointestinal stromal tumor, gastric cancer, glioblastoma, lung cancer, lymphoma, melanoma, myeloma, non-small cell lung cancer, renal cancer, small cell lung cancer, blast-phase chronic myelogenous leukemia, leukemia, lymphoproliferative disorder, metastatic melanoma, relapsed multiple myeloma, refractory multiple myeloma, myeloproliferative disorders, pancreatic cancer, small intestine cancer, or solid tumor.

142. The compound of embodiment 134, where the disorder is an infectious disease.

143. The compound of embodiment 142, where the infectious disease is a viral infection.

144. The compound of embodiment 143, where the viral infection is an infection by a virus of a family selected from the group consisting of Herpesviridae, Polyomaviridae, Poxviridae, Reoviridae, Birnaviridae, Picornaviridae, Flaviviridae, Arenaviridae, Hepeviridae, Rhabdoviridae, Paramoxyviridae, Bunyaviridae, Orthomoxyviridae, Filoviridae, Retroviridae, and Hepadnaviridae.

145. The compound of embodiment 144, where the virus of a family Herpesviridae is herpes simplex virus-1, herpes simplex virus-2, herpes herpesvirus-5, Kaposi's sarcoma-associated herpesvirus, varicella zoster virus, or Epstein-Barr virus.

146. The compound of embodiment 144, where the virus of Polyomaviridae family is SV40.

147. The compound of embodiment 144, where the virus of Poxviridae family is vaccinia virus.

148. The compound of embodiment 144, where the virus of Reoviridae family is rotavirus.

149. The compound of embodiment 144, where the virus of Birnaviridae family is infectious bursal disease virus.

150. The compound of embodiment 144, where the virus of Picornaviridae family is poliovirus, rhinovirus, or coxsackievirus.

141. The compound of embodiment 144, where the virus of Flaviviridae family is hepatitis C virus or dengue virus.

152. The compound of embodiment 144, where the virus of Arenaviridae family is lymphocytic choriomeningitis virus.

153. The compound of embodiment 144, where the virus of Hepeviridae family is Hepatitis E virus.

154. The compound of embodiment 144, where the virus of Rhabdoviridae family is vesicular stomatitis virus.

155. The compound of embodiment 144, where the virus of Paramoxyviridae family is human parainfluenza virus 2, human parainfluenza virus 3, SV5, SV41, measles virus, or Sendai virus.

156. The compound of embodiment 144, where the virus of Bunyaviridae family is La Crosse virus.

157. The compound of embodiment 144, where the virus of Orthomoxyviridae family is influenza A virus.

158. The compound of embodiment 144, where the virus of Filoviridae family is Ebola virus.

159. The compound of embodiment 144, where the virus of Retroviridae family is HTLV1 or HIV1.

160. The compound of embodiment 144, where the virus of Hepadnaviridae family is hepatitis B virus.

161. The compound of embodiment 134, where the infectious disease is a fungal infection.

162. The compound of embodiment 161, where the fungal infection is a *Candida albicans* infection, an *Aspergillus fumigates* infection, or *Pneumocystis jiroveci* infection.

163. The compound of embodiment 134, where the infectious disease is a bacterial infection.

165. The compound of embodiment 163, where the bacterial infection is a mycobacteria infection or anthrax infection.

166. The compound of embodiment 163, where the bacterial infection is a bacterial pneumonia.

167. The compound of embodiment 134, where the disorder an inflammatory or autoimmune disease.

168. The compound of embodiment 167, where the inflammatory or autoimmune disease is rheumatoid arthritis, systemic lupus erythermatosus, or asthma.

169. The compound of embodiment 134, where the disorder is a cardiovascular disease.

170. The compound of embodiment 169, where the cardiovascular disease is atherosclerosis or cardiomyopathy.

171. The compound of embodiment 170, where the disorder is an allergy.

172. Use of a compound in the manufacture of a medicament for treating a disorder in a mammal caused by the action of heat shock protein 90 (Hsp90), where the compound is the compound of any one of embodiments 1 to 87 or a pharmaceutically acceptable salt thereof.

173. Use of a compound for treating a disorder in a mammal caused by the action of heat shock protein 90 (Hsp90), where the compound is the compound of any one of embodiments 1 to 87 or a pharmaceutically acceptable salt thereof.

174. The use of embodiment 172 or 173, where the disorder is a neurodegenerative disorder.

175. The use of embodiment 174, where the neurodegenerative disorder is a tauopathy.

176. The use of embodiment 174 or 175, where the neurodegenerative disorder is Alzheimer's disease, Huntington's disease, progressive supranuclear palsy, Parkinson's disease, Pick's disease, corticobasal degeneration, chronic traumatic encephalopathy, traumatic brain injury, or frontotemporal dementia.

177. The use of embodiment 176, where the neurodegenerative disorder is Alzheimer's disease.

178. The use of embodiment 172 or 173, where the disorder is a proliferative disorder.

179. The use of embodiment 178, where the proliferative disorder is a cancer.

180. The use of embodiment 179, where the cancer is acute myeloid leukemia, gastrointestinal stromal tumor, gastric cancer, glioblastoma, lung cancer, lymphoma, melanoma, myeloma, non-small cell lung cancer, renal cancer, small cell lung cancer, blast-phase chronic myelogenous leukemia, leukemia, lymphoproliferative disorder, metastatic melanoma, relapsed multiple myeloma, refractory multiple myeloma, myeloproliferative disorders, pancreatic cancer, small intestine cancer, or solid tumor.

181. Use of a compound for treating, or in the manufacture of a meadicament for treating, an infectious disease, where the compound is the compound of any one of embodiments 1 to 87.

182. The use of embodiment 181, where the infectious disease is a viral infection.

183. The use of embodiment 182, where the viral infection is an infection by a virus of a family selected from the group consisting of Herpesviridae, Polyomaviridae, Poxviridae, Reoviridae, Birnaviridae, Picornaviridae, Flaviviridae, Arenaviridae, Hepeviridae, Rhabdoviridae, Paramoxyviridae, Bunyaviridae, Orthomoxyviridae, Filoviridae, Retroviridae, and Hepadnaviridae.

184. The use of embodiment 183, where the virus of a family Herpesviridae is herpes simplex virus-1, herpes simplex virus-2, herpes herpesvirus-5, Kaposi's sarcoma-associated herpesvirus, varicella zoster virus, or Epstein-Barr virus.

185. The use of embodiment 183, where the virus of Polyomaviridae family is SV40.

186. The use of embodiment 183, where the virus of Poxviridae family is vaccinia virus.

187. The use of embodiment 183, where the virus of Reoviridae family is rotavirus.

188. The use of embodiment 183, where the virus of Birnaviridae family is infectious bursal disease virus.

189. The use of embodiment 183, where the virus of Picornaviridae family is poliovirus, rhinovirus, or coxsackievirus.

190. The use of embodiment 183, where the virus of Flaviviridae family is hepatitis C virus or dengue virus.

191. The use of embodiment 183, where the virus of Arenaviridae family is lymphocytic choriomeningitis virus.

192. The use of embodiment 183, where the virus of Hepeviridae family is Hepatitis E virus.

193. The use of embodiment 183, where the virus of Rhabdoviridae family is vesicular stomatitis virus.

194. The use of embodiment 183, where the virus of Paramoxyviridae family is human parainfluenza virus 2, human parainfluenza virus 3, SV5, SV41, measles virus, or Sendai virus.

195. The use of embodiment 183, where the virus of Bunyaviridae family is La Crosse virus.

196. The use of embodiment 183, where the virus of Orthomoxyviridae family is influenza A virus.

197. The use of embodiment 183, where the virus of Filoviridae family is Ebola virus.

198. The use of embodiment 183, where the virus of Retroviridae family is HTLV1 or HIV1.

199. The use of embodiment 183, where the virus of Hepadnaviridae family is hepatitis B virus.

200. The use of embodiment 172 or 173, where the infectious disease is a fungal infection.

201. The use of embodiment 200, where the fungal infection is a *Candida albicans* infection, an *Aspergillus fumigates* infection, or *Pneumocystis jiroveci* infection.

202. The use of embodiment 172 or 173, where the infectious disease is a bacterial infection.

203. The use of embodiment 202, where the bacterial infection is a mycobacteria infection or anthrax infection.

204. The use of embodiment 203, where the bacterial infection is a bacterial pneumonia.

205. The use of embodiment 172 or 173, where the disorder an inflammatory or autoimmune disease.

206. The use of embodiment 205, where the inflammatory or autoimmune disease is rheumatoid arthritis, systemic lupus erythermatosus, or asthma.

207. The use of embodiment 172 or 173, where the disorder is a cardiovascular disease.

208. The use of embodiment 207, where the cardiovascular disease is atherosclerosis cardiomyopathy.

209. The use of embodiment 172 or 173, where the disorder is an allergy.

210. The compound of any one of embodiments 134 to 171 or the use of any one of embodiments 172 to 209, where the compound is formulated for administration by a route selected from the group consistin of oral, sublingual, buccal, transdermal, intradermal, intramuscular, parenteral, intravenous, intra-arterial, intracranial, subcutaneous, intraorbital, intraventricular, intraspinal, intraperitoneal, intranasal, by inhalation, and topical.

211. The compound or the use of embodiment 128, where the compound is formulated for oral administration.

212. A method of inhibiting Hsp90, the method including contacting a cell with the compound of any one of embodiments 1 to 87 or a pharmaceutically acceptable salt thereof.

213. The method of embodiment 212, where the cell is in vitro.

214. A compound for use in inhibiting Hsp90, where the compound is the compound of any one of embodiments 1 to 87 or a pharmaceutically acceptable salt thereof.

215. Use of a compound for inhibiting Hsp90, where the compound is the compound of any one of embodiments 1 to 87 or a pharmaceutically acceptable salt thereof.

216. A kit including:
(i) the pharmaceutical composition of any one of embodiments 88 to 90; and
(ii) instructions for use of the pharmaceutical compositions of (i) to treat a disorder in a mammal caused by the action of Hsp90.

All publications, patents, and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are in the claims.

The invention claimed is:

1. A compound according to formula (I):

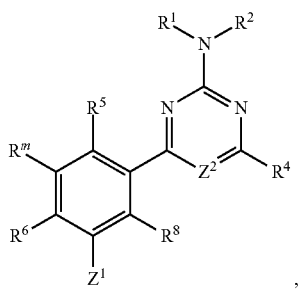

(I)

or a pharmaceutically acceptable salt thereof,
wherein
$Z^1$ is —$OR^7$ or —$SR^7$;
$Z^2$ is —$C(R^3)=$ or —N=;
each $R^1$ and $R^2$ is, independently, H, optionally substituted $C_{1-3}$ acyl, or optionally substituted $C_{1-3}$ alkyl;
$R^3$ and $R^4$ combine to form —$X^1$—$X^2$—$X^3$—; or $R^3$ is H, halogen, cyano, optionally substituted $C_{1-6}$ alkyl, optionally substituted $C_{1-3}$ alkoxy, or optionally substituted amino, and $R^4$ is halogen, cyano, optionally substituted $C_{1-6}$ alkyl, optionally substituted $C_{1-3}$ alkoxy, optionally substituted amino, or optionally substituted $C_{1-6}$ thioalkoxy;
wherein
$X^1$ is —S—, —O—, —$(CR^{14}R^{15})$—, —$C(R^{16})=$, —$N(R^9)$—, or —N=;
$X^2$ is —$(CR^{17}R^{18})_n$—, —S—, —O—, —$N(R^9)$—, —$C(R^{19})=$, =$C(R^{20})$—, or =$C(R^{21})$—$C(R^{22})=$;
$X^3$ is —$(CR^{14}R^{15})$—, —S—, —O—, —$N(R^9)$—, =N—, =$C(R^{23})$—;
each $R^{14}$ and $R^{15}$ is, independently, H or optionally substituted $C_{1-3}$ alkyl, or $R^{14}$ and $R^{15}$ combine to form =O or =S;
each $R^{17}$ and $R^{18}$ is, independently, H or optionally substituted $C_{1-3}$ alkyl, or $R^{17}$ and $R^{18}$ combine to form =O or =S;
each $R^{16}$, $R^{19}$, $R^{20}$, $R^{21}$, $R^{22}$, and $R^{23}$ is, independently, H or optionally substituted $C_{1-3}$ alkyl; and
n is 1 or 2;
$R^5$ is halogen, H, optionally substituted $C_{1-3}$ alkyl, optionally substituted $C_{1-3}$ alkoxy, or CN;
$R^6$ is halogen, H, optionally substituted $C_{1-3}$ alkyl, optionally substituted $C_{1-3}$ alkoxy, or CN;
$R^7$ and $R^8$, together with the atoms to which each is attached, join to form an optionally substituted five membered ring comprising one or two heteroatoms selected from the group consisting of oxygen and sulfur;
$R^9$ is H, optionally substituted $C_{1-3}$ alkyl, optionally substituted $C_{3-8}$ cycloalkyl, optionally substituted $C_{6-10}$ aryl, optionally substituted $C_{2-9}$ heteroaryl, optionally substituted $C_{2-9}$ heterocyclyl, optionally substituted $C_{1-3}$ alkcycloalkyl, optionally substituted $C_{1-3}$ alkheterocyclyl, or optionally substituted $C_{1-3}$ alkaryl; and
$R^m$ is H, halogen, cyano, optionally substituted $C_{1-4}$ acyl, optionally substituted $C_{1-4}$ alkyl, or optionally substituted $C_{1-3}$ alkoxy;
wherein
when each $R^5$ and $R^6$ is chloro, Z is —$OR^7$, $R^7$ and $R^8$ combine to form —$CH_2$—$CH_2$—, $Z^2$ is $CR^3$, and $R^3$ and $R^4$ combine to form a group according to formula (IIa),

(IIa)

wherein $R^9$ is H or —C(O)—N(H)-(linear $C_{1-3}$ alkyl).

2. The compound of claim 1, wherein $R^m$ is H.

3. The compound of claim 1, wherein the compound is according to formula (Ia):

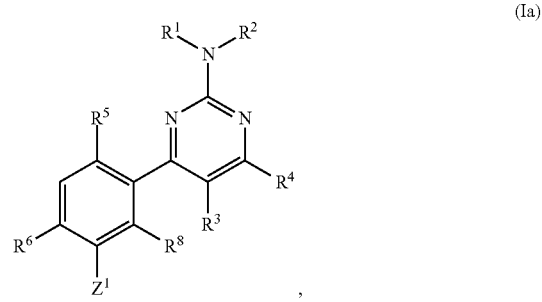

(Ia)

or a pharmaceutically acceptable salt thereof.

4. The compound of claim 1, wherein the compound is according to formula (Ib):

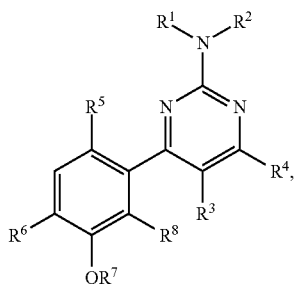

(Ib)

or a pharmaceutically acceptable salt thereof.

5. The compound of claim 1, wherein $R^3$ and $R^4$ combine to form $-X^1-X^2-X^3-$, wherein $-X^1-X^2-X^3-$ comprises one nitrogen, one oxygen, or one sulfur atom; or $R^3$ is H, halogen, optionally substituted $C_{1-3}$ acyl, optionally substituted $C_{1-3}$ alkyl, or optionally substituted $C_{1-3}$ alkoxy, and $R^4$ is halogen, optionally substituted $C_{1-3}$ acyl, optionally substituted $C_{1-3}$ alkyl, optionally substituted $C_{1-3}$ alkoxy, optionally substituted amino, or optionally substituted $C_{1-6}$ thioalkyl.

6. The compounds of claim 1, wherein $R^3$ and $R^4$ combine to form $-X^1-X^2-X^3-$, wherein $-X^1-X^2-X^3-$ comprises one sulfur atom.

7. The compound of claim 1, wherein $R^3$ and $R^4$ combine to form $-C(R^{13A})=C(R^{13B})-S-$ group, wherein $R^{13A}$ is H, and $R^{13B}$ is optionally substituted $C_{1-3}$ alkyl or H.

8. The compound of claim 7, wherein $R^{13B}$ is optionally substituted $C_{1-3}$ alkyl.

9. The compound of claim 8, wherein $R^{13B}$ is $-C(O)-R^{13C}$, wherein $R^{13C}$ is optionally substituted amino or optionally substituted $C_{1-3}$ alkoxy.

10. The compound of claim 1, wherein $R^3$ and $R^4$ combine to form $-C(R^{13A})=C(R^{13B})-S-$ group, wherein $R^{13A}$ is H, and $R^{13B}$ is $-C(O)-R^{13C}$, H, or $C_{1-6}$ aminoalkyl, wherein $R^{13C}$ is optionally substituted $C_{1-3}$ alkyl, optionally substituted $C_{1-3}$ alkoxy, optionally substituted amino, or optionally substituted $C_{2-9}$ heterocyclyl.

11. The compound of claim 1, wherein $R^3$ and $R^4$ combine to form $-CH_2CH_2CH_2-$ group.

12. The compound of claim 1, wherein $R^3$ and $R^4$ combine to form $-X^1-X^2-X^3-$, wherein $-X^1-X^2-X^3-$ comprises one nitrogen.

13. The compound of claim 12, wherein $R^3$ and $R^4$ combine to form $-N(R^9)-CH=CH-$ group.

14. The compound of claim 1, wherein $R^3$ and $R^4$ combine to form $-X^1-X^2-X^3-$, wherein $X^1$ is $-S-$, $-O-$, $-(CR^{14}R^{15})-$, $-C(R^{16})=$, $-N(R^9)-$, or $-N=$ $X^2$ is $-(CR^{17}R^{18})_n-$, $-C(R^{19})=$, $=C(R^{20})-$, or $=C(R^{21})-C(R^{22})=$;

$X^3$ is $-(CR^{14}R^{15})-$, $-S-$, $-O-$, $-N(R^9)-$, $=N-$, or $=C(R^{23})-$.

15. The compound of claim 1, wherein $R^7$ and $R^8$ form a group $-Y^1-Y^2-$, wherein:

$Y^1$ is $-(CR^{26}R^{27})_m-$; and $Y^2$ is $-(CR^{26}R^{27})-$; wherein each $R^{26}$ and $R^{27}$ is, independently, H or optionally substituted $C_{1-3}$ alkyl;

m is 1.

16. The compound of claim 1, wherein $Z^1$ and $R^8$ combine to form $-Z^3-Y^1-Y^2-$, wherein $Z^3$ is $-O-$ or $-S-$;

$Y^1$ is $-(CR^{26}R^{27})_m-$ or $-C(R^{20})=$; and $Y^2$ is $-O-$, $-S-$, $-(CR^{26}R^{27})-$, or $=C(R^{20})-$;

wherein each $R^{20}$ is, independently, H or optionally substituted $C_{1-3}$ alkyl; and each $R^{26}$ and $R^{27}$ is, independently, H or optionally substituted $C_{1-3}$ alkyl, or $R^{26}$ and $R^{27}$ combine to form $=O$ or $=S$;

m is 1 or 2.

17. A compound:

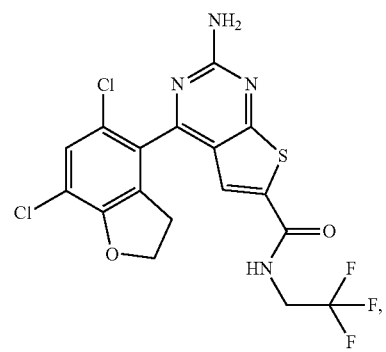

61

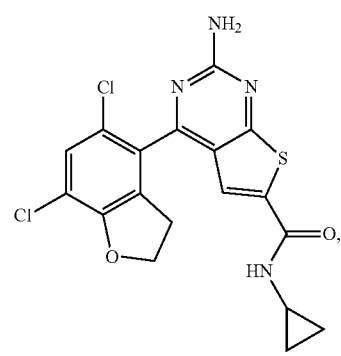

62

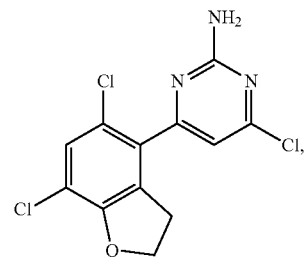

49

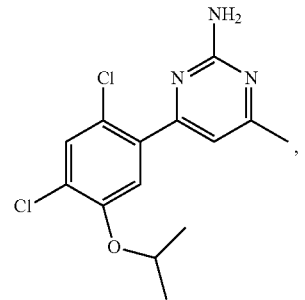

2

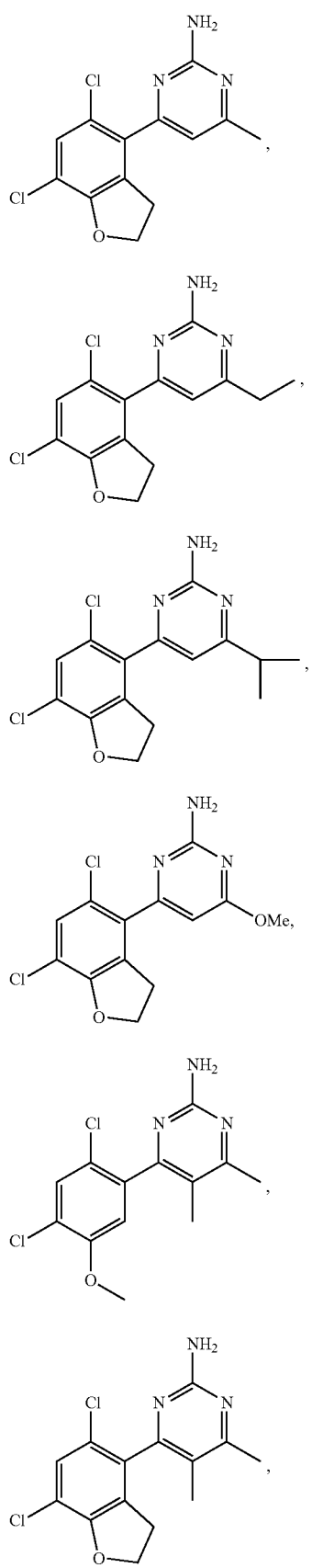
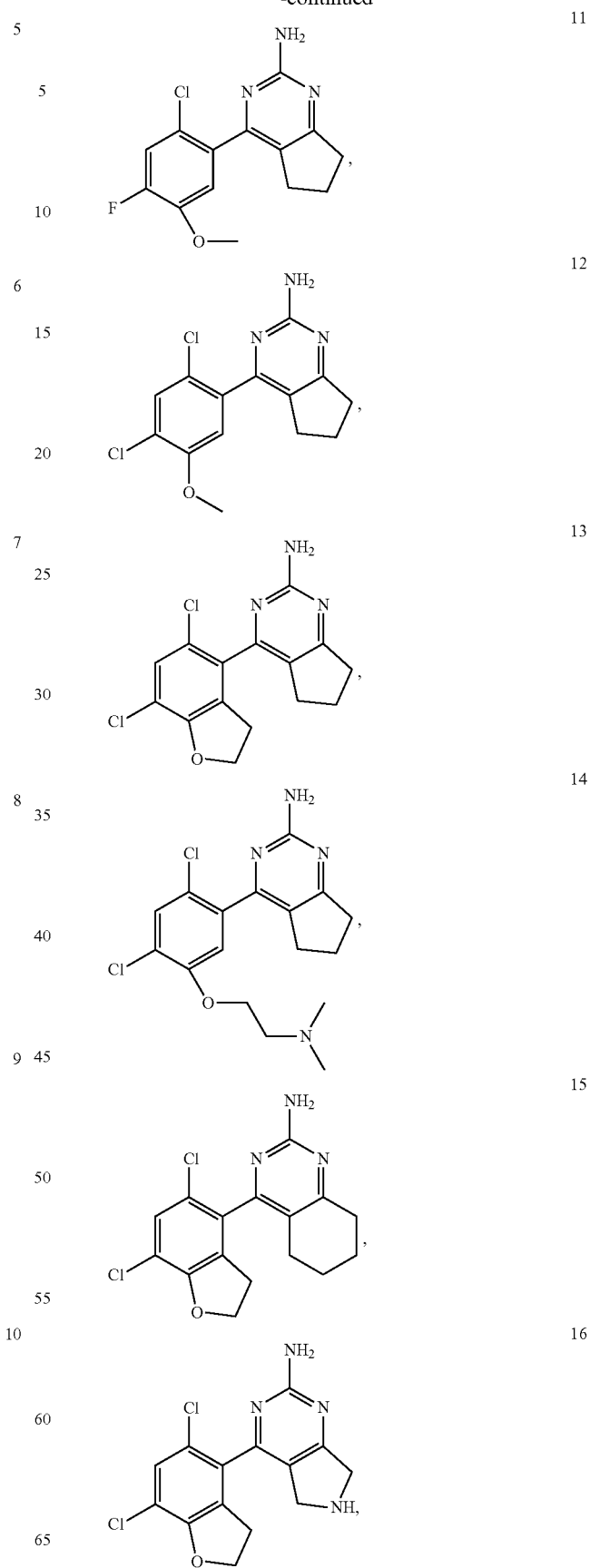

17
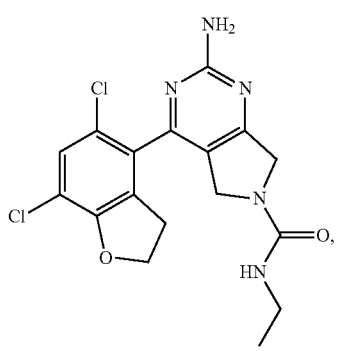
18
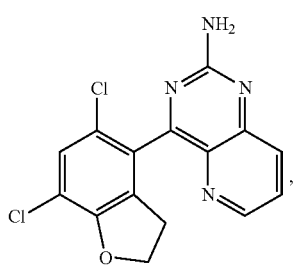
19
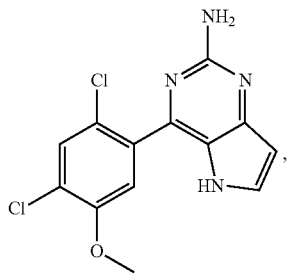
20
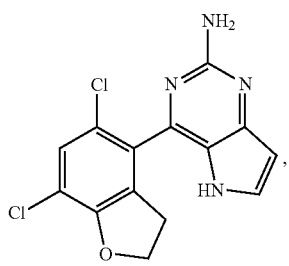
21
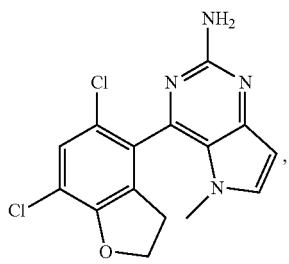
22
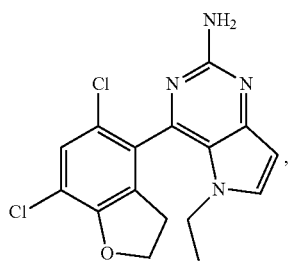
23
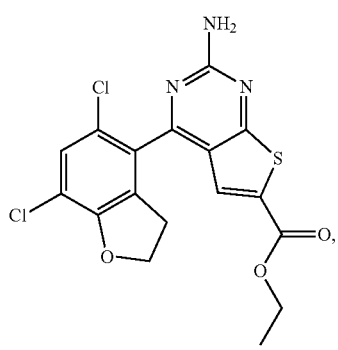
24
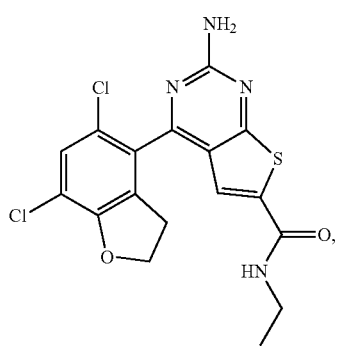
25
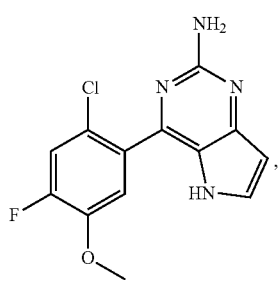
26
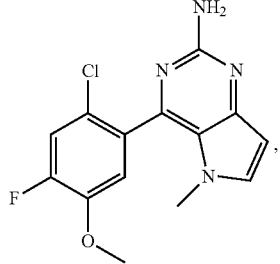

229
-continued
27
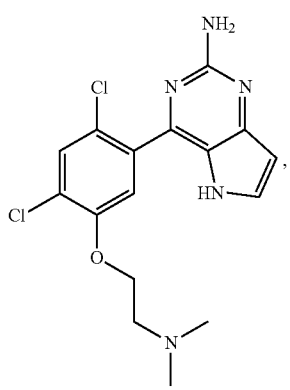
28
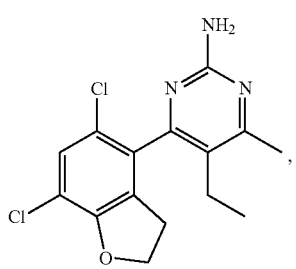
29
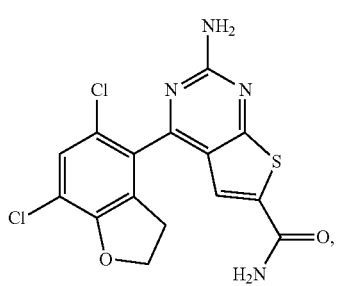
33
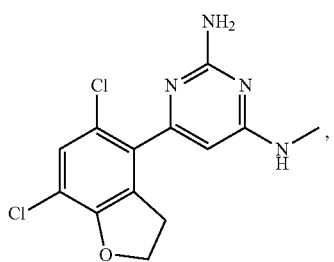
34
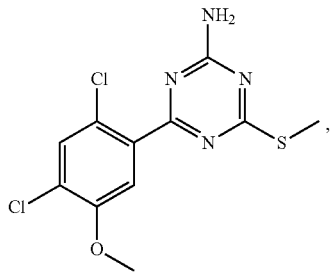
230
-continued
35
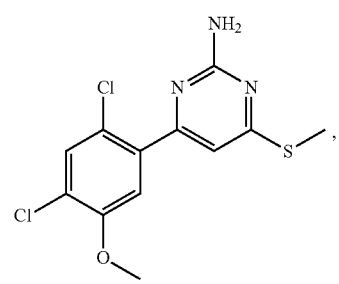
36
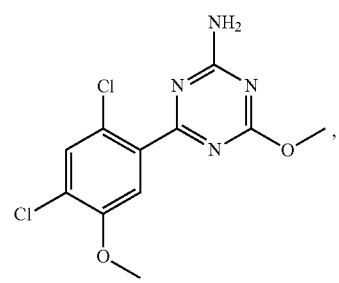
40
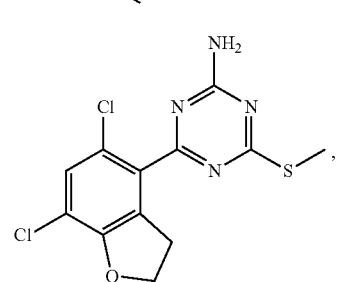
41
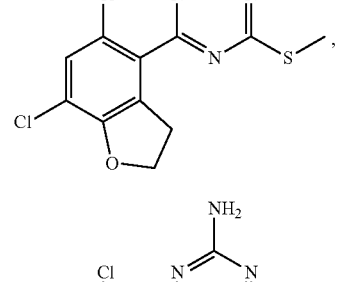
42
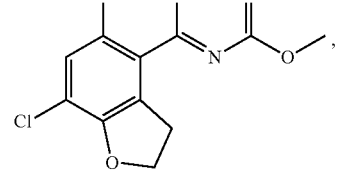
43
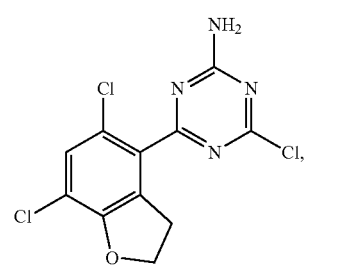

44
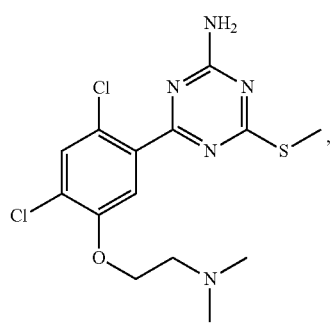
45
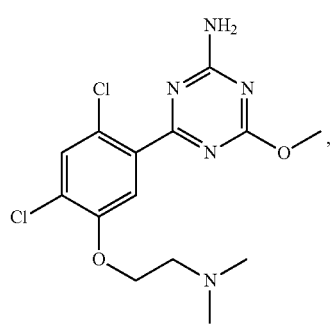
46
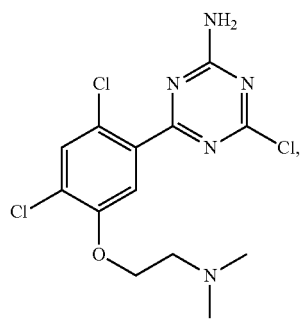
47
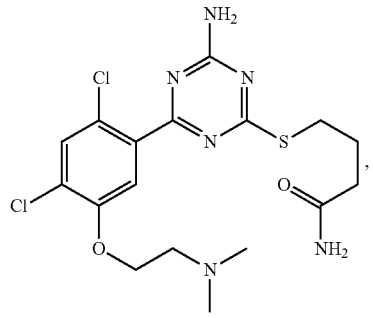
48
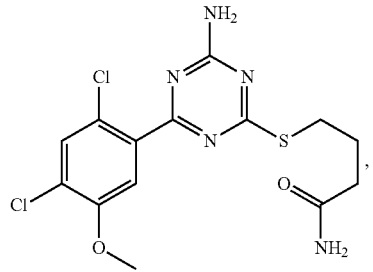
60
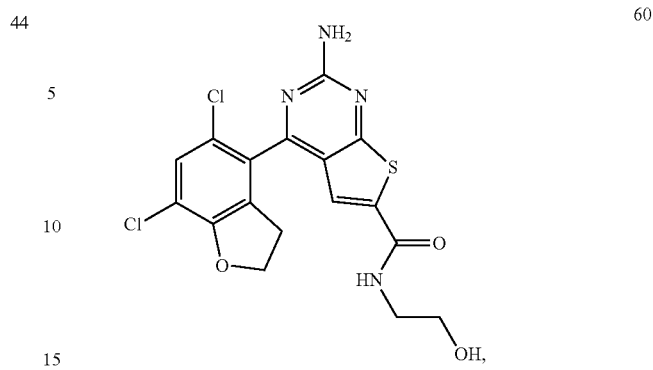
50
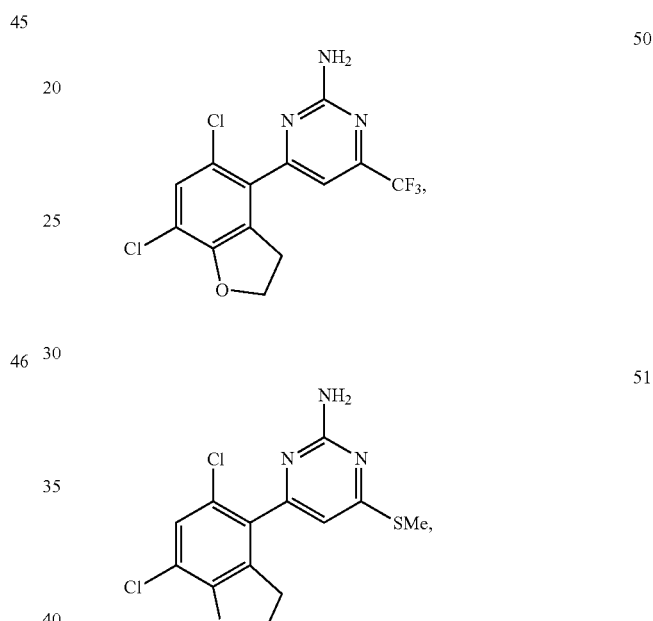
51
52
53
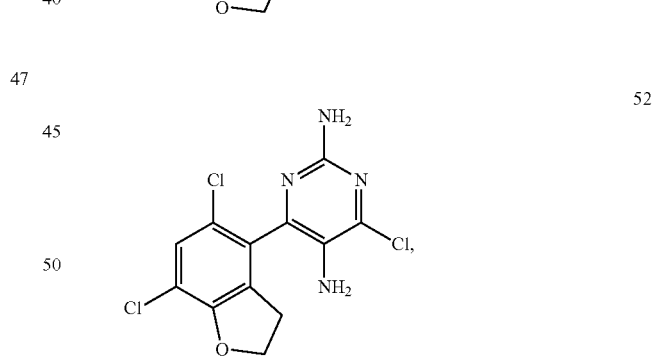
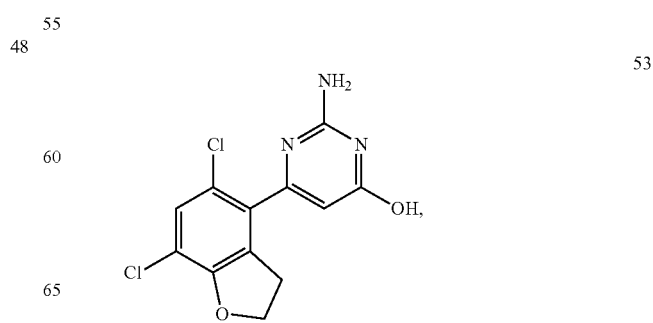

54
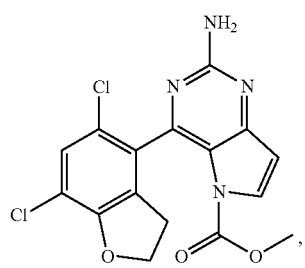
55
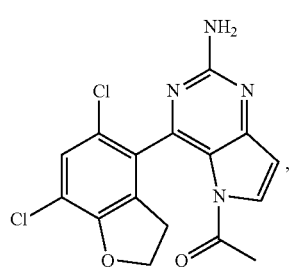
56
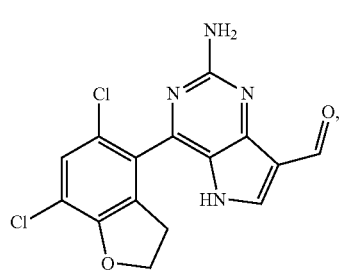
57
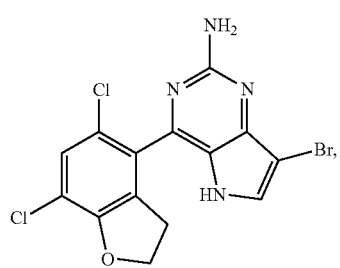
58
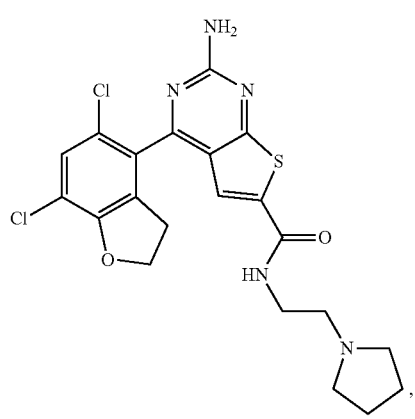
59
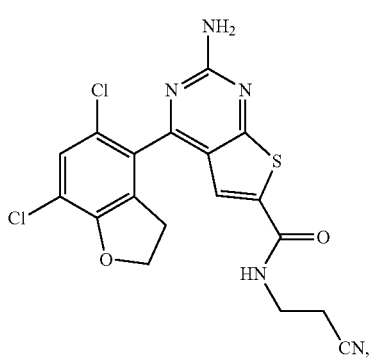
63
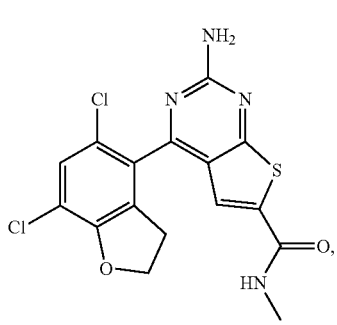
64
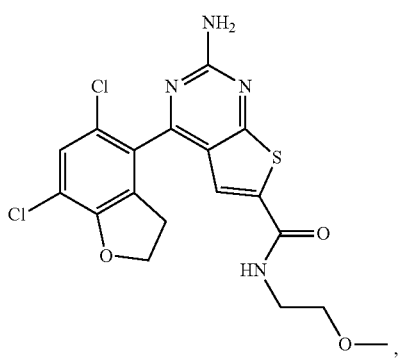
65
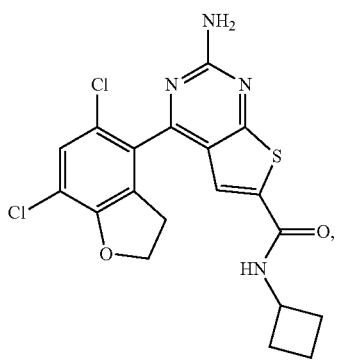

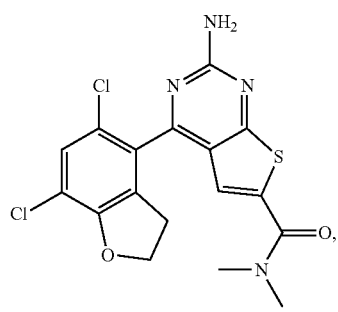
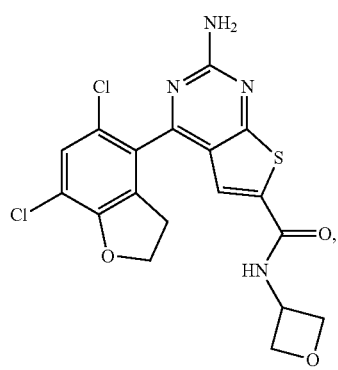
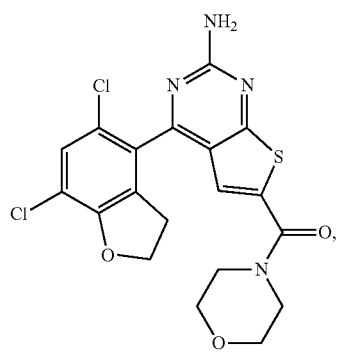
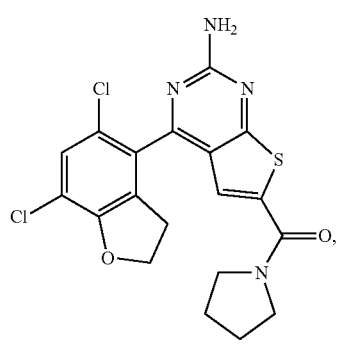
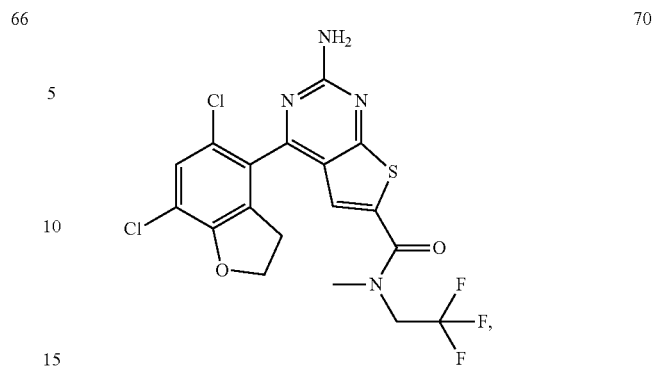
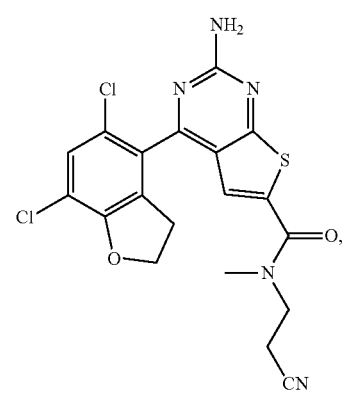
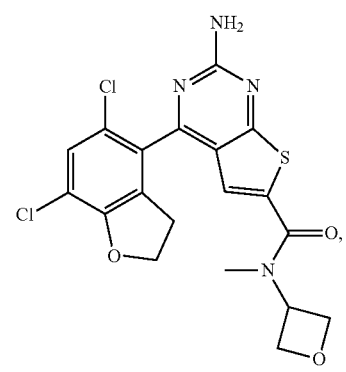
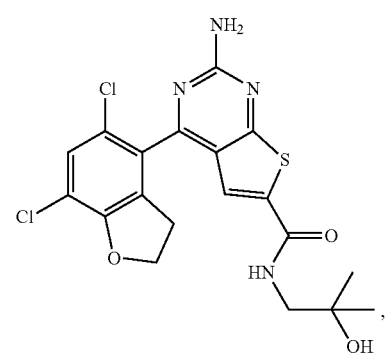

-continued
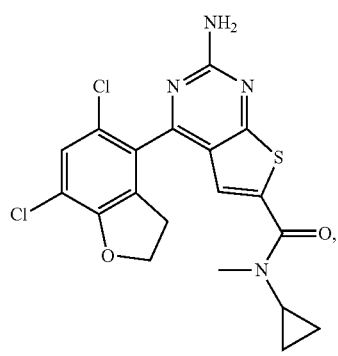
74
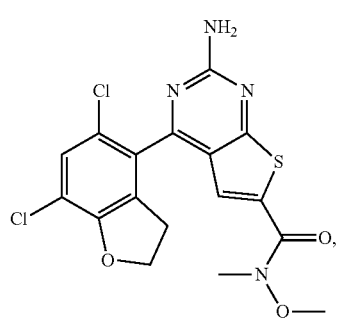
75
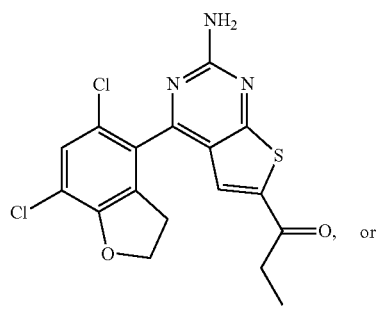
76
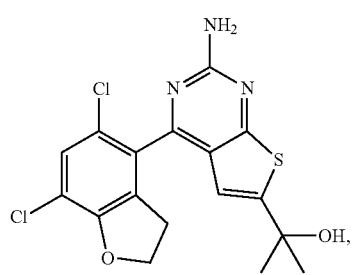
77
or a pharmaceutically acceptable salt thereof.
18. The compound of claim 17 having the formula:
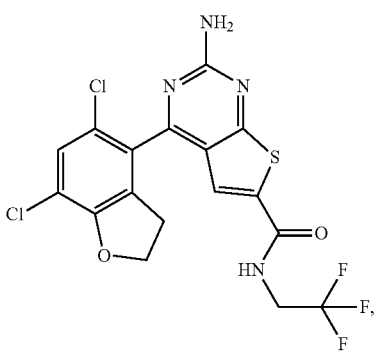
61
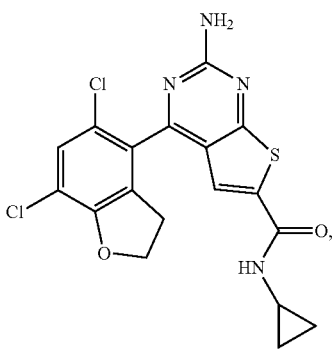
62
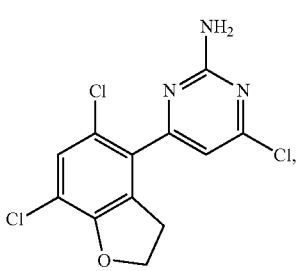
49
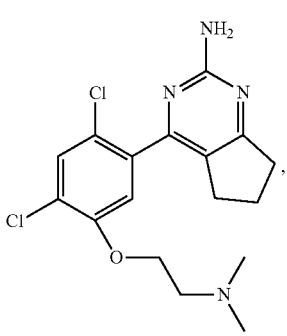
14
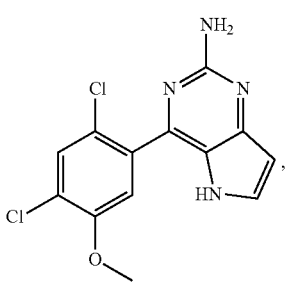
19

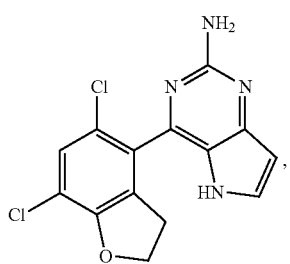
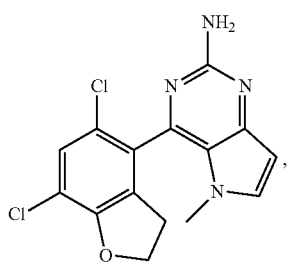
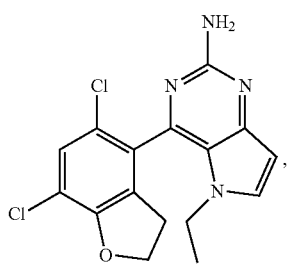
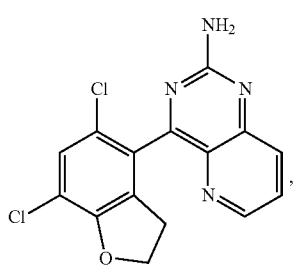
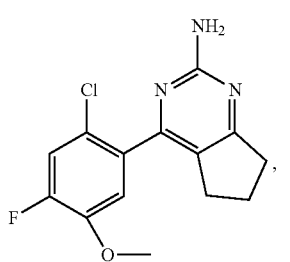
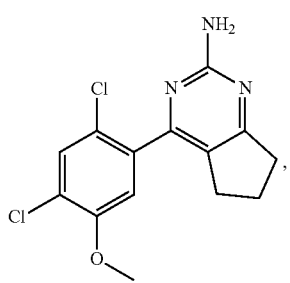
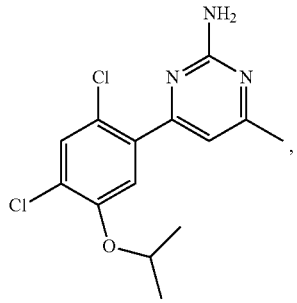
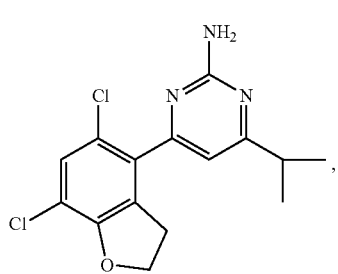
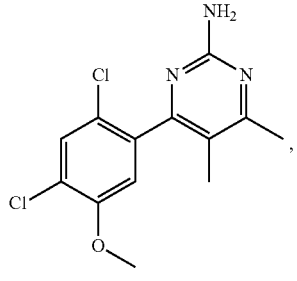
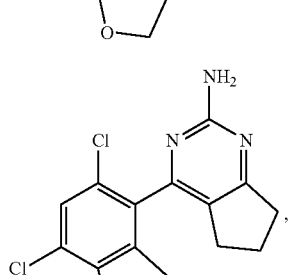
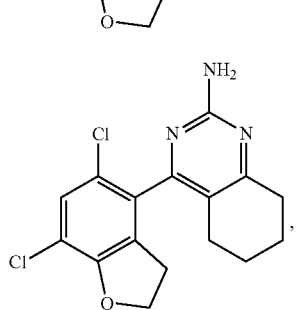

16
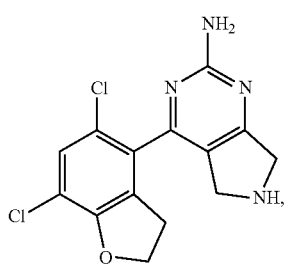
5
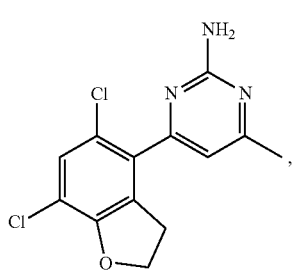
6
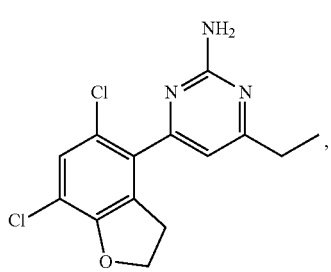
8
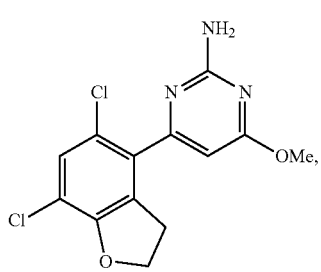
23
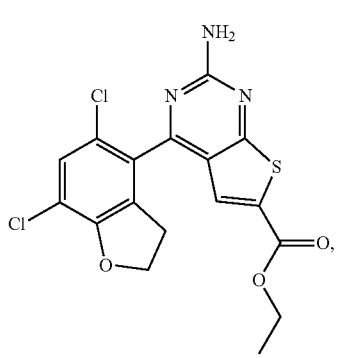
24
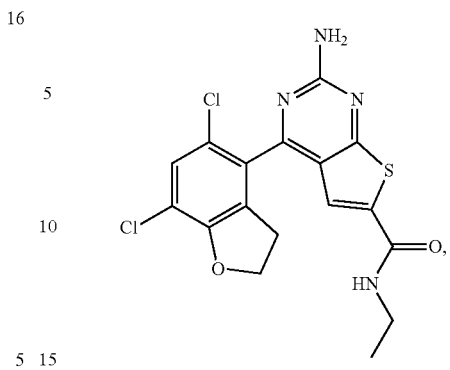
30
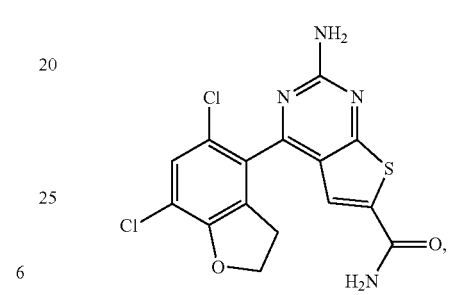
25
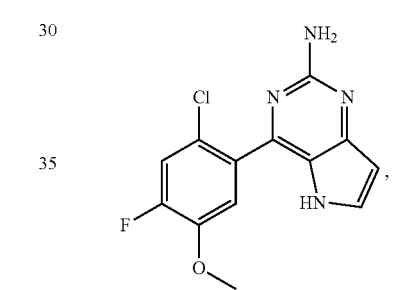
26
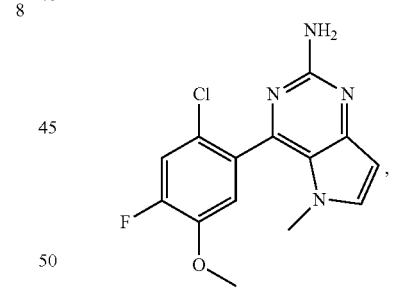
27
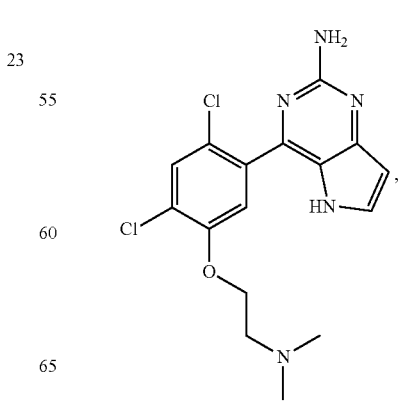

-continued
33
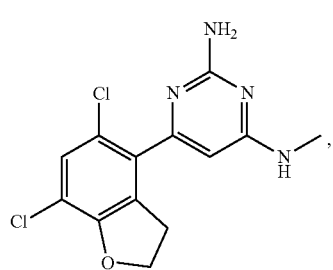
34
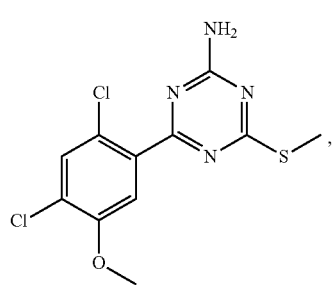
35
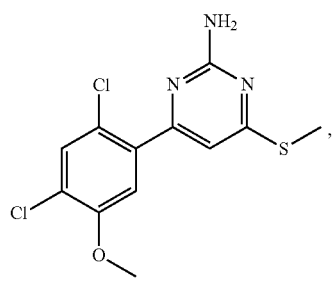
36
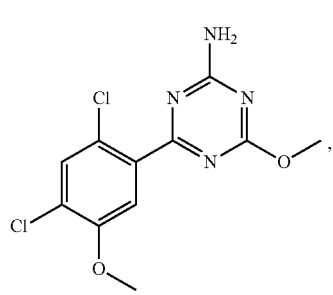
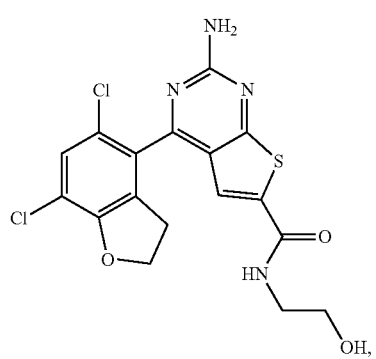
-continued
50
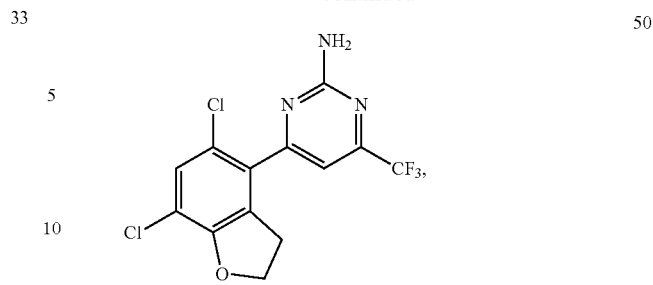
51
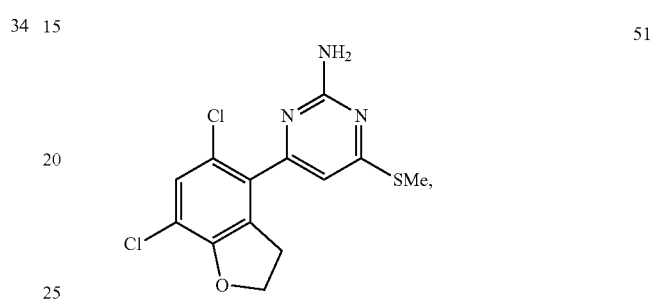
52
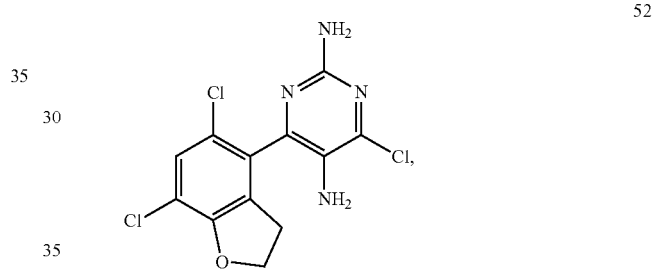
58
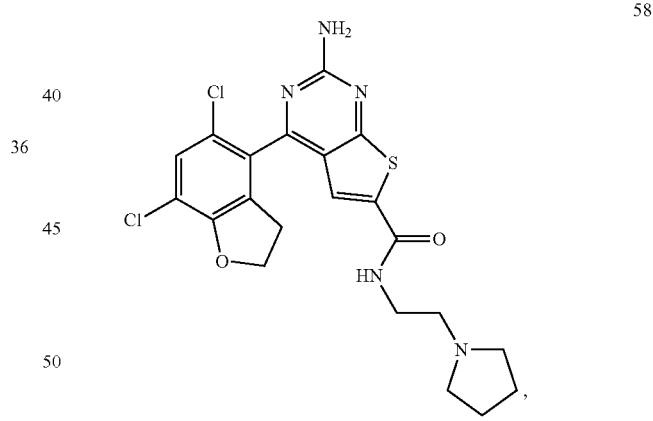
59
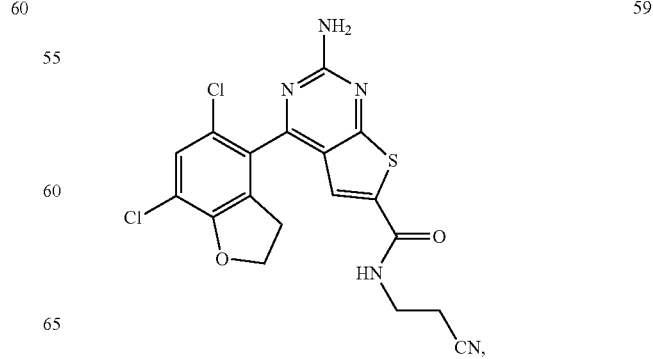

63
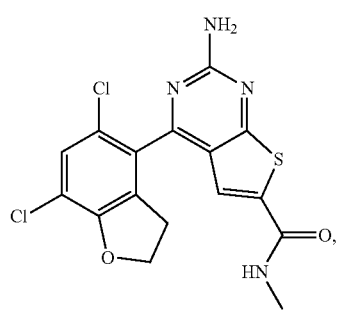
64
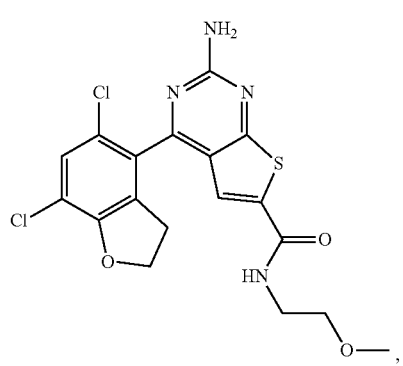
65
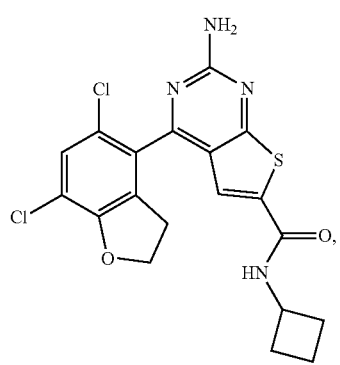
66
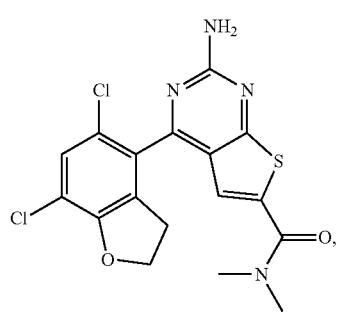
67
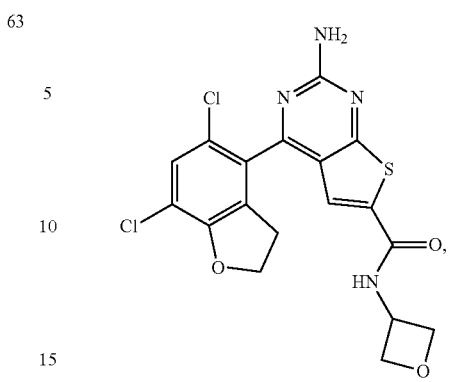
68
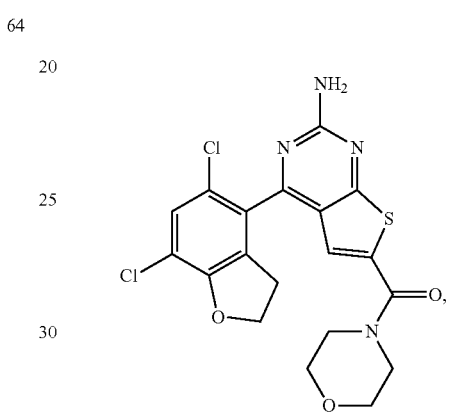
69
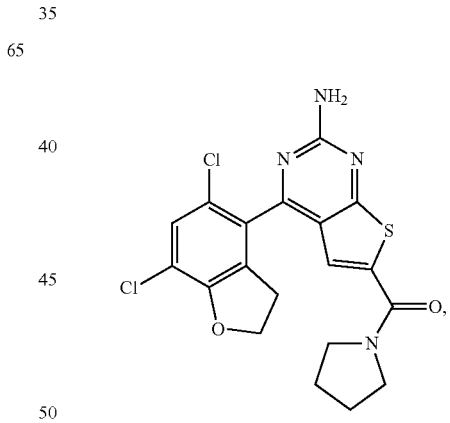
70
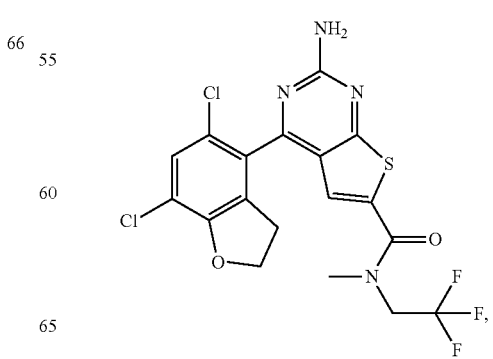

247
-continued
71
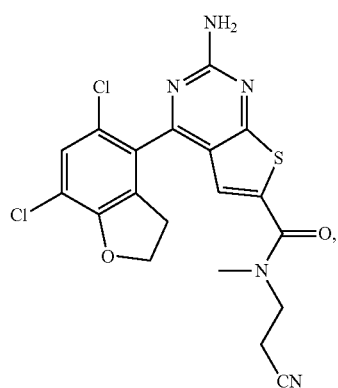
72
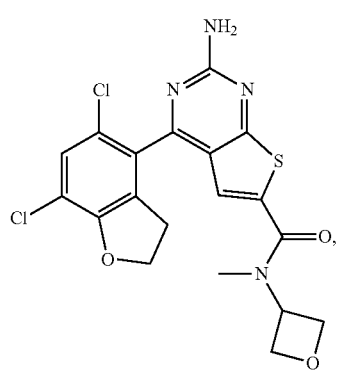
73
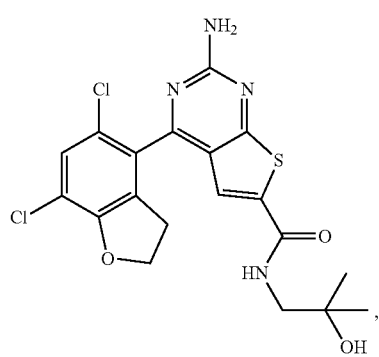
74
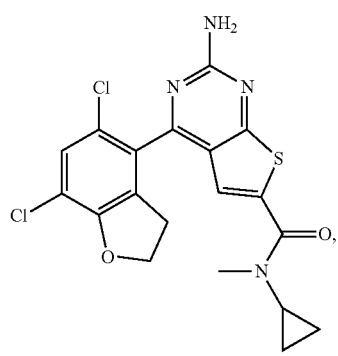
248
-continued
75
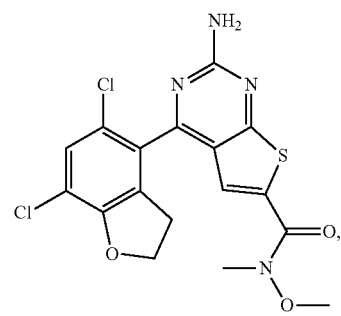
76
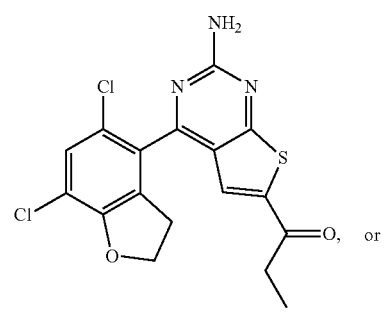
77
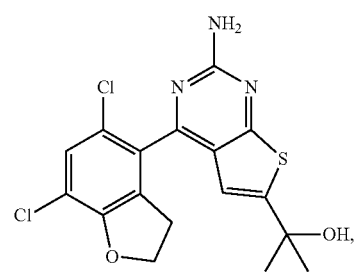
or a pharmaceutically acceptable salt thereof.
19. A compound according to the structure:
61
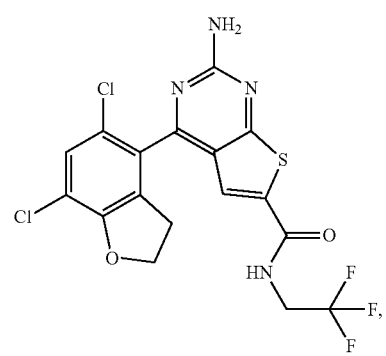

-continued

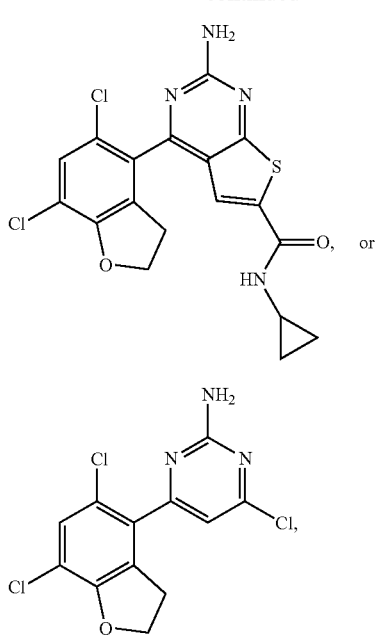

or a pharmaceutically acceptable salt thereof.

20. A pharmaceutical composition comprising the compound of claim 1, or a pharmaceutically acceptable salt thereof, and one or more of pharmaceutically acceptable carriers or excipients.

21. A method of treating a disorder in a mammal caused by the action of heat shock protein 90 (Hsp90), said method comprising administering an effective amount of the compound of claim 1 or a pharmaceutically acceptable salt thereof to said mammal, wherein said disorder is Alzheimer's disease, Huntington's disease, progressive supranuclear palsy, Parkinson's disease, Pick's disease, corticobasal degeneration, chronic traumatic encephalopathy, traumatic brain injury, or frontotemporal dementia.

22. The method of claim 21, wherein said disorder is Alzheimer's disease.

23. A method of treating a disorder in a mammal caused by the action of heat shock protein 90 (Hsp90), said method comprising administering an effective amount of the compound of claim 1 or a pharmaceutically acceptable salt thereof to said mammal, wherein said disorder is cancer.

24. A method of treating an infectious disease in a mammal, said method comprising administering an effective amount of the compound of claim 1 or a pharmaceutically acceptable salt thereof to said mammal.

25. The method of claim 24, wherein said infectious disease is a viral, fungal, or bacterial infection.

26. The method of claim 25, wherein said infectious disease is an infection by a virus of a family selected from the group consisting of Herpesviridae, Polyomaviridae, Poxviridae, Reoviridae, Birnaviridae, Picornaviridae, Flaviviridae, Arenaviridae, Hepeviridae, Rhabdoviridae, Paramoxyviridae, Bunyaviridae, Orthomoxyviridae, Filoviridae, Retroviridae, and Hepadnaviridae.

27. A method of treating a disorder in a mammal caused by the action of heat shock protein 90 (Hsp90), said method comprising administering an effective amount of the compound of claim 1 or a pharmaceutically acceptable salt thereof to said mammal, wherein said disorder is an inflammatory or autoimmune disease.

28. The method of claim 27, wherein said inflammatory or autoimmune disease is rheumatoid arthritis, systemic lupus erythermatosus, or asthma.

29. A method of treating a disorder in a mammal caused by the action of heat shock protein 90 (Hsp90), said method comprising administering an effective amount of the compound of claim 1 or a pharmaceutically acceptable salt thereof to said mammal, wherein said disorder is a cardiovascular disease.

30. The method of claim 29, wherein said cardiovascular disease is atherosclerosis.

31. A method of treating a disorder in a mammal caused by the action of heat shock protein 90 (Hsp90), said method comprising administering an effective amount of the compound of claim 1 or a pharmaceutically acceptable salt thereof to said mammal, wherein said disorder is an allergy.

32. A method of inhibiting Hsp90, said method comprising contacting a cell with the compound of claim 1 or a pharmaceutically acceptable salt thereof.

33. A kit comprising:
(i) the pharmaceutical composition of claim 20; and
(ii) instructions for use of the pharmaceutical compositions of (i) to treat a disorder in a mammal caused by the action of Hsp90.

* * * * *